US011858930B2

(12) United States Patent
Belfield et al.

(10) Patent No.: US 11,858,930 B2
(45) Date of Patent: Jan. 2, 2024

(54) FUSED BICYCLIC RAF INHIBITORS AND METHODS FOR USE THEREOF

(71) Applicant: JAZZ PHARMACEUTICALS IRELAND LIMITED, Dublin (IE)

(72) Inventors: Andrew Belfield, Macclesfield (GB); Clifford David Jones, Macclesfield (GB); Jean-François Margathe, Macclesfield (GB); Chiara Colletto, Macclesfield (GB)

(73) Assignee: JAZZ PHARMACEUTICALS IRELAND LIMITED, Dublin (IE)

( * ) Notice: Subject to any disclaimer, the term of this patent is extended or adjusted under 35 U.S.C. 154(b) by 0 days.

(21) Appl. No.: 17/387,049

(22) Filed: Jul. 28, 2021

(65) Prior Publication Data
US 2022/0033398 A1 Feb. 3, 2022

Related U.S. Application Data

(60) Provisional application No. 63/057,536, filed on Jul. 28, 2020.

(51) Int. Cl.
| | | |
|---|---|---|
| *C07D 471/04* | (2006.01) | |
| *A61K 31/4375* | (2006.01) | |
| *A61K 45/06* | (2006.01) | |
| *C07D 405/14* | (2006.01) | |

(52) U.S. Cl.
CPC ............ *C07D 471/04* (2013.01); *A61K 45/06* (2013.01); *C07D 405/14* (2013.01)

(58) Field of Classification Search
CPC .... C07D 471/04; A61K 31/4375; A61P 35/00
USPC .......................................... 546/123; 514/300
See application file for complete search history.

(56) References Cited

U.S. PATENT DOCUMENTS

| | | | |
|---|---|---|---|
| 5,698,550 A | 12/1997 | Eggler et al. | |
| 10,183,939 B2 | 1/2019 | Bingham et al. | |
| 2022/0041595 A1 | 2/2022 | Belfield et al. | |

FOREIGN PATENT DOCUMENTS

| | | |
|---|---|---|
| CN | 1690056 A | 11/2005 |
| CN | 109503659 A | 3/2019 |
| JP | 2009-519908 A | 5/2009 |
| WO | WO 1999/063974 A2 | 12/1999 |
| WO | WO 2003/006452 A1 | 1/2003 |
| WO | WO 2004/063191 A1 | 7/2004 |
| WO | WO 2006/087229 A1 | 8/2006 |
| WO | WO 2006/124874 A2 | 11/2006 |
| WO | WO 2008/009079 A2 | 1/2008 |
| WO | WO 2008/009079 A3 | 1/2008 |
| WO | WO 2013/097224 A1 | 7/2013 |
| WO | WO 2016/038389 A1 | 3/2016 |

OTHER PUBLICATIONS

Gilchrist, T, "Six-membered ring compounds with two or more heteroatoms," Heterocyclic Chemistry, Third Edition, Addison-Wesley Longman, 1992, Chapter 7, p. 257 (3 total pages).
Lewis et al., "The pharmacokinetics and metabolism of idazoxan in the rat," Xenobiotica, 1988, 18(5) pp. 519-532.
GB Search Report for GB Application No. GB1416186.3, dated May 26, 2015, 22 pages.
International Search Report and Written Opinion of the International Searching Authority for International Application No. PCT/EP2021/071212 dated Jan. 24, 2022, 15 pages.
International Search Report and Written Opinion of the International Searching Authority for International Application No. PCT/EP2021/071219 dated Dec. 7, 2021, 11 pages.
Suzuki et al., "Syntheses of 2-Aryl-4-(3-thienyl)imidazole Derivatives with Antiinflammatory Properties," Chem. Pharm. Bull. 1986, 34(8), 3111-3120.

*Primary Examiner* — Charanjit Aulakh
(74) *Attorney, Agent, or Firm* — COOLEY LLP

(57) ABSTRACT

The present disclosure generally relates to improved synthesis of fused bicyclic Raf inhibitors of formula (I), (I-A), (I-B), (II), or (III), or a pharmaceutically acceptable salt, tautomer, or stereoisomer thereof. The disclosure also relates to method of using the compound of formula (I), (I-A), (I-B), (II), or (III), or a pharmaceutically acceptable salt, tautomer, or stereoisomer thereof, for treating diseases such as cancer, including colorectal cancer.

17 Claims, No Drawings

FUSED BICYCLIC RAF INHIBITORS AND METHODS FOR USE THEREOF

CROSS-REFERENCE TO RELATED APPLICATIONS

This application claims the benefit of U.S. Provisional Application No. 63/057,536, filed Jul. 28, 2020, the disclosures of which are incorporated by reference herein in its entirety.

FIELD OF THE INVENTION

The present disclosure generally relates to novel RAF inhibitors and method of use thereof for treatment of various diseases, including but not limited to, colorectal cancer and melanoma.

BACKGROUND OF THE INVENTION

Mutations leading to uncontrolled signaling via the RAS-RAF-MAPK pathway are seen in more than one third of all cancers. The RAF kinases (A-RAF, B-RAF and C-RAF) are an integral part of this pathway, with B-RAF mutations commonly seen in the clinic. Although most B-RAF V600E mutant skin cancers are sensitive to approved B-RAF selective drugs, B-RAF V600E mutant colorectal cancers are surprisingly insensitive to these agents as monotherapy due to the functions of other RAF family members and require combination therapy. B-RAF selective therapies fail to show clinical benefit against atypical B-RAF (non-V600E), other RAF and RAS driven tumors.

U.S. Pat. No. 10,183,939 discloses racemic Raf inhibitors that demonstrated binding affinity for B-RAF V600E and C-RAF, the disclosures of which are hereby incorporated by reference in its entirety. These pan-RAF inhibitors are identified to be promising candidates in overcome resistance mechanisms associated with clinically approved B-RAF selective drugs.

SUMMARY OF THE INVENTION

The present disclosure relates to compounds that are Raf inhibitors. In embodiments, the compounds of the disclosure are pan-Raf inhibitors.

The present disclosure relates to a compound of formula (I), or a pharmaceutically acceptable salt, tautomer, or stereoisomer thereof,

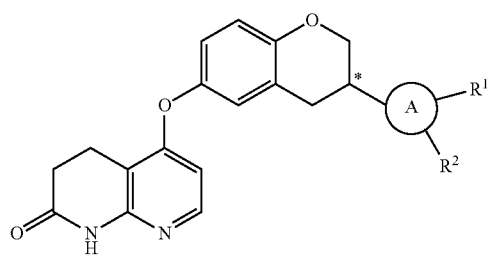

(I)

wherein:
ring A is a 5-membered heterocycle containing 1, 2, or 3, nitrogen atom as a ring member;
one of $R^1$ or $R^2$ is selected from substituted $C_{1-8}$ alkyl, unsubstituted $C_{5-8}$ alkyl, substituted or unsubstituted $C_{1-8}$ haloalkyl, substituted or unsubstituted aryl, substituted or unsubstituted heterocyclyl, or substituted heteroaryl, and the other $R^1$ or $R^2$ is H;
or alternatively, $R^1$ and $R^2$ together with the atoms to which they are attached forms a 5- or 6-membered saturated, partially unsaturated, or unsaturated ring containing 0, 1, or 2 heteroatoms selected from N, O, or S, wherein the ring is substituted or unsubstituted; and
wherein when ring A is an imidazole, then the substituted aryl is not

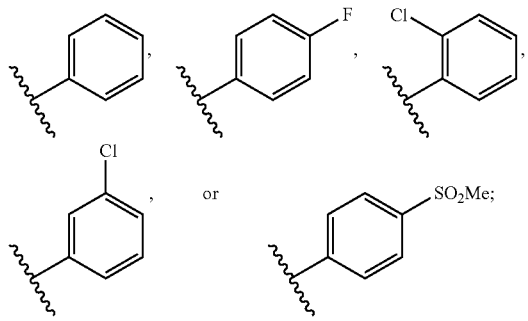

and
wherein when ring A is an imidazole, $R^1$ and $R^2$ together with the atoms to which they are attached do not form an unsubstituted phenyl ring.

In embodiments of compound of formula (I), ring A is imidazole, pyrazole, or triazole. In embodiments, ring A is

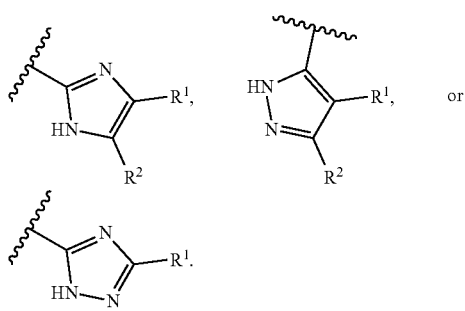

In embodiments, $R^1$ is a monocyclic or bicyclic, substituted or unsubstituted aryl. In embodiments, the bicyclic aryl is a fused bicyclic aryl.

The present disclosure also relates to a compound of formula (I-A), or a pharmaceutically acceptable salt, tautomer, or stereoisomer thereof,

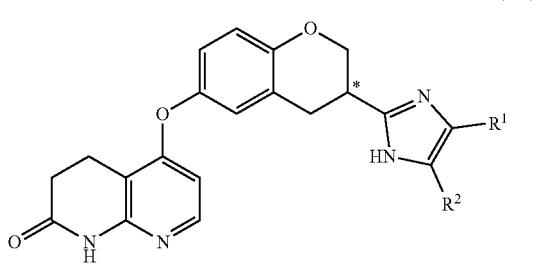

(I-A)

wherein:
one of $R^1$ or $R^2$ is selected from substituted or unsubstituted $C_{5-8}$ alkyl, substituted or unsubstituted $C_{1-8}$ haloalkyl, substituted aryl, substituted or unsubstituted heterocyclyl, or substituted heteroaryl, and the other $R^1$ or $R^2$ is H;
or alternatively, $R^1$ and $R^2$ together with the atoms to which they are attached forms a 5- or 6-membered saturated, partially unsaturated, or unsaturated ring containing 0, 1, or 2 heteroatoms selected from N, O, or S, wherein the ring is substituted or unsubstituted; and
wherein substituted aryl is not

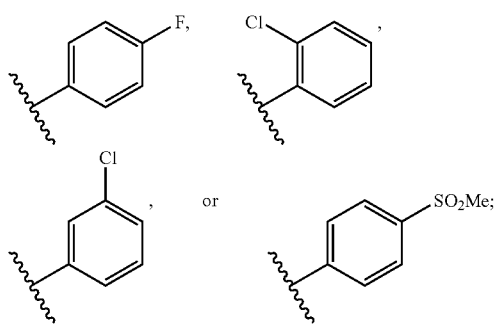

and
wherein $R^1$ and $R^2$ together with the atoms to which they are attached do not form an unsubstituted phenyl.

In embodiments of compound of formula (I) or (I-A), $R^1$ and $R^2$ together with the atoms to which they are attached forms a 5- or 6-membered partially unsaturated or unsaturated ring containing 0, 1, or 2 heteroatoms selected from N, O, or S, wherein the ring is substituted or unsubstituted. In embodiments, $R^1$ and $R^2$ together with the atoms to which they are attached forms a 6-membered partially unsaturated or unsaturated ring containing 0 or 1 nitrogen atom in the ring, wherein the ring is substituted or unsubstituted. In embodiments, $R^1$ and $R^2$ together with the atoms to which they are attached forms a substituted or unsubstituted phenyl ring or a substituted or unsubstituted pyridyl ring. In embodiments, $R^1$ and $R^2$ together with the atoms to which they are attached forms a substituted or unsubstituted tetrahydropyridyl ring.

The present disclosure also relates to a compound of formula (I-B), or a pharmaceutically acceptable salt, tautomer, or stereoisomer thereof,

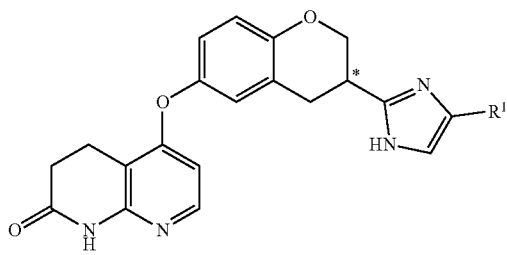

(I-B)

wherein:
one of $R^1$ or $R^2$ is selected from substituted aryl, substituted or unsubstituted heterocyclyl, or substituted heteroaryl; and wherein substituted aryl is not

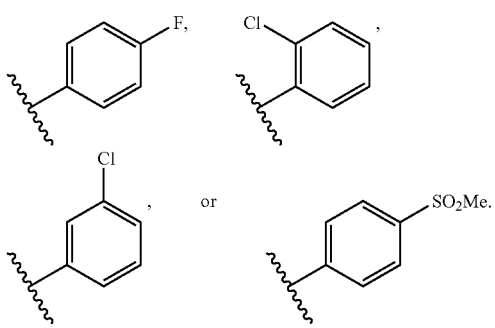

In embodiments of formula (I), (I-A), or (I-B), $R^1$ is substituted aryl, substituted or unsubstituted heterocyclyl, or substituted heteroaryl. In embodiments, $R^1$ is substituted phenyl or substituted 5- or 6-membered N-heteroaryl. In embodiments, $R^1$ is substituted phenyl, substituted pyridyl, substituted pyrazole, substituted pyrimidinyl, or substituted thiophenyl. In embodiments, $R^1$ is a monocyclic or bicyclic substituted aryl or a monocyclic or bicyclic substituted heteroaryl. In embodiments, the bicyclic aryl or the bicyclic heteroaryl is a fused bicyclic aryl or fused bicyclic heteroaryl. In embodiments, $R^1$ is substituted indazole or substituted benzoimidazole. In embodiments, In embodiments of formula (I), (I-A), or (I-B), $R^1$ is unsubstituted or substituted heterocyclyl containing 0, 1, or 2 heteroatoms selected from N, O, or S. In embodiments, $R^1$ is substituted or unsubstituted tetrahydropyran.

In embodiments of formula (I), (I-A), or (I-B), $R^1$ is substituted or unsubstituted $C_{5-6}$ alkyl.

In embodiments of formula (I), (I-A), or (I-B), $R^1$ is substituted with 1 or 2 substituents.

In embodiments of formula (I), (I-A), or (I-B), the substituent is selected from halogen, $—OR^A$, $—NR^AR^B$, $—SO_2R^C$, $—SOR^C$, $—CN$, $C_{1-6}$ alkyl, $C_{1-6}$ haloalkyl, $C_{3-6}$ cycloalkyl, or $—C(O)C_{1-6}$ alkyl; wherein:
$R^A$ and $R^B$ are each independently selected from H, $C_{1-6}$ alkyl and $C_{1-6}$ haloalkyl; and
$R^C$ is selected from $C_{1-6}$ alkyl and $C_{1-6}$ haloalkyl; and
wherein the alkyl, haloalkyl and cycloalkyl groups are optionally substituted with 1 to 3 groups independently selected from: $—OR^A$, $—CN$, $—SOR^C$, $—NR^AR^B$, or $—NR^DR^E$;
$R^D$ and $R^E$ together with the N atom to which they are attached forms a 5- or 6-membered saturated or partially unsaturated ring containing 1 or 2 heteroatoms selected from N, O, or S; wherein the saturated or partially unsaturated ring is optionally substituted with $C_{1-6}$ alkyl.

In embodiments of formula (I), (I-A), or (I-B), the substituent is selected from halogen, methyl, ethyl, propyl, isopropyl, n-butyl, s-butyl, t-butyl, cyclopropyl, methoxy, ethoxy, isopropoxy, $—CH_2F$, $—CHF_2$, $—CF_3$, $—CH_2CH_2F$, $—CH_2CHF_2$, $—CH_2CF_3$, $—C(O)CH_3$, $—CN$, $—OH$, $—NH_2$, $—NH(C_{1-3}$ alkyl), $—N(C_{1-3}$ alkyl$)_2$, $—CH_2NH_2$, $—CH_2NH(C_{1-3}$ alkyl), or $—CH_2N(C_{1-3}$ alkyl$)_2$.

In embodiments of formula (I), (I-A), or (I-B), the substituent on the substituted aryl or the substituted heteroaryl is selected from methyl, ethyl, propyl, isopropyl, n-butyl, s-butyl, t-butyl, cyclopropyl, methoxy, ethoxy, isopropoxy, $—CH_2F$, $—CHF_2$, $—CF_3$, $—CH_2CH_2F$, $—CH_2CHF_2$, —CH$_2$CF$_3$, —C(O)CH$_3$, —CN, —OH, —NH$_2$, —NH(C$_{1-3}$ alkyl), —N(C$_{1-3}$ alkyl)$_2$, —CH$_2$NH$_2$, —CH$_2$NH(C$_{1-3}$ alkyl), or —CH$_2$N(C$_{1-3}$ alkyl)$_2$.

In embodiments of formula (I), (I-A), or (I-B), the compound has (R) or (S) stereochemistry at the carbon indicated by *.

The present disclosure also relates to a compound selected from Table A-1, Table A-2, or Table A-3, or a pharmaceutically acceptable salt, tautomer, or stereoisomer thereof.

The present disclosure also relates to a compound of formula (II), or a pharmaceutically acceptable salt, tautomer, or stereoisomer thereof,

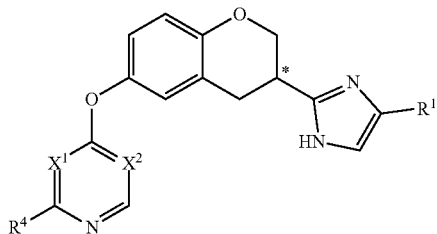

(II)

wherein:
X$^1$ and X$^2$ are each N or CH;
R$^1$ is selected from substituted C$_{1-8}$ alkyl, unsubstituted C$_{5-8}$ alkyl, substituted or unsubstituted C$_{1-8}$ haloalkyl, substituted or unsubstituted aryl, substituted or unsubstituted heterocyclyl, or substituted or unsubstituted heteroaryl; and
R$^4$ is —NR$^F$C(O)R$^5$, —NR$^F$C(O)CH$_2$R$^5$, —NR$^F$C(O)CH(CH$_3$)R$^5$, or —NR$^F$R$^5$;
R$^5$ is substituted or unsubstituted group selected from alkyl, carbocyclyl, aryl, heterocyclyl, or heteroaryl; and
R$^F$ is selected from H or C$_{1-3}$ alkyl.

In embodiments of formula (II), one of X$^1$ and X$^2$ is N. In embodiments, X$^1$ and X$^2$ are both CH.

In embodiments of formula (II), R$^1$ is substituted or unsubstituted aryl, substituted or unsubstituted heterocyclyl, or substituted or unsubstituted heteroaryl. In embodiments, R$^1$ is substituted or unsubstituted phenyl, substituted or unsubstituted pyridyl, substituted or unsubstituted pyrazole, substituted or unsubstituted pyrimidinyl, or substituted or unsubstituted thiophenyl.

In embodiments of formula (II), R$^4$ is —NHC(O)R$^5$, —NHC(O)CH$_2$R$^5$, —NHC(O)CH(CH$_3$)R$^5$, or —NHR$^5$.

In embodiments of formula (II), R$^5$ is substituted or unsubstituted group selected from alkyl, 3-6 membered carbocyclyl, phenyl, 3-6 membered heterocyclyl, or 5-6 membered heteroaryl. In embodiments, R$^5$ is substituted or unsubstituted group selected from methyl, cyclopropyl, cyclobutyl, cyclopentyl, or cyclohexyl, azetidine, pyrrolidine, piperidine, piperazine, morpholine, pyridine, thiazole, imidazole, pyrazole, or triazole.

In embodiments of formula (II), R$^F$ is H or methyl.

In embodiments of formula (II), the substituent is selected from halogen, —OR$^A$, —NR$^A$R$^B$, —SO$_2$R$^C$, —SOR$^C$, —CN, C$_{1-6}$ alkyl, C$_{1-6}$ haloalkyl, C$_{3-6}$ cycloalkyl, or —C(O)C$_{1-6}$ alkyl;
  wherein R$^A$ and R$^B$ are each independently selected from H, C$_{1-6}$ alkyl and C$_{1-6}$ haloalkyl; and
  R$^C$ is selected from C$_{1-6}$ alkyl and C$_{1-6}$ haloalkyl; wherein the alkyl, haloalkyl and cycloalkyl groups are optionally substituted with 1 to 3 groups independently selected from: —OR$^A$, —CN, —SOR$^C$, or —NR$^A$R$^B$.

In embodiments of formula (II), the substituent is selected from halogen, methyl, ethyl, propyl, isopropyl, n-butyl, s-butyl, t-butyl, cyclopropyl, methoxy, ethoxy, isopropoxy, —CH$_2$F, —CHF$_2$, —CF$_3$, —CH$_2$CH$_2$F, —CH$_2$CHF$_2$, —CH$_2$CF$_3$, —C(O)CH$_3$, —CN, —OH, —NH$_2$, —NH(C$_{1-3}$ alkyl), —N(C$_{1-3}$ alkyl)$_2$, —CH$_2$NH$_2$, —CH$_2$NH(C$_{1-3}$ alkyl), or —CH$_2$N(C$_{1-3}$ alkyl)$_2$.

In embodiments of formula (II), R$^5$ is substituted with one or more substituents selected from halogen, methyl, ethyl, propyl, isopropyl, —CN, —OH, or —NH$_2$.

In embodiments of formula (II), the compound has (R) or (S) stereochemistry at the carbon indicated by *.

The present disclosure also relates to a compound selected from Table B, or a pharmaceutically acceptable salt, tautomer, or stereoisomer thereof.

The present disclosure also relates to a compound of formula (III), or a pharmaceutically acceptable salt, tautomer, or stereoisomer thereof,

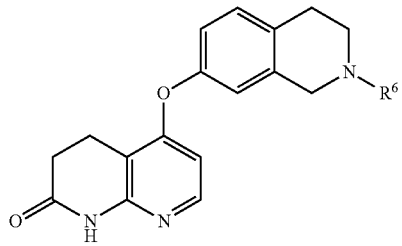

(III)

wherein:
R$^6$ is —C(O)NR$^F$R$^5$, —C(O)NR$^F$CH$_2$R$^5$, substituted or unsubstituted aryl, substituted or unsubstituted heterocyclyl, or substituted or unsubstituted heteroaryl;
R$^5$ is substituted or unsubstituted group selected from carbocyclyl, aryl, heterocyclyl, or heteroaryl; and
R$^F$ is selected from H or C$_{1-3}$ alkyl.

In embodiments of formula (III), R$^6$ is —C(O)NHR$^5$ or —C(O)NHCH$_2$R$^5$.

In embodiments of formula (III), R$^5$ is substituted or unsubstituted aryl. In embodiments, R$^5$ is substituted or unsubstituted phenyl.

In embodiments of formula (III), R$^6$ is substituted or unsubstituted aryl or substituted or unsubstituted heteroaryl. In embodiments, R$^6$ is a monocyclic or bicyclic substituted aryl or a monocyclic or bicyclic substituted heteroaryl. In embodiments, the bicyclic aryl or the bicyclic heteroaryl is a fused bicyclic aryl or fused bicyclic heteroaryl. In embodiments, R$^6$ is substituted or unsubstituted indazole or substituted or unsubstituted benzoimidazole.

In embodiments of formula (III), the substituent is selected from halogen, —OR$^A$, —NR$^A$R$^B$, —SO$_2$R$^C$, —SOR$^C$, —CN, C$_{1-6}$ alkyl, C$_{1-6}$ haloalkyl, C$_{3-6}$ cycloalkyl, or —C(O)C$_{1-6}$ alkyl;
  wherein R$^A$ and R$^B$ are each independently selected from H, C$_{1-6}$ alkyl and C$_{1-6}$ haloalkyl; and
  R$^C$ is selected from C$_{1-6}$ alkyl and C$_{1-6}$ haloalkyl; wherein the alkyl, haloalkyl and cycloalkyl groups are optionally substituted with 1 to 3 groups independently selected from: —OR$^A$, —CN, —SOR$^C$, or —NR$^A$R$^B$.

In embodiments of formula (III), the substituent is selected from halogen, methyl, ethyl, propyl, isopropyl, n-butyl, s-butyl, t-butyl, cyclopropyl, methoxy, ethoxy, isopropoxy, —CH$_2$F, —CHF$_2$, —CF$_3$, —CH$_2$CH$_2$F, —CH$_2$CHF$_2$, —CH$_2$CF$_3$, —C(O)CH$_3$, —CN, —OH, —NH$_2$, —NH(C$_{1-3}$ alkyl), —N(C$_{1-3}$ alkyl)$_2$, —CH$_2$NH$_2$, —CH$_2$NH(C$_{1-3}$ alkyl), or —CH$_2$N(C$_{1-3}$ alkyl)$_2$.

In embodiments of formula (III), R$^6$ is substituted aryl, substituted heterocyclyl, or substituted heteroaryl; wherein the substituent is selected from halogen, methyl, ethyl, propyl, isopropyl, n-butyl, s-butyl, t-butyl, cyclopropyl, methoxy, ethoxy, isopropoxy, —CH$_2$F, —CHF$_2$, —CF$_3$, —CH$_2$CH$_2$F, —CH$_2$CHF$_2$, —CH$_2$CF$_3$, —C(O)CH$_3$, —CN, —OH, —NH$_2$, —NH(C$_{1-3}$ alkyl), —N(C$_{1-3}$ alkyl)$_2$, —CH$_2$NH$_2$, —CH$_2$NH(C$_{1-3}$ alkyl), —CH$_2$N(C$_{1-3}$ alkyl)$_2$, optionally substituted phenyl, or optionally substituted heteroaryl. In embodiments, R$^6$ is a substituted aryl or a substituted heteroaryl, wherein the substituent is a phenyl or a pyrazole substituted with one or two C$_{1-3}$ alkyl groups.

The present disclosure also relates to a compound selected from Table C, or a pharmaceutically acceptable salt, tautomer, or stereoisomer thereof.

The present disclosure also relates to a compound selected from Table D, or a pharmaceutically acceptable salt, tautomer, or stereoisomer thereof.

The present disclosure relates to a pharmaceutical composition comprising any one of the compounds as disclosed herein and a pharmaceutically acceptable excipient or carrier.

In embodiments of the pharmaceutical composition, the composition further comprises an additional therapeutic agent. In embodiments, the additional therapeutic agent is selected from an antiproliferative or an antineoplastic drug, a cytostatic agent, an anti-invasion agent, an inhibitor of growth factor function, an antiangiogenic agent, a steroid, a targeted therapy agent, or an immunotherapeutic agent.

The present disclosure relates to a method of treating a condition which is modulated by a RAF kinase, comprising administering an effective amount of any one of the compounds disclosed herein.

In embodiments of the method of treatment, the condition treatable by the inhibition of one or more Raf kinases. In embodiments, the condition is selected from cancer, sarcoma, melanoma, skin cancer, haematological tumors, lymphoma, carcinoma or leukemia. In embodiments, the condition is selected from Barret's adenocarcinoma; biliary tract carcinomas; breast cancer; cervical cancer; cholangiocarcinoma; central nervous system tumors; primary CNS tumors; glioblastomas, astrocytomas; glioblastoma multiforme; ependymomas; secondary CNS tumors (metastases to the central nervous system of tumors originating outside of the central nervous system); brain tumors; brain metastases; colorectal cancer; large intestinal colon carcinoma; gastric cancer; carcinoma of the head and neck; squamous cell carcinoma of the head and neck; acute lymphoblastic leukemia; acute myelogenous leukemia (AML); myelodysplastic syndromes; chronic myelogenous leukemia; Hodgkin's lymphoma; non-Hodgkin's lymphoma; megakaryoblastic leukemia; multiple myeloma; erythroleukemia; hepatocellular carcinoma; lung cancer; small cell lung cancer; non-small cell lung cancer; ovarian cancer; endometrial cancer; pancreatic cancer; pituitary adenoma; prostate cancer; renal cancer; metastatic melanoma or thyroid cancers.

The present disclosure relates to a method of treating cancer, comprising administering an effective amount of any one of the compounds disclosed herein.

In embodiments of the method of treating cancer, the cancer comprises at least one mutation of the BRAF kinase. In embodiments, the cancer comprises a BRAF$^{V600E}$ mutation.

In embodiments, the cancer is selected from melanomas, thyroid cancer, Barret's adenocarcinoma, biliary tract carcinomas, breast cancer, cervical cancer, cholangiocarcinoma, central nervous system tumors, glioblastomas, astrocytomas, ependymomas, colorectal cancer, large intestine colon cancer, gastric cancer, carcinoma of the head and neck, hematologic cancers, leukaemia, acute lymphoblastic leukaemia, myelodysplastic syndromes, chronic myelogenous leukaemia, Hodgkin's lymphoma, non-Hodgkin's lymphoma, megakaryoblastic leukaemia, multiple myeloma, hepatocellular carcinoma, lung cancer, ovarian cancer, pancreatic cancer, pituitary adenoma, prostate cancer, renal cancer, sarcoma, uveal melanoma or skin cancer. In embodiments, the cancer is BRAF$^{V600E}$ melanoma, BRAF$^{V600E}$ colorectal cancer, BRAF$^{V600E}$ papillary thyroid cancers, BRAF$^{V600E}$ low grade serous ovarian cancers, BRAF$^{V600E}$ glioma, BRAF$^{V600E}$ hepatobiliary cancers, BRAF$^{V600E}$ hairy cell leukaemia, BRAF$^{V600E}$ non-small cell cancer, or BRAF$^{V600E}$ pilocytic astrocytoma. In embodiments, the cancer is colorectal cancer.

DETAILED DESCRIPTION

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a RAF inhibitor" refers to one or more RAF inhibitor or at least one RAF inhibitor. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The term "treating" means one or more of relieving, alleviating, delaying, reducing, improving, or managing at least one symptom of a condition in a subject. The term "treating" may also mean one or more of arresting, delaying the onset (i.e., the period prior to clinical manifestation of the condition) or reducing the risk of developing or worsening a condition.

The compounds of the invention, or their pharmaceutically acceptable salts contain at least one asymmetric center. The compounds of the invention with one asymmetric center give rise to enantiomers, where the absolute stereochemistry can be expressed as (R)- and (S)-, or (+) and (−). When the compounds of the invention have more than two asymmetric centers, then the compounds can exist as diastereomers or other stereoisomeric forms. The present disclosure is meant to include all such possible isomers, as well as their racemic and optically pure forms whether or not they are specifically depicted herein. Optically active (+) and (−) or (R)- and (S)-isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present disclosure includes tautomers of any said compounds.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or pharmaceutical formulation that is sufficient to result in a desired clinical benefit after administration to a patient in need thereof.

As used herein, a "subject" can be a human, non-human primate, mammal, rat, mouse, cow, horse, pig, sheep, goat, dog, cat and the like. The subject can be suspected of having or at risk for having a cancer, including but not limited to colorectal cancer and melanoma.

"Mammal" includes humans and both domestic animals such as laboratory animals (e.g., mice, rats, monkeys, dogs, etc.) and household pets (e.g., cats, dogs, swine, cattle, sheep, goats, horses, rabbits), and non-domestic animals such as wildlife and the like.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

The term "halo" refers to a halogen. In particular the term refers to fluorine, chlorine, bromine and iodine.

"Alkyl" or "alkyl group" refers to a fully saturated, straight or branched hydrocarbon chain group, and which is attached to the rest of the molecule by a single bond. Alkyls comprising any number of carbon atoms, including but not limited to from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-Nonyl, n-decyl, n-undecyl, and n-dodecyl. Unless stated otherwise specifically in the specification, an alkyl group can be optionally substituted.

"Cycloalkyl" refers to a stable non-aromatic monocyclic or polycyclic fully saturated hydrocarbon group consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl groups include, for example, cyclopropyl, cyclobutyl, cyclopentyl, cyclohexyl, cycloheptyl, and cyclooctyl. Polycyclic cycloalkyl groups include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Haloalkyl" refers to an alkyl group, as defined above, that is substituted by one or more halo groups, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Aryl" refers to a hydrocarbon ring system group comprising hydrogen, 6 to 18 carbon atoms and at least one aromatic ring. For purposes of this invention, the aryl group can be a monocyclic, bicyclic, tricyclic or tetracyclic ring system, which can include fused or bridged ring systems. Aryl groups include, but are not limited to, aryl groups derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl groups that are optionally substituted.

"Heterocyclyl," "heterocyclic ring" or "heterocycle" refers to a stable 3- to 20-membered ring group which consists of two to twelve carbon atoms and from one to six heteroatoms selected from the group consisting of nitrogen, oxygen and sulfur. Heterocyclcl or heterocyclic rings include heteroaryls as defined below. Unless stated otherwise specifically in the specification, the heterocyclyl group can be a monocyclic, bicyclic, tricyclic or tetracyclic ring system, which can include fused or bridged ring systems; and the nitrogen, carbon or sulfur atoms in the heterocyclyl group can be optionally oxidized; the nitrogen atom can be optionally quaternized; and the heterocyclyl group can be partially or fully saturated. Examples of such heterocyclyl groups include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted. In embodiments, heterocyclyl, heterocyclic ring or heterocycle is a stable 3- to 20-membered non-aromatic ring group which consists of two to twelve carbon atoms and from one to six heteroatoms selected from the group consisting of nitrogen, oxygen and sulfur.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heteroaryl" refers to a 5- to 20-membered ring system group comprising hydrogen atoms, one to thirteen carbon atoms, one to six heteroatoms selected from the group consisting of nitrogen, oxygen and sulfur, and at least one aromatic ring. For purposes of this invention, the heteroaryl group can be a monocyclic, bicyclic, tricyclic or tetracyclic ring system, which can include fused or bridged ring systems; and the nitrogen, carbon or sulfur atoms in the heteroaryl group can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1, 4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo [1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, $C_1$, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)$ $R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing groups can also be optionally substituted with one or more of the above groups.

Compounds of the Invention

The present disclosure relates to pan-RAF inhibitors having the structure of formula (I), or a pharmaceutically acceptable salt, tautomer, or stereoisomer thereof,

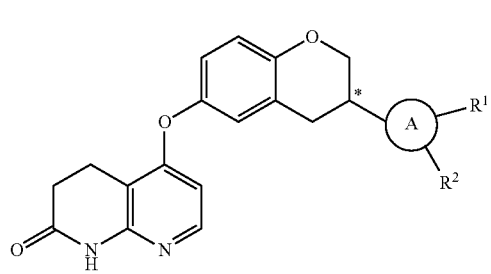

(I)

wherein ring A is a 5-membered heterocycle or heteroaryl containing 1, 2, or 3, nitrogen atom as a ring member;

wherein one of $R^1$ or $R^2$ is selected from substituted $C_{1-8}$ alkyl, unsubstituted $C_{5-8}$ alkyl, substituted or unsubstituted $C_{1-8}$ haloalkyl, substituted or unsubstituted aryl, substituted or unsubstituted heterocyclyl, or substituted heteroaryl, and the other $R^1$ or $R^2$ is H;

or alternatively, $R^1$ and $R^2$ together with the atoms to which they are attached forms a 5- or 6-membered saturated, partially unsaturated, or unsaturated ring containing 0, 1, or 2 heteroatoms selected from N, O, or S, wherein the ring is substituted or unsubstituted;

wherein when ring A is an imidazole, then the substituted aryl (e.g., $R^1$ or $R^2$) is not

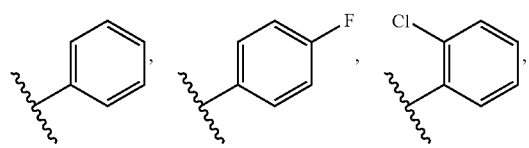

-continued

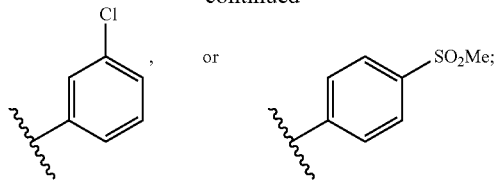

and wherein when ring A is an imidazole, $R^1$ and $R^2$ together with the atoms to which they are attached do not form an unsubstituted phenyl ring.

In embodiments of formula (I), ring A is imidazole, pyrazole, or triazole. In embodiments of formula (I), ring A is

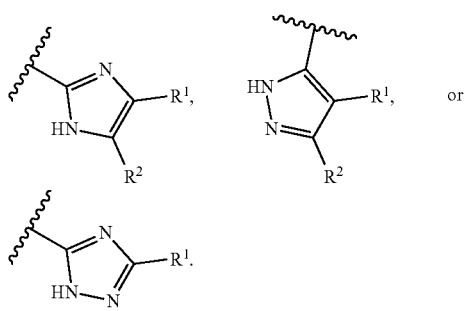

In embodiments, the present disclosure relates compounds of formula (I-A), or a pharmaceutically acceptable salt, tautomer, or stereoisomer thereof,

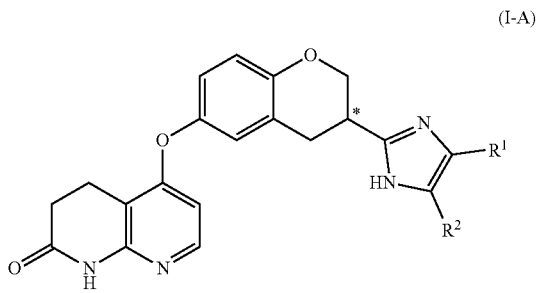

(I-A)

wherein one of $R^1$ or $R^2$ is selected from substituted or unsubstituted $C_{5-8}$ alkyl, substituted or unsubstituted $C_{1-8}$ haloalkyl, substituted aryl, substituted or unsubstituted heterocyclyl, or substituted heteroaryl, and the other $R^1$ or $R^2$ is H;

or alternatively, $R^1$ and $R^2$ together with the atoms to which they are attached forms a 5- or 6-membered saturated, partially unsaturated, or unsaturated ring containing 0, 1, or 2 heteroatoms selected from N, O, or S, wherein the ring is substituted or unsubstituted;

wherein the substituted aryl (e.g., $R^1$ or $R^2$) is not

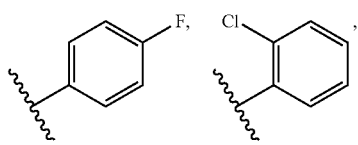

15

-continued

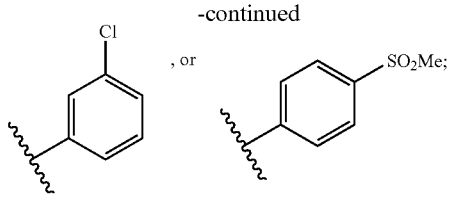

and
wherein R¹ and R² together with the atoms to which they are attached do not form an unsubstituted phenyl.

In embodiments of formula (I) or (I-A), substituent is selected from halogen, —OR$^A$, —NR$^A$R$^B$, —SO$_2$R$^C$, —SOR$^C$, —CN, C$_{1-6}$ alkyl, C$_{1-6}$ haloalkyl, C$_{3-6}$ cycloalkyl, or —C(O)C$_{1-6}$ alkyl; wherein:
  R$^A$ and R$^B$ are each independently selected from H, C$_{1-6}$ alkyl and C$_{1-6}$ haloalkyl; and
  R$^C$ is selected from C$_{1-6}$ alkyl and C$_{1-6}$ haloalkyl; and
  wherein the alkyl, haloalkyl and cycloalkyl groups are optionally substituted with 1 to 3 groups independently selected from: —OR$^A$, —CN, —SOR$^C$, —NR$^A$R$^B$, or —NR$^D$R$^E$;
  R$^D$ and R$^E$ together with the N atom to which they are attached forms a 5- or 6-membered saturated or partially unsaturated ring containing 1 or 2 heteroatoms selected from N, O, or S; wherein the saturated or partially unsaturated ring is optionally substituted with C$_{1-6}$ alkyl.

In embodiments, the present disclosure relates compounds of formula (I-B), or a pharmaceutically acceptable salt, tautomer, or stereoisomer thereof, (I-B)

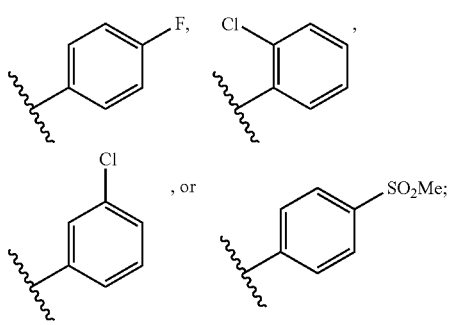

wherein one of R¹ or R² is selected from substituted aryl, substituted or unsubstituted heterocyclyl, or substituted heteroaryl; and
wherein the substituted aryl is not In embodiments of formula (I), (I-A), or (I-B), substituent is selected from halogen, —OR$^A$, —NR$^A$R$^B$, —SO$_2$R$^C$, —SOR$^C$, —CN, C$_{1-6}$ alkyl, C$_{1-6}$ haloalkyl, C$_{3-6}$ cycloalkyl, or —C(O)C$_{1-6}$ alkyl; wherein R$^A$ and R$^B$ are each independently selected from H, C$_{1-6}$ alkyl and C$_{1-6}$ haloalkyl; and R$^C$ is selected from C$_{1-6}$ alkyl and C$_{1-6}$ haloalkyl; wherein the alkyl, haloalkyl and cycloalkyl groups are optionally substituted with 1 to 3 groups independently selected from: —OR$^A$, —CN, —SOR$^C$, or —NR$^A$R$^B$.

In embodiments of formula (I), (I-A), or (I-B), substituent is selected from halogen, methyl, ethyl, propyl, isopropyl, n-butyl, s-butyl, t-butyl, cyclopropyl, methoxy, ethoxy, isopropoxy, —CH$_2$F, —CHF$_2$, —CF$_3$, —CH$_2$CH$_2$F, —CH$_2$CHF$_2$, —CH$_2$CF$_3$, —C(O)CH$_3$, —CN, —OH, —NH$_2$, —NH(C$_{1-3}$ alkyl), —N(C$_{1-3}$ alkyl)$_2$, —CH$_2$NH$_2$, —CH$_2$NH(C$_{1-3}$ alkyl), or —CH$_2$N(C$_{1-3}$ alkyl)$_2$.

In embodiments of formula (I), (I-A), or (I-B), substituent on the substituted aryl or the substituted heteroaryl is selected from halogen, —OR$^A$, —NR$^A$R$^B$, —SO$_2$R$^C$, —SOR$^C$, —CN, C$_{1-6}$ alkyl, C$_{1-6}$ haloalkyl, C$_{3-6}$ cycloalkyl, or —C(O)C$_{1-6}$ alkyl; wherein R$^A$ and R$^B$ are each independently selected from H, C$_{1-6}$ alkyl and C$_{1-6}$ haloalkyl; and R$^C$ is selected from C$_{1-6}$ alkyl and C$_{1-6}$ haloalkyl. In embodiments, substituent is selected from methyl, ethyl, propyl, isopropyl, n-butyl, s-butyl, t-butyl, cyclopropyl, methoxy, ethoxy, isopropoxy, —CH$_2$F, —CHF$_2$, —CF$_3$, —CH$_2$CH$_2$F, —CH$_2$CHF$_2$, —CH$_2$CF$_3$, —C(O)CH$_3$, —CN, —OH, —NH$_2$, —NH(C$_{1-3}$ alkyl), —N(C$_{1-3}$ alkyl)$_2$, —CH$_2$NH$_2$, —CH$_2$NH(C$_{1-3}$ alkyl), or —CH$_2$N(C$_{1-3}$ alkyl)$_2$.

In embodiments of formula (I), (I-A), or (I-B), substituent on the substituted aryl is selected from C$_{1-6}$ alkyl, C$_{1-6}$ haloalkyl, C$_{3-6}$ cycloalkyl, —OR$^A$, —NR$^A$R$^B$, —CN, - or —C(O)C$_{1-6}$ alkyl.

In embodiments of formula (I) or (I-A), R¹ is substituted aryl, substituted or unsubstituted heterocyclyl, or substituted heteroaryl. In embodiments, substituted aryl is substituted phenyl. In embodiments, substituted heteroaryl is substituted N-heteroaryl. In embodiments, substituted heteroaryl is substituted 5- or 6-membered N-heteroaryl.

In embodiments of formula (I), (I-A), or (I-B), R¹ is substituted phenyl, substituted pyridyl, substituted pyrazole, substituted pyrimidinyl, or substituted thiophenyl. In embodiments of formula (I), (I-A), or (I-B), R¹ is substituted phenyl, substituted pyridyl, or substituted pyrazole.

In embodiments of formula (I), (I-A), or (I-B), R¹ is substituted or unsubstituted heterocyclyl containing 0, 1, or 2 heteroatoms selected from N, O, or S. In embodiments, R¹ is substituted or unsubstituted tetrahydropyran. In embodiments, R¹ is substituted or unsubstituted In embodiments of formula (I-B), R¹ is substituted or unsubstituted heterocyclyl containing 0, 1, or 2 heteroatoms selected from N, O, or S. In embodiments, R¹ is substituted or unsubstituted 5- or 6-membered heterocyclyl containing 0, 1, or 2 heteroatoms selected from N, O, or S. In embodiments, R¹ is substituted or unsubstituted saturated heterocyclyl containing 0, 1, or 2 heteroatoms selected from N, O, or S. In embodiments, R¹ is substituted or unsubstituted saturated 5- or 6-membered heterocyclyl containing 0, 1, or 2 heteroatoms selected from N, O, or S. In embodiments, $R^1$ is substituted or unsubstituted tetrahydropyran.

In embodiments of formula (I) or (I-A), $R^1$ is substituted or unsubstituted $C_{5-6}$ alkyl. In embodiments, $C_{5-6}$ alkyl is linear or branched.

In embodiments of formula (I), (I-A), or (I-B), $R^1$ is a monocyclic substituted aryl or a monocyclic substituted heteroaryl. In embodiments of formula (I), $R^1$ is a bicyclic substituted aryl or a bicyclic substituted heteroaryl. In embodiments of formula (I), (I-A), or (I-B), $R^1$ is a bicyclic substituted aryl or a bicyclic substituted heteroaryl. In embodiments of formula (I), (I-A), or (I-B), $R^1$ is a fused bicyclic substituted aryl or a fused bicyclic substituted heteroaryl. In embodiments of formula (I), $R^1$ is substituted or unsubstituted indazole or substituted or unsubstituted benzoimidazole. In embodiments of formula (I), (I-A), or (I-B), $R^1$ is substituted indazole or substituted benzoimidazole.

In embodiments of formula (I) or (I-A), $R^1$ or $R^2$ is substituted with 1, 2, or 3 substituents. In embodiments of formula (I) or (I-A), $R^1$ or $R^2$ is substituted with 1 or 2 substituents.

In embodiments of formula (I-B), $R^1$ is substituted with 1, 2, or 3 substituents. In embodiments of formula (I-B), $R^1$ is substituted with 1 or 2 substituents.

In embodiments of formula (I) or (I-A), $R^1$ and $R^2$ together with the atoms to which they are attached forms a 5- or 6-membered partially unsaturated or unsaturated ring containing 0, 1, or 2 heteroatoms selected from N, O, or S, wherein the ring is substituted or unsubstituted. In embodiments, $R^1$ and $R^2$ together with the atoms to which they are attached forms a 6-membered partially unsaturated or unsaturated ring containing 0 or 1 nitrogen atom in the ring, wherein the ring is substituted or unsubstituted.

In embodiments of formula (I-A), $R^1$ and $R^2$ together with the atoms to which they are attached forms a phenyl ring, which is substituted or unsubstituted. In embodiments, $R^1$ and $R^2$ together with the atoms to which they are attached forms a phenyl ring thereby forming a benzoimidazole ring with the imidazole ring depicted in formula (I-A), which is substituted or unsubstituted.

In embodiments of formula (I-A), $R^1$ and $R^2$ together with the atoms to which they are attached forms a pyridyl ring, which is substituted or unsubstituted. In embodiments, $R^1$ and $R^2$ together with the atoms to which they are attached forms a pyridyl ring thereby forming a imidazopyridine ring with the imidazole ring depicted in formula (I-A), which is substituted or unsubstituted.

In embodiments of formula (I-A), $R^1$ and $R^2$ together with the atoms to which they are attached forms a tetrahydropyridyl ring, which is substituted or unsubstituted. In embodiments, $R^1$ and $R^2$ together with the atoms to which they are attached forms a tetrahydropyridyl ring thereby forming a tetrahydroimidazopyridine ring with the imidazole ring depicted in formula (I-A), which is substituted or unsubstituted.

In embodiments of formula (I) or (I-A), $R^1$ and $R^2$ together with the atoms to which they are attached forms a 5- or 6-membered saturated, partially unsaturated, or unsaturated ring containing 0, 1, or 2 heteroatoms selected from N, O, or S, wherein the ring is unsubstituted.

In embodiments of formula (I) or (I-A), $R^1$ and $R^2$ together with the atoms to which they are attached forms a 5- or 6-membered saturated, partially unsaturated, or unsaturated ring containing 0, 1, or 2 heteroatoms selected from N, O, or S, wherein the ring is substituted with 1, 2, 3, or 4 substituents. In embodiments, the ring is substituted with 1 or 2 substituents.

In embodiments, any substituents listed in embodiments of formula (I), (I-A), or (I-B) can be applicable to embodiments of formula (II) or (III).

In embodiments of formula (I), (I-A), or (I-B), the compound is a racemate. In embodiments, the compound is an (R) stereoisomer. In embodiments, the compound is an (S) stereoisomer.

In embodiments, the compound of formula (I), (I-A), or (I-B) is selected from Tables A-1, A-2, or A-3, or a pharmaceutically acceptable salt, tautomer, or stereoisomer thereof.

TABLE A-1

| No | Structure |
|---|---|
| 1 | 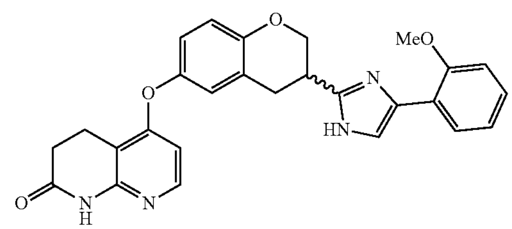 [SMILES: COc1ccccc1-c1c[nH]c(C2COc3ccc(Oc4ccnc5c4CCC(=O)N5)cc3C2)n1] |
| 2 | 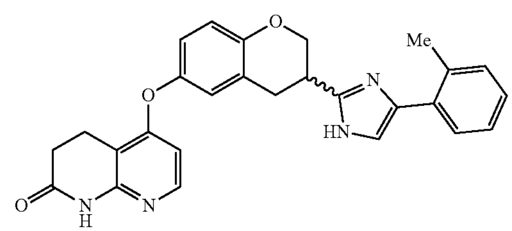 [SMILES: Cc1ccccc1-c1c[nH]c(C2COc3ccc(Oc4ccnc5c4CCC(=O)N5)cc3C2)n1] |
| 3 | 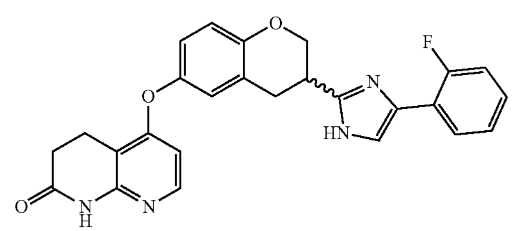 [SMILES: O=C1CCc2c(Oc3ccc4c(c3)CC(c3nc(-c5ccccc5F)c[nH]3)CO4)ccnc2N1] |
| 4 | 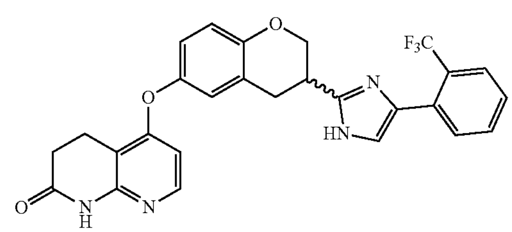 [SMILES: O=C1CCc2c(Oc3ccc4c(c3)CC(c3nc(-c5ccccc5C(F)(F)F)c[nH]3)CO4)ccnc2N1] |
| 5 | 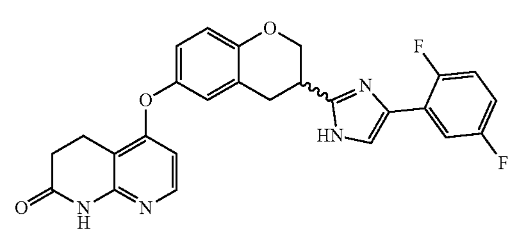 [SMILES: O=C1CCc2c(Oc3ccc4c(c3)CC(c3nc(-c5cc(F)ccc5F)c[nH]3)CO4)ccnc2N1] |

TABLE A-1-continued
| No | Structure |
|---|---|
| 6 | 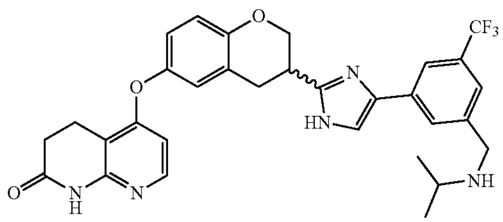 [SMILES: CC(C)NCc1cc(-c2c[nH]c(C3COc4ccc(Oc5ccnc6c5CCC(=O)N6)cc4C3)n2)cc(C(F)(F)F)c1] |
| 7 | 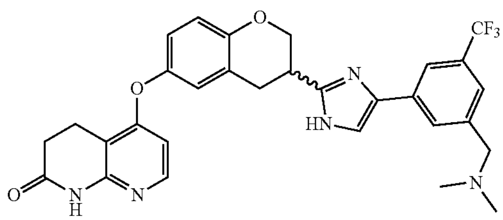 [SMILES: CN(C)Cc1cc(-c2c[nH]c(C3COc4ccc(Oc5ccnc6c5CCC(=O)N6)cc4C3)n2)cc(C(F)(F)F)c1] |
| 8 | 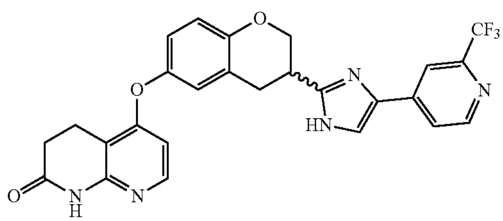 [SMILES: O=C1CCc2c(Oc3ccc4c(c3)CC(c3nc(-c5ccnc(C(F)(F)F)c5)c[nH]3)CO4)ccnc2N1] |
| 9 | 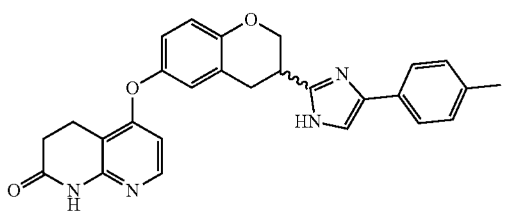 [SMILES: Cc1ccc(-c2c[nH]c(C3COc4ccc(Oc5ccnc6c5CCC(=O)N6)cc4C3)n2)cc1] |
| 10 | 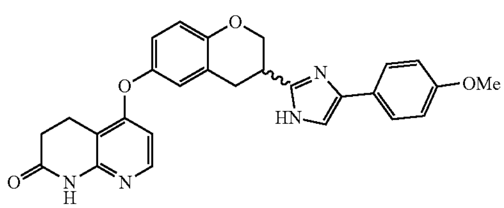 [SMILES: COc1ccc(-c2c[nH]c(C3COc4ccc(Oc5ccnc6c5CCC(=O)N6)cc4C3)n2)cc1] |
| 11 | 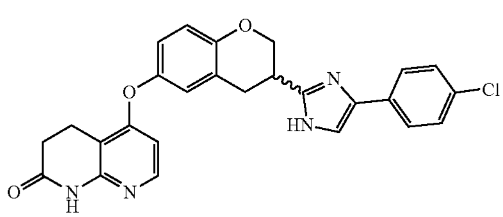 [SMILES: O=C1CCc2c(Oc3ccc4c(c3)CC(c3nc(-c5ccc(Cl)cc5)c[nH]3)CO4)ccnc2N1] |
| 12 | 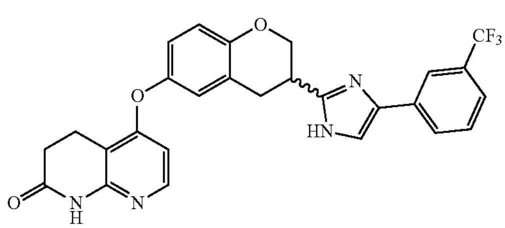 [SMILES: O=C1CCc2c(Oc3ccc4c(c3)CC(c3nc(-c5cccc(C(F)(F)F)c5)c[nH]3)CO4)ccnc2N1] |
| 13 | |
| 14 | |
| 15 | |
| 16 | |
| 17 | |
| 18 | |
| 19 | |
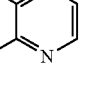

TABLE A-1-continued
| No | Structure |
|---|---|
| 20 | 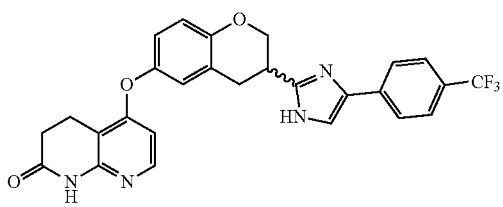 [SMILES: O=C1CCc2c(Oc3ccc4c(c3)CC(c3nc(-c5ccc(C(F)(F)F)cc5)c[nH]3)CO4)ccnc2N1] |
| 21 | 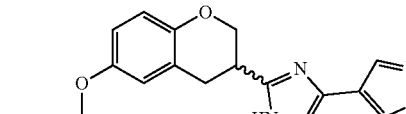 |
| 101 | 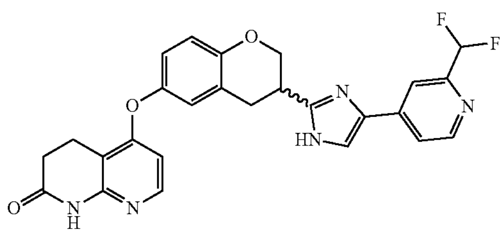 [SMILES: O=C1CCc2c(Oc3ccc4c(c3)CC(c3nc(-c5ccnc(C(F)F)c5)c[nH]3)CO4)ccnc2N1] |
| 103 | 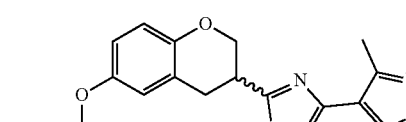 |
| 104 | 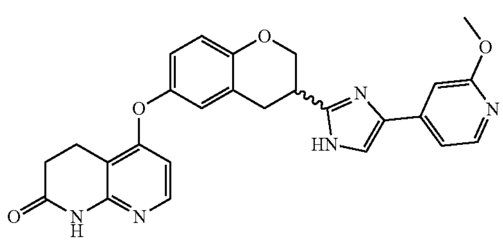 [SMILES: COc1cc(-c2c[nH]c(C3COc4ccc(Oc5ccnc6c5CCC(=O)N6)cc4C3)n2)ccn1] |
| 105 | 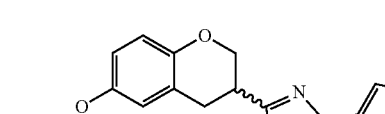 |
| 106 | 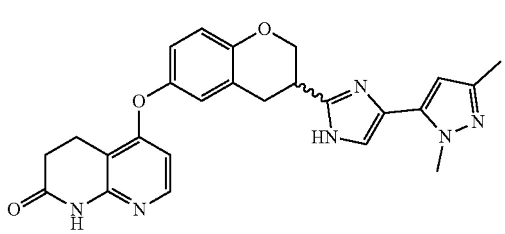 [SMILES: Cc1cc(-c2c[nH]c(C3COc4ccc(Oc5ccnc6c5CCC(=O)N6)cc4C3)n2)n(C)n1] |
| 107 | |
| 108 | |
| 109 | |
| 110 | |
| 111 | |
| 112 | |
| 113 | |

TABLE A-1-continued

| No | Structure |
|---|---|
| 114 | |
| 115 | |
| 116 | |
| 117 | |
| 118 | |
| 119 | |
| 120 | |️
| 121 | 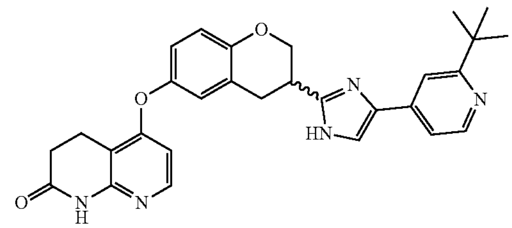 [SMILES: CC(C)(C)c1cc(-c2c[nH]c(C3COc4ccc(Oc5ccnc6c5CCC(=O)N6)cc4C3)n2)ccn1] |
| 122 | 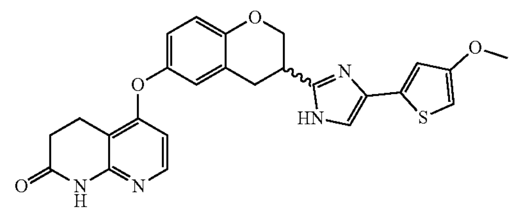 [SMILES: COc1csc(-c2c[nH]c(C3COc4ccc(Oc5ccnc6c5CCC(=O)N6)cc4C3)n2)c1] |
| 123 | 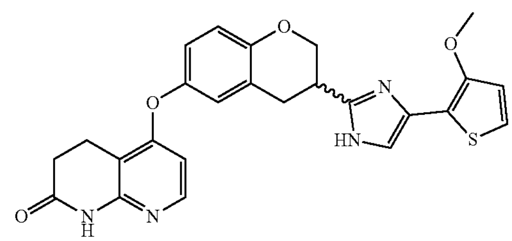 [SMILES: COc1ccsc1-c1c[nH]c(C2COc3ccc(Oc4ccnc5c4CCC(=O)N5)cc3C2)n1] |
| 124 | 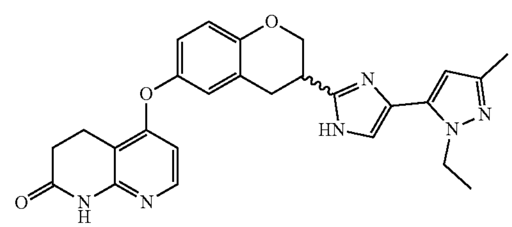 [SMILES: CCn1nc(C)cc1-c1c[nH]c(C2COc3ccc(Oc4ccnc5c4CCC(=O)N5)cc3C2)n1] |
| 125 | 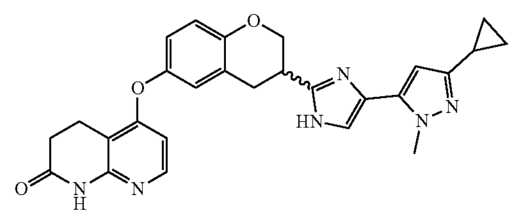 [SMILES: Cn1nc(C2CC2)cc1-c1c[nH]c(C2COc3ccc(Oc4ccnc5c4CCC(=O)N5)cc3C2)n1] |
| 126 | 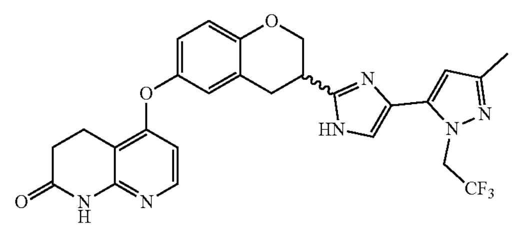 [SMILES: Cc1cc(-c2c[nH]c(C3COc4ccc(Oc5ccnc6c5CCC(=O)N6)cc4C3)n2)n(CC(F)(F)F)n1] |
| 127 | 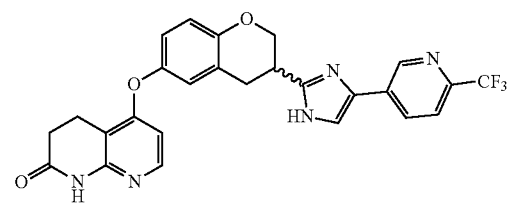 [SMILES: O=C1CCc2c(Oc3ccc4c(c3)CC(c3nc(-c5ccc(C(F)(F)F)nc5)c[nH]3)CO4)ccnc2N1] |

TABLE A-1-continued

| No | Structure |
|---|---|
| 128 | 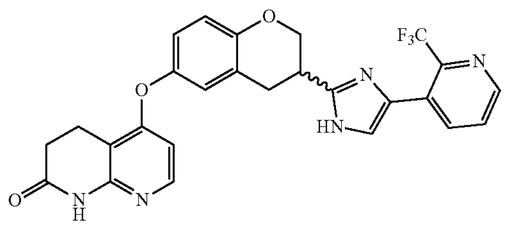 [SMILES: O=C1CCc2c(Oc3ccc4c(c3)CC(c3nc(-c5cccnc5C(F)(F)F)c[nH]3)CO4)ccnc2N1] |
| 129 | 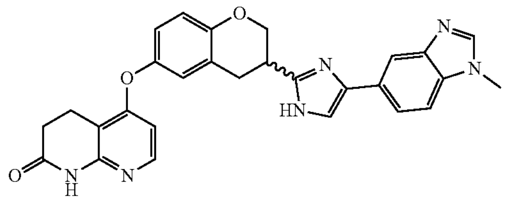 [SMILES: Cn1cnc2cc(-c3c[nH]c(C4COc5ccc(Oc6ccnc7c6CCC(=O)N7)cc5C4)n3)ccc21] |
| 130 | 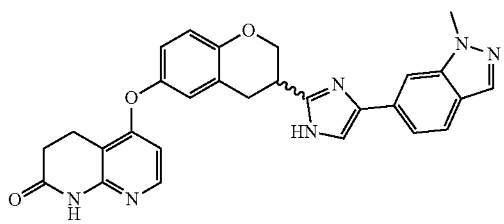 [SMILES: Cn1ncc2ccc(-c3c[nH]c(C4COc5ccc(Oc6ccnc7c6CCC(=O)N7)cc5C4)n3)cc21] |
| 131 | 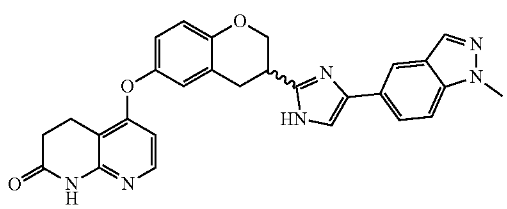 [SMILES: Cn1ncc2cc(-c3c[nH]c(C4COc5ccc(Oc6ccnc7c6CCC(=O)N7)cc5C4)n3)ccc21] |
| 132 | 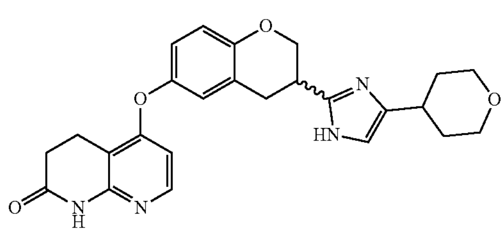 [SMILES: O=C1CCc2c(Oc3ccc4c(c3)CC(c3nc(C5CCOCC5)c[nH]3)CO4)ccnc2N1] |

TABLE A-2

| No | Structure |
|---|---|
| 22 | 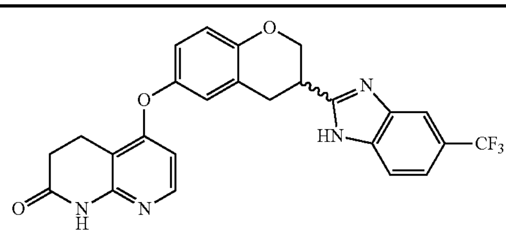 |

TABLE A-2-continued

| No | Structure |
|---|---|
| 23 | 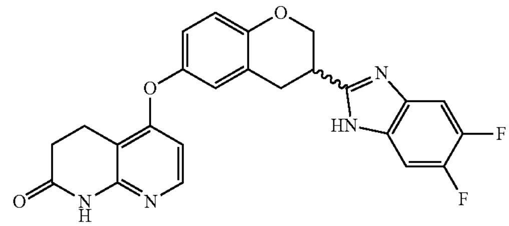 [SMILES: O=C1CCc2c(Oc3ccc4c(c3)CC(c3nc5cc(F)c(F)cc5[nH]3)CO4)ccnc2N1] |
| 24 | 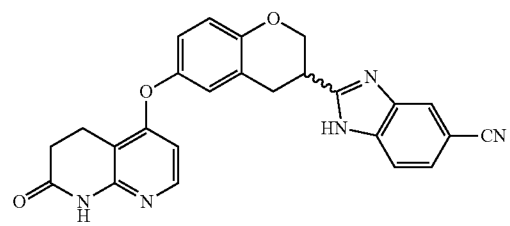 [SMILES: N#Cc1ccc2[nH]c(C3COc4ccc(Oc5ccnc6c5CCC(=O)N6)cc4C3)nc2c1] |
| 25 | 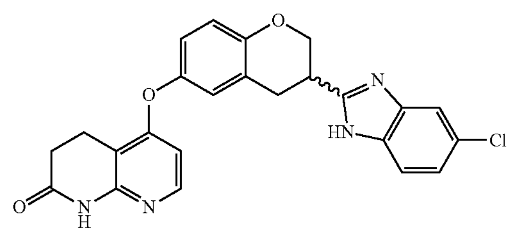 [SMILES: O=C1CCc2c(Oc3ccc4c(c3)CC(c3nc5cc(Cl)ccc5[nH]3)CO4)ccnc2N1] |
| 26 | 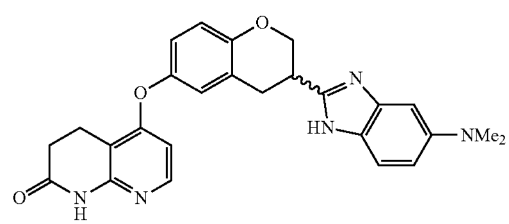 [SMILES: CN(C)c1ccc2[nH]c(C3COc4ccc(Oc5ccnc6c5CCC(=O)N6)cc4C3)nc2c1] |
| 27 | 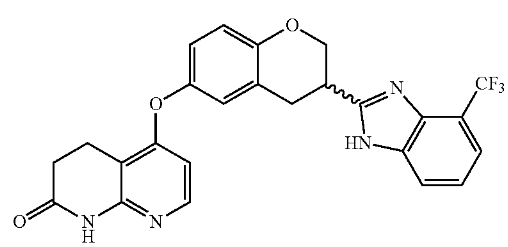 [SMILES: O=C1CCc2c(Oc3ccc4c(c3)CC(c3nc5c(C(F)(F)F)cccc5[nH]3)CO4)ccnc2N1] |
| 28 | 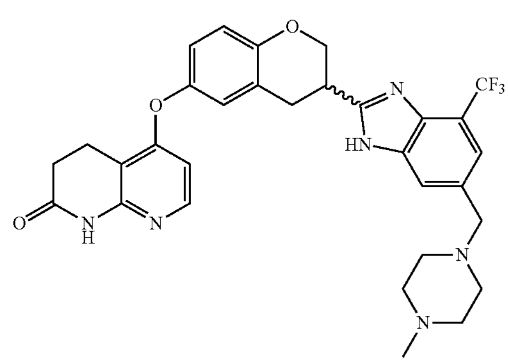 [SMILES: CN1CCN(Cc2cc(C(F)(F)F)c3nc(C4COc5ccc(Oc6ccnc7c6CCC(=O)N7)cc5C4)[nH]c3c2)CC1] |

TABLE A-2-continued
| No | Structure |
|---|---|
| 29 | 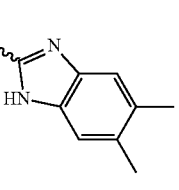 |
| 30 | 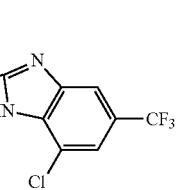 |
| 31 | 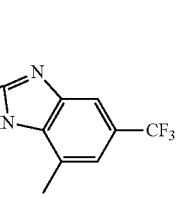 |
| 32 | 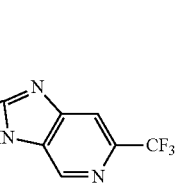 |
| 33 | 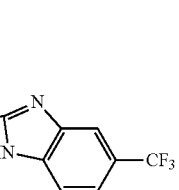 |
| 34 | 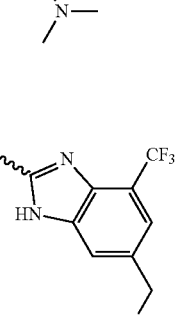 |
TABLE A-2-continued
| No | Structure |
|---|---|
| 133 | 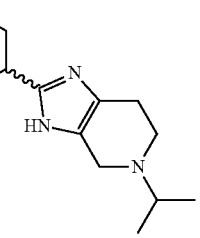 |
| 134 | 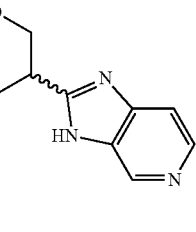 |
| 135 | 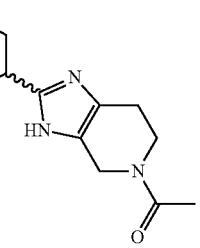 |
TABLE A-3
| No | Structure |
|---|---|
| 35 | 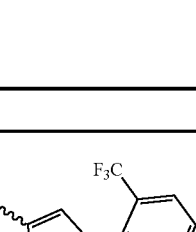 |
| 36 | 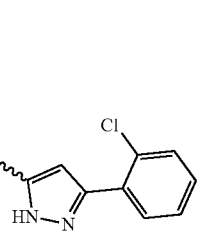 |
| 37 | 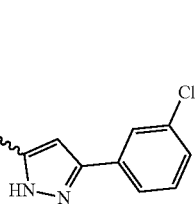 |

TABLE A-3-continued

| No | Structure |
|---|---|
| 38 | 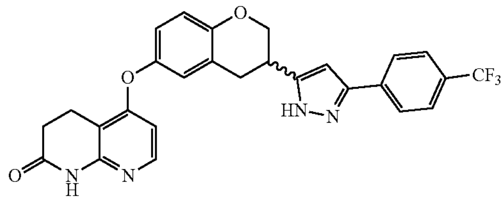 [SMILES: O=C1CCc2c(Oc3ccc4c(c3)CC(c3cc(-c5ccc(C(F)(F)F)cc5)n[nH]3)CO4)ccnc2N1] |
| 39 | 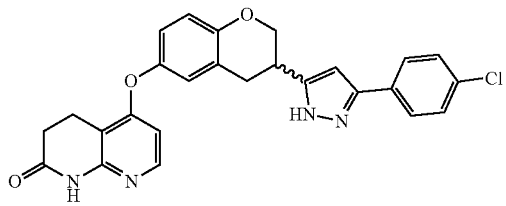 [SMILES: O=C1CCc2c(Oc3ccc4c(c3)CC(c3cc(-c5ccc(Cl)cc5)n[nH]3)CO4)ccnc2N1] |
| 40 | 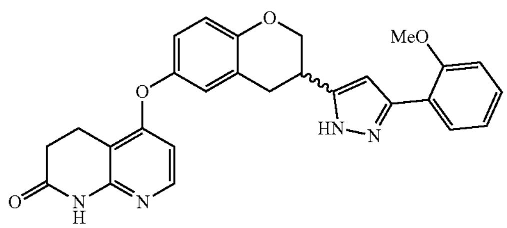 [SMILES: COc1ccccc1-c1cc(C2COc3ccc(Oc4ccnc5c4CCC(=O)N5)cc3C2)[nH]n1] |
| 41 | 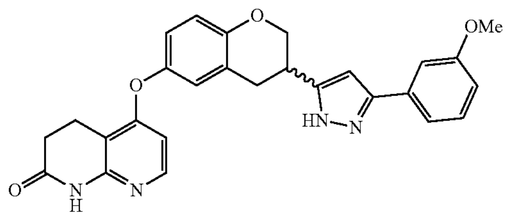 [SMILES: COc1cccc(-c2cc(C3COc4ccc(Oc5ccnc6c5CCC(=O)N6)cc4C3)[nH]n2)c1] |
| 42 | 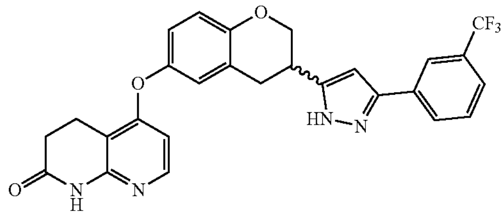 [SMILES: O=C1CCc2c(Oc3ccc4c(c3)CC(c3cc(-c5cccc(C(F)(F)F)c5)n[nH]3)CO4)ccnc2N1] |
| 43 | 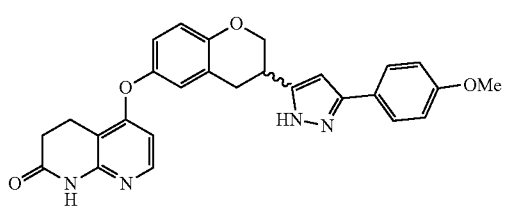 [SMILES: COc1ccc(-c2cc(C3COc4ccc(Oc5ccnc6c5CCC(=O)N6)cc4C3)[nH]n2)cc1] |
| 44 | 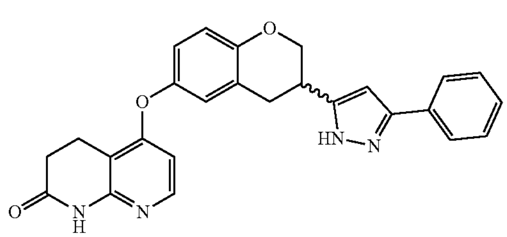 [SMILES: O=C1CCc2c(Oc3ccc4c(c3)CC(c3cc(-c5ccccc5)n[nH]3)CO4)ccnc2N1] |

In embodiments, the present disclosure relates compounds of formula (II), or a pharmaceutically acceptable salt, tautomer, or stereoisomer thereof,

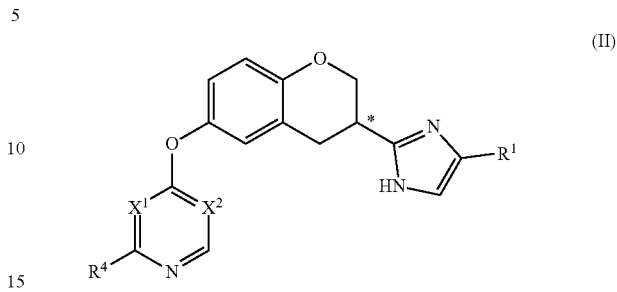

(II)

wherein: $X^1$ and $X^2$ are each N or CH;

$R^1$ is selected from substituted $C_{1-8}$ alkyl, unsubstituted $C_{5-8}$ alkyl, substituted or unsubstituted $C_{1-8}$ haloalkyl, substituted or unsubstituted aryl, substituted or unsubstituted heterocyclyl, or substituted or unsubstituted heteroaryl; and $R^4$ is $-NR^FC(O)R^5$, $-NR^FC(O)CH_2R^5$, $-NR^FC(O)CH(CH_3)R^5$, or $-NR^FR^5$;

$R^5$ is substituted or unsubstituted group selected from carbocyclyl, aryl, heterocyclyl, or heteroaryl; and $R^F$ is selected from H or $C_{1-3}$ alkyl.

In embodiments of the compounds of formula (II), one of $X^1$ and $X^2$ is N. In embodiments, $X^1$ is N and $X^2$ CH. In embodiments, $X^2$ is N and $X^1$ CH. In embodiments, $X^1$ and $X^2$ are both CH.

In embodiments of the compounds of formula (II), $R^1$ is substituted or unsubstituted aryl, substituted or unsubstituted heterocyclyl, or substituted or unsubstituted heteroaryl. In embodiments, $R^1$ is substituted or unsubstituted phenyl, substituted or unsubstituted pyridyl, substituted or unsubstituted pyrazole, substituted or unsubstituted pyrimidinyl, or substituted or unsubstituted thiophenyl. In embodiments, $R^1$ is substituted or unsubstituted phenyl. In embodiments, $R^1$ is substituted phenyl.

In embodiments of the compounds of formula (II), $R^4$ is $-NHC(O)R^5$, $-NHC(O)CH_2R^5$, $-NHC(O)CH(CH_3)R^5$, or $-NHR^5$. In embodiments, $R^4$ is $-NHC(O)R^5$, $-NHC(O)CH_2R^5$, or $-NHR^5$.

In embodiments of the compounds of formula (II), $R^5$ is substituted or unsubstituted group selected from alkyl, 3-6 membered carbocyclyl, phenyl, 3-6 membered heterocyclyl, or 5-6 membered heteroaryl. In embodiments, $R^5$ is substituted or unsubstituted group selected from 3-6 membered carbocyclyl, phenyl, 3-6 membered heterocyclyl, or 5-6 membered heteroaryl. In embodiments, $R^5$ is substituted or unsubstituted cyclopropyl, cyclobutyl, cyclopentyl, or cyclohexyl. In embodiments, $R^5$ is substituted or unsubstituted heterocyclyl containing 1 or 2 heteroatoms selected from N, O, or S. In embodiments, $R^5$ is substituted or unsubstituted 5- or 6-membered heterocyclyl containing 1 or 2 heteroatoms selected from N, O, or S. In embodiments, $R^5$ is substituted or unsubstituted saturated heterocyclyl containing 1 or 2 heteroatoms selected from N, O, or S. In embodiments, $R^5$ is substituted or unsubstituted saturated 5- or 6-membered heterocyclyl containing 1 or 2 heteroatoms selected from N, O, or S. In embodiments, $R^5$ is substituted or unsubstituted azetidine, pyrrolidine, piperidine, piperazine, or morpholine moiety. In embodiments, $R^5$ is substituted or unsubstituted group selected from methyl, cyclopropyl, cyclobutyl, cyclopentyl, or cyclohexyl, azetidine, pyrrolidine, piperidine, piperazine, or morpholine, pyridine, thiazole, imidazole, pyrazole, or triazole.

In embodiments of the compounds of formula (II), $R^5$ is substituted or unsubstituted 5-6 membered heteroaryl. In embodiments, $R^5$ is substituted or unsubstituted 5-6 membered heteroaryl containing at least 1 nitrogen atom as a ring member. In embodiments, $R^5$ is substituted or unsubstituted pyridine, thiazole, imidazole, pyrazole, or triazole.

In embodiments of the compounds of formula (II), $R^F$ is H or methyl. In embodiments, $R^F$ is H.

In embodiments of formula (II), substituent is selected from halogen, —$OR^A$, —$NR^AR^B$, —$SO_2R^C$, —$SOR^C$, —CN, $C_{1-6}$ alkyl, $C_{1-6}$ haloalkyl, $C_{3-6}$ cycloalkyl, or —C(O) $C_{1-6}$ alkyl; wherein $R^A$ and $R^B$ are each independently selected from H, $C_{1-6}$ alkyl and $C_{1-6}$ haloalkyl; and $R^C$ is selected from $C_{1-6}$ alkyl and $C_{1-6}$ haloalkyl; wherein the alkyl, haloalkyl and cycloalkyl groups are optionally substituted with 1 to 3 groups independently selected from: —$OR^A$, —CN, —$SOR^C$, or —$NR^AR^B$.

In embodiments of formula (II), substituent is selected from halogen, methyl, ethyl, propyl, isopropyl, n-butyl, s-butyl, t-butyl, cyclopropyl, methoxy, ethoxy, isopropoxy, —$CH_2F$, —$CHF_2$, —$CF_3$, —$CH_2CH_2F$, —$CH_2CHF_2$, —$CH_2CF_3$, —$C(O)CH_3$, —CN, —OH, —$NH_2$, —$NH(C_{1-3}$ alkyl), —$N(C_{1-3}$ alkyl)$_2$, —$CH_2NH_2$, —$CH_2NH(C_{1-3}$ alkyl), or —$CH_2N(C_{1-3}$ alkyl)$_2$.

In embodiments of formula (II), $R^5$ is substituted with a substituent selected from methyl, ethyl, propyl, isopropyl, n-butyl, s-butyl, t-butyl, cyclopropyl, methoxy, ethoxy, isopropoxy, —$CH_2F$, —$CHF_2$, —$CF_3$, —$CH_2CH_2F$, —$CH_2CHF_2$, —$CH_2CF_3$, —$C(O)CH_3$, —CN, —OH, —$NH_2$, —$NH(C_{1-3}$ alkyl), —$N(C_{1-3}$ alkyl)$_2$, —$CH_2NH_2$, —$CH_2NH(C_{1-3}$ alkyl), or —$CH_2N(C_{1-3}$ alkyl)$_2$. In embodiments, $R^5$ is substituted with one or more substituent selected from halogen, methyl, ethyl, propyl, isopropyl, —CN, —OH, or —$NH_2$.

In embodiments of formula (II), $R^1$ is substituted with 1, 2, or 3 substituents. In embodiments of formula (II), $R^1$ is substituted with 1 or 2 substituents. In embodiments of formula (II), $R^1$ is unsubstituted.

In embodiments of formula (II), $R^5$ is substituted with 1, 2, or 3 substituents. In embodiments of formula (II), $R^5$ is substituted with 1 or 2 substituents. In embodiments of formula (II), $R^5$ is unsubstituted.

In embodiments, any substituents listed in embodiments of formula (II) can be applicable to embodiments of formula (I), (I-A), (I-B) or (III).

In embodiments of formula (II), the compound is a racemate. In embodiments, the compound is an (R) stereoisomer. In embodiments, the compound is an (S) stereoisomer.

In embodiments, the compound of formula (II) is selected from Table B, or a pharmaceutically acceptable salt, tautomer, or stereoisomer thereof.

TABLE B

| No | Structure | No | Structure |
|---|---|---|---|
| 45 | 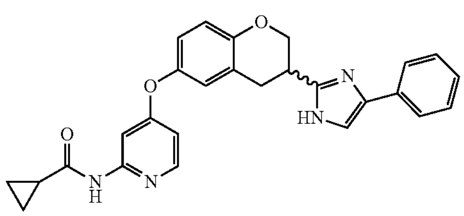 [SMILES: O=C(Nc1cc(Oc2ccc3c(c2)CC(c2nc(-c4ccccc4)c[nH]2)CO3)ccn1)C1CC1] | | |
| 136 | 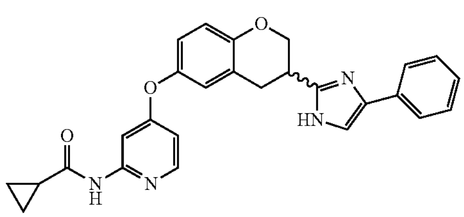 [SMILES: O=C(Nc1cc(Oc2ccc3c(c2)CC(c2nc(-c4ccccc4)c[nH]2)CO3)ccn1)C1CC1] | 148 | 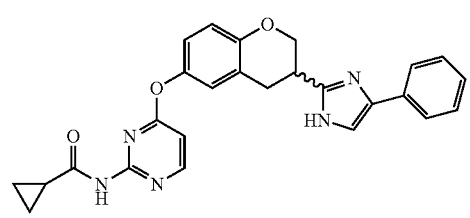 [SMILES: O=C(Nc1nccc(Oc2ccc3c(c2)CC(c2nc(-c4ccccc4)c[nH]2)CO3)n1)C1CC1] |
| 137 | 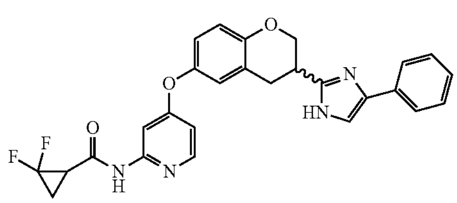 [SMILES: O=C(Nc1cc(Oc2ccc3c(c2)CC(c2nc(-c4ccccc4)c[nH]2)CO3)ccn1)C1CC1(F)F] | 149 | 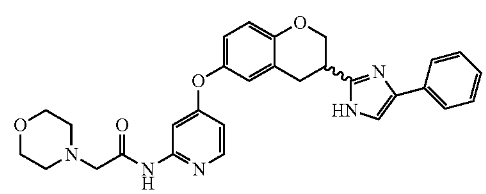 [SMILES: O=C(CN1CCOCC1)Nc1cc(Oc2ccc3c(c2)CC(c2nc(-c4ccccc4)c[nH]2)CO3)ccn1] |
| 138 | 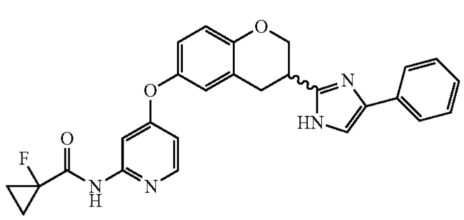 [SMILES: O=C(Nc1cc(Oc2ccc3c(c2)CC(c2nc(-c4ccccc4)c[nH]2)CO3)ccn1)C1(F)CC1] | 150 | 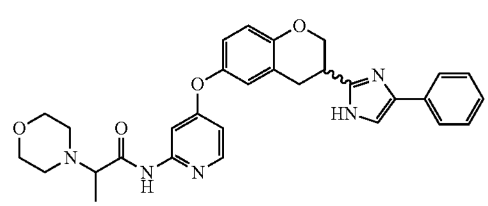 [SMILES: CC(C(=O)Nc1cc(Oc2ccc3c(c2)CC(c2nc(-c4ccccc4)c[nH]2)CO3)ccn1)N1CCOCC1] |

TABLE B-continued

| No | Structure | No | Structure |
|---|---|---|---|
| 139 | 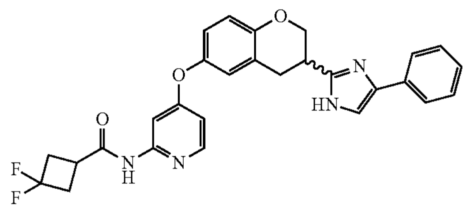 [SMILES: O=C(Nc1cc(Oc2ccc3c(c2)CC(c2nc(-c4ccccc4)c[nH]2)CO3)ccn1)C1CC(F)(F)C1] | 151 | 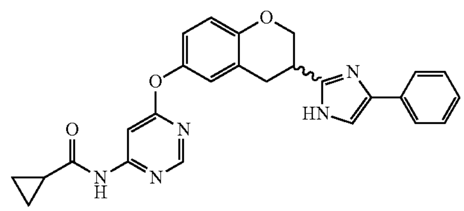 [SMILES: O=C(Nc1cc(Oc2ccc3c(c2)CC(c2nc(-c4ccccc4)c[nH]2)CO3)ncn1)C1CC1] |
| 140 | 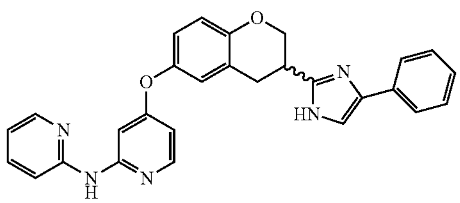 [SMILES: c1ccc(-c2c[nH]c(C3COc4ccc(Oc5ccnc(Nc6ccccn6)c5)cc4C3)n2)cc1] | 152 | 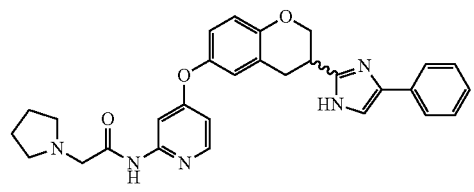 [SMILES: O=C(CN1CCCC1)Nc1cc(Oc2ccc3c(c2)CC(c2nc(-c4ccccc4)c[nH]2)CO3)ccn1] |
| 141 | 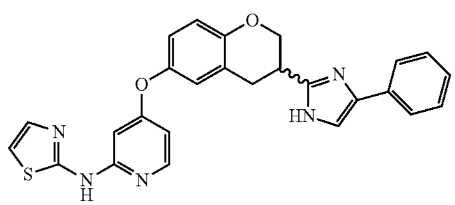 [SMILES: c1ccc(-c2c[nH]c(C3COc4ccc(Oc5ccnc(Nc6nccs6)c5)cc4C3)n2)cc1] | 153 | 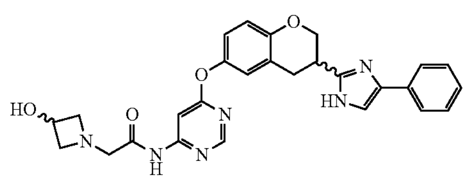 [SMILES: O=C(CN1CC(O)C1)Nc1cc(Oc2ccc3c(c2)CC(c2nc(-c4ccccc4)c[nH]2)CO3)ncn1] |
| 142 | 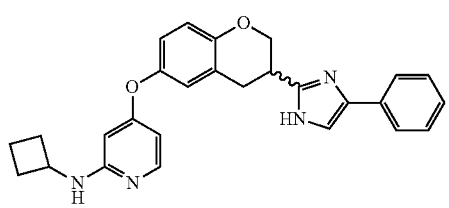 [SMILES: c1ccc(-c2c[nH]c(C3COc4ccc(Oc5ccnc(NC6CCC6)c5)cc4C3)n2)cc1] | 154 | 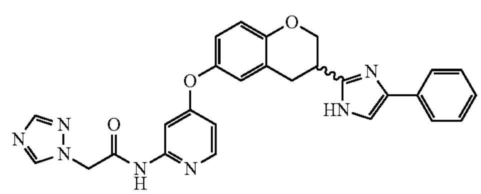 [SMILES: O=C(Cn1cncn1)Nc1cc(Oc2ccc3c(c2)CC(c2nc(-c4ccccc4)c[nH]2)CO3)ccn1] |
| 143 | 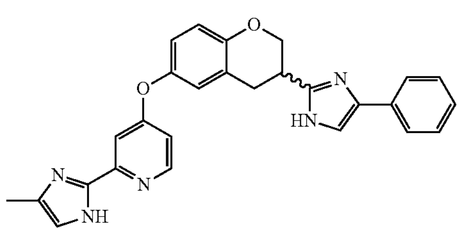 [SMILES: Cc1c[nH]c(-c2cc(Oc3ccc4c(c3)CC(c3nc(-c5ccccc5)c[nH]3)CO4)ccn2)n1] | 155 | 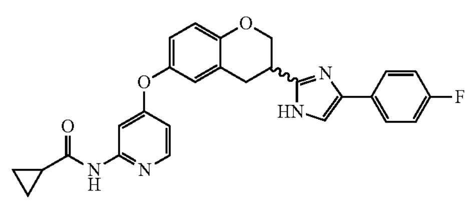 [SMILES: O=C(Nc1cc(Oc2ccc3c(c2)CC(c2nc(-c4ccc(F)cc4)c[nH]2)CO3)ccn1)C1CC1] |
| 144 | 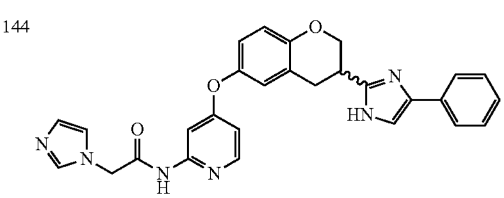 | 156 | 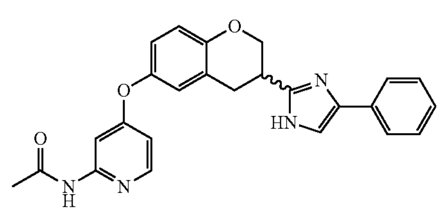 [SMILES: CC(=O)Nc1cc(Oc2ccc3c(c2)CC(c2nc(-c4ccccc4)c[nH]2)CO3)ccn1] |
| 145 | 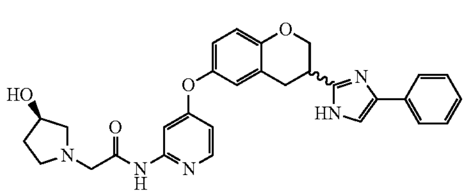 [SMILES: O=C(CN1CC[C@@H](O)C1)Nc1cc(Oc2ccc3c(c2)CC(c2nc(-c4ccccc4)c[nH]2)CO3)ccn1] | 157 | 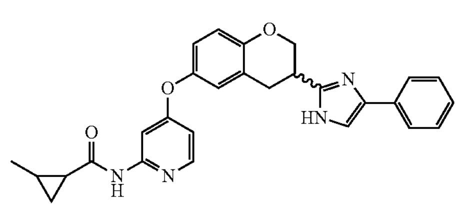 [SMILES: CC1CC1C(=O)Nc1cc(Oc2ccc3c(c2)CC(c2nc(-c4ccccc4)c[nH]2)CO3)ccn1] |

TABLE B-continued

| No | Structure | No | Structure |
|---|---|---|---|
| 146 | 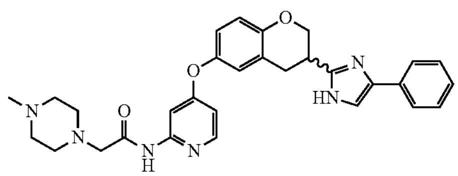 [SMILES: CN1CCN(CC(=O)Nc2cc(Oc3ccc4c(c3)CC(c3nc(-c5ccccc5)c[nH]3)CO4)ccn2)CC1] | 158 | 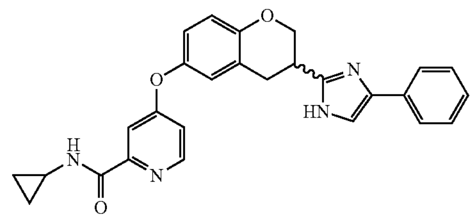 [SMILES: O=C(NC1CC1)c1cc(Oc2ccc3c(c2)CC(c2nc(-c4ccccc4)c[nH]2)CO3)ccn1] |
| 147 | 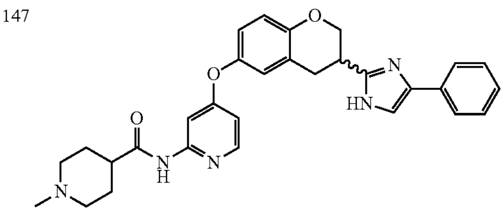 | | |

In embodiments, the present disclosure relates compounds of formula (III), or a pharmaceutically acceptable salt, tautomer, or stereoisomer thereof,

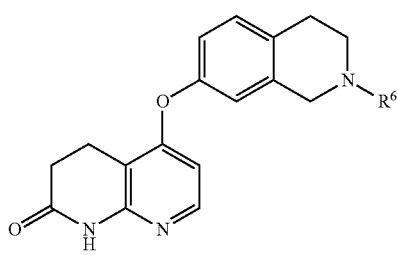

(III)

wherein: $R^6$ is —C(O)NR$^F$R$^5$, —C(O)NR$^F$CH$_2$R$^5$, substituted or unsubstituted aryl, substituted or unsubstituted heterocyclyl, or substituted or unsubstituted heteroaryl;
$R^5$ is substituted or unsubstituted group selected from carbocyclyl, aryl, heterocyclyl, or heteroaryl; and
$R^F$ is selected from H or C$_{1-3}$ alkyl.

In embodiments of the compounds of formula (III), $R^6$ is —C(O)NR$^F$R$^5$ or —C(O)NR$^F$CH$_2$R$^5$. In embodiments, $R^6$ is —C(O)NHR$^5$ or —C(O)NHCH$_2$R$^5$.

In embodiments of the compounds of formula (III), $R^5$ is substituted or unsubstituted aryl. In embodiments, $R^5$ is substituted or unsubstituted phenyl.

In embodiments of the compounds of formula (III), $R^6$ is substituted or unsubstituted aryl or substituted or unsubstituted heteroaryl. In embodiments, a monocyclic substituted aryl or a monocyclic substituted heteroaryl. In embodiments, $R^6$ is a bicyclic substituted aryl or a monocyclic substituted heteroaryl. In embodiments, $R^6$ is a fused bicyclic substituted aryl or a fused bicyclic substituted heteroaryl. In embodiments, $R^6$ is substituted or unsubstituted indazole or substituted or unsubstituted benzoimidazole.

In embodiments of the compounds of formula (III), $R^6$ is substituted aryl or substituted heteroaryl, wherein the substituent is selected from halogen, methyl, ethyl, propyl, isopropyl, n-butyl, s-butyl, t-butyl, cyclopropyl, methoxy, ethoxy, isopropoxy, —CH$_2$F, —CHF$_2$, —CF$_3$, —CH$_2$CH$_2$F, —CH$_2$CHF$_2$, —CH$_2$CF$_3$, —C(O)CH$_3$, —CN, —OH, —NH$_2$, —NH(C$_{1-3}$ alkyl), —N(C$_{1-3}$ alkyl)$_2$, —CH$_2$NH$_2$, —CH$_2$NH(C$_{1-3}$ alkyl), —CH$_2$N(C$_{1-3}$ alkyl)$_2$, optionally substituted phenyl, optionally substituted heteroaryl. In embodiments of the compounds of formula (III), $R^6$ is substituted aryl or substituted heteroaryl, wherein the substituent is selected from optionally substituted phenyl or optionally substituted 5- or 6-membered heteroaryl. In embodiments, $R^6$ is substituted aryl or substituted heteroaryl, wherein the substituent is selected from phenyl or optionally substituted 5- or 6-membered N-heteroaryl. In embodiments, $R^6$ is substituted aryl or substituted heteroaryl, wherein the substituent is selected from phenyl or optionally substituted 5-membered N-heteroaryl. In embodiments, $R^6$ is substituted aryl or substituted heteroaryl, wherein the substituent is selected from phenyl or pyrazole substituted with one or two C$_{1-3}$ alkyl groups.

In embodiments of formula (III), substituent is selected from halogen, —OR$^A$, —NR$^A$R$^B$, —SO$_2$R$^C$, —SOR$^C$, —CN, C$_{1-6}$ alkyl, C$_{1-6}$ haloalkyl, C$_{3-6}$ cycloalkyl, —C(O)C$_{1-6}$ alkyl, aryl, or heteroaryl; wherein R$^A$ and R$^B$ are each independently selected from H, C$_{1-6}$ alkyl and C$_{1-6}$ haloalkyl; and R$^C$ is selected from C$_{1-6}$ alkyl and C$_{1-6}$ haloalkyl; wherein the alkyl, haloalkyl, cycloalkyl, aryl, and heteroaryl groups are optionally substituted with 1 to 3 groups independently selected from: C$_{1-6}$ alkyl, —OR$^A$, —CN, —SOR$^C$, or —NR$^A$R$^B$.

In embodiments of formula (II), substituent is selected from halogen, methyl, ethyl, propyl, isopropyl, n-butyl, s-butyl, t-butyl, cyclopropyl, methoxy, ethoxy, isopropoxy, —CH$_2$F, —CHF$_2$, —CF$_3$, —CH$_2$CH$_2$F, —CH$_2$CHF$_2$, —CH$_2$CF$_3$, —C(O)CH$_3$, —CN, —OH, —NH$_2$, —NH(C$_{1-3}$ alkyl), —N(C$_{1-3}$ alkyl)$_2$, —CH$_2$NH$_2$, —CH$_2$NH(C$_{1-3}$ alkyl), —CH$_2$N(C$_{1-3}$ alkyl)$_2$, optionally substituted phenyl, optionally substituted heteroaryl.

In embodiments of formula (III), $R^5$ is substituted with 1, 2, or 3 substituents. In embodiments of formula (III), $R^5$ is substituted with 1 or 2 substituents. In embodiments of formula (III), $R^5$ is unsubstituted.

In embodiments, any substituents listed in embodiments of formula (III) can be applicable to embodiments of formula (I), (I-A), (I-B) or (II).

In embodiments, the compound of formula (III) is selected from Table C, or a pharmaceutically acceptable salt, tautomer, or stereoisomer thereof.

TABLE C

| No | Structure | No | Structure |
|---|---|---|---|
| 46 | 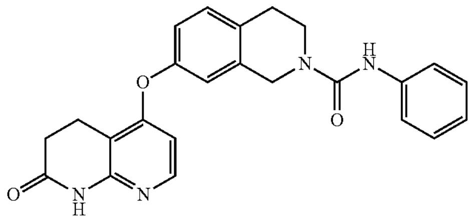 [SMILES: O=C1CCc2c(Oc3ccc4c(c3)CN(C(=O)Nc3ccccc3)CC4)ccnc2N1] | 49 | 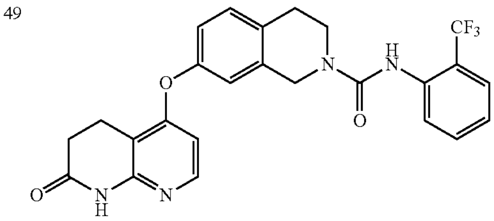 |
| 47 | 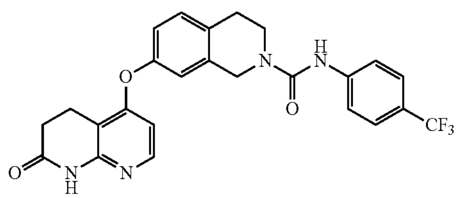 [SMILES: O=C1CCc2c(Oc3ccc4c(c3)CN(C(=O)Nc3ccc(C(F)(F)F)cc3)CC4)ccnc2N1] | 50 | 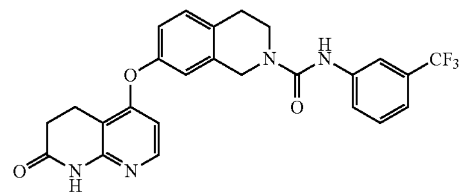 [SMILES: O=C1CCc2c(Oc3ccc4c(c3)CN(C(=O)Nc3cccc(C(F)(F)F)c3)CC4)ccnc2N1] |
| 48 | 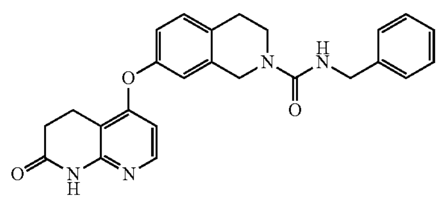 [SMILES: O=C1CCc2c(Oc3ccc4c(c3)CN(C(=O)NCc3ccccc3)CC4)ccnc2N1] | | |
| 159 | 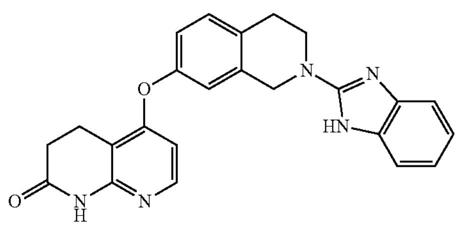 [SMILES: O=C1CCc2c(Oc3ccc4c(c3)CN(c3nc5ccccc5[nH]3)CC4)ccnc2N1] | 162 | 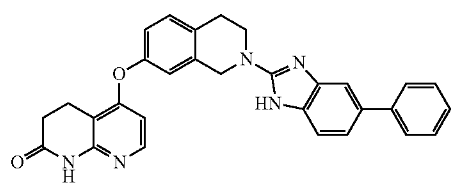 [SMILES: O=C1CCc2c(Oc3ccc4c(c3)CN(c3nc5cc(-c6ccccc6)ccc5[nH]3)CC4)ccnc2N1] |
| 160 | 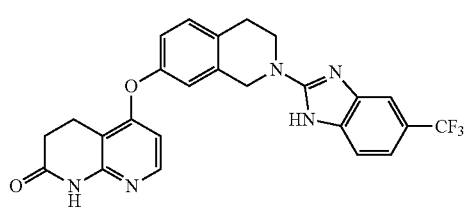 [SMILES: O=C1CCc2c(Oc3ccc4c(c3)CN(c3nc5cc(C(F)(F)F)ccc5[nH]3)CC4)ccnc2N1] | 163 | 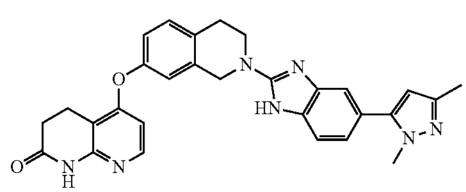 [SMILES: Cc1cc(-c2ccc3[nH]c(N4CCc5ccc(Oc6ccnc7c6CCC(=O)N7)cc5C4)nc3c2)n(C)n1] |
| 161 | 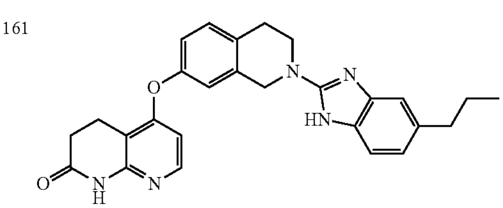 | | |

In embodiments, the present disclosure relates a compound in Table D, or a pharmaceutically acceptable salt, tautomer, or stereoisomer thereof.

TABLE D

| No | Structure |
|---|---|
| 51 | (structure) |

In embodiments, the compounds of the present disclosure have pERK A375 (1 hr) $pIC_{50}$ in the range of about 4 to about 9, including any values and subranges therebetween. In embodiments, the compounds of the present disclosure have pERK A375 (1 hr) $pIC_{50}$ in the range of about 5 to about 8, including any values and subranges therebetween. In embodiments, the compounds of the present disclosure have pERK A375 (1 hr) $pIC_{50}$ value of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0, including any values therebetween.

In embodiments, the compounds of the present disclosure have pERK HCT116 dimer (1 hr) $pIC_{50}$ in the range of about 4 to about 9 including any values and subranges therebetween. In embodiments, the compounds of the present disclosure have pERK HCT116 dimer (1 hr) $pIC_{50}$ in the range of about 5 to about 8, including any values and subranges therebetween. In embodiments, the compounds of the present disclosure have pERK HCT116 dimer (1 hr) $pIC_{50}$ of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2 about 7.3, about 7.4, about 7.5, about 7.6, about 7.7, about 7.8, about 7.9, or about 8.0 including any values therebetween.

In embodiments, the compounds of the present disclosure have a pERK A375 monomer/pERK HCT116 dimer ratio in the range of about 0.01 to about 2.5, including any values and subranges therebetween. In embodiments, the compounds of the present disclosure have a pERK A375 monomer/pERK HCT116 dimer ratio in the range of about 0.03 to about 2.0, including any values and subranges therebetween. In embodiments, the compounds of the present disclosure have a pERK monomer/dimer ratio of about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0, including any values therebetween. In embodiments, the compounds of the present disclosure have a pERK A375 monomer/pERK HCT116 dimer ratio of 2 or less. A pERK A375 monomer/pERK HCT116 dimer ratio is calculated using the potency in nM.

In embodiments, the compounds of the present disclosure have pERK HCT116 (2 hr) absolute $pIC_{50}$ in the range of about 6 to about 9, including any values and subranges therebetween. In embodiments, the compounds of the present disclosure have pERK HCT116 (2 hr) absolute $pIC_{50}$ in the range of about 6.5 to about 8, including any values and subranges therebetween. In embodiments, the compounds of the present disclosure have pERK HCT116 (2 hr) absolute $pIC_{50}$ of about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0, including any values therebetween. In embodiments, the compounds of the present disclosure have pERK HCT116 (2 hr) absolute $pIC_{50}$ of about 6.5 or greater.

In embodiments, the compounds of the present disclosure have pERK WiDr (2 hr) absolute $pIC_{50}$ in the range of about 6 to about 9, including any values and subranges therebetween. In embodiments, the compounds of the present disclosure have pERK WiDr (2 hr) absolute $pIC_{50}$ in the range of about 6.5 to about 8, including any values and subranges therebetween. In embodiments, the compounds of the present disclosure have pERK WiDr (2 hr) absolute $pIC_{50}$ of about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0, including any values therebetween. In embodiments, the compounds of the present disclosure have pERK WiDr (2 hr) absolute $pIC_{50}$ of about 6.5 or greater.

In embodiments, the compounds of the present disclosure have pGI50 3D HCT116 in the range of about 6 to about 9, including any values and subranges therebetween. In embodiments, the compounds of the present disclosure have pGI50 3D HCT116 in the range of about 6.5 to about 8, including any values and subranges therebetween. In embodiments, the compounds of the present disclosure have pGI50 3D HCT116 of about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0, including any values therebetween. In embodiments, the compounds of the present disclosure have pGI50 3D HCT116 of about 6.5 or greater.

In embodiments, the compounds of the present disclosure have pGI50 3D WiDr in the range of about 6 to about 9, including any values and subranges therebetween. In embodiments, the compounds of the present disclosure have pGI50 3D WiDr in the range of about 6.5 to about 8, including any values and subranges therebetween. In embodiments, the compounds of the present disclosure have pGI50 3D WiDr of about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0, including any values therebetween. In embodiments, the compounds of the present disclosure have pGI50 3D WiDr of about 6.5 or greater.

In embodiments, the compounds of the present disclosure have human liver microsome (HLM) intrinsic clearance (CLint) in the range of about 1 µL/min/mg to about 25 µL/min/mg, including any values and subranges therebetween. In embodiments, the compounds of the present disclosure have HLM CLint in the range of about 1 µL/min/mg to about 20 µL/min/mg, including any values and subranges therebetween. In embodiments, the compounds of the present disclosure have HLM CLint in the range of about 1 µL/min/mg to about 15 µL/min/mg, including any values and subranges therebetween. In embodiments, the compounds of the present disclosure have HLM CLint in the range of about 1 µL/min/mg to about 10 µL/min/mg, including any values and subranges therebetween. In embodiments, the compounds of the present disclosure have HLM CLint of about 1 µL/min/mg, about 2 µL/min/mg, about 3

μL/min/mg, about 4 μL/min/mg, about 5 μL/min/mg, about 6 μL/min/mg, about 7 μL/min/mg, about 8 μL/min/mg, about 9 μL/min/mg, about 10 μL/min/mg, about 11 μL/min/mg, about 12 μL/min/mg, about 13 μL/min/mg, about 14 μL/min/mg, or about 15 μL/min/mg, including any values therebetween. In embodiments, the compounds of the present disclosure have HLM CLint of less than about 15 μL/min/mg. In embodiments, the compounds of the present disclosure have HLM CLint of less than about 20 μL/min/mg.

In embodiments, the compounds of the present disclosure have mouse liver microsome (MLM) intrinsic clearance (CLint) in the range of about 1 μL/min/mg to about 130 μL/min/mg, including any values and subranges therebetween. In embodiments, the compounds of the present disclosure have MLM CLint in the range of about 1 μL/min/mg to about 50 μL/min/mg, including any values and subranges therebetween. In embodiments, the compounds of the present disclosure have MLM CLint in the range of about 1 μL/min/mg to about 30 μL/min/mg, including any values and subranges therebetween. In embodiments, the compounds of the present disclosure have MLM CLint in the range of about 1 μL/min/mg to about 20 μL/min/mg, including any values and subranges therebetween. In embodiments, the compounds of the present disclosure have MLM CLint of about 1 μL/min/mg, about 2 μL/min/mg, about 3 μL/min/mg, about 4 μL/min/mg, about 5 μL/min/mg, about 6 μL/min/mg, about 7 μL/min/mg, about 8 μL/min/mg, about 9 μL/min/mg, about 10 μL/min/mg, about 11 μL/min/mg, about 12 μL/min/mg, about 13 μL/min/mg, about 14 μL/min/mg, about 15 μL/min/mg, about 16 μL/min/mg, about 17 μL/min/mg, about 18 μL/min/mg, about 19 μL/min/mg, or about 20 μL/min/mg, including any values therebetween. In embodiments, the compounds of the present disclosure have MLM CLint of less than about 30 μL/min/mg. In embodiments, the compounds of the present disclosure have MLM CLint of less than about 25 μL/min/mg. In embodiments, the compounds of the present disclosure have MLM CLint of less than about 20 μL/min/mg.

In embodiments, the compounds of the present disclosure have human plasma protein binding (hPPB) percent free value in the range of about 0.01% to about 15%, including any values and subranges therebetween. In embodiments, the compounds of the present disclosure have hPPB percent free value in the range of about 0.05% to about 10%, including any values and subranges therebetween. In embodiments, the compounds of the present disclosure have hPPB percent free value in the range of about 0.1% to about 8%, including any values and subranges therebetween. In embodiments, the compounds of the present disclosure have hPPB percent free value in the range of about 0.10% to about 5%, including any values and subranges therebetween.

In embodiments, the compounds of the present disclosure have mouse plasma protein binding (mPPB) percent free value in the range of about 0.01% to about 15%, including any values and subranges therebetween. In embodiments, the compounds of the present disclosure have mPPB percent free value in the range of about 0.05% to about 10%, including any values and subranges therebetween. In embodiments, the compounds of the present disclosure have mPPB percent free value in the range of about 0.1% to about 8%, including any values and subranges therebetween. In embodiments, the compounds of the present disclosure have mPPB percent free value in the range of about 0.10% to about 5%, including any values and subranges therebetween.

In embodiments, the compounds of the present disclosure have fed state simulated intestinal fluid (FESSIF) solubility in the range of about 10 mg/L to about 1000 mg/L, including any values and subranges therebetween. In embodiments, the compounds of the present disclosure have FESSIF solubility in the range of about 20 mg/L to about 750 mg/L, including any values and subranges therebetween. In embodiments, the compounds of the present disclosure have FESSIF solubility in the range of about 25 mg/L to about 600 mg/L, including any values and subranges therebetween. In embodiments, the compounds of the present disclosure have FESSIF solubility of about 10 mg/L or greater. In embodiments, the compounds of the present disclosure have FESSIF solubility of about 20 mg/L or greater. In embodiments, the compounds of the present disclosure have FESSIF solubility of about 25 mg/L or greater. In embodiments, the compounds of the present disclosure have FESSIF solubility of about 30 mg/L or greater.

Therapeutic Use

The present disclosure also relates to method of using compounds of formula (I), (I-A), (I-B), (II), or (III), or pharmaceutically acceptable salt, tautomer, or stereoisomer thereof, for treating various diseases and conditions. In embodiments, compounds of formula (I), (I-A), (I-B), (II), or (III), or pharmaceutically acceptable salt, tautomer, or stereoisomer thereof, are useful for treating a disease or a condition implicated by abnormal activity of one or more Raf kinase. In embodiments, compounds of formula (I), (I-A), (I-B), (II), or (III), or pharmaceutically acceptable salt, tautomer, or stereoisomer thereof, are useful for treating a disease or a condition treatable by the inhibition of one or more Raf kinase. RAF kinase inhibition is relevant for the treatment of many different diseases associated with the abnormal activity of the MAPK pathway. In embodiments the condition treatable by the inhibition of RAF kinases, such as B-RAF or C-RAF.

The present disclosure also relates to method of using compounds of Tables A1-A3 and B-D, or pharmaceutically acceptable salt, tautomer, or stereoisomer thereof, for treating various diseases and conditions. In embodiments, compounds of Tables A1-A3 and B-D, or pharmaceutically acceptable salt, tautomer, or stereoisomer thereof, are useful for treating a disease or a condition implicated by abnormal activity of one or more Raf kinase. In embodiments, compounds of Tables A1-A3 and B-D, or pharmaceutically acceptable salt, tautomer, or stereoisomer thereof, are useful for treating a disease or a condition treatable by the inhibition of one or more Raf kinase. RAF kinase inhibition is relevant for the treatment of many different diseases associated with the abnormal activity of the MAPK pathway. In embodiments the condition treatable by the inhibition of RAF kinases, such as B-RAF or C-RAF.

In embodiments, the disease or the condition is cancer. In embodiments, the disease or the condition is selected from Barret's adenocarcinoma; biliary tract carcinomas; breast cancer; cervical cancer; cholangiocarcinoma; central nervous system tumors; primary CNS tumors; glioblastomas, astrocytomas; glioblastoma multiforme; ependymomas; secondary CNS tumors (metastases to the central nervous system of tumors originating outside of the central nervous system); brain tumors; brain metastases; colorectal cancer; large intestinal colon carcinoma; gastric cancer; carcinoma of the head and neck; squamous cell carcinoma of the head and neck; acute lymphoblastic leukemia; acute myelogenous leukemia (AML); myelodysplastic syndromes; chronic myelogenous leukemia; Hodgkin's lymphoma; non-Hodgkin's lymphoma; megakaryoblastic leukemia; multiple myeloma; erythroleukemia; hepatocellular carcinoma; lung cancer; small cell lung cancer; non-small cell lung cancer; ovarian cancer; endometrial cancer; pancreatic cancer; pituitary adenoma; prostate cancer; renal cancer; metastatic melanoma or thyroid cancers.

In embodiments, the disease or the condition is melanoma, non-small cell cancer, colorectal cancer, ovarian cancer, thyroid cancer, breast cancer or cholangiocarcinoma. In embodiments, the disease or the condition is colorectal cancer. In embodiments, the disease or the condition is melanoma.

In embodiments, the disease or the condition is cancer comprising a $BRAF^{V600E}$ mutation. In embodiments, the disease or the condition is modulated by $BRAF^{V600E}$ In embodiments, the disease or the condition is $BRAF^{V600E}$ melanoma, $BRAF^{V600E}$ colorectal cancer, $BRAF^{V600E}$ papillary thyroid cancers, $BRAF^{V600E}$ low grade serous ovarian cancers, $BRAF^{V600E}$ glioma, $BRAF^{V600E}$ hepatobiliary cancers, $BRAF^{V600E}$ hairy cell leukaemia, $BRAF^{V600E}$ non-small cell cancer, or $BRAF^{V600E}$ pilocytic astrocytoma.

In embodiments, the disease or the condition is cardio-facio cutaneous syndrome and polycystic kidney disease.

Pharmaceutical Compositions

The present disclosure also relates to pharmaceutical compositions comprising the compounds of formula (I), (I-A), (I-B), (II), or (III), or a pharmaceutically acceptable salt, tautomer, or stereoisomer thereof, and a pharmaceutically acceptable carrier or excipient. The present disclosure also relates to pharmaceutical compositions comprising the compounds of Tables A1-A3 and B-D, or a pharmaceutically acceptable salt, tautomer, or stereoisomer thereof, and a pharmaceutically acceptable carrier or excipient.

In embodiments, the pharmaceutical composition may further comprise an additional pharmaceutically active agent. The additional pharmaceutically active agent may be an anti-tumor agent.

In embodiments, the additional pharmaceutically active agent is an antiproliferative/antineoplastic drug. In embodiments, antiproliferative/antineoplastic drug is alkylating agent (for example cis-platin, oxaliplatin, carboplatin, cyclophosphamide, nitrogen mustard, bendamustin, melphalan, chlorambucil, busulphan, temozolamide and nitrosoureas); antimetabolite (for example gemcitabine and antifolates such as fluoropyrimidines like 5-fluorouracil and tegafur, raltitrexed, methotrexate, pemetrexed, cytosine arabinoside, and hydroxyurea); antibiotic (for example anthracyclines like adriamycin, bleomycin, doxorubicin, daunomycin, epirubicin, idarubicin, mitomycin-C, dactinomycin and mithramycin); antimitotic agent (for example vinca alkaloids like vincristine, vinblastine, vindesine and vinorelbine and taxoids like TAXOL® (paclitaxel) and taxotere and polokinase inhibitors); proteasome inhibitor, for example carfilzomib and bortezomib; interferon therapy; or topoisomerase inhibitor (for example epipodophyllotoxins like etoposide and teniposide, amsacrine, topotecan, mitoxantrone and camptothecin).

In embodiments, the additional pharmaceutically active agent is a cytostatic agent. In embodiments, cytostatic agent is antiestrogen (for example tamoxifen, fulvestrant, toremifene, raloxifene, droloxifene and iodoxyfene), antiandrogen (for example bicalutamide, flutamide, nilutamide and cyproterone acetate), LHRH antagonist or LHRH agonist (for example goserelin, leuprorelin and buserelin), progestogen (for example megestrol acetate), aromatase inhibitor (for example as anastrozole, letrozole, vorazole and exemestane) or inhibitor of 5a-reductase such as finasteride.

In embodiments, the additional pharmaceutically active agent is an anti-invasion agent. In embodiments, the anti-invasion agent is dasatinib and bosutinib (SKI-606), metalloproteinase inhibitor, or inhibitor of urokinase plasminogen activator receptor function or antibody to Heparanase.

In embodiments, the additional pharmaceutically active agent is an inhibitor of growth factor function. In embodiments, the inhibitor of growth factor function is growth factor antibody and growth factor receptor antibody, for example the anti-erbB2 antibody trastuzumab [Herceptin™], the anti-EGFR antibody panitumumab, the anti-erbB1 antibody cetuximab, tyrosine kinase inhibitor, for example inhibitors of the epidermal growth factor family (for example EGFR family tyrosine kinase inhibitor such as gefitinib, erlotinib and 6-acrylamido-N-(3-chloro-4-fluorophenyl)-7-(3-morpholinopropoxy)-quinazolin-4-amine (CI 1033), erbB2 tyrosine kinase inhibitor such as lapatinib); inhibitor of the hepatocyte growth factor family; inhibitor of the insulin growth factor family; modulator of protein regulators of cell apoptosis (for example Bcl-2 inhibitors); inhibitor of the platelet-derived growth factor family such as imatinib and/or nilotinib (AMN107); inhibitor of serine/threonine kinases (for example Ras/RAF signalling inhibitors such as famesyl transferase inhibitor, for example sorafenib, tipifarnib and lonafarnib), inhibitor of cell signalling through MEK and/or AKT kinase, c-kit inhibitor, abl kinase inhibitor, Pl3 kinase inhibitor, Plt3 kinase inhibitor, CSF-1R kinase inhibitor, IGF receptor, kinase inhibitor; aurora kinase inhibitor or cyclin dependent kinase inhibitor such as CDK2 and/or CDK4 inhibitor.

In embodiments, the additional pharmaceutically active agent is an antiangiogenic agent. In embodiments, the antiangiogenic agent inhibits the effects of vascular endothelial growth factor, for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib.

In embodiments, the additional pharmaceutically active agent is a cIn embodiments, the cytotoxic agent is fludarib-ine (fludara), cladribine, or pentostatin (Nipent™)

In embodiments, the additional pharmaceutically active agent is a steroid. In embodiments, the steroid is corticosteroid, including glucocorticoid and mineralocorticoid, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids as described herein.

In embodiments, the additional pharmaceutically active agent is a targeted therapy agent. In embodiments, the targeted therapy agent is a PI3 Kd inhibitor, for example idelalisib and perifosine.

In embodiments, the additional pharmaceutically active agent is an immunotherapeutic agent. In embodiments, the immunotherapeutic agent is antibody therapy agent such as alemtuzumab, rituximab, ibritumomab tiuxetan (Zevalin®) and ofatumumab; interferon such as interferon $\alpha$; interleukins such as IL-2 (aldesleukin); interleukin inhibitors for example IRAK4 inhibitors; cancer vaccine including prophylactic and treatment vaccines such as HPV vaccines, for example Gardasil, Cervarix, Oncophage and Sipuleucel-T (Provenge); toll-like receptor modulator for example TLR-7 or TLR-9 agonist; and PD-1 antagonist, PDL-1 antagonist, and IDO-1 antagonist.

In embodiments, the pharmaceutical composition may be used in combination with another therapy. In embodiments, the other therapy is gene therapy, including for example approaches to replace aberrant genes such as aberrant p53 or aberrant BRCA1 or BRCA2.

In embodiments, the other therapy is immunotherapy approaches, including for example antibody therapy such as alemtuzumab, rituximab, ibritumomab tiuxetan (Zevalin®) and ofatumumab; interferons such as interferon $\alpha$; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); toll-like receptor modulators for example TLR-7 or TLR-9 agonists; and PD-1 antagonists, PDL-1 antagonists, and IDO-1 antagonists.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight ($\mu$g/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

Pharmaceutical compositions can be prepared as liposome and encapsulation therapeutic agents. For various methods of preparing liposomes and encapsulation of therapeutic agents: see, for example, U.S. Pat. Nos. 3,932,657, 4,311,712, 4,743,449, 4,452,747, 4,830,858, 4,921,757, and 5,013,556. Known methods include the reverse phase evaporation method as described in U.S. Pat. No. 4,235,871. Also, U.S. Pat. No. 4,744,989 covers use of, and methods of preparing, liposomes for improving the efficiency or delivery of therapeutic compounds, drugs and other agents.

Compounds of the invention can be passively or actively loaded into liposomes. Active loading is typically done using a pH (ion) gradient or using encapsulated metal ions, for example, pH gradient loading may be carried out according to methods described in U.S. Pat. Nos. 5,616,341, 5,736,155, 5,785,987, and 5,939,096. Also, liposome loading using metal ions may be carried out according to methods described in U.S. Pat. Nos. 7,238,367, and 7,744,921.

Inclusion of cholesterol in liposomal membranes has been shown to reduce release of drug and/or increase stability after intravenous administration (for example, see: U.S. Pat.

Nos. 4,756,910, 5,077,056, and 5,225,212). Inclusion of low cholesterol liposomal membranes continuing charged lipids has been shown to provide cryostability as well as increase circulation after intravenous administration (see: U.S. Pat. No. 8,518,437).

Pharmaceutical compositions can comprise nanoparticles. The formation of nanoparticles has been achieved by various methods. Nanoparticles can be made by precipitating a molecule in a water-miscible solvent, and then drying and pulverizing the precipitate to form nanoparticles. (U.S. Pat. No. 4,726,955). Similar techniques for preparing nanoparticles for pharmaceutical preparations include wet grinding or milling. Other methods include mixing low concentrations of polymers dissolved in a water-miscible solution with an aqueous phase to alter the local charge of the solvent and form a precipitate through conventional mixing techniques. (U.S. Pat. No. 5,766,635). Other methods include the mixing of copolymers in organic solution with an aqueous phase containing a colloid protective agent or a surfactant for reducing surface tension. Other methods of incorporating additive therapeutic agents into nanoparticles for drug delivery require that nanoparticles be treated with a liposome or surfactant before drug administration (U.S. Pat. No. 6,117,454). Nanoparticles can also be made by flash nanoprecipitation (U.S. Pat. No. 8,137,699).

U.S. Pat. No. 7,850,990 covers methods of screening combinations of agents and encapsulating the combinations in delivery vehicles such as liposomes or nanoparticles.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient. The standard duration of treatment with compounds of the invention is expected to vary between one and seven days for most clinical indications. It may be necessary to extend the duration of treatment beyond seven days in instances of recurrent infections or infections associated with tissues or implanted materials to which there is poor blood supply including bones/joints, respiratory tract, endocardium, and dental tissues.

EXAMPLES

The disclosure now being generally described, it will be more readily understood by reference to the following examples which are included merely for purposes of illustration of certain aspects and embodiments of the present invention, and are not intended to limit the invention.

As used herein the following terms have the meanings given: "Boc" refers to tert-butyloxycarbonyl; "Cbz" refers to carboxybenzyl; "dba" refers to dibenzylideneacetone; "DCM" refers to dichloromethane; "DIPEA" refers to N,N-diisopropylethylamine; "DMA" refers to dimethylacetamide; "DMF" refers to N,N-dimethylformamide; "DMSO" refers to dimethyl sulfoxide; "dppf" refers to 1,1'-bis(diphenylphosphino)ferrocene; "EtOAc" refers to ethyl acetate; "EtOH" refers to ethanol; "Et2O" refers to diethyl ether; "IPA" refers to isopropyl alcohol; "LiHMDS" refers to lithium bis(trimethylsilyl)amide; "mCPBA" refers to meta-chloroperoxybenzoic acid; "MeCN" refers to acetonitrile; "MeOH" refers to methanol; "min" refers to minutes; "NMR" refers to nuclear magnetic resonance; "PhMe" refers to toluene; "pTsOH" refers to p-toluenesulfonic acid; "py" refers to pyridine; "r.t." refers to room temperature; "SCX" refers to strong cation exchange; "T3P" refers to propylphosphonic anhydride; "Tf2O" refers to trifluoromethanesulfonic anhydride; "THF" refers to tetrahydrofuran; "THP" refers to 2-tetrahydropyranyl; "(UP)LC-MS" refers to (ultra performance) liquid chromatography/mass spectrometry. Solvents, reagents and starting materials were purchased from commercial vendors and used as received unless otherwise described. All reactions were performed at room temperature unless otherwise stated. Compound identity and purity confirmations were performed by LC-MS UV using a Waters Acquity SQ Detector 2 (ACQ-SQD2 #LCA081). The diode array detector wavelength was 254 nM and the MS was in positive and negative electrospray mode (m/z: 150-800). A 2 µL aliquot was injected onto a guard column (0.2 µm×2 mm filters) and UPLC column (C18, 50×2.1 mm, <2 µm) in sequence maintained at 40° C. The samples were eluted at a flow rate of 0.6 mL/min with a mobile phase system composed of A (0.1% (v/v) formic acid in water) and B (0.10% (v/v) formic acid in MeCN) according to the gradients outlined below. Retention times RT are reported in minutes.

| Time (min) | % A | % B |
|---|---|---|
| Final purity | | |
| 0 | 95 | 5 |
| 1.1 | 95 | 5 |
| 6.1 | 5 | 95 |
| 7 | 5 | 95 |
| 7.5 | 95 | 5 |
| 8 | 95 | 5 |
| Short acidic | | |
| 0 | 95 | 5 |
| 0.3 | 95 | 5 |
| 2 | 5 | 95 |
| 2.6 | 95 | 5 |
| 3 | 95 | 5 |

NMR was also used to characterise final compounds. NMR spectra were obtained on a Bruker AVIII 400 Nanobay with 5 mm BBFO probe. Optionally, compound Rf values on silica thin layer chromatography (TLC) plates were measured.

Compound purification was performed by flash column chromatography on silica or by preparative LC-MS. LC-MS purification was performed using a Waters 3100 Mass detector in positive and negative electrospray mode (m z: 150-800) with a Waters 2489 UV/Vis detector. Samples were eluted at a flow rate of 20 mL/min on a Xbridgerm prep C18 5 µM OBD 19×100 mm column with a mobile phase system composed of A (0.1% (v/v) formic acid in water) and B (0.1% (v/v) formic acid in MeCN) according to the gradient outlined below:

| Time (min) | % A | % B |
|---|---|---|
| 0 | 90 | 10 |
| 1.5 | 90 | 10 |
| 11.7 | 5 | 95 |
| 13.7 | 5 | 95 |
| 14 | 90 | 90 |
| 15 | 90 | 90 |

Chemical names in this document were generated using mol2nam—Structure to Name Conversion by OpenEye Scientific Software. Starting materials were purchased from commercial sources or synthesised according to literature procedures.

Synthesis of Common Intermediates

Example 1. Synthesis of 5-fluoro-3,4-dihydro-1H-1,8-naphthyridin-2-one

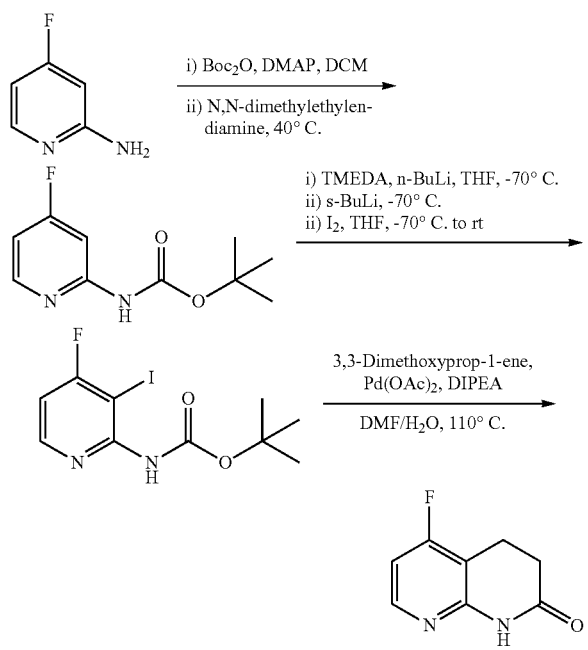

Step 1—tert-butyl N-(4-fluoro-2-pyridyl)carbamate

2-Amino-4-fluoropyridine (400 g, 3.57 mol) was charged into a 10 L fixed reactor vessel and then taken up in DCM (4 L) under a nitrogen atmosphere. DMAP (43.6 g, 357 mmol) was added and the reaction cooled to 10° C. Boc$_2$O (934 g, 4.2 mol) was added as a solution in DCM (1 L) over 1.5 hours. The reaction was stirred at rt for 2 hours. The reaction was then treated with N,N-dimethylethylenediamine (390 mL, 3.57 mmol) and heated to 40° C. overnight. The reaction was cooled to rt, diluted with DCM (2 L) and washed with water. The aqueous layer was extracted with further DCM (2 L) and the organics washed with water, brine and dried over MgSO$_4$. During evaporation of the solvent, a solid crashed out, which was filtered, washed with petroleum ether to give tert-butyl N-(4-fluoro-2-pyridyl) carbamate (505 g, 2.38 mol, 67% yield) as a cream solid product. UPLC-MS (ES+, Short acidic): 1.64 min, m/z 213.1 [M+H]+. $^1$H NMR (400 MHz, DMSO-d$_6$) δ/ppm: 10.13 (1H, d, J=1.7 Hz), 8.26 (1H, dd, J=9.4 Hz, 5.7 Hz), 7.60 (1H, dd, J=12.3 Hz, 2.4 Hz), 6.94 (1H, ddd, J=8.2 Hz, 5.7 Hz, 2.4 Hz), 1.47 (9H, s).

Step 2—tert-butyl N-(4-fluoro-3-iodo-2-pyridyl)carbamate

Tert-butyl N-(4-fluoro-2-pyridyl)carbamate (126 g, 593.7 mmol) and N,N,N,N-tetramethylethylenediamine (223 mL, 1.48 mol) were taken up in dry THF (1.7 L) and then cooled to −78° C. under a nitrogen atmosphere. To this solution was added n-BuLi (2.5M in hexane—285 mL, 712.5 mmol) and then allowed to stir for a further 10 minutes. sec-BuLi (1.2M in cyclohexane—509 mL, 712.5 mmol) was then added keeping the reaction temperature below −70° C. and stirred for 1 hour. After this time, iodine (226 g, 890.6 mmol) in THF (300 mL) was added dropwise over 30 minutes and the temperature kept below −65° C. The reaction was stirred at −70° C. for another 10 minutes then quenched by the addition of sat. aq. NH$_4$Cl (400 mL) and then a solution of sodium thiosulphate (134.1 g, 848.2 mmol) dissolved in water (600 mL) which raised the temperature to −25° C. The reaction was warmed to rt, transferred to a 5 L separator and extracted with EtOAc (2×1.5 L) and then washed with brine (500 ml). The organic phase was dried over MgSO$_4$ and the solvent removed in vacuo. The residue was taken up in DCM (500 mL) and passed through a 2 Kg silica pad, which was washed with DCM (10×1 L) and then the product was eluted from the column using as eluent a gradient 10-100% EtOAc in petroleum ether (1 L at each 10% increase) tert-butyl N-(4-fluoro-3-iodo-2-pyridyl)carbamate (154.6 g, 457.1 mmol, 77% yield) as a white solid. UPLC-MS (ES+, Short acidic): 1.60 min, m/z 339.1 [M+H]+. $^1$H NMR (400 MHz, DMSO-d$_6$) δ/ppm: 9.47 (1H, s), 8.33 (1H, dd, J=8.7 Hz, 5.5 Hz), 7.19 (1H, dd, J=7.3 Hz, 5.5 Hz), 1.46 (9H, s).

Step 3—5-fluoro-3,4-dihydro-1H-1,8-naphthyridin-2-one tert-butyl N-(4-fluoro-3-iodo-2-pyridyl)carbamate (263.3 g, 778.72 mmol) and 3,3-dimethoxyprop-1-ene (120 mL, 1.01 mol) and DIPEA (285 mL, 1.64 mol) were taken up in DMF (2.2 L) and water (440 mL) and degassed under a nitrogen atmosphere for 20 minutes. To this mixture, palladium (II) acetate (17.5 g, 77.9 mmol) was added, the reaction degassed for 15 minutes and then heated to 110° C. for 18 hours. The reaction was cooled to rt and filtered through celite. The solvent was removed under reduce pressure, the residue was taken up in water and acidified to pH-1-2 with 2N HCl solution. It was then basified to pH-9 with solid NaHCO$_3$ solution followed by extraction with DCM (2×2 L). The organic phases were combined, washed with water, brine and dried over MgSO$_4$. EtOAc (2 L) was added to the solution and the organics were passed through a silica plug eluting with 40% EtOAc in DCM. Fractions containing the product were combined and the solvent removed in vacuo to give a solid, which was slurried in cold Et20 (300 mL) and filtered. The solid was washed with Et20 and then petroleum ether, pulled dry to give 5-fluoro-3,4-dihydro-1H-1,8-naphthyridin-2-one (5.7 mg, 343.1 mmol, 44% yield) as a pale yellow solid. UPLC-MS (ES+, Short acidic): 1.04 min, m/z 167.0 [M+H]+. $^1$H NMR (400 MHz, DMSO-d$_6$) δ/ppm: 10.69 (1H, s), 8.29-7.90 (1H, m), 6.92 (1H, dd, J=8.8 Hz, 5.7 Hz, 1H), 2.88 (2H, dd, J=8.3 Hz, 7.1 Hz), 2.57-2.47 (2H, m).

Example 2. Synthesis of 6-hydroxychromane-3-carboxylic Acid

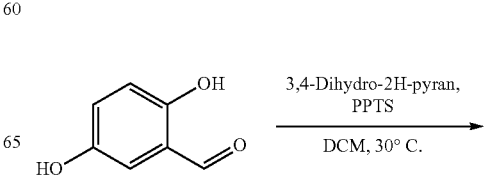

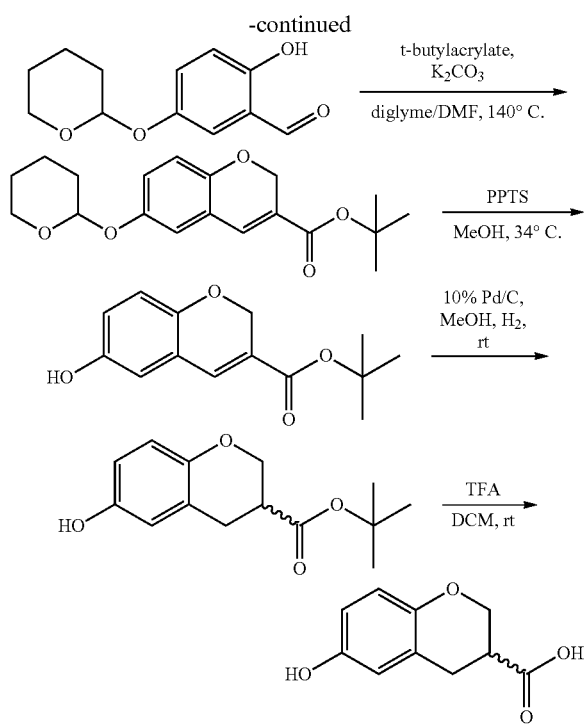

Step 1—2-hydroxy-5-tetrahydropyran-2-yloxy-benzaldehyde

To a solution of 2,5-dihydroxybenzaldehyde (400 g, 2.90 mol) and pyridinium p-toluenesulfonate (36.4 g, 144.8 mmol) in DCM (7.5 L) was added 3,4-dihydro-2H-pyran (396.3 mL, 4.34 mol) dropwise over 10 minutes and the reaction stirred at 30° C. overnight. The reaction was washed with water (1.5 L), the organic layer separated and passed through a 1.5 Kg silica pad, which was washed with DCM (2.5 L), 25% EtOAc in petroleum ether (2.5 L) and finally 50% EtOAc in petroleum ether (2.5 L). Fractions containing the product were combined and the solvent removed in vacuo. The residue was slowly diluted with petroleum ether (1.75 L) and cooled to 10° C. to give a thick slurry. The product was filtered, washed with petroleum ether (2×150 mL) and dried to give 2-hydroxy-5-tetrahydropyran-2-yloxy-benzaldehyde (570.7 g, 2.57 mol, 89% yield) as a yellow solid. UPLC-MS (ES+, Short acidic): 1.64 min, m/z 223.0 [M+H]+. $^1$H NMR (400 MHz, DMSO-$d_6$) δ/ppm: 10.35 (1H, s), 10.23 (1H, s), 7.32-7.19 (2H, m), 6.94 (1H, d, J=8.9 Hz), 5.36 (1H, t, J=3.3 Hz), 3.77 (1H, ddd, J=11.2 Hz, 8.8 Hz, 3.6 Hz), 3.59-3.49 (1H, m), 1.94-1.45 (6H, m).

Step 2—tert-butyl 6-tetrahydropyran-2-yloxy-2H-chromene-3-carboxylate 2-hydroxy-5-tetrahydropyran-2-yloxy-benzaldehyde (107 g, 481.5 mmol) was dissolved in diglyme (750 mL) and $K_2CO_3$ (133 g, 962.9 mmol) was added. The reaction was then heated to 140° C. and tert-butyl acrylate (155 mL, 1059.2 mmol) in DMF (75 mL) was added over 10 minutes at −110° C.; the reaction was stirred at 140° C. for a further 5 hour. The reaction was cooled to rt overnight, filtered and the solvent removed in vacuo. The reaction was suspended in EtOAc (2.5 L) and water (2.5 L) and the phases separated. The aqueous phase was extracted with EtOAc (2.5 L) and the combined organic layers were washed with brine (50%) and the solvent removed in vacuo. The crude was dissolved in DCM, loaded onto a 2 Kg silica pad, which was flushed with a gradient from 10-25% EtOAc in petroleum ether to give tert-butyl 6-tetrahydropyran-2-yloxy-2H-chromene-3-carboxylate (122.5 g, 368.5 mmol, 77% yield) as a yellow solid. UPLC-MS (ES+, Short acidic): 2.18 min, m/z nd. $^1$H NMR (400 MHz, DMSO-$d_6$) δ/ppm: 7.38 (1H, s), 7.05 (1H, d, J=2.9 Hz), 6.94 (1H, dd, J=8.8, 2.9 Hz), 6.79 (1H, dd, J=8.8, 0.7 Hz), 5.35 (1H, t, J=3.3 Hz), 4.82 (2H, d, J=1.4 Hz), 3.78 (1H, ddd, J=11.8, 8.6, 3.6 Hz), 3.58-3.49 (1H, m), 1.92-1.66 (3H, m), 1.66-1.52 (3H, m), 1.49 (s, 9H).

Step 3—tert-butyl 6-hydroxy-2H-chromene-3-carboxylate tert-Butyl 6-tetrahydropyran-2-yloxy-2H-chromene-3-carboxylate (110.4 g, 332.1 mmol) was suspended in MeOH (1.2 L) at rt and pyridinium p-toluenesulfonate (8.35 g, 33.2 mmol) was added. The reaction was warmed to 34° C. for 3 hours. The solvent was removed in vacuo, the crude dissolved in EtOAc (1 L) and washed with water (750 mL). The organic layer was dried over $MgSO_4$, filtered and the solvent removed under reduce pressure to give a yellow solid. This solid was suspended in petroleum ether and the solvent removed in vacuo to give tert-butyl 6-hydroxy-2H-chromene-3-carboxylate (82 g, 330.3 mmol, 99% yield) as a yellow solid. UPLC-MS (ES−, Short acidic): 1.71 min, m/z 247.2 [M−H]−. 1H NMR (400 MHz, DMSO-$d_6$) δ/ppm: 9.17 (1H, s), 7.33 (1H, s), 6.76-6.64 (3H, m), 4.77 (2H, d, J=1.4 Hz), 1.49 (9H, s).

Step 4—tert-butyl 6-hydroxychromane-3-carboxylate tert-Butyl 6-hydroxy-2H-chromene-3-carboxylate (177.3 g, 714.1 mmol) was suspended in MeOH (2.5 L) at rt and palladium, 10 wt. % on carbon powder, 50% wet (15.2 g, 142.8 mmol) added. The reaction was fitted with a $H_2$ balloon, extra $H_2$ added and subjected to 3×vacuum/$H_2$ cycles and then left to stir under a $H_2$ atmosphere for 5 hours. The crude was filtered over celite, washed with MeOH and the filtrate concentrated in vacuo to give tert-butyl 6-hydroxychromane-3-carboxylate (171 g, 683.2 mmol, 96% yield) as a pale cream solid. UPLC-MS (ES+, Short acidic): 1.64 min, m/z nd. $^1$H NMR (400 MHz, DMSO-$d_6$) δ/ppm: 8.81 (1H, s), 6.60-6.52 (1H, m), 6.47 (2H, d, J=7.7 Hz), 4.19 (1H, dd, J=10.6 Hz, 3.0 Hz), 3.96 (1H, dd, J=10.6 Hz, 7.4 Hz), 2.96-2.73 (3H, m), 1.40 (9H, s).

Step 5-6-hydroxychromane-3-carboxylic Acid tert-Butyl 6-hydroxychromane-3-carboxylate (23 g, 91.9 mmol) was dissolved in DCM (250 mL) and TFA (48.3 mL, 630.35 mmol) added and the reaction stirred at rt overnight. Solvents were removed in vacuo and azeotroped with toluene (100 mL); the residue was slurried with Et20 and filtered to give 6-hydroxychromane-3-carboxylic acid (16.8 g, 86.5 mmol, 94% yield) as a pink solid. UPLC-MS (ES+, Short acidic): 1.08 min, m/z 194.1 [M+H]+. $^1$H NMR (400 MHz, DMSO-$d_6$) δ/ppm: 12.60 (1H, s), 8.81 (1H, s), 6.60-6.53 (1H, m), 6.52-6.45 (2H, m), 4.22 (1H, dd, J=10.7 Hz, 3.0 Hz), 4.06-3.96 (1H, m), 2.97-2.77 (3H, m).

Example 3. Synthesis of 6-[(7-oxo-6,8-dihydro-5H-1,8-naphthyridin-4-yl)oxy]chromane-3-carboxylic Acid

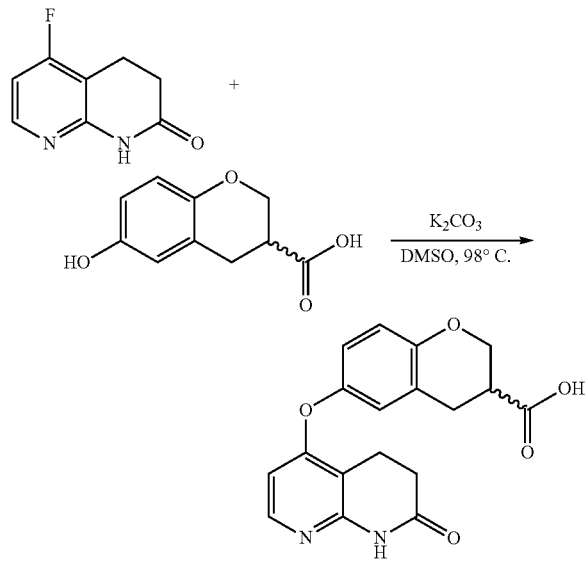

6-hydroxychromane-3-carboxylic acid (45.3 g, 233.3 mmol), 5-fluoro-3,4-dihydro-1H-1,8-naphthyridin-2-one (38.8 g, 233.3 mmol) were suspended in DMSO (230 mL) and K₂CO₃ (119.7 g, 865.8 mmol) was added in portions. The reaction was heated to 98° C. for 48h. It was then cooled to 60° C., diluted with water (2 L) and extracted with EtOAc (750 mL). The aqueous layer was separated and slowly added to a solution of citric acid (179.3 g, 933.2 mmol) in water (400 mL) to give a cream solid, which was filtered, washed with water/acetone (1:1) and Et2O and dried to give 6-[(7-oxo-6,8-dihydro-5H-1,8-naphthyridin-4-yl)oxy]chromane-3-carboxylic acid (74.7 g, 219.5 mmol, 94% yield) as a cream solid. UPLC-MS (ES+, Short acidic): 1.26 min, m/z 341.2 [M+H]+. ¹H NMR (400 MHz, DMSO-$d_6$) δ/ppm: 12.69 (1H, s), 10.46 (1H, s), 7.95 (1H, d, J=5.8 Hz), 6.97 (1H, d, J=2.8 Hz), 6.89 (1H, dd, J=8.8 Hz, 2.8 Hz), 6.84 (1H, t, J=8.8 Hz), 6.24 (1H, d, J=5.8 Hz), 4.33 (1H, dd, J=10.9 Hz, 3.1 Hz), 4.20-4.10 (1H, m), 3.06-2.95 (3H, m), 2.92 (2H, t, J=8.4 Hz, 7.0 Hz), 2.59-2.51 (2H, m).

Example 4. Synthesis of 3-[4-bromo-1-(2-trimethylsilylethoxymethyl)imidazol-2-yl]chroman-6-ol and 5-[3-[4-bromo-1-(2-trimethylsilylethoxymethyl)imidazol-2-yl]chroman-6-yl]oxy-3,4-dihydro-1H-1,8-naphthyridin-2-one

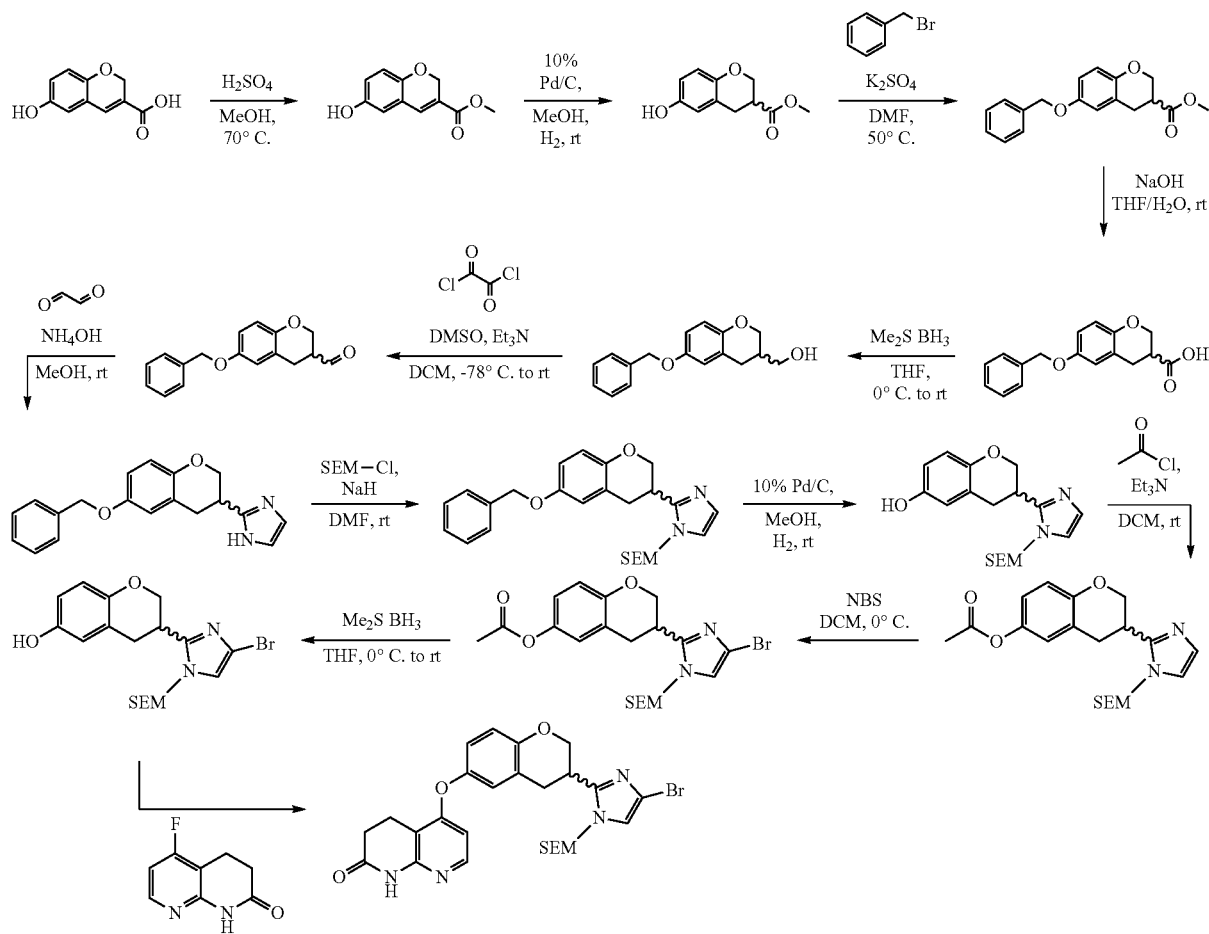

Step 1—methyl 6-hydroxy-2H-chromene-3-carboxylate

To 6-hydroxy-2H-chromene-3-carboxylic acid (16 g, 83.3 mmol) in MeOH (200 mL) was added sulfuric acid (0.44 mL, 8.33 mmol) and the reaction heated to 70° C. until completion. The solvent was removed in vacuo and the residue dissolved in DCM and washed with water. The organic layer was separated and passed through a 100 g silica pad eluting with DCM (500 mL) and then with 50% EtOAc in petroleum ether (2×500 mL). The solid obtained was slurried with petroleum ether, filtering and dried to give methyl 6-hydroxy-2H-chromene-3-carboxylate (14.1 g, 68.4 mmol, 82% yield) as a yellow solid. UPLC-MS (ES+, Short acidic): 1.38 min, m/z 207.1 [M+H]+. $^1$H NMR (400 MHz, DMSO-$d_6$) δ/ppm: 9.19 (1H, s), 7.46 (1H, d, J=1.4 Hz), 6.79-6.65 (2H, m), 6.70 (1H, s), 4.82 (2H, d, J=1.4 Hz), 3.75 (3H, s).

Step 2—methyl 6-hydroxychromane-3-carboxylate methyl 6-hydroxy-2H-chromene-3-carboxylate (53.3 g, 258.3 mmol) was suspended in MeOH (600 mL) at rt and palladium, 10 wt. % on carbon powder, 50% wet (2.75 g, 25.8 mmol) was added under a nitrogen atmosphere. The reaction was fitted with a $H_2$ balloon, extra $H_2$ added and subjected to 3×vacuum/$H_2$ cycles and then left to stir under a $H_2$ atmosphere for 3 hours. The crude was filtered over celite, washed with MeOH and the solvent removed in vacuo to give methyl 6-hydroxychromane-3-carboxylate (50.1 g, 233.9 mmol, 91% yield) as a cream solid. UPLC-MS (ES+, Short acidic): 1.27 min, m/z 209.1 [M+H]+. $^1$H NMR (400 MHz, DMSO-$d_6$) δ/ppm: 8.83 (1H, s), 6.56 (1H, dd, J=8.1, 1.0 Hz), 6.48 (2H, dd, J=9.7 Hz, 1.8 Hz), 4.22 (1H, dd, J=10.8 Hz, 3.2 Hz), 4.04 (1H, dd, J=10.7 Hz, 7.6 Hz), 3.64 (3H, s), 3.10-2.98 (1H, m), 2.89 (2H, d, J=6.9 Hz).

Step 3—methyl 6-benzyloxychromane-3-carboxylate

Benzyl bromide (2.85 mL, 23.97 mmol) was slowly added to a stirred mixture of methyl 6-hydroxychromane-3-carboxylate (4.16 g, 19.98 mmol), $K_2CO_3$ (8.28 g, 59.93 mmol) and DMF (100 mL) at rt under a nitrogen atmosphere. The reaction was heated to 50° C. and stirred for 1.5 hour, after which time it was cooled to rt and the solvent removed in vacuo. The residue was partitioned between water (300 mL) and DCM (300 mL). The organic layer was separated and the aqueous extracted with DCM (300 mL). The combined organic layers were dried over $Na_2SO_4$, filtered and solvent removed in vacuo. The residue was purified by column chromatography using as eluent a gradient of 0-50% EtOAc in petroleum ether to give methyl 6-benzyloxychromane-3-carboxylate (5.9 g, 19.78 mmol, 99% yield) as a colourless oil which solidified to a white solid on standing. UPLC-MS (ES+, short acidic): 1.92 min, m/z 299.2 [M+H]+. $^1$H NMR (400 MHz, CDCl$_3$) δ/ppm: 7.46-7.32 (5H, m), 6.79-6.77 (2H, m), 6.73 (1H, d, J=7.2 Hz), 5.02 (2H, s), 4.44-4.39 (1H, m), 4.14-4.08 (1H, m), 3.75 (3H, s), 3.14-2.97 (3H, m).

Step 4-6-benzyloxychromane-3-carboxylic Acid

Methyl 6-benzyloxychromane-3-carboxylate (5.9 g, 19.78 mmol) was stirred in a solution of aq. NaOH (100 mL, 100 mmol) and THF (100 mL) at rt for 18 hours. The organic solvent was removed in vacuo and the resulting mixture stirred, cooled in ice, followed by acidification to ~pH 5 using conc. HCl. The resulting solid was filtered off and dried to give 6-benzyloxychromane-3-carboxylic acid (5.1 g, 17.94 mmol, 91% yield) as a white solid. UPLC-MS (ES−, short acidic): 1.71 min, m/z 283.2 [M−H]−. $^1$H NMR (400 MHz, CDCl$_3$) δ/ppm: 12.64 (1H, br s), 7.46-7.37 (4H, m), 7.35-7.30 (1H, m), 6.80 (1H, d, J=2.8 Hz), 6.74 (1H, dd, J=9.2 Hz, 2.8 Hz), 6.67 (1H, d, J=9.2 Hz), 5.02 (2H, s), 4.27-4.22 (1H, m), 4.09-4.04 (1H, m), 2.99-2.91 (3H, m).

Step 5—6-benzyloxychroman-3-yl)methanol

Di-methylsulfide borane (13.45 mL, 26.91 mmol) was added to a stirred solution of 6-benzyloxychromane-3-carboxylic acid (5.1 g, 17.94 mmol) and THF (200 mL) at 0° C. under a nitrogen atmosphere and stirred at rt for 3 hours. The reaction was cooled to 0° C. and quenched carefully with water (500 mL). This was extracted with EtOAc (2×500 mL). the combined organic layers were dried over $Na_2SO_4$, filtered and solvent removed in vacuo. The residue was purified by column chromatography using as eluent a gradient of 0-10% EtOAc in petroleum ether to give 6-benzyloxychroman-3-yl)methanol (4.5 g, 16.65 mmol, 93% yield) as a yellow solid. UPLC-MS (ES+, short acidic): 1.69 min, m/z 271.2 [M+H]+. $^1$H NMR (400 MHz, CDCl$_3$) δ/ppm: 7.46-7.31 (5H, m), 6.78-6.75 (2H, m), 6.72-6.69 (1H, m), 5.01 (2H, s), 4.27 (1H, ddd, J=10.8 Hz, 2.8 Hz, 1.2 Hz), 3.99 (1H, dd, J=10.8 Hz, 2.8 Hz), 3.77-3.65 (2H, m), 2.92-2.85 (1H, m), 2.59 (1H, dd, J=16.8 Hz, 7.6 Hz), 2.33-2.23 (1H, m). Exchangeable proton not seen.

Step 6-6-benzyloxychromane-3-carbaldehyde

A solution of DMSO (1.77 mL, 24.97 mmol) in DCM (200 mL) was stirred under a nitrogen atmosphere at −78° C. Oxalyl chloride (2.11 mL, 24.97 mmol) was then added and left stirring for 20 min; a solution of (6-benzyloxychroman-3-yl)methanol in DCM (50 mL) was then added dropwise whilst maintaining the temperature below −70° C. Upon completion of addition, the reaction was stirred for 30 minutes and triethylamine (5.8 mL, 41.62 mmol) was added dropwise. The reaction was left stirring at −78° C. for 20 min after which time it was allowed to warm to rt. The reaction was diluted with water (200 mL) and the organic layer separated, passed through a phase separator and the solvent removed in vacuo. The residue was purified by column chromatography using as eluent a gradient of 0-50% EtOAc in petroleum ether to give 6-benzyloxychromane-3-carbaldehyde (4.4 g, 16.4 mmol, 99% yield) as a yellow oil. UPLC-MS (ES+, short acidic): 1.82 min, m/z 268.2 [M]+. $^1$H NMR (400 MHz, CDCl$_3$) δ/ppm: 9.86 (1H, s), 7.47-7.32 (5H, m), 6.81-6.74 (3H, m), 5.02 (2H, s), 4.42-4.32 (2H, m), 3.17-3.09 (1H, m), 3.04-2.93 (2H, m).

Step 7—2-(6-benzyloxychroman-3-yl)-1H-imidazole

Ammonium Hydroxide (25 mL, 750 mmol) was added to a stirred solution of 6-benzyloxychromane-3-carbaldehyde (3.9 g, 14.54 mmol), glyoxal (9.96 mL, 87.21 mmol) and MeOH (25 mL) at rt. After 1 hour, the reaction was diluted with water (200 mL) and extracted with DCM (2×200 mL). The combined organic layers were dried over $Na_2SO_4$, filtered and solvent removed in vacuo to give 2-(6-benzyloxychroman-3-yl)-1H-imidazole (2.4 g, 7.83 mmol, 54% yield) as a yellow solid. UPLC-MS (ES+, short acidic), 1.28 min, m/z 307.3 [M+H]+. $^1$H NMR (400 MHz, DMSO-$d_6$)

δ/ppm: 7.46-7.30 (6H, m), 7.08 (1H, d, J=9.2 Hz), 6.83-6.80 (1H, d), 6.79-6.75 (1H, d), 6.71 (1H, d, J=8.8 Hz), 5.03 (2H, s), 4.40-4.35 (1H, m), 3.97 (1H, t, J=10.0 Hz), 3.31-3.26 (1H, m), 3.15-3.10 (1H, m), 3.05-2.97 (1H, m). Exchangeable proton not seen.

Step 8—2-[[2-(6-benzyloxychroman-3-yl)imidazol-1-yl]methoxy]ethyl-trimethyl-silane Sodium hydride (60% dispersed in mineral oil—895.6 mg, 22.39 mmol) was added to a stirred solution of 2-(6-benzyloxychroman-3-yl)-1H-imidazole (3.43 g, 11.2 mmol) in DMF (5 mL) at rt under a nitrogen atmosphere. After 20 minutes, 2-(trimethylsilyl)ethoxymethyl chloride (2.97 mL, 16.79 mmol) was added. The reaction was allowed to stir for 1 hour, then quenched with water (1 mL) and solvent removed in vacuo. The residue was partitioned between water (20 mL) and DCM (20 mL). The organic layer was separated and the aqueous extracted with DCM (20 mL). The combined organic layers were dried over $Na_2SO_4$, filtered and solvent removed in vacuo. The residue was purified by column chromatography using as eluent a gradient of 0-5% MeOH in DCM to give 2-[[2-(6-benzyloxychroman-3-yl)imidazol-1-yl]methoxy]ethyl-trimethyl-silane (4.3 g, 9.85 mmol, 88% yield) as a yellow solid. UPLC-MS (ES+, short acidic): 1.67 min, m/z 437.7 [M+H]+. $^1$H NMR (400 MHz, $CDCl_3$) δ/ppm: 7.45-7.29 (5H, m), 7.03-7.01 (1H, m), 6.99-6.97 (1H, m), 6.80-6.78 (2H, m), 6.73-6.71 (1H, m), 5.31-5.28 (2H, m), 5.01 (2H, s), 4.44-4.38 (1H, m), 4.12 (1H, t, J=10.4 Hz), 3.55-3.50 (2H, m), 3.48-3.33 (2H, m), 2.99-2.92 (1H, m), 0.96-0.87 (2H, m), 0.00 (9H, s).

Step 9—3-[1-(2-trimethylsilylethoxymethyl)imidazol-2-yl]chroman-6-ol

Palladium, 10 wt. % on carbon powder, dry (400 mgl) was added to a stirred solution of 2-[[2-(6-benzyloxychroman-3-yl)imidazol-1-yl]methoxy]ethyl-trimethyl-silane (4.3 g, 9.85 mmol) in MeOH (50 mL) at rt. The reaction was fitted with a $H_2$ balloon and subjected to 3×vacuum/$H_2$ cycles and then left to stir under a $H_2$ atmosphere for 2 hours. The crude was filtered over celite, washed with MeOH and the filtrate concentrated in vacuo to give 3-[1-(2-trimethylsilylethoxymethyl)imidazol-2-yl]chroman-6-ol (3.32 g, 9.58 mmol, 97% yield) as a yellow solid. The compound was used directly in the next step without further purification. UPLC-MS (ES+, short acidic): 1.36 min, m/z 347.7 [M+H]+. $^1$H NMR (400 MHz, $CDCl_3$) δ/ppm: 6.98 (1H, d, J=1.6 Hz), 6.99 (1H, d, J=1.6 Hz), 6.69 (1H, d, J=8.8 Hz), 6.63 (1H, dd, J=8.8 Hz, 3.2 Hz), 6.56 (1H, d, J=3.2 Hz), 5.32 (1H, d, J=10.8 Hz), 5.28 (1H, d, J=10.8 Hz), 4.33 (1H, ddd, J=10.8 Hz, 3.2 Hz, 2.4 Hz), 4.10 (1H, t, J=10.4 Hz), 3.55-3.50 (3H, m), 3.33-3.24 (1H, m), 2.94-2.87 (1H, m), 0.91-0.95 (2H, m), 0.10 (9H, s). Exchangeable proton not seen.

Step 10—[3-[1-(2-trimethylsilylethoxymethyl)imidazol-2-yl]chroman-6-yl] acetate Acetyl chloride (0.94 mL, 13.29 mmol) was added to a stirred solution of 2-(1-benzylimidazol-2-yl)-3,4-dihydro-1H-isoquinolin-7-ol (3.07 g, 8.86 mmol), Et3N (1.85 mL, 13.29 mmol) and DCM (100 mL) at rt under a nitrogen atmosphere. The reaction was stirred for 30 minutes, after which time water (100 mL) was added. The mixture was extracted with DCM (2×100 mL). The combined organic extracts were dried over $Na_2SO_4$, filtered and solvent removed in vacuo. The residue was purified by column chromatography using as eluent a gradient of 0-100% EtOAc in petroleum ether to give [3-[1-(2-trimethylsilylethoxymethyl)imidazol-2-yl]chroman-6-yl] acetate (2.93 g, 7.53 mmol, 85% yield) as a yellow solid. UPLC-MS (ES+, short acidic): 1.48 min, m/z 389.5 [M+H]+. $^1$H NMR (400 MHz, $CDCl_3$) δ/ppm: 7.07-6.99 (2H, m), 6.88-6.81 (3H, m), 5.33-5.27 (2H, m), 4.46-4.41 (1H, m), 4.25-4.18 (1H, m), 3.57-3.50 (2H, m), 3.48-3.38 (2H, m), 3.03-2.95 (1H, m), 2.25 (3H, s), 0.96-0.89 (2H, m), 0.00 (9H, s).

Step 11—[3-[4-bromo-1-(2-trimethylsilylethoxymethyl)imidazol-2-yl]chroman-6-yl]acetate N-Bromosuccinimide (0.46 g, 2.57 mmol) was added to a stirred solution of [3-[1-(2-trimethylsilylethoxymethyl)imidazol-2-yl]chroman-6-yl] acetate (1 g, 2.57 mmol) and DCM (100 mL) at 0° C. under a nitrogen atmosphere. The reaction was stirred for 30 minutes and then diluted with water (100 mL). The organic layer was separated, dried over $Na_2SO_4$, filtered and solvent removed in vacuo. The residue was purified by column chromatography using as eluent a gradient of 0-50% EtOAc in petroleum ether to give [3-[4-bromo-1-(2-trimethylsilylethoxymethyl)imidazol-2-yl]chroman-6-yl] acetate (684 mg, 1.46 mmol, 57% yield) as a yellow oil. UPLC-MS (ES+, short acidic): 2.07 min, m/z 467.2, 469.2 [M+H]+. $^1$H NMR (400 MHz, $CDCl_3$) δ/ppm: 6.98 (1H, s), 6.85-6.80 (3H, m), 5.33 (2H, s), 4.46-4.41 (1H, m), 4.15-4.07 (2H, m), 3.62-3.56 (1H, m), 3.51-3.41 (1H, m), 3.38-3.30 (1H, m), 3.00-2.94 (1H, m), 2.27 (3H, s), 0.96-0.89 (2H, m), 0.00 (9H, s).

Step 12—3-[4-bromo-1-(2-trimethylsilylethoxymethyl)imidazol-2-yl]chroman-6-ol

[3-[4-bromo-1-(2-trimethylsilylethoxymethyl)imidazol-2-yl]chroman-6-yl] acetate (800 mg, 1.71 mmol) was stirred in a mixture of aq. 1M NaOH (10 mL, 10 mmol) and THF (10 mL) at rt. After 30 minutes, the reaction was taken to ~pH 5 using aq. 1M HCl and then it was diluted with water (50 ml) and extracted with DCM (2×50 mL). The combined organic layers were dried over $Na_2SO_4$, filtered and solvent removed in vacuo to give 3-[4-bromo-1-(2-trimethylsilylethoxymethyl)imidazol-2-yl]chroman-6-ol (728 mg, 1.71 mmol, 100% yield) as a yellow oil. The compound was used in the next step without further purification. UPLC-MS (ES+, short acidi): 1.87 min, m/z 425.1, 427.1 [M+H]+. $^1$H NMR (400 MHz, $CDCl_3$) δ/ppm: 6.99 (1H, s), 6.75-6.73 (1H, m), 6.64-6.60 (1H, m), 6.58-6.56 (1H, m), 5.34 (2H, s), 4.80-4.71 (1H, m), 4.42-4.36 (1H, m), 4.06 (1H, t, J=10.4 Hz), 3.61-3.57 (2H, m), 3.51-3.40 (1H, m), 3.37-3.28 (1H, m), 2.95-2.88 (1H, m), 0.96-0.89 (2H, m), 0.00 (9H, s).

Step 13—5-[3-[4-bromo-1-(2-trimethylsilylethoxymethyl)imidazol-2-yl]chroman-6-yl]oxy-3,4-dihydro-1H-1,8-naphthyridin-2-one 3-[4-bromo-1-(2-trimethylsilylethoxymethyl)imidazol-2-yl]chroman-6-ol (2 g, 4.7 mmol), 5-fluoro-3,4-dihydro-1H-1,8-naphthyridin-2-one (781.2 mg, 4.7 mmol), $K_2CO_3$ (2.6 g, 18.81 mmol) and DMSO (5 mL) were combined and stirred at 110° C. under a nitrogen atmosphere for 1 hour. The reaction was cooled to rt and poured into a solution of water (100 mL) and citric acid monohydrate (3.95 g, 18.81 mmol). The resultant mixture was extracted with DCM (2×100 mL) and the combined organic layers dried over Na$_2$SO$_4$, filtered and solvent removed in vacuo. The residue was purified by column chromatography using as eluent a gradient of 0-10% MeOH in DCM to give 5-[3-[4-bromo-1-(2-trimethylsilylethoxymethyl)imidazol-2-yl]chroman-6-yl]oxy-3,4-dihydro-1H-1,8-naphthyridin-2-one (230 mg, 0.40 mmol, 9% yield) as a yellow solid. UPLC-MS (ES+, short acidic), 1.96 min, m/z 571.2, 573.2 [M+H]+.

Example 5. Synthesis of 6-[(2-chloro-4-pyridyl)oxy]chromane-3-carboxylic Acid and 6-[[2-(cyclopropanecarbonylamino)-4-pyridyl]oxy]chromane-3-carboxylic Acid

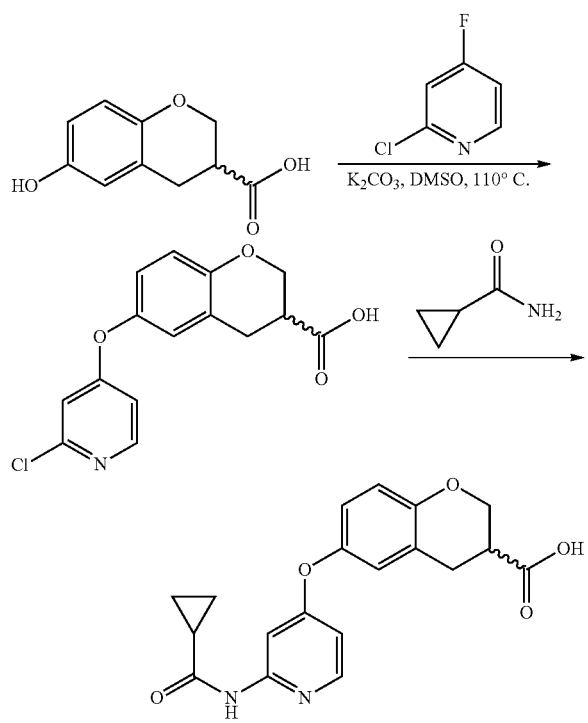

Step 1—6-[2-chloro-4-pyridyl)oxy]chromane-3-carboxylic Acid

A solution of 6-hydroxychromane-3-carboxylic acid hydrochloride (1.4 g, 6.07 mmol), 2-chloro-4-fluoropyridine (550 μL, 6.09 mmol) and K$_2$CO$_3$ (3.36 g, 24.28 mmol) in DMSO (7.6 mL) was heated to 110° C. under a nitrogen atmosphere for 1.5 hours. The reaction mixture was cooled to rt and poured into a solution of citric acid (4.67 g, 24.28 mmol) in water (100 mL). The resulting precipitate was filtered, washed with water and dried to give 6-[(2-chloro-4-pyridyl)oxy]chromane-3-carboxylic acid (1.74 g, 5.69 mmol, 94% yield) as a brown solid. The compound was used in the next step without further purification. UPLC-MS (ES+, Short acidic): 1.55 min, m/z 306.1 [M+H]+. $^1$H NMR (400 MHz, DMSO-d$_6$) δ/ppm: 12.69 (1H, br s), 8.27 (1H, d, J=5.7 Hz), 7.04 (1H, d, J=2.9 Hz), 6.97-6.89 (3H, m), 6.86 (1H, d, J=8.8 Hz), 4.34 (1H, dd, J=10.9, 3.2 Hz), 4.19-4.13 (1H, m), 3.05-2.95 (3H, m).

Step 2—6-[[2-(cyclopropanecarbonylamino)-4-pyridyl]oxy]chromane-3-carboxylic Acid To a solution of 6-[(2-chloro-4-pyridyl)oxy]chromane-3-carboxylic acid (500 mg, 1.64 mmol), cyclopropanecarboxamide (278.4 mg, 3.27 mmol) and Cs$_2$CO$_3$ (1.07 g, 3.27 mmol) in 1,4-dioxane (16 mL) was added (+/−)-BINAP (203.7 mg, 0.33 mmol) and tris(dibenzylideneacetone)dipalladium (0) (149.7 mg, 0.16 mmol) under a nitrogen atmosphere. The mixture was heated at 100° C. for 20 hrs. After cooling to rt, the mixture was filtered through celite and washed with methanol. The solvent was removed under reduce pressure and the residue purified by column chromatography using as eluent a gradient 0-20% MeOH in DCM. Fractions containing the product were combined, solvent removed in vacuo, the residue suspended in DCM and filtered. The precipitate was washed with DCM and dried to give 6-[[2-(cyclopropanecarbonylamino)-4-pyridyl]oxy]chromane-3-carboxylic acid (272.3 mg, 0.77 mmol, 47% yield) as an off-white solid. UPLC-MS (ES+, Short acidic): 1.23 min, m/z 355.2 [M+H]+. $^1$H NMR (400 MHz, DMSO-d$_6$) δ/ppm: 12.69 (1H, br s), 10.81 (1H, s), 8.15 (1H, d, J=5.7 Hz), 7.63 (1H, d, J=2.4 Hz), 6.97 (1H, d, J=2.7 Hz), 6.88 (1H, dd, J=8.8 Hz, 2.7 Hz), 6.83 (1H, d, J=8.8 Hz), 6.59 (1H, dd, J=5.7 Hz, 2.4 Hz), 4.34 (1H, dd, J=10.7 Hz, 2.8 Hz), 4.14 (1H, dd, J=10.7 Hz, 6.7 Hz), 3.04-2.92 (3H, m), 1.97 (1H, quint, J=6.2 Hz), 0.77 (4H, d, J=6.2 Hz).

Example 6. Synthesis of 7-benzyloxy-1,2,3,4-tetrahydroisoquinoline Hydrochloride

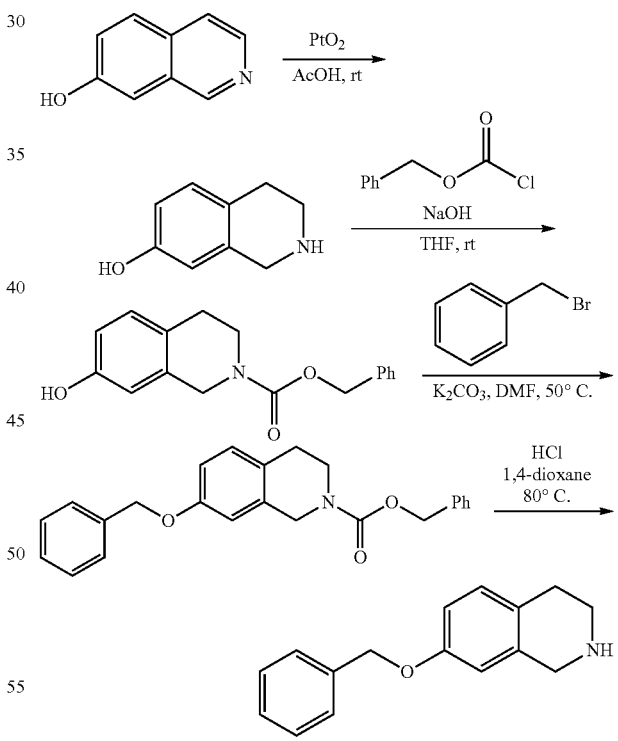

Step 1—acetic acid; 1,2,3,4-tetrahydroisoquinolin-7-ol

Platinum(IV) oxide (Adam's Catalyst) (500 mg, 2.2 mmol) was added to 7-hydroxyisoquinoline (5. g, 34.45 mmol) in acetic acid (20 mL) at rt. The reaction was fitted with a H$_2$ balloon and subjected to 3×vacuum/H$_2$ cycles and then left to stir under a H$_2$ atmosphere for 18 hours. The crude was filtered over celite and the filtrate concentrated in vacuo. The residue was stirred in an acetone/petroleum ether mixture (1:2, 15 mL) for 1 hour, causing a solid to crash out which was filtered off and dried in vacuo to give acetic acid; 1,2,3,4-tetrahydroisoquinolin-7-ol (6.53 g, 31.2 mmol, 91% yield) as a light yellow solid. The compound was used in the next step without further purification. UPLC-MS (ES+, short acidic): 0.36 min, m/z 150.2 [M+H]+.

Step 2—benzyl 7-hydroxy-3,4-dihydro-1H-isoquinoline-2-carboxylate

Benzyl chloroformate (2.05 mL, 14.34 mmol) was added to a stirred solution of THF (15 mL), acetic acid; 1,2,3,4-tetrahydroisoquinolin-7-ol (2.5 g, 11.95 mmol) and NaOH (35.84 mL, 35.84 mmol) at rt. The reaction was stirred for 1 hour and then diluted with water (200 mL) and EtOAc (200 mL). The organic layer was separated, dried over $Na_2SO_4$, filtered and solvent removed in vacuo. The residue was purified by column chromatography using an eluent of 0-100% EtOAc in petroleum ether to give benzyl 7-hydroxy-3,4-dihydro-1H-isoquinoline-2-carboxylate (3.3 g, 11.65 mmol, 97% yield) as a white solid. UPLC-MS (ES+, short acidic): 1.65 min, m/z 284.2 [M+H]+. $^1$H NMR (400 MHz, $CDCl_3$) δ/ppm: 7.40-7.29 (5H, m), 6.98 (1H, d, J=8.4 Hz), 6.70-6.54 (2H, m), 5.18 (2H, s), 4.61-4.56 (2H, m), 3.75-3.66 (2H, m), 2.81-2.73 (2H, m). Exchangeable proton not seen.

Step 3—benzyl 7-benzyloxy-3,4-dihydro-1H-isoquinoline-2-carboxylate

Benzyl 7-hydroxy-3,4-dihydro-1H-isoquinoline-2-carboxylate (569 mg, 1.45 mmol) was dissolved in DMF (8 mL) followed by addition of benzyl bromide (0.21 mL, 1.74 mmol) and $K_2CO_3$ (600 mg, 4.34 mmol). The reaction was left stirring at 50° C. for 1.5 hour and then at rt overnight. The solvent was removed under reduce pressure. Water was added, followed by extraction with EtOAc (2×). The organic layers were combined, washed with brine (2×), dried over $Na_2SO_4$ and the solvent removed in vacuo. The crude was purified by column chromatography using as eluent a gradient 0-25% EtOAc in petroleum ether to give benzyl 7-benzyloxy-3,4-dihydro-1H-isoquinoline-2-carboxylate (428 mg, 1.15 mmol, 79% yield) as a colourless oil. UPLC-MS (ES+, short acidic): 2.12 min, m/z 374.2 [M+H]+. $^1$H-NMR (400 MHz, $CDCl_3$) δ/ppm: 7.50-7.28 (10H, m), 7.04 (1H, d, J=8.4 Hz), 6.81 (1H, dd, J=8.4 Hz, 2.4 Hz), 6.72 (1H, br d, J=12.0 Hz), 5.18 (2H, s), 5.04 (2H, s), 4.61 (2H, s), 3.71 (2H, br s), 2.78 (2H, br s).

Step 4—7-benzyloxy-1,2,3,4-tetrahydroisoquinoline Hydrochloride

To benzyl 7-benzyloxy-3,4-dihydro-1H-isoquinoline-2-carboxylate (196 mg, 0.52 mmol) was added HCl (4N in 1,4-dioxane—6 mL, 24 mmol) and the reaction heated to 80° C. for 72 hours. The solvent was removed under reduce pressure to give 7-benzyloxy-1,2,3,4-tetrahydroisoquinoline hydrochloride (144.7 mg, 0.52 mmol, 100% yield) as a cream solid. The compound was used in the next step without further purification. UPLC-MS (ES+, short acidic): 1.27 min, m/z 240.2 [M+H]+. $^1$H-NMR (400 MHz, DMSO-$d_6$) δ/ppm: 9.18 (1H, br s), 7.52-7.37 (4H, m), 7.36-7.27 (1H, m), 7.14 (1H, d, J=8.4 Hz), 6.96-6.89 (2H, m), 5.10 (2H, s), 4.21 (2H, br s), 3.35-3.28 (2H, t, (under water)), 2.92 (2H, t, J=6.0 Hz).

Example 7. Synthesis of 3-methyl-5-(trifluoromethyl)benzene-1,2-diamine

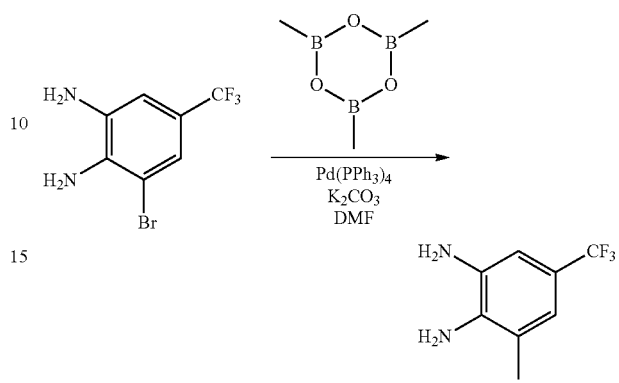

3-Bromo-4,5-diaminobenzotrifluoride (500 mg, 1.96 mmol), $K_2CO_3$ (542 mg, 3.92 mmol), tetrakis(triphenylphosphine)palladium(0) (227 mg, 0.20 mmol) were mixed under $N_2$ followed by the addition of 2,4,6-Trimethylboroxin (0.27 mL, 1.96 mmol). The reaction was left stirring for 72 hours at 110° C., after which time a second portion of 2,4,6-trimethylboroxin (0.14 mL, 0.98 mmol), $K_2CO_3$ (271 mg, 1.96 mmol) and tetrakis(triphenylphosphine)palladium(0) (113 mg, 0.10 mmol) were added. The reaction was stirred at 110° C. overnight, after which time water was added (20 mL) followed by extraction with EtOAc (2×). The organic phases were combined, washed with brine, dried over $Na_2SO_4$, filtered and the solvent removed in vacuo. The crude was purified by column chromatography using as eluent a gradient 0-5% MeOH in DCM to give 3-methyl-5-(trifluoromethyl)benzene-1,2-diamine (82 mg, 0.43 mmol, 22% yield) as a brown oil. UPLC-MS (ES+, short acidic): 1.37 min, m/z 191.1 [M+H]+. $^1$H-NMR (400 MHz, DMSO-$d_6$) δ/ppm: 6.70-6.67 (1H, m), 6.63-6.59 (1H, m), 4.81 (2H, s), 4.79 (2H, s), 2.07 (3H, s).

Example 8. Synthesis of 6-(trifluoromethyl)pyridine-3,4-diamine

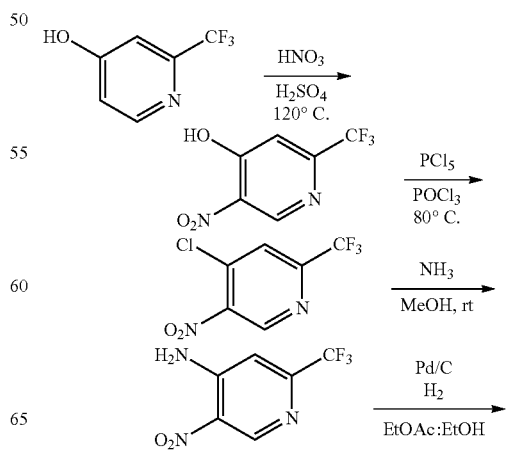

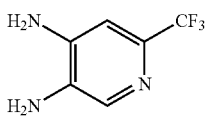

Step 1—5-nitro-2-(trifluoromethyl)pyridin-4-ol

To a cooled solution of 2-(trifluoromethyl)pyridin-4-ol (1000 mg, 6.13 mmol) at 0° C. in sulfuric acid (2.46 mL, 46.15 mmol) was added nitric acid, fuming, 90% (6.12 mL, 144.04 mmol) dropwise over 15 min, after which time the reaction was heated to 120° C. overnight. The reaction mixture was cooled to rt and poured into ice water. The mixture was brought to neutral pH by addition of a solution 32% of aq. NaOH and extracted with EtOAc (3×) and n-BuOH. The combined organic phases were dried over $Na_2SO_4$, filtered and the solvent removed in vacuo to give 5-nitro-2-(trifluoromethyl)pyridin-4-ol (1.27 g, 6.10 mmol, 100% yield) as a yellow solid. The compound was used without further purification in the following step. UPLC-MS (ES−, short acidic): 1.17 min, m/z 207.1 [M−H]−. $^1$H-NMR (400 MHz, DMSO-$d_6$) δ/ppm: 9.00 (1H, s), 7.30 (1H, s).

Step 2—4-chloro-5-nitro-2-(trifluoromethyl)pyridine 5-nitro-2-(trifluoromethyl)pyridin-4-ol (1.28 g, 6.13 mmol), phosphorus pentachloride (1.91 g, 9.19 mmol) and phosphorus oxychloride (0.86 mL, 9.19 mmol) were stirred at 80° C. overnight. The mixture was cooled to rt, diluted with DCM and washed with water, sat. aq. $Na_2CO_3$ and brine. The organic phase was dried over $Na_2SO_4$, filtered and the solvent removed in vacuo. The compound was re-dissolved in DCM and poured into water-ice, followed by addition of aq. 1M NaOH. The organic phase was washed with brine, dried over $Na_2SO_4$, filtered and the solvent removed under reduce pressure to give 4-chloro-5-nitro-2-(trifluoromethyl)pyridine (804 mg, 3.55 mmol, 58% yield) as a yellow oil. UPLC-MS (ES−, short acidic): 1.68 min, m/z nd. $^1$H-NMR (400 MHz, DMSO-$d_6$) δ/ppm: 9.43 (1H, s), 8.58 (1H, s).

Step 3—5-nitro-2-(trifluoromethyl)pyridin-4-amine 4-chloro-5-nitro-2-(trifluoromethyl)pyridine (752 mg, 3.32 mmol) was dissolved with ammonia in MeOH (30.08 mL, 69.19 mmol) and left stirring at rt for 3 hours. The solvent was removed in vacuo to give 5-nitro-2-(trifluoromethyl)pyridin-4-amine (687 mg, 3.32 mmol, 100% yield) as a yellow solid. The product was used without further purification in the following step. UPLC-MS (ES+, short acidic): 1.36 min, m/z 208.1 [M+H]+. $^1$H-NMR (400 MHz, DMSO-$d_6$) δ/ppm: 9.07 (1H, s), 7.44 (1H, s).

Step 4—6-(trifluoromethyl)pyridine-3,4-diamine 5-nitro-2-(trifluoromethyl)pyridin-4-amine (734 mg, 3.54 mmol) was dissolved in EtOAc (15 mL) and Ethanol (25 mL) followed by the addition of palladium, 10 wt. % on carbon powder, (238 mg) under a nitrogen atmosphere. The reaction was fitted with a $H_2$ balloon and subjected to 3×vacuum/$H_2$ cycles and then left to stir under a $H_2$ atmosphere for 72 hours. A second portion of palladium, 10 wt. % on carbon powder, dry (238 mg) was added and left stirring overnight. The crude was filtered over celite, washed with EtOAc and the solvent removed under reduce pressure to give 6-(trifluoromethyl)pyridine-3,4-diamine (571 mg, 3.22 mmol, 91% yield) as a colourless oil. $^1$H-NMR (400 MHz, DMSO-$d_6$) δ/ppm: 7.69 (1H, s), 6.83 (1H, s), 5.79 (2H, br s), 5.21 (2H, br s).

Example 9. Synthesis of 5-[(dimethylamino)methyl]-3-(trifluoromethyl)benzene-1,2-diamine

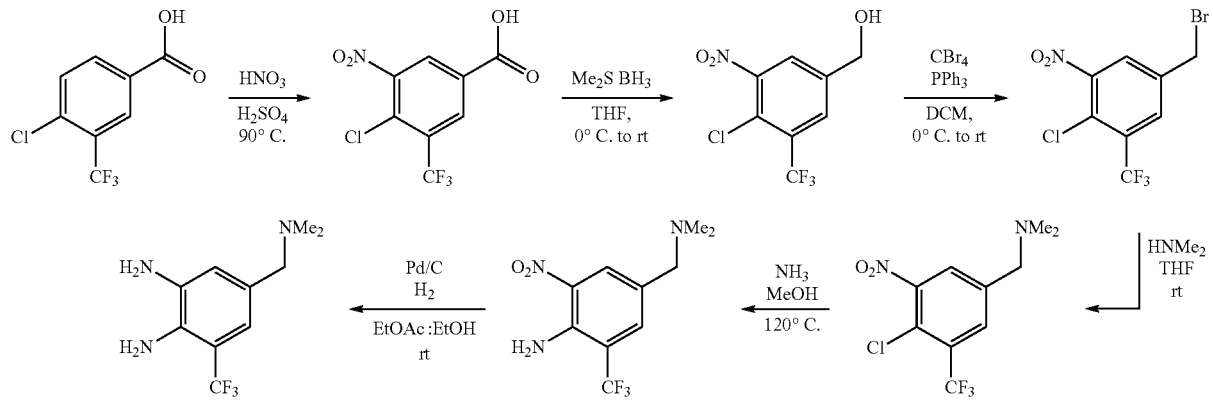

Step 1—4-chloro-3-nitro-5-(trifluoromethyl)benzoic Acid

To 4-chloro-3-(trifluoromethyl)benzoic acid (1.5 g, 6.68 mmol) was added sulfuric acid (5.34 mL, 100.20 mmol) and nitric acid, fuming, 90% (0.85 mL, 20.04 mmol) and the reaction mixture was heated at 90° C. for 1 hour. The crude was poured in ice-cold water (150 mL), filtered and dried in vacuo to give 4-chloro-3-nitro-5-(trifluoromethyl)benzoic acid (1.66 g, 6.15 mmol, 92% yield) as a white solid. UPLC-MS (ES−, short acidic): 1.66 min, m/z 268.1 [M−H]−. $^1$H-NMR (400 MHz, DMSO-$d_6$) δ/ppm: 14.22 (1H, br s), 8.78 (1H, d, J=2.0 Hz), 8.44 (1H, d, J=1.6 Hz).

Step 2—[4-chloro-3-nitro-5-(trifluoromethyl)phenyl]methanol 4-chloro-3-nitro-5-(trifluoromethyl)benzoic acid (1.66 g, 6.15 mmol) was dissolved in THF (20 mL) and cooled to 0°

C., followed by dropwise addition of di-methylsulfide borane (9.24 mL, 18.46 mmol). The reaction was stirred at rt for 72 hours, after which time it was quenched by slow addition of a sat. aq. NaHCO$_3$ and extracted with EtOAc (×2). The organic layers were combined, dried over Na$_2$SO$_4$, filtered and the solvent removed under reduce pressure to give 4-chloro-3-nitro-5-(trifluoromethyl)phenyl]methanol (1.31 g, 5.11 mmol, 83% yield) as a pale yellow oil. $^1$H-NMR (400 MHz, CDCl$_3$) δ/ppm: 7.94 (1H, s), 7.91 (1H, s), 4.84 (2H, s). Exchangeable proton missing.

Step 3—5-(bromomethyl)-2-chloro-1-nitro-3-(trifluoromethyl)benzene

A solution of [4-chloro-3-nitro-5-(trifluoromethyl)phenyl]methanol (1.31 g, 5.11 mmol) in DCM (15 mL) was cooled to 0° C. followed by the addition of triphenylphosphine (1.61 g, 6.13 mmol) and tetrabromomethane (1864.1 mg, 5.62 mmol). The reaction was left stirring at rt overnight, after which time it was washed with sat. aq. NaHCO$_3$. The organic layer was separated, dried over Na$_2$SO$_4$ and the solvent removed in vacuo to give 5-(bromomethyl)-2-chloro-1-nitro-3-(trifluoromethyl)benzene (3.94 g, 5.07 mmol, 99% yield) as a yellow oil. $^1$H-NMR (400 MHz, CDCl$_3$) δ/ppm: 7.97 (1H, d, J=2.0 Hz), 7.95 (1H, d, J=2.0 Hz), 4.52 (2H, s).

Step 4—1-[4-chloro-3-nitro-5-(trifluoromethyl)phenyl]-N,N-dimethyl-methanamine

To 5-(bromomethyl)-2-chloro-1-nitro-3-(trifluoromethyl)benzene (500. mg, 0.6300 mmol) was added dimethylamine (2M in THF-3.14 mL, 62.8 mmol) and the reaction was stirred at rt for 2 hours. The solvent was removed in vacuo and the crude purified by column chromatography using as eluent a gradient 0-100% EtOAc in petroleum ether. Fractions containing the product were loaded into an SCX-2 column and flushed at first with MeOH (20 mL) and then NH$_3$ in MeOH (20 mL) to give 1-[4-chloro-3-nitro-5-(trifluoromethyl)phenyl]-N,N-dimethyl-methanamine (101 mg, 0.36 mmol, 57% yield) as a pale yellow oil. UPLC-MS (ES+, short acidic): 1.19 min, m/z 283.1 [M+H]+. $^1$H-NMR (400 MHz, CDCl$_3$) δ/ppm: 7.91-7.90 (1H, m), 7.89-7.87 (1H, m), 3.50 (2H, s), 2.27 (6H, s).

Step 5—4-[(dimethylamino)methyl]-2-nitro-6-(trifluoromethyl)aniline

1-[4-Chloro-3-nitro-5-(trifluoromethyl)phenyl]-N,N-dimethyl-methanamine (101 mg, 0.36 mmol) was dissolved in 1,4-dioxane (1 mL) in a seal tube followed by addition of NH$_3$ (28% in H$_2$O-0.99 mL, 7.15 mmol). The reaction was stirred at 120° C. overnight, after which time a second portion of NH$_3$ (28% in H$_2$O-0.99 mL, 7.15 mmol) was added. The reaction was left stirring overnight at 120° C. The crude was filtered over a phase separator to give 4-[(dimethylamino)methyl]-2-nitro-6-(trifluoromethyl)aniline (94 mg, 0.36 mmol, 100% yield) as a yellow solid. UPLC-MS (ES+, short acidic): 0.90 min, m/z 264.2 [M+H]+. $^1$H-NMR (400 MHz, DMSO-d$_6$) δ/ppm: 8.36 (1H, s), 7.95 (1H, s), 7.42 (2H, s), 3.78 (2H, s), 2.40 (6H, s).

Step 6—5-[(dimethylamino)methyl]-3-(trifluoromethyl)benzene-1,2-diamine

4-[(Dimethylamino)methyl]-2-nitro-6-(trifluoromethyl)aniline (94 mg, 0.36 mmol) was dissolved in EtOAc (10 mL) and EtOH (17 mL) followed by the addition of palladium, 10 wt. % on carbon powder, (12.1 mg) under a nitrogen atmosphere. The reaction was fitted with a H$_2$ balloon and subjected to 3×vacuum/H$_2$ cycles and then left to stir under a H$_2$ atmosphere overnight. The crude was filtered over celite and the solvent removed under reduce pressure to give 5-[(dimethylamino)methyl]-3-(trifluoromethyl)benzene-1, 2-diamine (77 mg, 0.33 mmol, 92% yield) as a yellow solid. $^1$H-NMR (400 MHz, DMSO-d$_6$) δ/ppm: 6.81 (1H, s), 6.77 (1H, s), 5.15-5.00 (4H, m), 3.83 (2H, br s), 2.50 (6H, s, (under DMSO)). UPLC-MS (ES+, short acidic): 0.76 min, m/z 234.2 [M+H]+.

Intermediates in the table below was made in an analogous manner, using 1-methylpiperazine in place of dimethylamine in step 4.

| Structure | Name | Data |
|---|---|---|
| 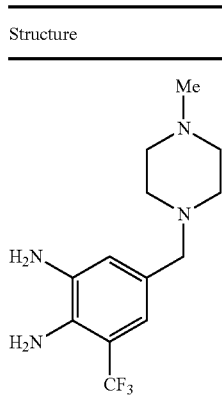 | 5-[(4-methylpiperazin-1-yl)methyl]-3-(trifluoromethyl)benzene-1,2-diamine | UPLC-MS (ES+, short acidic): 0.49 min, m/z 289.3 [M + H]+. |

Example 10. Synthesis of 3-[(dimethylamino)methyl]-5-(trifluoromethyl)benzene-1,2-diamine

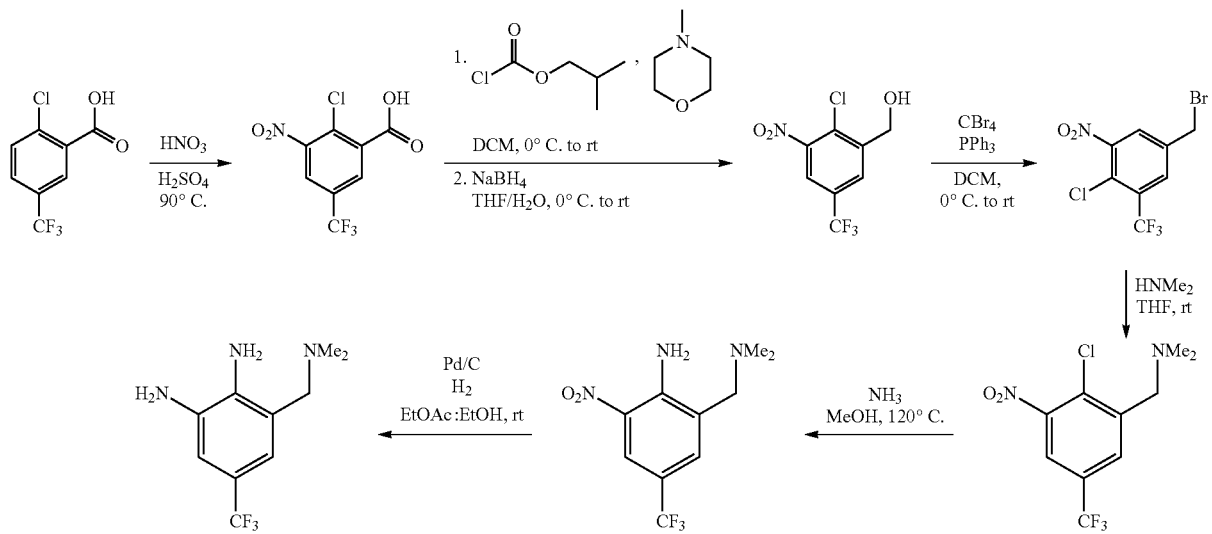

Step 1—2-chloro-3-nitro-5-(trifluoromethyl)benzoic Acid 2-(Trifluoromethyl)pyridin-4-ol (1 g, 6.13 mmol) was dissolved in sulfuric acid (10.68 mL, 200.39 mmol) following by the addition of nitric acid, fuming, 90% (1.7 mL, 40.08 mmol). The reaction mixture was then heated to 90° C. for 45 min, after which time the reaction mixture was cooled to rt and poured into ice-cold water (250 mL). The product was filtered, washed with ice-cold water (40 mL) and dried in vacuo to give 2-chloro-3-nitro-5-(trifluoromethyl)benzoic acid (3.36 g, 12.48 mmol, 93% yield) as a white solid in 93% yield. UPLC-MS (ES−, short acidic): 1.46 min, m/z 268.1 [M−H]−. $^1$H-NMR (400 MHz, DMSO-$d_6$) δ/ppm: 8.73-8.70 (1H, m), 8.43-8.39 (1H, m). Exchangeable proton not seen.

Step 2—[2-chloro-3-nitro-5-(trifluoromethyl)phenyl]methanol

Isobutyl chloroformate (3.41 mL, 26.31 mmol) was added to a stirred solution of 4-methylmorpholine (4.82 mL, 43.85 mmol), 2-chloro-3-nitro-5-(trifluoromethyl)benzoic acid (2.36 g, 8.77 mmol) in DCM (70 mL) at 0° C. under a nitrogen atmosphere. The reaction was stirred at rt overnight after which time the solvent was evaporated under reduce pressure. The crude was dissolved in THF (50 mL) and slowly added to a solution of NaBH$_4$ (497.64 mg, 13.16 mmol) in H$_2$O (50 mL) at 0° C. The reaction was stirred for 1 h at rt, after which time it was quenched by carefully adding to sat. aq. NH$_4$Cl (100 mL), followed by extraction with DCM (2×100 mL). The combined organic layers were dried over Na$_2$SO$_4$, filtered and solvent removed in vacuo. The crude was purified by column chromatography using an eluent of 0-50% EtOAc in petroleum ether to give [2-chloro-3-nitro-5-(trifluoromethyl)phenyl]methanol (1.21 g, 1.51 mmol, 17%) yield as a yellow oil. UPLC-MS (ES+/−, short acidic): 1.63 min, m/z nd. $^1$H-NMR (400 MHz, DMSO-$d_6$) δ/ppm: 8.13 (1H, s), 8.00 (1H, s), 4.93 (2H, s).

Step 3—1-(bromomethyl)-2-chloro-3-nitro-5-(trifluoromethyl)benzene

A solution of [2-chloro-3-nitro-5-(trifluoromethyl)phenyl]methanol (1.21 g, 1.51 mmol) in DCM (10 mL) was cooled to 0° C. followed by the addition of triphenylphosphine (475 mg, 1.81 mmol) and tetrabromomethane (551 mg, 1.66 mmol). The reaction was left stirring at rt overnight, after which time a second portion of triphenylphosphine (475 mg, 1.81 mmol) and tetrabromomethane (551 mg, 1.66 mmol) were added and left stirring for 4h. The reaction was washed with a sat. aq. NaHCO$_3$; the organic phase was separated, dried over Na$_2$SO$_4$ and the solvent removed in vacuo to give 1-(bromomethyl)-2-chloro-3-nitro-5-(trifluoromethyl)benzene (2.71 g, 1.49 mmol, 99% yield) as a yellow oil. UPLC-MS (ES+/−, short acidic): 1.26 min, m/z nd.

Step 4—1-[2-chloro-3-nitro-5-(trifluoromethyl)phenyl]-N,N-dimethyl-methanamine To 1-(Bromomethyl)-2-chloro-3-nitro-5-(trifluoromethyl)benzene (1 g, 0.55 mmol) was added dimethylamine (2M in THF-2.74 mL, 54.95 mmol). The reaction was left stirring at rt for 5 min, after which time the solvent was removed in vacuo and the crude purified by column chromatography using as eluent a gradient 0-20% EtOAc in petroleum ether. Fractions containing the product were loaded into an SCX-2 column and flushed at first with MeOH (10 mL) and then NH$_3$ in MeOH (10 mL) to give 1-[2-chloro-3-nitro-5-(trifluoromethyl)phenyl]-N,N-dimethyl-methanamine (82 mg, 0.29 mmol, 53% yield) as an orange oil. UPLC-MS (ES+, short acidic): 1.07 min, m/z 283.1 [M+H]+. $^1$H-NMR (400 MHz, DMSO-$d_6$) δ/ppm: 8.08-8.05 (1H, m), 7.94-7.90 (1H, m), 3.65 (2H, s), 2.34 (6H, s).

Step 5—2-[(dimethylamino)methyl]-6-nitro-4-(trifluoromethyl)aniline

1-[2-chloro-3-nitro-5-(trifluoromethyl)phenyl]-N,N-dimethyl-methanamine (82 mg, 0.29 mmol) was dissolved in 1,4-dioxane (0.8100 mL) in a seal tube followed by addition of NH$_3$ (28% in H$_2$O-0.81 mL, 5.8 mmol) and the reaction was left stirring at 120° C. overnight. The crude was filtered over a phase separator to give 2-[(dimethylamino)methyl]-6-nitro-4-(trifluoromethyl)aniline (76 mg, 0.29 mmol, 100% yield) as a yellow oil. UPLC-MS (ES+, short acidic): 1.11 min, m/z 264.2 [M+H]+. $^1$H-NMR (400 MHz, DMSO-d$_6$) δ/ppm: 8.24 (1H, s), 8.12 (2H, s), 7.70 (1H, s), 3.66 (2H, br s), 2.23 (6H, s).

Step 6—3-[(dimethylamino)methyl]-5-(trifluoromethyl)benzene-1,2-diamine

2-[(Dimethylamino)methyl]-6-nitro-4-(trifluoromethyl) aniline (75 mg, 0.28 mmol) was dissolved in EtOAc (5 mL) and EtOH (9 mL) followed by the addition of palladium, 10 wt. % on carbon powder, (10 mg) under a nitrogen atmosphere. The reaction was fitted with a H$_2$ balloon and subjected to 3×vacuum/H$_2$ cycles and then left to stir under a H$_2$ atmosphere for 4 hours. The crude was filtered over celite and the solvent removed under reduce pressure to give 3-[(dimethylamino)methyl]-5-(trifluoromethyl)benzene-1,2-diamine (66 mg, 0.28 mmol, 99% yield) as a yellow solid. UPLC-MS (ES+, short acidic): 0.91 min, m/z 234.2 [M+H]+. $^1$H-NMR (400 MHz, DMSO-d$_6$) δ/ppm: 6.78 (2H, s), 6.70 (2H, br s), 4.98 (4H, br s), 2.28 (6H, br s).

Example 11. Synthesis of N-[[3-(4,4,5,5-tetramethyl-1,3,2-dioxaborolan-2-yl)-5-(trifluoromethyl)phenyl]methyl]propan-2-amine

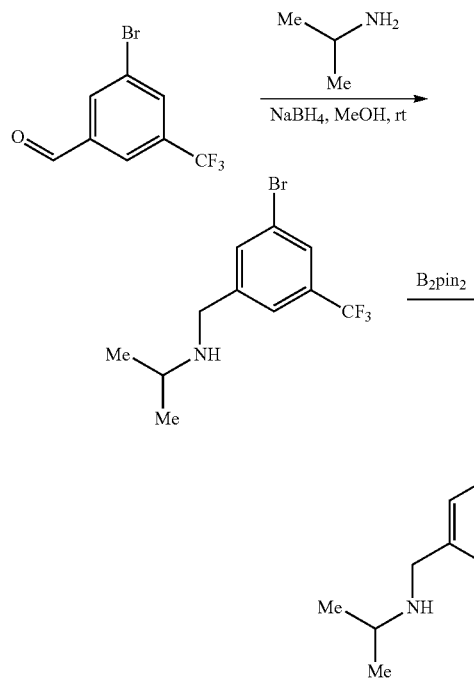

Step 1—N-[[3-bromo-5-(trifluoromethyl)phenyl]methyl]propan-2-amine

2-Aminopropane (0.34 mL, 3.95 mmol) was added to a stirred solution of 3-Bromo-5-(trifluoromethyl)benzaldehyde (0.6 mL, 3.95 mmol) and MeOH (10 mL) at rt under a nitrogen atmosphere for 18 hours. NaBH$_4$ (224.3 mg, 5.93 mmol) was then added and the resulting mixture stirred for 10 minutes and quenched with water (5 mL). Organic solvent was then removed in vacuo and the remaining mixture partitioned between water (50 mL) and EtOAc (50 mL). The aqueous layer was further extracted with EtOAc (50 mL). The combined organic layers were dried over Na$_2$SO$_4$, filtered and solvent removed in vacuo. The residue was purified by column chromatography using an eluent of 0-10% MeOH in DCM to give N-[[3-bromo-5-(trifluoromethyl)phenyl]methyl]propan-2-amine (665 mg, 2.25 mmol, 57% yield) as a yellow oil. UPLC-MS (ES+, short acidic): 1.13 min, m/z 295.9, 297.9 [M+H]+. $^1$H NMR (400 MHz, CDCl$_3$) δ/ppm: 7.72 (1H, s), 7.66 (1H, s), 7.56 (1H, s), 3.84 (2H, s), 2.86 (1H, septet, J=6.4 Hz), 1.12 (6H, d, J=6.4 Hz). Exchangeable proton not seen.

Step 2—N-[[3-(4,4,5,5-tetramethyl-1,3,2-dioxaborolan-2-yl)-5-(trifluoromethyl)phenyl]methyl]propan-2-amine N-[[3-bromo-5-(trifluoromethyl)phenyl]methyl]propan-2-amine (300 mg, 1.01 mmol), bis(pinacolato)diboron (283 mg, 1.11 mmol), KOAc (298.3 mg, 3.04 mmol), [1,1'-bis(diphenylphosphino)ferrocene]palladium(II) chloride dichloromethane complex (82.7 mg, 0.10 mmol) and 1,4-dioxane (10 mL) were stirred at 90° C. under a nitrogen atmosphere for 2 hours, after which time the reaction was cooled to rt and solvent removed in vacuo. The residue was dissolved in DCM (10 mL), filtered over celite, which was washed with DCM (10 mL). The filtrate was concentrated in vacuo and the residue purified by column chromatography using an eluent of 0-5% MeOH in DCM to give N-[[3-(4,4,5,5-tetramethyl-1,3,2-dioxaborolan-2-yl)-5-(trifluoromethyl)phenyl]methyl]propan-2-amine (185 mg, 0.54 mmol, 53% yield) as a yellow oil. UPLC-MS (ES+, short acidic): 1.02 min, m/z 262.1 [M-pinacol+H]+; 1.41 min, m/z 344.3 [M+H]+. $^1$H NMR (400 MHz, CDCl$_3$) δ/ppm: 7.96-7.93 (2H, m), 7.71 (1H, s), 3.85 (2H, s), 2.88 (1H, septet, J=6.4 Hz), 1.38 (12H, s), 1.13 (6H, d, J=6.4 Hz). Exchangeable proton not seen.

Example 12. Synthesis of [3-[(dimethylamino)methyl]-5-(trifluoromethyl)phenyl]boronic Acid

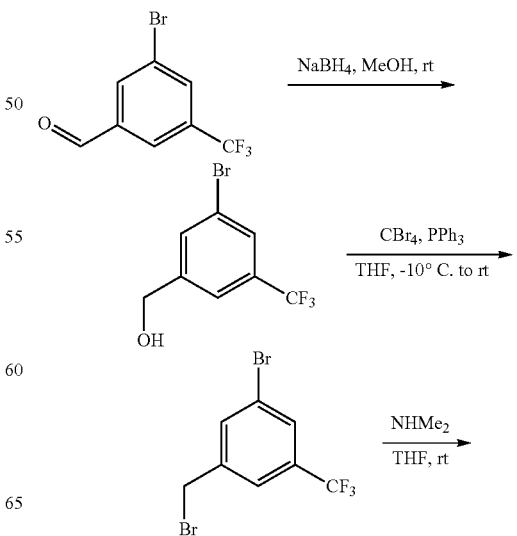

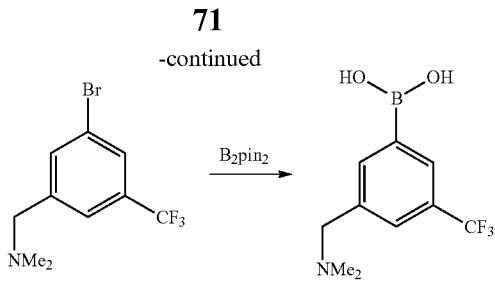

Step 1—[3-bromo-5-(trifluoromethyl)phenyl]methanol

Sodium Borohydride (149.5 mg, 3.95 mmol) was added to a stirred solution of 3-bromo-5-(trifluoromethyl)benzaldehyde (500 mg, 1.98 mmol) and MeOH (10 mL) at rt for 1 hour. The reaction was poured into water (50 mL) and the resulting mixture was extracted with EtOAc (2×50 mL). The combined organic layers were dried over $Na_2SO_4$, filtered and solvent removed in vacuo to give [3-bromo-5-(trifluoromethyl)phenyl]methanol (444 mg, 1.74 mmol, 88% yield) as a colourless oil. The product was used in the next step without further purification. UPLC-MS (ES+, short acidic): 1.68 min, m/z nd. $^1$H NMR (400 MHz, $CDCl_3$) δ/ppm: 7.74 (1H, s), 7.71 (1H, s), 7.59 (1H, s), 4.79 (2H, s). Exchangeable proton not seen.

Step 2—1-bromo-3-(bromomethyl)-5-(trifluoromethyl)benzene

[3-Bromo-5-(trifluoromethyl)phenyl]methanol (444 mg, 1.74 mmol) was added to a stirred solution of triphenylphosphine (685 mg, 2.61 mmol), tetrabromomethane (866 mg, 2.61 mmol) and THF (20 mL) at −10° C. under a nitrogen atmosphere. The reaction was allowed to warm to rt and stir for 2 hours. It was then concentrated in vacuo and partitioned between water (100 mL) and DCM (100 mL). The organic layer was separated, dried over $Na_2SO_4$, filtered and solvent removed in vacuo. The residue was purified by column chromatography using an eluent of 0-50% EtOAc in petroleum ether to give 1-bromo-3-(bromomethyl)-5-(trifluoromethyl)benzene (469 mg, 1.48 mmol, 85% yield) as a yellow oil. UPLC-MS (ES+, short acidic): 2.06 min, m/z nd. $^1$H NMR (400 MHz, $CDCl_3$) δ/ppm: 7.76-7.72 (2H, m), 7.60 (1H, s), 4.47 (2H, s).

Step 3—1-[3-bromo-5-(trifluoromethyl)phenyl]-N,N-dimethyl-methanamine

1-Bromo-3-(bromomethyl)-5-(trifluoromethyl)benzene (469 mg, 1.48 mmol) was added to a stirred solution of dimethylamine (2M in THF-3 mL, 6 mmol) at rt under a nitrogen atmosphere and left stirring for 10 min. Solvent was removed in vacuo and the residue partitioned between water (20 mL) and DCM (20 mL). The organic layer was separated, dried over $Na_2SO_4$, filtered and solvent removed in vacuo. The residue was purified by column chromatography using an eluent of 0-10% MeOH in DCM to give 1-[3-bromo-5-(trifluoromethyl)phenyl]-N,N-dimethyl-methanamine (337 mg, 1.19 mmol, 81% yield) as a yellow oil. UPLC-MS (ES+, short acidic): 1.13 min, m/z 281.9, 283.9 [M+H]+. $^1$H NMR (400 MHz, $CDCl_3$) δ/ppm: 7.70-7.67 (2H, m), 7.54 (1H, s), 3.46 (2H, s), 2.27 (6H, s).

Step 4—[3-[(dimethylamino)methyl]-5-(trifluoromethyl)phenyl]boronic acid

1-[3-Bromo-5-(trifluoromethyl)phenyl]-N,N-dimethyl-methanamine (337 mg, 1.19 mmol), bis(pinacolato)diboron (334 mg, 1.31 mmol), KOAc (352 mg, 3.58 mmol), [1,1'-bis(diphenylphosphino)ferrocene]palladium(II) chloride dichloromethane complex (98 mg, 0.1200 mmol) and 1,4-dioxane (10 mL) under a nitrogen atmosphere and stirred at 90° C. for 2 hours. The reaction was cooled to rt and solvent removed in vacuo. The residue was suspended in DCM (10 mL), filtered over celite, which was washed with DCM (10 mL). The filtrate was concentrated in vacuo and the residue purified by column chromatography using an eluent of 0-5% MeOH in DCM to give [3-[(dimethylamino)methyl]-5-(trifluoromethyl)phenyl]boronic acid (109 mg, 0.44 mmol, 37% yield) as a yellow oil. UPLC-MS (ES+, short acidic): 0.93 min, m/z 248.1 [M+H]+.

Example 13. Synthesis of 2-ethyl-4-(4,4,5,5-tetramethyl-1,3,2-dioxaborolan-2-yl)pyridine

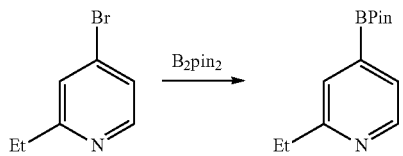

Step 1—2-ethyl-4-(4,4,5,5-tetramethyl-1,3,2-dioxaborolan-2-yl)pyridine

[1,1'-Bis(diphenylphosphino)ferrocene]palladium(II) chloride dichloromethane complex (0.09 g, 0.11 mmol) was added to a stirred solution of bis(pinacolato)diboron (0.3 g, 1.18 mmol), 4-bromo-2-ethylpyridine (0.2 g, 1.07 mmol), KOAc (0.16 g, 1.61 mmol) and 1,4-dioxane (20 mL) under a nitrogen atmosphere and the reaction was heated to 100° C. for 2 hours. The reaction was cooled to rt and solvent removed in vacuo. The residue was taken up in DCM (50 mL), filtered over celite, which was washed with DCM (10 mL). The filtrate was concentrated in vacuo to give 2-ethyl-4-(4,4,5,5-tetramethyl-1,3,2-dioxaborolan-2-yl)pyridine (250 mg, 1.0725 mmol, 99.765% yield) as a black oil. The product was used in the next step without further purification. UPLCMS (ES+, short acidic): 0.83 min, m/z 151.9 [M-pinacol]+. $^1$H NMR (400 MHz, $CDCl_3$) δ/ppm: 8.57 (1H, d, J=9.2 Hz), 7.54 (1H, d, J=6.4 Hz), 7.47 (1H, d, J=9.2 Hz), 2.85 (2H, q, J=8.0 Hz), 1.39 (12H, s), 1.33 (3H, t, J=8.0 Hz).

Intermediates in the table below was made in an analogous manner, using the appropriate (hetero)aryl bromide in place of 4-bromo-2-ethylpyridine:

| Structure | Name | Data |
|---|---|---|
| (2-(difluoromethyl)-4-BPin-pyridine structure) | 2-(difluoromethyl)-4-(4,4,5,5-tetramethyl-1,3,2-dioxaborolan-2-yl)pyridine | UPLCMS (ES+, short acidic): 1.02 min, m/z 173.9 [M-pinacol]+. |
| (1-methyl-5-BPin-benzimidazole structure) | 1-methyl-5-(4,4,5,5-tetramethyl-1,3,2-dioxaborolan-2-yl)benzimidazole | UPLCMS (ES+, short acidic): 1.23 min, m/z 259.0 [M + H]+. <br> 1H NMR (400 MHz, CDCl3) δ/ppm: 8.30 (1H, s), 7.88 (1H, s), 7.76 (1H, d, J =8.0 Hz), 7.38 (1H, d, J = 8.0 Hz), 3.71 (3H, s), 1.38 (12H, s). |
| (3-methyl-5-BPin-1-(2,2,2-trifluoroethyl)pyrazole structure) | 3-methyl-5-(4,4,5,5-tetramethyl-1,3,2-dioxaborolan-2-yl)-1-(2,2,2-trifluoroethyl)pyrazole <br> *Reaction performed at 90° C. | UPLC-MS (ES+, Short acidic): 1.16 min, m/z 208.7 [M + H]+. |

Example 14. Synthesis of 1-ethyl-3-methyl-5-(4,4,5,5-tetramethyl-1,3,2-dioxaborolan-2-yl)pyrazole

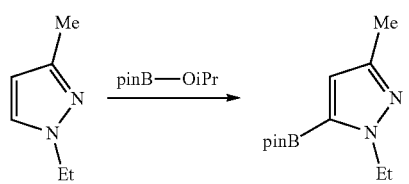

n-Butyllithium solution (0.4 mL, 1 mmol) was added to a stirred solution of 1-ethyl-3-methyl-pyrazole (0.1 mL, 0.91 mmol) and THF (5 mL) at 0° C. under a nitrogen atmosphere. The mixture was allowed to warm to 25° C. for 1 hour and then cooled back to −78° C. 2-Isopropoxy-4,4,5,5-tetramethyl-1,3,2-dioxaborolane (0.22 mL, 1.09 mmol) was added; after 10 mins at −78° C. the reaction was allowed to warm to room temperature and stir for 2 hours. The reaction was quenched with water and the resulting mixture reduced in vacuo. The residue was azeotroped with toluene to give 1-ethyl-3-methyl-5-(4,4,5,5-tetramethyl-1,3,2-dioxaborolan-2-yl)pyrazole (214 mg, 0.91 mmol, 100% yield) as an off white solid. The compound was used in the next step without further purification. UPLC-MS (ES+, Short acidic): 0.83 min, m/z 154.6 [M+H]+.

Example 15. Synthesis of 1-cyclopropyl-3-ethyl-5-(4,4,5,5-tetramethyl-1,3,2-dioxaborolan-2-yl)pyrazole

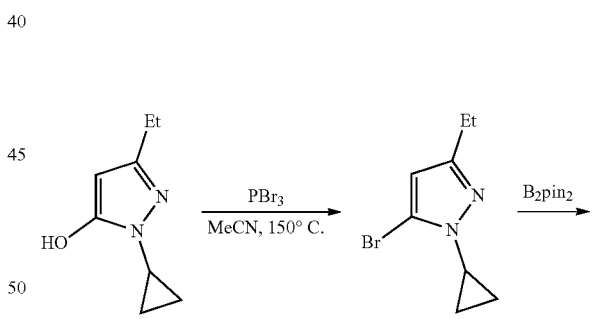

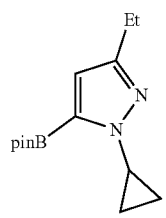

Step 1—5-bromo-1-cyclopropyl-3-ethyl-pyrazole 2-cyclopropyl-5-ethyl-pyrazol-3-ol (730 mg, 4.8 mmol) was suspended in PBr$_3$ (3.05 mL, 16.79 mmol) with MeCN (3 mL) in a sealable vial. The vial was sealed and the reaction was heated thermally to 150° C. for 1.5 hours. After cooling to rt, the reaction separates into two layers; the top layer (MeCN) was quenched into iced saturated aq. NaHCO$_3$ to pH ~7-8. The aqueous layer was separated, extracted with EtOAc (3×); the organics were combined, dried through a phase separator and reduced in vacuo to give 5-bromo-1-cyclopropyl-3-ethyl-pyrazole (340 mg, 1.58 mmol, 33% yield) as an orange oil. The compound was used in the next step without further purification. UPLC-MS (ES+, Short acidic): 1.75 min, m/z 214.9, 216.9 [M+H]$^+$.

Step 2—1-cyclopropyl-3-ethyl-5-(4,4,5,5-tetramethyl-1,3,2-dioxaborolan-2-yl)pyrazole

[1,1'-Bis(diphenylphosphino)ferrocene]palladium(II) chloride dichloromethane complex (129.1 mg, 0.16 mmol) was added to a stirred solution of bis(pinacolato)diboron (401.4 mg, 1.58 mmol), 5-bromo-1-cyclopropyl-3-ethyl-pyrazole (340 mg, 1.58 mmol), potassium acetate (310.3 mg, 3.16 mmol) and 1,4-dioxane (10 mL) at room temperature under inert atmosphere. The reaction was heated to 85° C. for 1 hour, cooled to room temperature and solvent removed in vacuo. The residue was taken up in DCM (20 mL), filtered through celite and the filter cake washed with DCM (10 mL). The filtrate was concentrated in vacuo to give 1-cyclopropyl-3-ethyl-5-(4,4,5,5-tetramethyl-1,3,2-dioxaborolan-2-yl)pyrazole (414 mg, 1.58 mmol, 100% yield) as a black oil. The compound was used in the next step without further purification. UPLCMS (ES+, short acidic): 1.05 min, m/z 180.7 [M-pinacol]$^+$.

Intermediates in the table below were made in an analogous manner, using the appropriate starting material in step 1:

Synthesis of Compounds of the Disclosure

Example 16. Synthesis of 5-[3-[4-[3-(trifluoromethyl)phenyl]-1H-imidazol-2-yl]chroman-6-yl]oxy-3,4-dihydro-1H-1,8-naphthyridin-2-one (Compound 12)

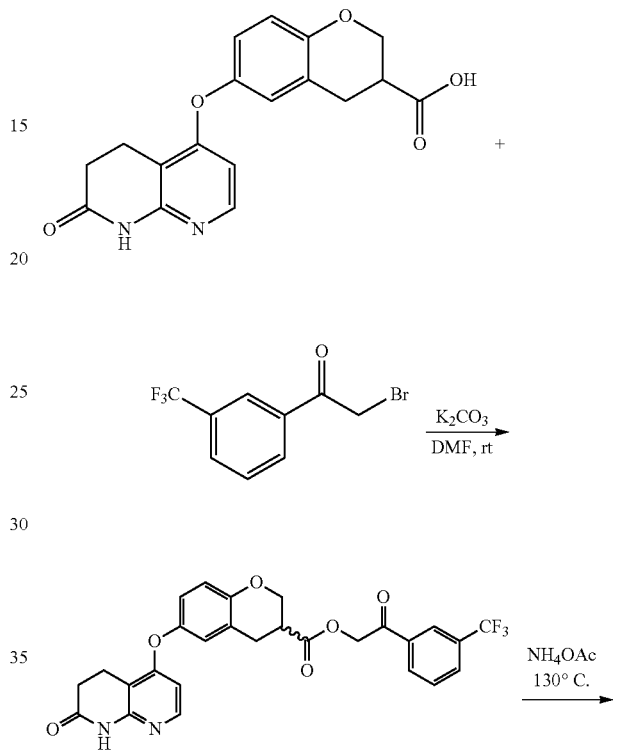

| Structure | Name | Data |
|---|---|---|
| Me, pinB, N, N, CF$_3$ | 3-methyl-5-(4,4,5,5-tetramethyl-1,3,2-dioxaborolan-2-yl)-1-(2,2,2-trifluoroethyl)pyrazole | UPLCMS (ES+, short acidic): 1.16 min, m/z 208.7 [M-pinacol]$^+$. |
| Et, pinB, N, N, Me | 3-ethyl-1-methyl-5-(4,4,5,5-tetramethyl-1,3,2-dioxaborolan-2-yl)pyrazole | UPLCMS (ES+, short acidic): 0.92 min, m/z 154.6 [M-pinacol]$^+$. |
| pinB, N, N, Me | 3-cyclopropyl-1-methyl-5-(4,4,5,5-tetramethyl-1,3,2-dioxaborolan-2-yl)pyrazole | UPLCMS (ES+, short acidic): 0.98 min, m/z 166.7 [M-pinacol]$^+$. |

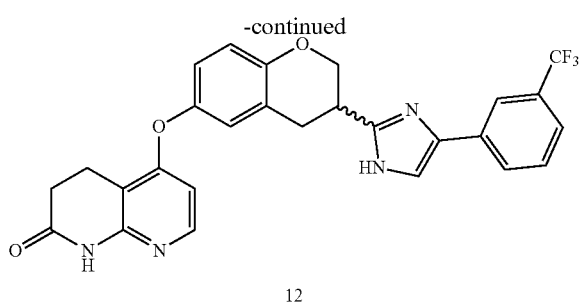

12

Step 1—[2-oxo-2-[3-(trifluoromethyl)phenyl]ethyl] 6-[(7-oxo-6,8-dihydro-5H-1,8-naphthyridin-4-yl)oxy]chromane-3-carboxylate 6-[(7-Oxo-6,8-dihydro-5H-1,8-naphthyridin-4-yl)oxy]chromane-3-carboxylic acid (200 mg, 0.59 mmol) and K₂CO₃ (244 mg, 1.76 mmol) were dissolved in dry DMF (5 mL) and treated with 3-(trifluoromethyl)phenacyl bromide (173 mg, 0.65 mmol) portionwise. The reaction was stirred for 2.5 hours at rt, after which time, a second portion of 3-(trifluoromethyl)phenacyl bromide was added (172 mg, 0.65 mmol) and the reaction was left stirring for 1h. Water (15 mL) was added and the product was extracted with DCM (×3). The combined organic phases were dried over Na₂SO₄, filtered and the solvent removed under reduce pressure. The product was purified by column chromatography using as eluent a gradient from 0-100% EtOAc in petroleum to give 2-oxo-2-[3-(trifluoromethyl)phenyl]ethyl]6-[(7-oxo-6,8-dihydro-5H-1,8-naphthyridin-4-yl)oxy]chromane-3-carboxylate (55 mg, 0.10 mmol, 18% yield) as yellow solid. UPLC-MS (ES+, short acidic): 1.78 min, m/z 527.4 [M+H]⁺.

Step 2—5-[3-[4-[3-(trifluoromethyl)phenyl]-1H-imidazol-2-yl]chroman-6-yl]oxy-3,4-dihydro-1H-1,8-naphthyridin-2-one

[2-oxo-2-[3-(trifluoromethyl)phenyl]ethyl] 6-[(7-oxo-6,8-dihydro-5H-1,8-naphthyridin-4-yl)oxy]chromane-3-carboxylate (55 mg, 0.10 mmol) and ammonium acetate (1.21 g, 15.67 mmol) were mixed in a sealed vial and the reaction heated to 130° C. for 8 hours. Water was added and the product extracted with EtOAc (×3). The organic phase was dried over Na₂SO₄, filtered and the solvent removed under reduce pressure. The product was purified by column chromatography using a gradient 0-100% EtOAc in petroleum ether followed by 0-5% MeOH in DCM to give 5-[3-[4-[3-(trifluoromethyl)phenyl]-1H-imidazol-2-yl]chroman-6-yl]oxy-3,4-dihydro-1H-1,8-naphthyridin-2-one (Compound 12) as a white solid. UPLC-MS (ES+, final purity) 3.17 min, m/z 507.3 [M+H]⁺. ¹H-NMR (400 MHz, DMSO-d₆) δ/ppm: 12.51 (0.10H, br s), 12.26 (0.90H, br s), 10.46 (1H, s), 8.10-7.99 (2H, m), 7.95 (1H, d, J=6.0 Hz), 7.82 (1H, s), 7.60-7.48 (2H, m), 7.02 (1H, s), 6.94-6.87 (2H, m), 6.26 (1H, d, J=5.6 Hz), 4.55-4.45 (1H, m), 4.19-4.09 (1H, m), 3.46-3.38 (1H, m), 3.30-3.20 (1H, m), 3.17-3.08 (1H, m), 2.93 (2H, t, J=7.6 Hz), 2.56-2.53 (m, 2H).

Example 17. Synthesis of 5-[3-[4-(3-methoxyphenyl)-1H-imidazol-2-yl]chroman-6-yl]oxy-3,4-dihydro-1H-1,8-naphthyridin-2-one (Compound 13)

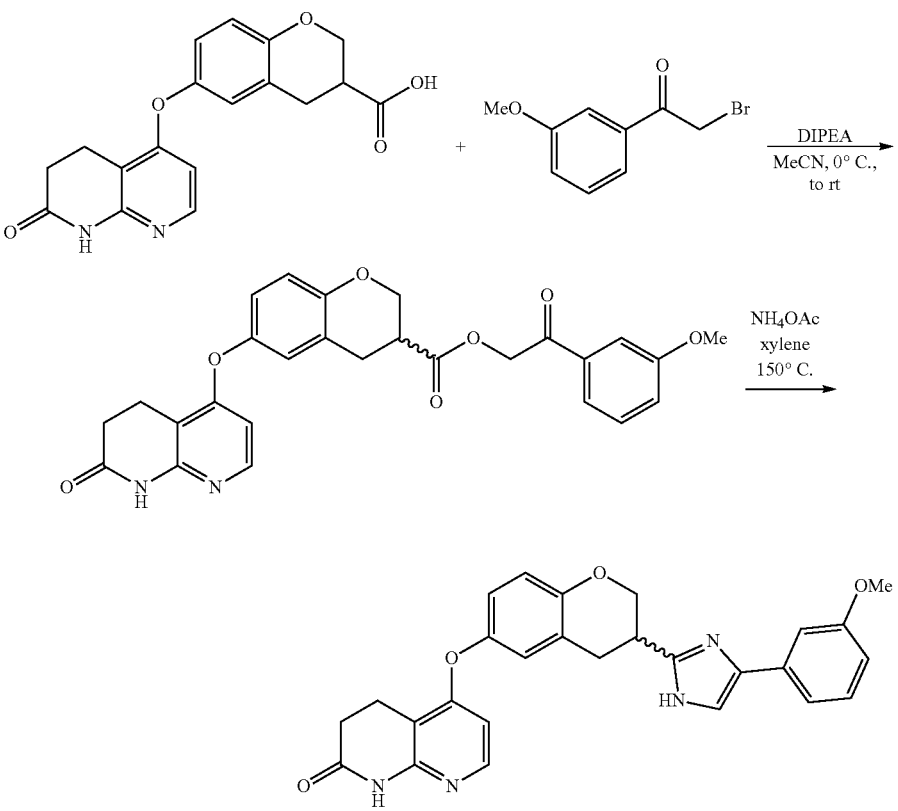

13

Step 1—[2-(3-methoxyphenyl)-2-oxo-ethyl] 6-[(7-oxo-6,8-dihydro-5H-1,8-naphthyridin-4-yl)oxy]chromane-3-carboxylate 6-[(7-oxo-6,8-dihydro-5H-1,8-naphthyridin-4-yl)oxy]chromane-3-carboxylic acid (200 mg, 0.59 mmol) and 2-bromo-1-(3-methoxyphenyl)ethanone (135 mg, 0.59 mmol) were dissolved in dry MeCN (10 mL) and cooled to 0° C. followed by dropwise addition of DIPEA (0.15 mL, 0.88 mmol). The reaction was stirred at rt for 2 hours. After this time, iced water was added followed by extraction with EtOAc (×3) and DCM (×2) The combined organic phases were dried over $Na_2SO_4$, filtered and the solvent evaporated under reduce pressure. The product was purified by column chromatography using as eluent a gradient 0-100% EtOAc in petroleum ether to give [2-(3-methoxyphenyl)-2-oxo-ethyl] 6-[(7-oxo-6,8-dihydro-5H-1,8-naphthyridin-4-yl)oxy]chromane-3-carboxylate (217 mg, 0.44 mmol, 76% yield) as a white solid. UPLC-MS (ES+, short acidic): 1.69 min, m/z 489.3 $[M+H]^+$. $^1$H-NMR (400 MHz, DMSO-$d_6$) δ/ppm: 10.46 (1H, s), 7.95 (1H, d, J=6.0 Hz), 7.59-7.55 (1H, m), 7.51-7.43 (2H, m), 7.27 (1H, ddd, J=8.2 Hz, 2.6 Hz, 0.8 Hz), 7.01 (1H, d, J=2.8 Hz), 6.93-6.85 (2H, m), 6.25 (1H, d, J=5.6 Hz), 5.57 (2H, s), 4.44 (1H, dd, J=10.8 Hz, 3.2 Hz), 4.24 (1H, dd, J=10.8 Hz, 8.0 Hz), 3.83 (3H, s), 3.31-3.25 (1H, m), 3.10-3.05 (2H, m), 2.92 (2H, t, J=8.0 Hz), 2.53 (2H, t, J=8.0 Hz, (partly under DMSO)).

Step 2—5-[3-[4-(3-methoxyphenyl)-1H-imidazol-2-yl]chroman-6-yl]oxy-3,4-dihydro-1H-1,8-naphthyridin-2-one

[2-(3-methoxyphenyl)-2-oxo-ethyl] 6-[(7-oxo-6,8-dihydro-5H-1,8-naphthyridin-4-yl)oxy]chromane-3-carboxylate (98 mg, 0.20 mmol) and ammonium acetate (309 mg, 4.01 mmol) were mixed in a sealed vial followed by addition of xylenes (1 mL) and heated to 150° C. for 30 min. Water was added and the product extracted with EtOAc (×3). The organic phase was dried over $Na_2SO_4$, filtered and the solvent removed under reduce pressure. The residue was loaded into an SCX-2 column and flushed at first with MeOH (10 mL) and then $NH_3$ in MeOH (10 mL) to elute the product. Fractions containing the product were combined and purified by column chromatography using as eluent a gradient 0-5% MeOH in DCM. Fractions containing the product were re-purified by reverse column chromatography using as eluent a gradient 5-100% of acetonitrile+0.1% formic acid in water+0.1% formic acid to give 5-[3-[4-(3-methoxyphenyl)-1H-imidazol-2-yl]chroman-6-yl]oxy-3,4-dihydro-1H-1,8-naphthyridin-2-one (Compound 13) (8 mg, 0.017 mmol, 9% yield) as a white solid. UPLC-MS (ES+, final purity) 2.76 min, m/z 469.3 $[M+H]^+$. $^1$H-NMR (400 MHz, DMSO-$d_6$) δ/ppm: 12.29 (br s, 0.2H), 12.09 (br s, 0.8H), 10.46 (s, 1H). 7.95 (d, J=5.6 Hz, 1H), 7.61 (d, J=2.0 Hz, 0.8H), 7.35-7.28 (m, 2H), 7.25-7.19 (m, 1.2H), 7.01 (d, J=2.4 Hz, 1H), 6.94-6.85 (m, 2H), 6.84-6.78 (m, 0.2H), 6.74 (ddd, J=8.4 Hz, 2.8 Hz, 1.2 Hz, 0.8H), 6.27 (d, J=5.6 Hz, 1H), 4.53-4.47 (m, 1H), 4.15-4.09 (m, 1H), 3.80 (s, 0.6H), 3.77 (s, 2.4H), 3.45-3.35 (m, 1H), 3.30-3.19 (m, 1H), 3.16-3.06 (m, 1H), 2.93 (t, J=7.2 Hz, 2H), 2.54-2.52 (m, 2H).

The compounds in the table below were made in an analogous manner to Example 17, using the appropriate 2-bromo-1-arylethanone in place of 2-bromo-1-(3-methoxyphenyl)ethanone in step 1:

| Comp. No | Structure and Name | Data |
|---|---|---|
| 9 | 5-[3-[4-(p-tolyl)-1H-imidazol-2-yl]chroman-6-yl]oxy-3,4-dihydro-1H-1,8-naphthyridin-2-one | UPLC-MS (ES+, final purity): 2.84 min, m/z 453.3 $[M + H]^+$. $^1$H-NMR (400 MHz, DMSO-$d_6$) δ/ppm: 12.24 (0.2H, br s), 12.03 (0.8H, br s), 10.46 (1H, s), 7.95 (1H, d, J = 6.0 Hz), 7.63 (1.6H, d, J = 8.0 Hz), 7.54-7.50 (1.2H, m), 7.23-7.18 (0.6H, m), 7.13 (1.6H, d, J = 8.0 Hz), 7.02-6.99 (1H, m), 6.94-6.86 (2H, m), 6.27 (1H, d, J = 5.6 Hz), 4.54-4.46 (1H, m), 4.16-4.06 (1H, m), 3.40-3.36 (1H, m), 3.26-3.18 (1H, m), 3.14-3.05 (1H, m), 2.93 (2H, t, J = 7.6 Hz), 2.53 (2H, t, J = 7.6 Hz, (partly under DMSO)), 2.30 (0.6H, s), 2.28 (2.4H, s). |
| 11 | 5-[3-[4-(4-chlorophenyl)-1H-imidazol-2-yl]chroman-6-yl]oxy-3,4-dihydro-1H-1,8-naphthyridin-2-one | UPLC-MS (ES+, final purity): 2.95 min, m/z 473.2 $[M + H]^+$. $^1$H-NMR (400 MHz, DMSO-$d_6$) δ/ppm: 12.22 (1H, br s), 10.47 (1H, s), 7.95 (1H, d, J = 5.6 Hz), 7.75 (2H, d, J = 8.4 Hz), 7.61 (1H, br s), 7.38 (2H, d, J= 8.4 Hz), 7.00 (1H, d, J = 2.4 Hz), 6.91 (1H, dd, J = 8.8 Hz, 2.4 Hz), 6.88 (1H, d, J = 8.8 Hz), 6.26 (1H, d, J = 6.0 Hz), 4.54-4.47 (1H, m), 4.12 (1H, t, J =10.0 Hz), 3.42-3.36 (1H, m), 3.23 (1H, dd, J = 16.8 Hz, 10.4 Hz), 3.11 (1H, dd, J = 16.8 Hz, 5.6 Hz), 2.93 (2H, t, J = 7.6 Hz), 2.53 (2H, t, J = 7.6 Hz, (partly under DMSO)). |

-continued

| Comp. No | Structure and Name | Data |
|---|---|---|
| 10 | 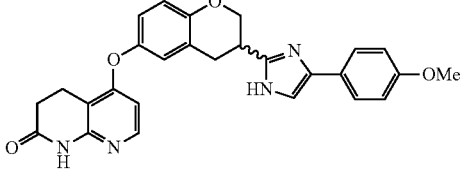<br>5-[3-[4-(4-methoxyphenyl)-1H-imidazol-2-yl]chroman-6-yl]oxy-3,4-dihydro-1H-1,8-naphthyridin-2-one | UPLC-MS (ES+, final purity): 2.72 min, m/z 469.3 [M + H]$^+$.<br>$^1$H-NMR (400 MHz, DMSO-d$_6$) δ/ppm: 12.19 (0.25H, br s), 12.00 (0.75H, br s), 10.46 (1H, s), 7.95 (1H, d, J = 5.6 Hz), 7.73-7.51 (2H, m), 7.45 (0.75H, br s), 7.14 (0.25H, br s), 7.00 (1H, d, J = 2.4 Hz), 6.94-6.85 (4H, m), 6.27 (1H, d, J = 5.6 Hz), 4.53-4.46 (1H, m), 4.11 (1H, t, J = 10.0Hz), 3.75 (3H, s), 4.42-3.37 (1H, m, (under water)), 3.28-3.18 (1H, m), 3.09 (1H, dd, J = 16.8 Hz, 5.2Hz), 2.93 (2H, t, J = 7.6 Hz), 2.53 (2H, t, J = 7.6 Hz, (partly under DMSO)). |
| 1 | 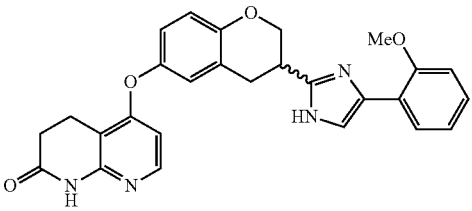 [SMILES: COc1ccccc1-c1c[nH]c(C2COc3ccc(Oc4ccnc5c4CCC(=O)N5)cc3C2)n1]<br>5-[3-[4-(2-methoxyphenyl)-1H-imidazol-2-yl]chroman-6-yl]oxy-3,4-dihydro-1H-1,8-naphthyridin-2-one | UPLC-MS (ES, final purity): 2.78 min, m/z 469.3 [M + H]$^+$.<br>$^1$H-NMR (400 MHz, DMSO-d$_6$) δ/ppm: 12.05-11.97 (1H, m), 10.46 (1H, br s), 8.17-8.14 (0.2H, m), 8.06 (0.8H, dd, J = 7.6 Hz, 1.6 Hz), 7.95 (1H, d, J = 6.0 Hz), 7.62-7.60 (0.2H, m), 7.50 (0.8H, d, J = 2.0 Hz), 7.30-6.87 (6H, m), 6.27 (1H, d, J = 6.0 Hz), 4.55-4.44 (1H, m), 4.13 (1H, t, J = 10.4 Hz), 3.89 (3H, s), 3.47-3.34 (1H, m), 3.29-3.20 (1H, m), 3.15-3.06 (1H, m), 2.93 (2H, t, J = 7.6 Hz), 2.53 (2H, t, J = 7.6 Hz, (partly under DMSO)). |
| 14 | 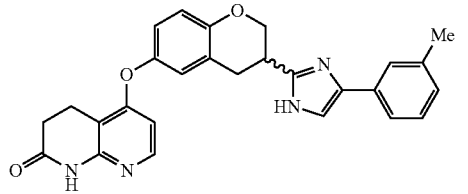 [SMILES: Cc1cccc(-c2c[nH]c(C3COc4ccc(Oc5ccnc6c5CCC(=O)N6)cc4C3)n2)c1]<br>5-[3-[4-(m-tolyl)-1H-imidazol-2-yl]chroman-6-yl]oxy-3,4-dihydro-1H-1,8-naphthyridin-2-one | UPLC-MS (ES+, final purity): 2.85 min, m/z 453.3 [M + H]$^+$.<br>$^1$H-NMR (400 MHz, DMSO-d$_6$) δ/ppm: 12.28 (0.2H, br s), 12.07 (0.8H, br s), 10.46 (1H, s), 7.95 (1H, d, J = 5.6 Hz), 7.61-7.39 (3H, m), 7.32-7.16 (1H, m), 7.07-6.95 (2H, m), 6.94-6.86 (2H, m), 6.27 (1H, d, J = 5.6 Hz), 4.53-4.47 (1H, m), 4.12 (1H, t, J = 10.0 Hz), 3.46-3.36 (1H, m), 3.29-3.19 (1H, m), 3.16-3.07 (1H, m), 2.93 (2H, t, J = 7.6 Hz), 2.53 (2H, t, J = 7.6 Hz, (partly under DMSO)), 2.32 (3H, s). |
| 2 | 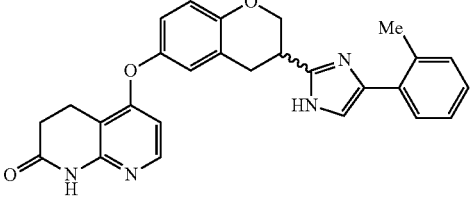<br>5-[3-[4-(o-tolyl)-1H-imidazol-2-yl]chroman-6-yl]oxy-3,4-dihydro-1H-1,8-naphthyridin-2-one | UPLC-MS (ES+, final purity): 2.75 min, m/z 453.3 [M + H]$^+$.<br>$^1$H-NMR (400 MHz, DMSO-d$_6$) δ/ppm: 12.17-12.08 (1H, m), 10.46 (1H, s), 7.97-7.94 (1H, m), 7.82-7.77 (0.75H, m), 7.45-7.42 (0.25H, m), 7.34-7.15 (3H, m), 7.14-7.07 (0.75H, m), 7.03-6.98 (1.25H, m), 6.95-6.86 (2H, m), 6.27 (1H, d, J = 5.6 Hz), 4.55-4.48 (1H, m), 4.19-4.08 (1H, m), 3.46-3.36 (1H, m), 3.29-3.19 (1H, m), 3.15-3.06 (1H, m), 2.93 (2H, t, J = 7.6 Hz), 2.53 (2H, t, J = 7.6 Hz, (partly under DMSO)), 2.43 (2.25H, s), 2.38 (0.75H, s). |
| 3 | 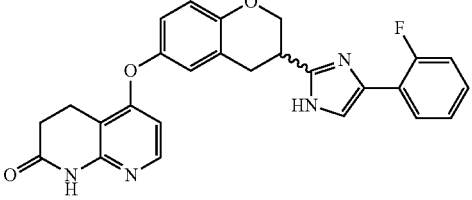<br>5-[3-[4-(2-fluorophenyl)-1H-imidazol-2-yl]chroman-6-yl]oxy-3,4-dihydro-1H-1,8-naphthyridin-2-one | UPLC-MS (ES+, final purity): 2.78 min, m/z 457.3 [M + H]$^+$.<br>$^1$H-NMR (400 MHz, CD$_3$OD) δ/ppm: 7.98-7.86 (2H, m), 7.39 (1H, d, J = 3.2 Hz), 7.30-7.11 (4H, m), 6.97-6.86 (3H, m), 6.35 (1H, d, J = 6.0 Hz), 4.55-4.48 (1H, m), 4.23 (1H, t, J = 10.8 Hz), 3.61-3.46 (1H, m), 3.30-3.24 (1H, m, (under water)) 3.20-3.11 (1H, m), 3.07 (2H, t, J = 7.6 Hz), 2.66 (2H, t, J = 7.6 Hz). Exchangeable proton missing. |

-continued

| Comp. No | Structure and Name | Data |
|---|---|---|
| 15 | 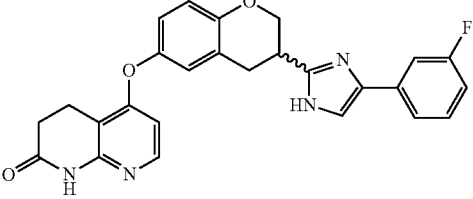<br>5-[3-[4-(3-fluorophenyl)-1H-imidazol-2-yl]chroman-6-yl]oxy-3,4-dihydro-1H-1,8-naphthyridin-2-one | UPLC-MS (ES+, final purity): 2.80 min, m/z 457.3 [M + H]$^+$.<br>$^1$H-NMR (400 MHz, DMSO-d$_6$) δ/ppm: 12.38 (0.15H, br s), 12.19 (0.85H, br s), 10.46 (1H, s), 7.95 (1H, d, J = 5.6 Hz), 7.70 (1H, s), 7.62-7.46 (2H, m), 7.40-7.32 (1H, m), 7.03-6.85 (4H, m), 6.26 (1H, d, J = 5.6 Hz), 4.53-4.45 (1H, m), 4.13 (1H, t, J = 10.0 Hz), 3.45-3.36 (1H, m), 3.28-3.19 (1H, m), 3.16-3.07 (1H, m), 2.93 (2H, t, J = 7.6 Hz), 2.53 (2H, t, J = 7.6 Hz, (partly under DMSO)). |
| 4 | 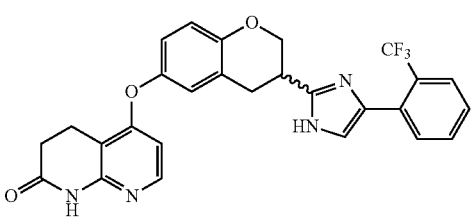 [SMILES: Cc1ccccc1-c1c[nH]c(C2COc3ccc(Oc4ccnc5c4CCC(=O)N5)cc3C2)n1]<br>5-[3-[4-[2-(trifluoromethyl)phenyl]-1H-imidazol-2-yl]chroman-6-yl]oxy-3,4-dihydro-1H-1,8-naphthyridin-2-one | UPLC-MS (ES+, final purity): 2.88 min, m/z 507.3 [M + H]$^+$.<br>$^1$H-NMR (400 MHz, DMSO-d$_6$) δ/ppm: 12.35 (0.15H, br s), 12.25 (0.85H, br s), 10.45 (1H, s), 7.95 (1H, d, J = 5.6 Hz), 7.90-7.82 (1H, m), 7.74 (1H, d, J = 7.6 Hz), 7.66 (1H, t, J = 7.6 Hz), 7.61-7.57 (0.15H, m), 7.45 (0.85H, t, J = 7.6 Hz), 7.30 (0.85H, br s), 7.00 (1H, d, J = 2.4 Hz), 6.98-6.86 (2.15H, m), 6.26 (1H, d, J = 5.6 Hz), 4.56-4.49 (1H, m), 4.13 (1H, t, J = 10.0 Hz), 3.47-3.39 (1H, m, (partly under water)), 3.28-3.19 (1H, m), 3.16-3.08 (1H, m), 2.93 (2H, t, J = 7.6 Hz), 2.56-2.53 (2H, m, (partly under DMSO)). |
| 20 | 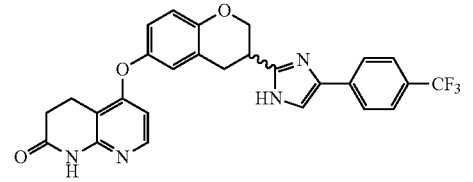 [SMILES: O=C1CCc2c(Oc3ccc4c(c3)CC(c3nc(-c5ccc(C(F)(F)F)cc5)c[nH]3)CO4)ccnc2N1]<br>5-[3-[4-[4-(trifluoromethyl)phenyl]-1H-imidazol-2-yl]chroman-6-yl]oxy-3,4-dihydro-1H-1,8-naphthyridin-2-one | UPLC-MS (ES, final purity): 3.21 min, m/z 507.2 [M + H]$^+$.<br>$^1$H-NMR (400 MHz, DMSO-d$_6$) δ/ppm: 12.30 (1H, br s), 10.46 (1H, s), 8.00-7.93 (3H, m), 7.81 (1H, s), 7.68 (2H, d, J = 8.4 Hz), 7.02 (1H, d, J = 2.4 Hz), 6.94-6.87 (2H, m), 6.27 (1H, d, J = 6.0 Hz), 4.56-4.49 (1H, m), 4.14 (1H, t, J = 10.0 Hz), 3.48-3.37 (1H, m), 3.29-3.21 (1H, m), 3.17-3.09 (1H, m), 2.93 (2H, t, J = 7.6 Hz), 2.56-2.53 (2H, m). |
| 5 | 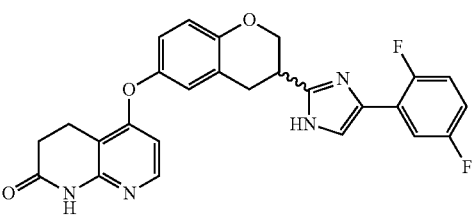 [SMILES: O=C1CCc2c(Oc3ccc4c(c3)CC(c3nc(-c5cc(F)ccc5F)c[nH]3)CO4)ccnc2N1]<br>5-[3-[4-(2,5-difluorophenyl)-1H-imidazol-2-yl]chroman-6-yl]oxy-3,4-dihydro-1H-1,8-naphthyridin-2-one | UPLC-MS (ES+, final purity): 2.96 min, m/z 475.3 [M + H]$^+$.<br>$^1$H-NMR (400 MHz, DMSO-d$_6$) δ/ppm: 12.37 (1H, br s), 10.46 (1H, s), 7.95 (1H, d, J = 5.6 Hz), 7.75-7.68 (1H, m), 7.55-7.49 (1H, m), 7.31-7.23 (1H, m), 7.09-6.99 (2H, m), 6.94-6.86 (2H, m), 6.26 (1H, d, J = 5.6 Hz), 4.55-4.47 (1H, m), 4.15 (1H, t, J = 10.4Hz), 3.47-3.38 (1H, m), 3.19-3.07 (2H, m, (partly under water), 2.93 (2H, t, J = 7.6 Hz), 2.57-2.52 (2H, t, J = 7.6 Hz, (partly under DMSO). |
| 16 | 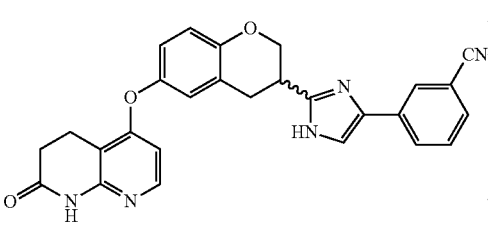 [SMILES: N#Cc1cccc(-c2c[nH]c(C3COc4ccc(Oc5ccnc6c5CCC(=O)N6)cc4C3)n2)c1]<br>3-[2-[6-[(7-oxo-6,8-dihydro-5H-1,8-naphthyridin-4-yl)oxy]chroman-3-yl]-1H-imidazol-4-yl]benzonitrile | UPLC-MS (ES+, final purity): 2.73 min, m/z 464.2 [M + H]$^+$.<br>$^1$H-NMR (400 MHz, DMSO-d$_6$) δ/ppm: 12.34 (1H, br s), 10.46 (1H, s), 8.15 (1H, s), 8.08 (1H, d, J = 8.0 Hz), 7.95 (1H, d, J = 5.6 Hz), 7.80 (1H, s), 7.61 (1H, d, J = 7.6 Hz), 7.54 (1H, t, J = 7.6 Hz), 7.02-6.99 (1H, m), 6.94-6.86 (2H, m), 6.26 (1H, d, J = 6.0 Hz), 4.54-4.47 (1H, m), 4.14 (1H, t, J = 10.0 Hz), 3.46-3.39 (1H, m), 3.26-3.19 (1H, m), 3.16-3.08 (1H, m), 2.93 (2H, t, J = 7.6 Hz), 2.57-5.53 (2H, m, (partly under DMSO)). |

The compound in the table below was made in an analogous manner, using the appropriate 6-[[2-(cyclopropanecarbonylamino)-4-pyridyl]oxy]chromane-3-carboxylic acid (Example 5) in place of 6-[(7-oxo-6,8-dihydro-5H-1,8-naphthyridin-4-yl)oxy]chromane-3-carboxylic in step 1 and using 2-bromo-1-phenylethanone in place of 2-bromo-1-(3-methoxyphenyl)ethanone in step 2:

complex (14.3 mg, 0.020 mmol), K₂CO₃ (72.6 mg, 0.52 mmol), 1,4-dioxane (5 mL) and water (1 mL) were combined under a nitrogen atmosphere and heated to 90° C. for 1 hour. The reaction was cooled to rt and solvent removed in vacuo. The residue was purified by column chromatography using an eluent of 0-10% MeOH in DCM to give 5-[3-[4-(2-methoxy-4-pyridyl)-1-(2-trimethylsilylethoxym-

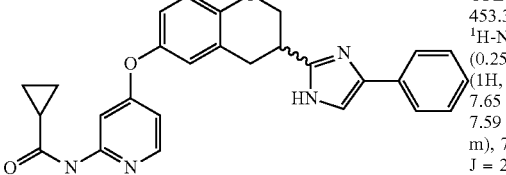

| Comp. No | Structure and Name | Data |
|---|---|---|
| 45 | N-[4-[3-(4-phenyl-1H-imidazol-2-yl)chroman-6-yl]oxy-2-pyridyl]cyclopropanecarboxamide | UPLC-MS (ES+, final purity): 2.66 min, m/z 453.3 [M + H]⁺. ¹H-NMR (400 MHz, DMSO-d₆) δ/ppm: 12.32 (0.25H, s), 12.10 (0.75H, s), 10.80 (1H, s), 8.16 (1H, d, J = 5.6 Hz), 7.75 (1.5H, d, J = 7.6 Hz), 7.65 (1H, d, J = 2.0 Hz), 7.63 (0.25H, br s), 7.59 (0.75H, d, J = 2.0 Hz), 7.43-7.20 (2.75H, m), 7.16 (0.75H, t, J = 7.6 Hz), 7.03 (1H, d, J = 2.4 Hz), 6.94-6.87 (2H, m), 6.62 (1H, dd, J = 5.6 Hz, 2.4 Hz), 4.56-4.49 (1H, m), 4.12 (1H, t, J = 10.4 Hz), 3.44-3.36 (1H, m), 3.24 (1H, dd, J = 16.4 Hz, 10.4 Hz), 3.12 (1H, dd, J = 16.4 Hz, 4.4 Hz), 1.07 (1H, q, J = 6.0 Hz), 0.77 (4H, d, J = 6.0 Hz). |

Example 18. Synthesis of 5-[3-[4-(2-methoxy-4-pyridyl)-1H-imidazol-2-yl]chroman-6-yl]oxy-3,4-dihydro-1H-1,8-naphthyridin-2-one (Compound 19)

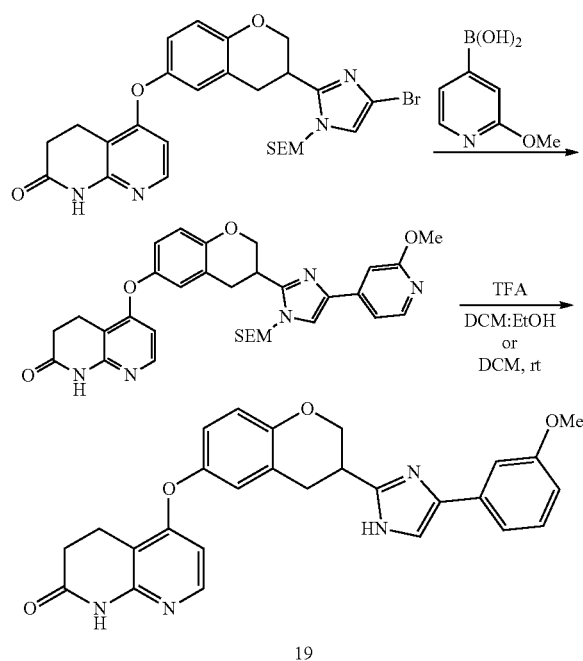

19

Step 1—5-[3-[4-(2-methoxy-4-pyridyl)-1-(2-trimethylsilylethoxymethyl)imidazol-2-yl]chroman-6-yl]oxy-3,4-dihydro-1H-1,8-naphthyridin-2-one 5-[3-[4-Bromo-1-(2-trimethylsilylethoxymethyl)imidazol-2-yl]chroman-6-yl]oxy-3,4-dihydro-1H-1,8-naphthyridin-2-one (100 mg, 0.18 mmol), 2-methoxypyridine-4-boronic acid (32.1 mg, 0.21 mmol), [1,1'-Bis(diphenylphosphino)ferrocene]palladium(II) chloride dichloromethane ethyl)imidazol-2-yl]chroman-6-yl]oxy-3,4-dihydro-1H-1,8-naphthyridin-2-one (96 mg, 0.16 mmol, 91% yield) as a orange oil. UPLC-MS (ES+, short acidic): 1.82 min, m/z 600.5 [M+H]⁺.

Step 2—5-[3-[4-(2-methoxy-4-pyridyl)-1H-imidazol-2-yl]chroman-6-yl]oxy-3,4-dihydro-1H-1,8-naphthyridin-2-one Trifluoroacetic acid (1 mL, 13.06 mmol) was added to a stirred solution of 5-[3-[4-(2-methoxy-4-pyridyl)-1-(2-trimethylsilylethoxymethyl)imidazol-2-yl]chroman-6-yl]oxy-3,4-dihydro-1H-1,8-naphthyridin-2-one (97 mg, 0.16 mmol) in DCM (4 mL) and EtOH (0.1 mL) at rt and stirred for 48 hours, after which time solvent and TFA were removed in vacuo. The residue was loaded into an SCX-2 column and flushed at first with MeOH (20 mL) and then NH₃ in MeOH (20 mL) to elute the product. Product containing fractions were combined and concentrated in vacuo. The residue was purified by column chromatography using an eluent of 0-10% MeOH in DCM to give 5-[3-[4-(2-methoxy-4-pyridyl)-1H-imidazol-2-yl]chroman-6-yl]oxy-3,4-dihydro-1H-1,8-naphthyridin-2-one (21 mg, 0.045 mmol, 28% yield) as a white solid. UPLC-MS (ES+, short acidic): 2.66 min m/z 470.3 [M+H]. ¹H NMR (400 MHz, DMSO-d₆) δ/ppm: 12.34 (1H, s), 10.47 (1H, s), 8.07 (1H, d, J=5.2 Hz), 7.96 (1H, d, J=5.6 Hz), 7.87 (1H, d, J=6. Hz), 7.34-7.31 (1H, 6), 7.10 (1H, d, J=8.0 Hz), 7.03-7.00 (1H, m), 6.95-6.87 (2H, m), 6.27 (1H, d, J=6.0 Hz), 4.54-4.48 (1H, n), 4.14 (1H, t, J=10.0 Hz), 3.88-3.83 (3H, in), 3.46-3.39 (1H, in), 3.28-3.09 (2H, in), 2.94 (2H, t, J=7.6 Hz), 2.62-2.57 (2H, m, (under DMSO peak).

The compounds in the table below were made in an analogous manner to Example 18, using the appropriate boronic acids/pinacol esters in place of 2-methoxypyridine-4-boronic acid in step 1:

| Comp. No. | Structure and Name | Data |
|---|---|---|
| 8 | 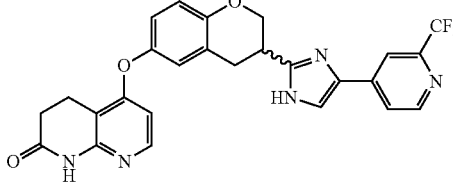<br>5-[3-[4-[2-(trifluoromethyl)-4-pyridyl]-1H-imidazol-2-yl]chroman-6-yl]oxy-3,4-dihydro-1H-1,8-naphthyridin-2-one | UPLC-MS (ES+, final acidic): 3.28 min, m/z 508.3 [M + H]$^+$.<br>$^1$H NMR (400 MHz, DMSO-d$_6$) δ/ppm: 12.60 (1H, s), 10.52 (1H, s), 8.72 (1H, s), 8.22-8.18 (2H, m), 8.05-8.04 (1H, m), 8.01 (1H, d, J = 6.0 Hz), 7.08 (1H, d, J = 7.6 Hz), 6.99 (1H, dd, J = 8.8 Hz, 2.4 Hz), 6.96 (1H, d, J = 8.8 Hz), 6.32 (1H, d, J = 6.0 Hz), 4.61-4.55 (1H, m), 4.22 (1H, t, J = 10.4 Hz), 3.55-3.45 (1H, m), 3.35-3.17 (2H, m), 2.99 (2H, t, J = 7.6 Hz), 2.62-2.58 (2H, m, (partly under DMSO)). |
| 103 | 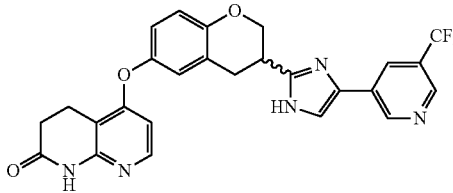<br>5-[3-[4-[5-(trifluoromethyl)-3-pyridyl]-1H-imidazol-2-yl]chroman-6-yl]oxy-3,4-dihydro-1H-1,8-naphthyridin-2-one | UPLC-MS (ES+, final purity): 3.14 min, m/z 508.2 [M + H]$^+$.<br>$^1$H NMR (400 MHz, DMSO-d$_6$) δ/ppm: 12.42 (1H, s), 10.47 (1H, s), 9.28-9.26 (1H, m), 8.78-8.75 (1H, m), 8.42-8.38 (1H, m), 8.00-7.94 (2H, m), 7.04-7.01 (1H, m), 6.95-6.88 (2H, m), 6.27 (1H, d, J = 6.0 Hz), 4.55-4.49 (1H, m), 4.19-4.13 (1H, m), 3.48-3.41 (1H, m), 3.29-3.23 (1H, m), 3.18-3.11 (1H, m), 2.94 (2H, t, J = 7.6 Hz), 2.54 (2H, t, J = 7.6 Hz (partly under DMSO)). |
| 17 | 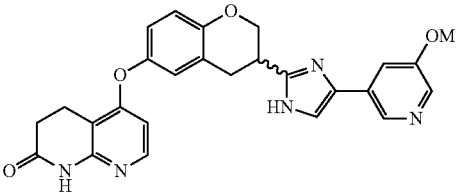 [SMILES: O=C1CCc2c(Oc3ccc4c(c3)CC(c3nc(-c5cncc(C(F)(F)F)c5)c[nH]3)CO4)ccnc2N1]<br>5-[3-[4-(5-methoxy-3-pyridyl)-1H-imidazol-2-yl]chroman-6-yl]oxy-3,4-dihydro-1H-1,8-naphthyridin-2-one | UPLC-MS (ES+, short acidic): 2.51 min, m/z 470.3 [M + H]$^+$.<br>$^1$H NMR (400 MHz, DMSO-d$_6$) δ/ppm: 12.47-12.26 (1H, m), 10.47 (1H, s), 8.58 (1H, d, J = 2.4 Hz), 8.10 (1H, d, J = 2.8 Hz), 7.96 (1H, d, J = 10.4 Hz), 7.80-7.77 (1H, m), 7.65-7.62 (1H, m), 7.03-7.01 (1H, m), 6.92 (1H, dd, J = 8.8 Hz, 3.2 Hz), 6.89 (1H, d, J = 8.8 Hz), 6.27 (1H, d, J = 6.0 Hz), 4.55-4.50 (1H, m), 4.15 (1H, t, J = 10.0 Hz), 3.90-3.85 (3H, m), 3.47-3.37 (1H, m), 3.30-3.21 (1H, m), 3.17-3.10 (1H, m), 2.94 (2H, t, J = 8.0 Hz), 2.56-2.50 (2H, m). |
| 117 | 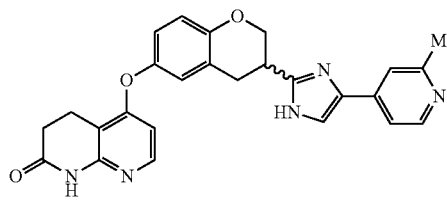<br>5-[3-[4-(2-methyl-4-pyridyl)-1H-imidazol-2-yl]chroman-6-yl]oxy-3,4-dihydro-1H-1,8-naphthyridin-2-one | UPLC-MS (ES+, final purity): 2.48 min, m/z 454.2 [M + H]$^+$.<br>$^1$H NMR (400 MHz, DMSO-d$_6$) δ/ppm: 12.33 (1H, s), 10.47 (1H, s), 8.35-8.34 (1H, m), 7.97-7.95 (1H, m), 7.85 (1H, s), 7.58 (1H, s), 7.51-7.47 (1H, m), 7.04-7.00 (1H, m), 6.95-6.88 (2H, m), 6.28-6.27 (1H, m), 4.54-4.49 (1H, m), 4.16-4.11 (1H, m), 3.44-3.36 (1H, m), 3.29-3.21 (1H, m), 3.17-3.09 (1H, m), 2.94 (2H, t, J = 8.0Hz), 2.54 (2H, t, J = 8.0 Hz, (partly under DMSO)), 2.46 (3H, s). |
| 18 | 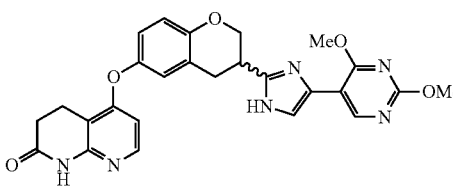<br>5-[3-[4-(2,4-dimethoxypyrimidin-5-yl)-1H-imidazol-2-yl]chroman-6-yl]oxy-3,4-dihydro-1H-1,8-naphthyridin-2-one | UPLC-MS (ES+, final compound acidic): 2.60 min, m/z 501.3 [M + H]$^+$.<br>$^1$H-NMR (400 MHz, DMSO-d$_6$) δ/ppm: 12.26 (1H, br s), 10.46 (1H, s), 8.81 (1H, s), 7.96 (1H, d, J = 6.0 Hz), 7.43 (1H, s), 7.00 (1H, s), 6.94-6.85 (2H, m), 6.26 (1H, d, J = 6.0 Hz), 4.53-4.46 (1H, m), 4.14 (1H, t, J = 10.0 Hz), 4.04 (3H, s), 3.91 (3H, s), 3.45-3.40 (1H, m, (partly under water)), 3.27-3.19 (1H, m), 3.16-3.06 (1H, m), 2.93 (2H, t, J = 7.6 Hz), 2.56-2.53 (2H, m, (partly under DMSO)). |

| Comp. No. | Structure and Name | Data |
|---|---|---|
| 6 | 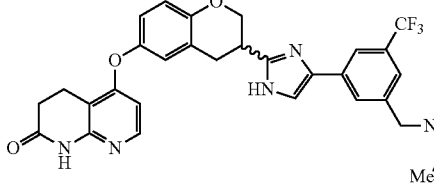<br><br>5-[3-[4-[3-[(isopropylamino)methyl]-5-(trifluoromethyl)phenyl]-1H-imidazol-2-yl]chroman-6-yl]oxy-3,4-dihydro-1H-1,8-naphthyridin-2-one | UPLC-MS (ES+, final acidic): 2.69 min, m/z 578.4 [M + H]$^+$.<br>$^1$H NMR (400 MHz, DMSO-$d_6$) δ/ppm: 12.26 (1H, s), 10.47 (1H, s), 8.06-8.00 (1H, m), 7.98-7.93 (2H, m), 7.83-7.80 (1H, m), 7.56-7.50 (1H, m), 7.03-7.00 (1H, m), 6.95-6.88 (2H, m), 6.27 (1H, d, J = 5.6 Hz), 4.55-4.59 (1H, m), 4.14 (1H, t, J = 10.4 Hz), 3.92-3.79 (2H, m), 3.47-3.37 (1H, m), 3.30-3.09 (3H, m), 2.94 (2H, t, J = 8.0 Hz), 2.56-2.53 (2H, m, (partly under DMSO peak)), 1.11-1.03 (6H, m). Exchangeable proton not seen. |
| 7 | 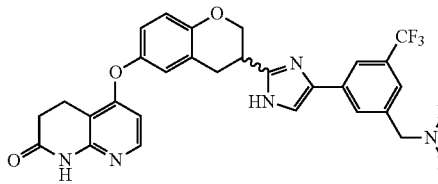<br><br>5-[3-[4-[3-[(dimethylamino)methyl]-5-(trifluoromethyl)phenyl]-1H-imidazol-2-yl]chroman-6-yl]oxy-3,4-dihydro-1H-1,8-naphthyridin-2-one | UPLC-MS (ES+, final acidic), 2.61 min, m/z 564.5 [M + H]$^+$.<br>$^1$H NMR (400 MHz, DMSO-$d_6$) δ/ppm: 12.26 (1H, s), 10.47 (1H, s), 7.99-7.94 (3H, m), 7.85-7.83 (1H, m), 7.43-7.39 (2H, m), 7.04-7.01 (1H, m), 6.95-6.88 (2H, m), 6.28 (1H, d, J = 5.6 Hz), 4.54-4.48 (1H, m), 4.14 (1H, t, J = 10.4 Hz), 3.51-3.47 (2H, m), 3.45-3.37 (1H, m), 3.30-3.22 (1H, m), 3.17-3.09 (1H, m), 2.94 (2H, t, J = 8.0 Hz), 2.55-2.50 (2H, m, (partly under DMSO)), 2.21-2.15 (6H, m). |
| 108 | 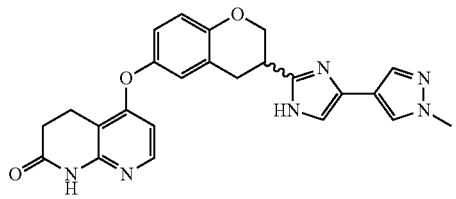 [SMILES: Cn1cc(-c2c[nH]c(C3COc4ccc(Oc5ccnc6c5CCC(=O)N6)cc4C3)n2)cn1]<br><br>5-[3-[4-(1-methylpyrazol-4-yl)-1H-imidazol-2-yl]chroman-6-yl]oxy-3,4-dihydro-1H-1,8-naphthyridin-2-one | UPLC-MS (ES+, final purity): 2.34 min, m/z 443.2 [M + H]$^+$.<br>$^1$H NMR (400 MHz, DMSO-$d_6$) δ/ppm: 12.06 (0.3H, s), 11.88 (0.7H, s), 10.47 (1H, s), 7.96 (1H, d, J = 6.0 Hz), 7.88 (0.3H, s), 7.81 (0.7H, s), 7.66 (0.3H, s), 7.58 (0.7H, s), 7.20 (0.7H, d, J = 2.0 Hz), 7.03-6.98 (1H, m), 6.94-6.87 (2.3H, m), 6.27 (1H, d, J = 6.0 Hz), 4.51-4.45 (1H, m), 4.08 (1H, t, J = 10.4 Hz), 3.86 (0.9H, s), 3.82 (2.1H, s), 3.39-3.34 (1H, m), 3.24-3.16 (1H, m), 3.12-3.04 (1H, m), 2.93 (2H, t, J = 7.6 Hz), 2.54 (2H, t, J = 7.6 Hz, (partly under DMSO)). |
| 125 | 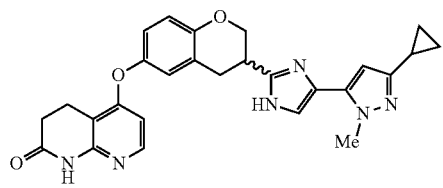 [SMILES: Cn1nc(C2CC2)cc1-c1c[nH]c(C2COc3ccc(Oc4ccnc5c4CCC(=O)N5)cc3C2)n1]<br><br>5-[3-[4-(5-cyclopropyl-2-methyl-pyrazol-3-yl)-1H-imidazol-2-yl]chroman-6-yl]oxy-3,4-dihydro-1H-1,8-naphthyridin-2-one | UPLC-MS (ES+, final purity): 2.80 min, m/z 483.2 [M + H]$^+$.<br>$^1$H NMR (400 MHz, DMSO-$d_6$) δ/ppm: 12.26 (1H, s), 10.46 (1H, s), 7.96 (1H, d, J = 6.0 Hz), 7.42 (1H, d, J = 2.0 Hz), 7.01-6.99 (1H, m), 6.91 (1H, dd, J = 8.8 Hz, 2.8 Hz), 6.87 (1H, d, J = 8.8 Hz), 6.26 (1H, d, J = 6.0 Hz), 6.05 (1H, s), 4.52-4.46 (1H, m), 4.17-4.10 (1H, m), 3.90 (3H, s), 3.45-3.37 (1H, m), 3.26-3.18 (1H, m), 3.16-3.09 (1H, m), 2.93 (2H, t, J = 8.0 Hz), 2.53 (2H, t, J = 7.6 Hz), 1.82-1.85 (1H, m), 0.89-0.79 (2H, m), 0.64-0.58 (2H, m). |

| Comp. No. | Structure and Name | Data |
|---|---|---|
| 126 | 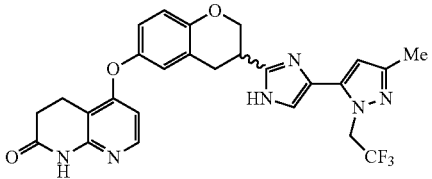 [SMILES: Cc1cc(-c2c[nH]c(C3COc4ccc(Oc5ccnc6c5CCC(=O)N6)cc4C3)n2)n(CC(F)(F)F)n1]<br>5-[3-[4-[5-methyl-2-(2,2,2-trifluoroethyl)pyrazol-3-yl]-1H-imidazol-2-yl]chroman-6-yl]oxy-3,4-dihydro-1H-1,8-naphthyridin-2-one<br>*Deprotection performed at 40° C. | UPLC-MS (ES+, final purity): 3.16 min, m/z 525.2 [M + H]$^+$.<br>$^1$H NMR (400 MHz, DMSO-d$_6$) δ/ppm: 12.37 (1H, s), 10.46 (1H, s), 7.96 (1H, d, J = 5.8 Hz), 7.54 (1H, d, J = 1.8 Hz), 6.99 (1H, d, J = 2.8 Hz), 6.91 (1H, dd, J = 8.8 Hz, 2.8 Hz), 6.86 (1H, d, J = 8.8 Hz), 6.29 (1H, s), 6.26 (1H, d, J = 5.7 Hz), 5.57-5.44 (2H, m), 4.52-4.43 (1H, m), 4.17 (1H, dd, J = 10.7 Hz, 9.1 Hz), 3.48-3.38 (1H, m), 3.26-3.07 (2H, m), 2.98-2.87 (2H, m), 2.57-2.52 (2H, m), 2.16 (3H, s). |
| 111 | 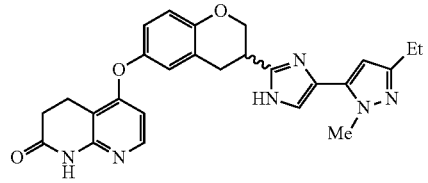 [SMILES: CCc1cc(-c2c[nH]c(C3COc4ccc(Oc5ccnc6c5CCC(=O)N6)cc4C3)n2)n(C)n1]<br>5-[3-[4-(5-ethyl-2-methyl-pyrazol-3-yl)-1-2) trimethylsilylethoxymethyl)imidazol-2-yl]chroman-6-yl]oxy-3,4-dihydro-1H-1,8-naphthyridin-2-one | UPLC-MS (ES+, final purity): 2.73 min, m/z 471.2 [M + H]$^+$.<br>$^1$H NMR (400 MHz, DMSO-d$_6$) δ/ppm: 12.64 (1H, s), 10.46 (1H, s), 7.96 (1H, d, J = 5.6 Hz), 7.45-7.43 (1H, m), 7.01-6.99 (1H, m), 6.91 (1H, dd, J = 8.8 Hz, 2.8 Hz), 6.88 (1H, d, J = 8.8 Hz), 6.26 (1H, d, J = 5.6 Hz), 6.18 (1H, s), 4.53-4.47 (1H, m), 4.14 (1H, t, J = 9.6 Hz), 3.92 (3H, s), 3.46-3.37 (1H, m), 3.27-3.19 (1H, m). 3.16-3.08 (1H, m), 2.93 (2H, t, J = 7.6 Hz), 2.53 (2H, t, J = 7.6 Hz), 2.52 (2H, m, (under DMSO)), 1.16 (3H, t, J = 7.6 Hz). |
| 112 | 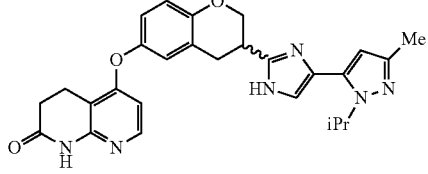<br>5-[3-[4-(2-isopropyl-5-methyl-pyrazol-3-yl)-1H-imidazol-2-yl]chroman-6-yl]oxy-3,4-dihydro-1H-1,8-naphthyridin-2-one | UPLC-MS (ES+, final purity): 2.86 min, m/z 485.2 [M + H]$^+$.<br>$^1$H NMR (400 MHz, DMSO-d$_6$) δ/ppm: 12.24 (1H, s), 10.46 (1H, s), 7.95 (1H, d, J = 6.0 Hz), 7.37 (1H, d, J = 2.0 Hz), 6.99 (1H, d, J = 2.4 Hz), 6.91 (1H, dd, J = 8.0 Hz, 2.4 Hz), 6.86 (1H, d, J = 8.0 Hz), 6.26 (1H, d, J = 6.0 Hz), 6.07 (1H, s), 5.24-5.17 (1H, m), 4.51-4.46 (1H, m), 4.19-4.13 (1H, m), 3.46-3.37 (1H, m), 3.25-3.17 (1H, m), 3.16-3.08 (1H, m), 2.93 (2H, t, J = 7.6 Hz), 2.53 (2H, t, J = 7.6 Hz), 2.52 (3H, s, (under DMSO), 1.33 (3H, d, J = 7.6 Hz), 1.31 (3H, d, J = 7.6 Hz). |
| 114 | 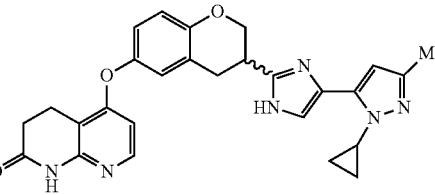<br>5-[3-[4-(2-cyclopropyl-5-methyl-pyrazol-3-yl)-1H-imidazol-2-yl]chroman-6-yl]oxy-3,4-dihydro-1H-1,8-naphthyridin-2-one | UPLC-MS (ES+, final purity): 2.74 min, m/z 483.4 [M + H]$^+$.<br>$^1$H NMR (400 MHz, DMSO-d$_6$) δ/ppm: 10.48 (1H, s), 7.96 (1H, d, J = 6.0 Hz), 7.72 (1H, s), 7.02 (1H, d, J = 2.8 Hz), 6.94 (1H, dd, J = 8.4 Hz, 2.4 Hz), 6.90 (1H, d, J = 8.4 Hz), 6.35 (1H, s), 6.27 (1H, d, J = 6.0 Hz), 4.55-450 (1H, m), 4.29-4.22 (1H, m), 3.78-3.75 (1H, m), 3.65-3.56 (1H, m), 3.32-3.17 (2H, m), 2.93 (2H, t, J = 7.6 Hz), 2.54 (2H, t, J = 7.6 Hz), 2.14 (3H, s), 1.06-0.96 (4H, m). One exchangeable proton not seen due to TFA salt. |

| Comp. No. | Structure and Name | Data |
|---|---|---|
| 113 | 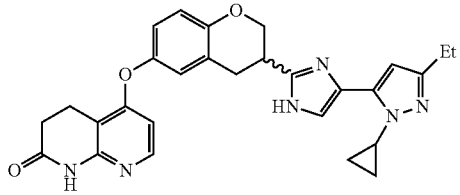 [SMILES: CCc1cc(-c2c[nH]c(C3COc4ccc(Oc5ccnc6c5CCC(=O)N6)cc4C3)n2)n(C2CC2)n1]<br>5-[3-[4-(2-cyclopropyl-5-ethyl-pyrazol-3-yl)-1H-imidazol-2-yl]chroman-6-yl]oxy-3,4-dihydro-1H-1,8-naphthyridin-2-one<br>*1st step at 85° C., 2nd step at 40° C. | UPLC-MS (ES+, final purity): 2.90 min, m/z 497.2 [M + H]+.<br>1H NMR (400 MHz, DMSO-d6) δ/ppm: 10.48 (1H, s), 7.96 (1H, d, J = 6.0 Hz), 7.76 (1H, s), 7.03 (1H, d, J = 2.4 Hz), 6.95 (1H, dd, J = 8.8 Hz, 2.8 Hz), 6.91 (1H, d, J = 8.8 Hz), 6.42 (1H, s), 6.27 (1H, d, J = 6.0 Hz), 4.58-450 (1H, m), 4.31-4.23 (1H, m), 3.78-3.72 (1H, m), 3.66-3.59 (1H, m), 3.34-3.18 (2H, m), 2.93 (2H, t, J = 7.6 Hz), 2.54 (2H, t, J = 7.6 Hz), 2.52 (2H, m, (under DMSO), 1.17 (3H, t, J = 7.6 Hz), 1.03-0.99 (4H, m). One exchangeable proton not seen due to TFA salt. |

Example 19. Synthesis of 5-[3-[4-(2,5-dimethylpyrazol-3-yl)-1H-imidazol-2-yl]chroman-6-yl]oxy-3-4-dihydro-1H-1,8-naphthyridin-2-one (Compound 106)

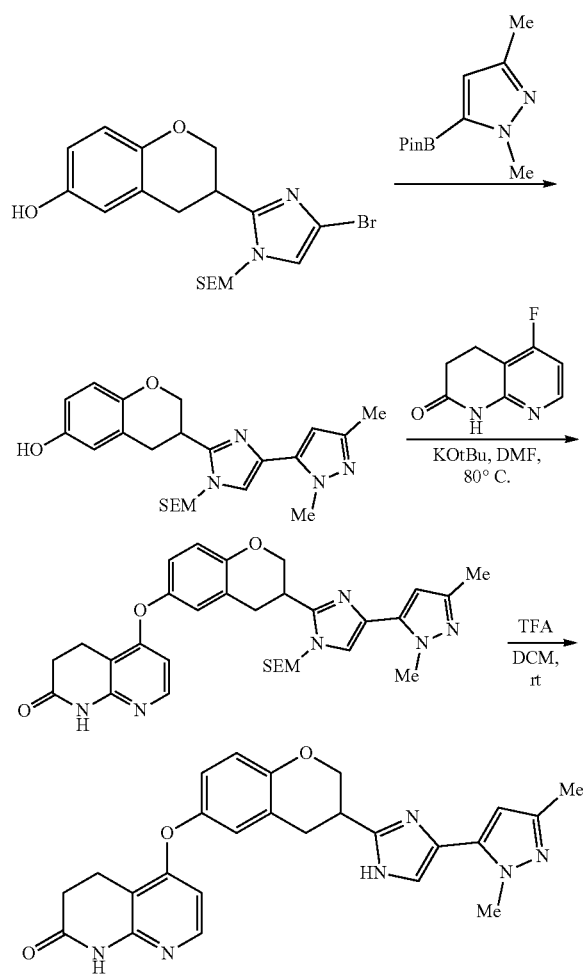

106

Step 1—3-[4-(2,5-dimethylpyrazol-3-yl)-1-(2-trimethylsilylethoxymethyl)imidazol-2-yl]chroman-6-ol 3-[4-bromo-1-(2-trimethylsilylethoxymethyl)imidazol-2-yl]chroman-6-ol (200 mg, 0.47 mmol), K2CO3 (195 mg, 1.41 mmol), 1,3-dimethyl-5-(4,4,5,5-tetramethyl-1,3,2-dioxaborolan-2-yl)-1H-pyrazole (104.4 mg, 0.47 mmol), 1,4-dioxane (4 mL) and water (1 mL) were combined and stirred at rt under a nitrogen atmosphere. [1,1'-Bis(diphenylphosphino)ferrocene]palladium(II) chloride dichloromethane complex (38.4 mg, 0.050 mmol) was added and the reaction heated to 100° C. for 2 hours. The reaction was cooled to rt and solvent removed in vacuo. The residue was purified by column chromatography using an eluent of 25-100% EtOAc in petroleum ether to give 3-[4-(2,5-dimethylpyrazol-3-yl)-1-(2-trimethylsilylethoxymethyl)imidazol-2-yl]chroman-6-ol (143 mg, 0.32 mmol, 69% yield) as an orange oil. UPLC-MS (ES+, short acidic): 1.74 min, m/z 441.8 [M+H]+.

Step 2—5-[3-[4-(2,5-dimethylpyrazol-3-yl)-1-(2-trimethylsilylethoxymethyl)imidazol-2-yl]chroman-6-yl]oxy-3,4-dihydro-1H-1,8-naphthyridin-2-one Potassium tert-Butoxide (40 mg, 0.36 mmol) was added to a stirred solution of 5-fluoro-3,4-dihydro-1H-1,8-naphthyridin-2-one (53.9 mg, 0.32 mmol) and 3-[4-(2,5-dimethylpyrazol-3-yl)-1-(2-trimethylsilylethoxymethyl)imidazol-2-yl]chroman-6-ol (143 mg, 0.32 mmol) in DMF (2 mL) and the reaction heated at 80° C. for 18 hours. The reaction was cooled to rt, solvent was reduced in vacuo and the residue partitioned between EtOAc and water. The organic layer was washed with sat. brine, separated, dried over a phase separator and the solvent reduced in vacuo. The residue was purified by column chromatography using as eluent a gradient 25-100% EtOAc in petroleum ether to give 5-[3-[4-(2,5-dimethylpyrazol-3-yl)-1-(2-trimethylsilylethoxymethyl)imidazol-2-yl]chroman-6-yl]oxy-3,4-dihydro-1H-1,8-naphthyridin-2-one (83 mg, 0.14 mmol, 44% yield) as a colourless gum. UPLC-MS (ES+, Short acidic): 1.83 min, m/z 587.5 [M+H]+.

Step 3—5-[3-[4-(2,5-dimethylpyrazol-3-yl)-1H-imidazol-2-yl]chroman-6-yl]oxy-3,4-dihydro-1H-1,8-naphthyridin-2-one Trifluoroacetic acid (0.54 mL, 7.08 mmol) was added to a stirred solution of 5-[3-[4-(2,5-dimethylpyrazol-3-yl)-1-

(2-trimethylsilylethoxymethyl)imidazol-2-yl]chroman-6-yl]oxy-3,4-dihydro-1H-1,8-naphthyridin-2-one (83 mg, 0.14 mmol) and DCM (2 mL) in a sealed vial and heated to 40° C. for 18 hours. The solvent was removed under reduce pressure and the residue was loaded into an SCX-2 column and flushed at first with MeOH (10 mL) and then NH$_3$ in MeOH (10 mL) to elute the product. The residue was purified by column chromatography using as eluent a gradient 1-8% MeOH in DCM. Fractions containing the product were combined, the solvent removed in vacuo and the residue was triturated in MeCN/Et20 to give a white solid, which was filtered and dried to give 5-[3-[4-(2,5-dimethylpyrazol-3-yl)-1H-imidazol-2-yl]chroman-6-yl]oxy-3,4-dihydro-1H-1,8-naphthyridin-2-one (33.5 mg, 0.073 mmol, 52% yield). UPLC-MS (ES+, final purity): 2.62 min, m/z 457.2 [M+H]$^+$. $^1$H NMR (400 MHz, DMSO-d$_6$) δ/ppm: 12.30 (0.13H, s), 12.26 (0.87H, s), 10.46 (1H, s), 7.96 (1H, d, J=6.0 Hz), 7.42 (0.87H, d, J=1.6 Hz), 7.13 (0.13H, d, J=1.6 Hz), 7.01-6.98 (1H, m), 6.94-6.81 (2H, m), 6.26-6.25 (1.13H, m), 6.14 (0.87H, s), 4.53-4.44 (1H, m), 4.13 (1H, t, J=10.4 Hz), 3.91 (2.61H, s), 3.80 (0.39H, s), 3.45-3.35 (1H, m), 3.27-3.06 (2H, m), 2.93 (2H, t, J=8.0 Hz), 2.53 (2H, t, J=8.0 Hz, (party under DMSO), 2.15 (2.61H, s), 2.11 (0.39H, s).

The compounds in the table below were made in an analogous manner to Example 19, using the appropriate boronic acids/pinacol esters in place of 1,3-dimethyl-5-(4,4,5,5-tetramethyl-1,3,2-dioxaborolan-2-yl)-1H-pyrazole in step 1:

| Comp. No | Structure and Name | Data |
|---|---|---|
| 107 | 5-[3-[4-[2-methyl-5-(trifluoromethyl)pyrazol-3-yl]-1H-imidazol-2-yl]chroman-6-yl]oxy-3,4-dihydro-1H-1,8-naphthyridin-2-one | UPLC-MS (ES+, final purity): 3.34 min, m/z 511.2 [M + H]$^+$. $^1$H NMR (400 MHz, DMSO-d$_6$) δ/ppm: 12.47 (1H, br s), 10.46 (1H, s), 7.96 (1H, d, J = 5.8 Hz), 7.66 (1H, br s), 7.01 (1H, d, J = 2.7 Hz), 6.92 (1H, dd, J = 8.8, 2.7 Hz), 6.88 (1H, d, J = 8.8 Hz), 6.83 (1H, s), 6.26 (1H, d, J = 5.8 Hz), 4.51 (1H, m), 4.16 (1H, dd, J = 10.7, 9.5 Hz), 4.11 (3H, s), 3.43 (1H, m), 3.28-3.09 (2H, m), 2.93 (2H, t, J = 8.0 Hz), 2.54 (2H, t, J = 8.0 Hz, (partly under DMSO)). |
| 110 | 5-[3-[4-(5-methyl-2-thienyl)-1H-imidazol-2-yl+chroman-6-yl+oxy-3,4-dihydro-1H-1,8-naphthyridin-2-one | UPLC-MS (ES+, final purity): 3.02 min, m/z 459.2 [M + H]$^+$. $^1$H NMR (400 MHz, DMSO-d$_6$) δ/ppm: 12.32 (0.16H, s), 12.07 (0.84H, s), 10.46 (1H, s), 7.96 (1H, d, J = 5.8 Hz), 7.36 (1H, d, J = 1.9 Hz), 7.07-6.83 (4H, m), 6.77 (0.16H, dd, J = 3.6 Hz, 1.3 Hz), 6.68 (0.84H, dd, J = 3.6 Hz, 1.3 Hz), 6.29-6.25 (1H, m), 4.52-4.44 (1H, m), 4.10 (1H, t, J = 10.3 Hz), 3.41-3.34 (1H, m), 3.25-3.05 (2H, m), 2.93 (2H, t, J = 7.7 Hz), 2.54 (2H, t, J = 7.7 Hz, (partly under DMSO)), 2.44 (0.48H, d, J = 1.1 Hz), 2.41 (2.52H, d, J = 1.1 Hz). |
| 118 | 5-[3-[4-(2-ethyl-4-pyridyl)-1H-imidazol-2-yl]chroman-6-yl]oxy-3,4-dihydro-1H-1,8-naphthyridin-2-one | UPLC-MS (ES+, final purity): 3.07 min, m/z 468.2 [M + H]$^+$. $^1$H NMR (400 MHz, DMSO-d$_6$) δ/ppm: 12.33 (1H, s), 10.47 (1H, s), 8.40-8.36 (1H, m), 7.96 (1H, d, J = 5.6 Hz), 7.87 (1H, s), 7.58 (1H, s), 7.52-7.48 (1H, m), 7.04-7.00 (1H, m), 6.95-6.87 (2H, m), 6.27 (1H, d, J = 5.6 Hz), 4.54-4.49 (1H, m), 4.14 (1H, t, J = 10.4 Hz), (3.47-3.38 (1H, m), 3.29-3.21 (1H, m), 3.17-3.09 (1H, m), 2.94 (2H, t, J = 7.6 Hz), 2.74 (2H, q, J = 7.6 Hz), 2.52 (2H, t, J =7.6 Hz), 1.25 (3H, t, J = 7.6 Hz). |
| 101 | 5-[3-[4-[2-(difluoromethyl)-4-pyridyl]-1H-imidazol-2-yl]chroman-6-yl]oxy-3,4-dihydro-1H-1,8-naphthyridin-2-one | UPLC-MS (ES+, final purity): 3.07 min, m/z 490.2 [M + H]$^+$. $^1$H NMR (400 MHz, DMSO d$_6$) δ/ppm: 12.48 (1H, s), 10.46 (1H, s), 8.58 (1H, d, J = 5.2 Hz), 8.07-8.05 (1H, m), 8.01-7.99 (1H, m), 7.96 (1H, d, J = 6.0 Hz), 7.87-7.84 (1H, m), 7.03-7.01 (1H, m), 6.96-6.88 (2H, m), 6.93 (1H, t, J = 55.0 Hz), 6.27 (1H, d, J = 5.2Hz), 4.55 (1H, m), 4.16 (1H, t, J = 10.4 Hz), 3.49-3.39 (1H, m), 3.28-3.22 (1H, m), 3.18-3.10 (1H, m), 2.93 (2H, t, J = 7.6 Hz), 2.54 (2H, t, J = 7.6 Hz). |

-continued

| Comp. No | Structure and Name | Data |
|---|---|---|
| 119 | 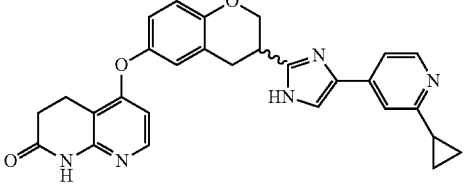<br>5-[3-[4-(2-cyclopropyl-4-pyridyl)-1H-imidazol-2-yl]chroman-6-yl]oxy-3,4-dihydro-1H-1,8-naphthyridin-2-one | UPLC-MS (ES+, final purity): 2.68 min, m/z 480.3 [M + H]⁺.<br>¹H NMR (400 MHz, DMSO-$d_6$) δ/ppm: 12.32 (1H, s), 10.46 (1H, s), 8.29 (1H, s), 7.96 (1H, dd, J = 5.6 Hz), 7.86 (1H, d, J = 2.0 Hz), 7.61 (1H, d, J = 5.2 Hz), 7.43 (1H, dd, J = 5.2 Hz, 1.6 Hz), 7.04-7.00 (1H, m), 6.96-6.89 (2H, m), 6.27 (1H, d, J = 5.6 Hz), 4.55-4.49 (1H, m), 4.14 (1H, t, J = 6.4 Hz), 3.48-3.73 (1H, m), 3.28-3.21 (1H, m), 3.17-3.09 (1H, m), 2.93 (2H, t, J = 7.6 Hz), 2.54 (2H, t, J = 7.6 Hz), 2.11-2.05 (1H, m), 0.92-0.91 (4H, m). |
| 120 | 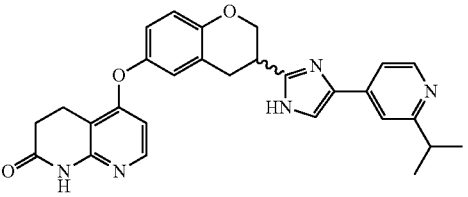 [SMILES: CC(C)c1cc(-c2c[nH]c(C3COc4ccc(Oc5ccnc6c5CCC(=O)N6)cc4C3)n2)ccn1]<br>5-[3-[4-(2-isopropyl-4-pyridyl)-1H-imidazol-2-yl]chroman-6-yl]oxy-3,4-dihydro-1H-1,8-naphthyridin-2-one | UPLC-MS (ES+, final purity): 2.76 min, m/z 482.3 [M + H]⁺.<br>¹H NMR (400 MHz, DMSO-$d_6$) δ/ppm: 12.32 (1H, s), 10.46 (1H, s), 8.39 (1H, d, J = 5.2 Hz), 7.96 (1H, J = 5.6 Hz), 7.88 (1H, d, J = 7.2 Hz), 7.58-7.56 (1H, m), 7.52-7.49 (1H, m), 7.03-7.01 (1H, m), 6.95-6.88 (2H, m), 6.27 (1H, d, J = 7.2 Hz), 4.55-4.49 (1H, m), 4.14 (1H, t, J = 10.4 Hz), 3.47-3.38 (1H, m), 3.28-3.21 (1H, m), 3.17-3.10 (1H, m), 3.04-2.99 (1H, m), 2.94 (2H, t, J = 8.0 Hz), 2.54 (2H, t, J = 8.0 Hz), 1.25 (6H, d, J = 6.8 Hz). |
| 121 | 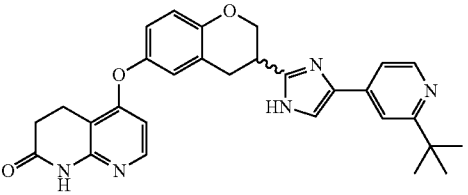 [SMILES: CC(C)(C)c1cc(-c2c[nH]c(C3COc4ccc(Oc5ccnc6c5CCC(=O)N6)cc4C3)n2)ccn1]<br>5-[3-[4-(2-tert-butyl-4-pyridyl)-1H-imidazol-2-yl]chroman-6-yl]oxy-3,4-dihydro-1H-1,8-naphthyridin-2-one | UPLC-MS (ES+, final purity): 2.84 min, m/z 496.3 [M + H]⁺.<br>¹H NMR (400 MHz, DMSO-$d_6$) δ/ppm: 12.32 (1H, s), 10.46 (1H, s), 8.41 (1H, d, J = 5.2 Hz), 7.96 (1H, d, J = 6.0 Hz), 7.90-7.89 (1H, m), 7.73-7.72 (1H, m), 7.50 (1H, dd, J = 4.8 Hz, 1.6 Hz), 7.03-7.01 (1H, m), 6.93 (1H, dd, J = 8.8 Hz, 2.8 Hz), 6.89 (1H, d, J = 8.8 Hz), 6.27 (1H, d, J = 5.6 Hz), 4.54-4.47 (1H, m), 4.15 (1H, t, J = 10.4 Hz), 3.47-3.38 (1H, m), 3.29-3.21 (1H, m), 3.17-3.10 (1H, m), 2.94 (2H, t, J = 7.6 Hz), 2.54 (2H, t, J = 7.6 Hz), 1.34 (9H, s). |
| 128 | 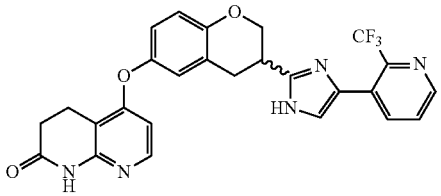 [SMILES: O=C1CCc2c(Oc3ccc4c(c3)CC(c3nc(-c5cccnc5C(F)(F)F)c[nH]3)CO4)ccnc2N1]<br>5-[3-[4-[2-(trifluoromethyl)-3-pyridyl]-1H-imidazol-2-yl]chroman-6-yl]oxy-3,4-dihydro-1H-1,8-naphthyridin-2-one | UPLC-MS (ES+, final purity): 2.79 min, m/z 508.2 [M + H]⁺.<br>¹H NMR (400 MHz, DMSO-$d_6$) δ/ppm: 12.40 (1H, s), 10.46 (1H, s), 8.60 (1H, dd, J = 4.8 Hz, 1.6 Hz), 8.32 (1H, d, J = 7.6 Hz), 7.95 (1H, d, J = 6.0 Hz), 7.72 (1H, dd, J = 8.0 Hz, 4.8 Hz), 7.43 (1H, s), 7.02-7.00 (1H, m), 6.92 (1H, dd, J = 8.8 Hz, 6.4 Hz), 6.89 (1H, d, J = 8.8 Hz), 6.27 (1H, d, J = 6.0 Hz), 4.55-4.50 (1H, m), 4.15 (1H, t, J = 10.4 Hz), 3.49-3.41 (1H, m), 3.28-3.20 (1H, m), 3.18-3.11 (1H, m), 2.93 (2H, t, J = 7.6 Hz), 2.54 (2H, t, J = 7.6 Hz). |
| 127 | 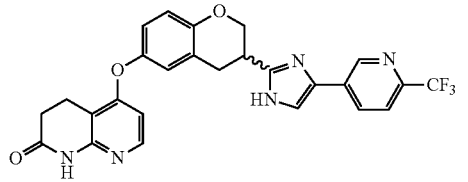 [SMILES: O=C1CCc2c(Oc3ccc4c(c3)CC(c3nc(-c5ccc(C(F)(F)F)nc5)c[nH]3)CO4)ccnc2N1]<br>5-[3-[4-[6-(trifluoromethyl)-3-pyridyl]-1H-imidazol-2-yl]chroman-6-yl]oxy-3,4-dihydro-1H-1,8-naphthyridin-2-one | UPLC-MS (ES+, final purity): 3.24 min, m/z 508.1 [M + H]⁺.<br>¹H NMR (400 MHz, DMSO-$d_6$) δ/ppm: 12.44 (1H, s), 10.46 (1H, s), 9.13 (1H, d, J = 2.4 Hz), 8.33 (1H, dd, J = 8.0 Hz, 2.0 Hz), 7.98-7.95 (2H, m), 7.86 (1H, d, J = 8.4 Hz), 7.02 (1H, d, J = 2.4 Hz), 6.92 (1H, dd, J = 8.8 Hz, 2.8 Hz), 6.89 (1H, d, J = 8.8 Hz), 6.27 (1H, d, J = 6.4 Hz), 4.56-4.50 (1H, m), 4.16 (1H, t, J = 10.0 Hz), 3.50-3.40 (1H, m), 3.30-3.22 (1H, m), 3.18-3.11 (1H, m), 2.93 (2H, t, J = 7.6 Hz), 2.54 (2H, t, J = 7.6 Hz). |

| Comp. No | Structure and Name | Data |
|---|---|---|
| 109 | 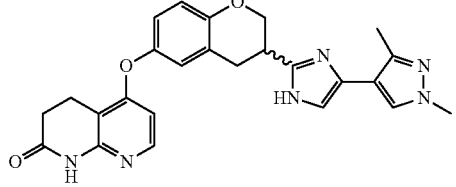<br>5-[3-[4-(1,3-dimethylpyrazol-4-yl)-1H-imidazol-2-yl]chroman-6-yl]oxy-3,4-dihydro-1H-1,8-naphthyridin-2-one | UPLC-MS (ES+, final purity): 2.39 min, m/z 457.2 [M + H]$^+$.<br>$^1$H NMR (400 MHz, DMSO-$d_6$) δ/ppm: 11.93-11.88 (1H, m), 10.46 (1H, s), 7.96 (1H, d, J = 6.0 Hz), 7.48 (0.35H, s), 7.72 (0.65H, s), 7.08-7.07 (0.65H, m), 7.01-6.99 (1H, m), 6.91 (1H, dd, J = 8.4 Hz, 2.8 Hz), 6.88 (1H, d, J = 8,4 Hz), 6.82-6.81 (0.35, m), 6.27 (1H, d, J = 6.0 Hz), 4.51-4.45 (1H, m), 4.09 (1H, t, J = 10.4 Hz), 3.79 (1.05H, s), 3.74 (1.95H, s), 3.39-3.34 (1H, m), 3.25-3.17 (1H, m), 3.12-3.05 (1H, m), 2.93 (2H, t, J = 8.4 Hz), 2.53 (2H, t, J = 8.4 Hz), 2.25 (1.95H, s), 2.23 (1.05H, s). |
| 129 | 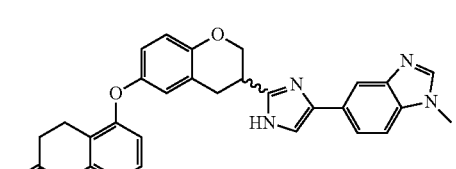<br>5-[3-[4-(1-methylbenzimidazol-5-yl)-1H-imidazol-2-yl]chroman-6-yl]oxy-3,4-dihydro-1H-1,8-naphthyridin-2-one | UPLC-MS (ES+, final purity): 2.24 min, m/z 493.2 [M + H]$^+$.<br>$^1$H NMR (400 MHz, DMSO-$d_6$) δ/ppm: 12.26 (0.3H, s), 12.01 (0.7H, s), 10.46 (1H, s), 8.18 (0.3H, s), 8.12 (0.7H, s), 8.01-7.93 (2H, m), 7.75-7.72 (0.6H, m), 7.60-7.58 (1.4H, m), 7.52-7.49 (0.7H, m), 7.26-7.25 (0.3H, m), 7.04-7.00 (1H, m), 6.92 (1H, dd, J = 8.8 Hz, 2.8 Hz), 6.89 (1H, d, J = 8.8 Hz), 6.28 (1H, d, J = 6.0 Hz), 4.55 (1H, m), 4.19-4.13 (1H, m), 3.85 (0.9H, s), 3.83 (2.1H, s), 3.44-3.35 (1H, m), 3.30-3.25 (1H, m), 3.18-3.10 (1H, m), 2.94 (2H, t, J = 7.6 Hz), 2.54 (2H, t, J = 7.6 Hz). |
| 130 | 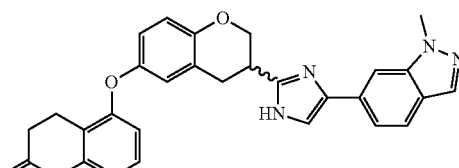<br>5-[3-[4-(1-methylindazol-6-yl)-1H-imidazol-2-yl]chroman-6-yl]oxy-3,4-dihydro-1H-1,8-naphthyridin-2-one | UPLC-MS (ES+, final purity): 2.66 min, m/z 493.1 [M + H]$^+$.<br>$^1$H NMR (400 MHz, CD$_3$OD) δ/ppm: 7.88-7.74 (3H, m), 7.67-7.61 (1H, m), 7.45-7.35 (2H, m), 6.88-6.78 (3H, m), 6.23 (1H, d, J = 6.0 Hz), 4.46-4.41 (1H, m), 4.16 (1H, t, J = 10.4 Hz), 3.99 (3H, s), 3.49-3.39 (1H, m), 3.27-3.23 (1H, m), 3.12-3.02 (1H, m), 2.97 (2H, t, J = 7.2 Hz), 2.57 (2H, t, J = 7.2 Hz). |
| 131 | 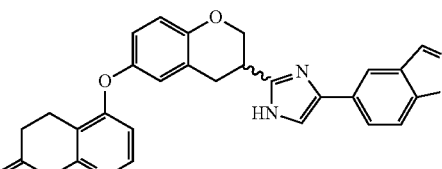<br>5-[3-[4-(1-methylindazol-5-yl)-1H-imidazol-2-yl]chroman-6-yl]oxy-3,4-dihydro-1H-1,8-naphthyridin-2-one | UPLC-MS (ES+, final purity): 2.60 min, m/z 493.2 [M + H]$^+$.<br>$^1$H NMR (400 MHz, DMSO-$d_6$) δ/ppm: 12.31 (0.2H, s), 12.05 (0.8H, s), 10.47 (1H, m), 8.11-8.07 (1H, m), 8.02-8.00 (0.8H, m), 7.99-7.95 (1.2H, m), 7.83 (0.8H, dd, J = 8.8 Hz, 1.6 Hz), 7.71-7.69 (0.4H, m), 7.61-7.57 (1.6H, m), 7.27-7.25 (0.2H, m), 7.04-7.01 (1H, m), 6.93 (1H, dd, J = 8.8 Hz, 2.4 Hz), 6.89 (1H, d, J = 8.8 Hz), 6.28 (1H, d, J = 6.0 Hz), 4.56 (1H, m), 4.15 (1H, t, J = 10.0 Hz), 4.06 (0.6H, s), 4.04 (2.4, s), 3.45-3.36 (1H, m), 3.29-3.22 (1H, m), 3.17-3.10 (1H, m), 2.94 (2H, t, J = 7.6 Hz), 2.54 (2H, t, J = 7.6 Hz). |
| 105 | 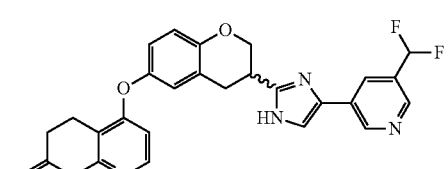 | UPLC-MS (ES+, final purity): 2.75 min, m/z 490.2 [M + H]$^+$.<br>$^1$NMR (400 MHz, DMSO-$d_6$) δ/ppm: 12.44 (1H, s), 10.47 (1H, s), 9.15-9.12 (1H, m), 8.61-8.58 (1H, m), 8.29-8.27 (1H, m), 7.97-7.87 (2H, m), 7.19 (1H, t, J = 55.2 Hz), 7.04-7.01 (1H, m), 6.96-6.88 (2H, m), 6.27 (1H, d, J = 5.2 Hz), 4.56-4.50 (1H, m), 4.17 |

| Comp. No | Structure and Name | Data |
|---|---|---|
| | 5-[3-[4-[5-(difluoromethyl)-3-pyridyl]-1H-imidazol-2-yl]chroman-6-yl]oxy-3,4-dihydro-1H-1,8-naphthyridin-2-one | (1H, t, J = 10.0 Hz), 3.51-3.41 (1H, m), 3.29-3.22 (1H, m), 3.19-3.11 (1H, m), 2.94 (2H, t, J = 7.2 Hz), 2.56-2.50 (2H, m). |
| 124 | 5-[3-[4-(2-ethyl-5-methyl-pyrazol-3-yl)-1H-imidazol-2-yl]chroman-6-yl]oxy-3,4-dihydro-1H-1,8-naphthyridin-2-one | UPLC-MS (ES+, final purity): 2.63 min, m/z 471.2 [M + H]+. <br> 1H NMR (400 MHz, DMSO-d6) δ/ppm: 12.25 (1H, s), 10.46 (1H, s), 7.96 (1H, d, J = 5.8 Hz), 7.40 (1H, s), 7.00 (1H, d, J = 2.8 Hz), 6.91 (1H, dd, J = 8.8 Hz, 2.8 Hz), 6.87 (1H, d, J = 8.8 Hz), 6.26 (1H, d, J = 5.8 Hz), 6.12 (1H, s), 4.54-4.44 (1H, m), 4.40-4.28 (2H, m), 4.16 (1H, t, J = 10.0 Hz), 3.40 (1H, m), 3.22 (1H, dd, J =16.7 Hz, 9.5 Hz), 3.12 (1H, dd, J = 16.6 Hz, 5.8 Hz), 2.93 (2H, dd, J = 8.4 Hz, 7.0 Hz), 2.57-2.53 (2H, m (partly under DMSO)), 2.12 (3H, s), 1.25 (3H, t, J = 7.1 Hz). |

Example 20. Synthesis of 5-[3-(4-tetrahydropyran-4-yl-1H-imidazol-2-yl)chroman-6-yl]oxy-3,4-dihydro-TH-1,8-naphthyridin-2-one (Compound 132)

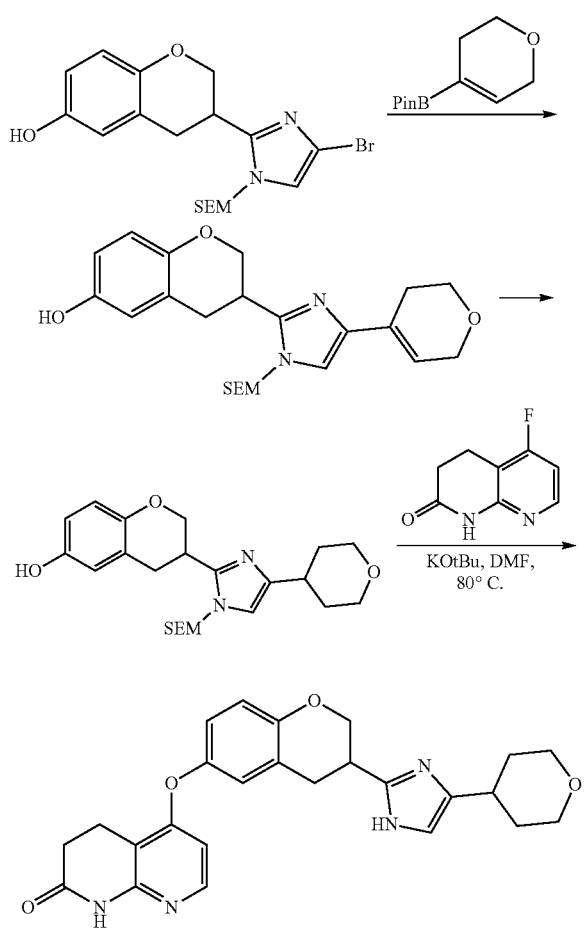

132

Step 1—3-[4-(3,6-dihydro-2H-pyran-4-yl)-1-(2-trimethylsilylethoxymethyl)imidazol-2-yl]chroman-6-ol 3,6-Dihydro-2H-pyran-4-boronic acid pinacol ester (108.7 mg, 0.52 mmol), 3-[4-bromo-1-(2-trimethylsilylethoxymethyl)imidazol-2-yl]chroman-6-ol (220 mg, 0.52 mmol), [1,1'-bis(diphenylphosphino)ferrocene]palladium (II) chloride dichloromethane complex (42.2 mg, 0.050 mmol), potassium carbonate (214.4 mg, 1.55 mmol), 1,4-dioxane (4 mL) and water (1 mL) were combined at room temperature under a nitrogen atmosphere in a sealable vial. The vial was sealed and the reaction was heated to 80° C. and allowed to stir for 2 hours. It was then cooled to room temperature and solvent removed in vacuo. The residue was taken up in DCM (20 mL) and filtered through celite and the filter cake washed with DCM (10 mL). The residue was purified by column chromatography using an eluent of 0-100% EtOAc in petroleum ether to give 3-[4-(3,6-dihydro-2H-pyran-4-yl)-1-(2-trimethylsilylethoxymethyl)imidazol-2-yl]chroman-6-ol (149 mg, 0.35 mmol, 67% yield) as a yellow solid. UPLCMS (ES+, short acidic): 1.53 min, m/z 429.7 [M+H]+.

Step 2—3-[4-tetrahydropyran-4-yl-1-(2-trimethylsilylethoxymethyl)imidazol-2-yl]chroman-6-ol 3-[4-(3,6-dihydro-2H-pyran-4-yl)-1-(2-trimethylsilylethoxymethyl)imidazol-2-yl]chroman-6-ol (149. mg, 0.35 mmol) was stirred in EtOAc (10 mL) at room temperature under a nitrogen atmosphere. Palladium, 10 wt. % on carbon powder, dry (20 mg) was added and the reaction fitted with a hydrogen balloon and subjected to 3×vacuum/hydrogen cycles and then allowed to stir under a hydrogen atmosphere for 18 hours. The reaction was then filtered through a celite plug and the plug washed with MeOH (10 mL). The filtrate was concentrated in vacuo to give 3-[4-tetrahydropyran-4-yl-1-(2-trimethylsilylethoxymethyl)imidazol-2-yl]chroman-6-ol (95 mg, 0.22 mmol, 63% yield) as a yellow solid. The compound was used directly in the next step without further purification. UPLC-MS (ES+, short acidic): 1.49 min, m/z 431.7 [M+H]+.

Step 3—5-[3-(4-tetrahydropyran-4-yl-1H-imidazol-2-yl)chroman-6-yl]oxy-3,4-dihydro-1H-1,8-naphthyridin-2-one Potassium tert-butoxide (75.4 mg, 0.67 mmol) was added to a stirred solution of 5-fluoro-3,4-dihydro-1H-1,8-naphthyridin-2-one (36.7 mg, 0.22 mmol) and 3-[4-tetrahydropyran-4-yl-1-(2-trimethylsilylethoxymethyl)imidazol-2-yl]chroman-6-ol (95 mg, 0.22 mmol) in DMF (2 mL) and the reaction was sealed in a tube and heated at 90° C. for 60 hours. Reaction was cooled to room temperature and the reaction was reduced in vacuo and partitioned between EtOAc and water. The organics were washed with saturated brine, separated, dried over a phase separator and reduced in vacuo. The residue was purified by column chromatography using as eluent a gradient 1-10% MeOH/DCM. Fractions containing the product were combined and re-purified by preparative HPLC (early method). Fractions containing the product were combined, solvent removed under reduce pressure and loaded onto a SCX column, which was flushed at first with MeOH and then 1.0 M MeOH/NH$_3$ to give 5-[3-(4-tetrahydropyran-4-yl-1H-imidazol-2-yl)chroman-6-yl]oxy-3,4-dihydro-1H-1,8-naphthyridin-2-one (5 mg, 0.011 mmol, 5% yield) as a white solid. UPLC-MS (ES+, Final purity): 2.36 min, m/z 447.2 [M+H]$^+$. $^1$H NMR (400 MHz, DMSO-d$_6$+CF$_3$CO$_2$D) δ/ppm: 14.11 (1H, s), 10.65 (1H, s), 8.00 (1H, d, J=6.0 Hz), 7.46 (1H, s), 7.03 (1H, d, J=2.8 Hz), 7.00-6.91 (2H, m), 6.30 (1H, d, J=6.0 Hz), 4.51 (1H, dd, J=10.9 Hz, 3.1 Hz), 4.34 (1H, dd, J=11.0 Hz, 8.1 Hz, 1H), 3.93 (2H, ddd, J=11.5 Hz, 4.5 Hz, 2.0 Hz), 3.83-3.73 (1H, m), 3.44 (2H, td, J=11.7 Hz, 2.1 Hz), 3.30-3.23 (2H, m), 3.01-2.89 (3H, m), 2.56 (2H, dd, J=8.4 Hz, 7.0 Hz), 1.92-1.82 (2H, m), 1.63 (2H, qd, J=12.1 Hz, 4.4 Hz).

Example 21. Synthesis of 5-[3-[5-(3-methoxy-2-thienyl)-1H-imidazol-2-yl]chroman-6-yl]oxy-3,4-dihydro-1H-1,8-naphthyridin-2-one (Compound 122)

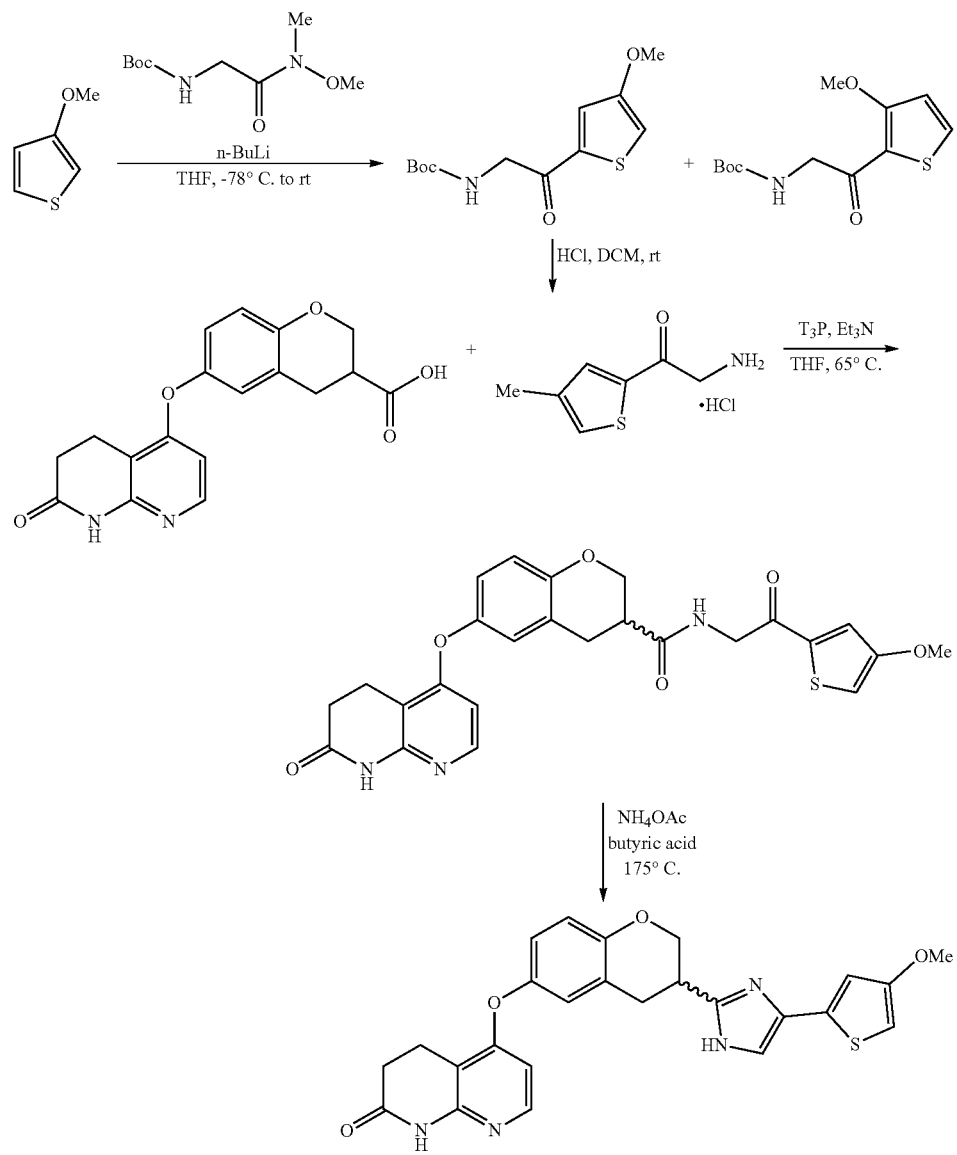

122

Step 1—tert-butyl N-[2-(4-methoxy-2-thienyl)-2-oxo-ethyl]carbamate and tert-butyl N-[2-(3-methoxy-2-thienyl)-2-oxo-ethyl]carbamate n-Butyllithium solution (3.5 mL, 8.76 mmol) was added to a stirred solution of 3-methoxythiophene (0.87 mL, 8.76 mmol) and THF (20 mL) at −78° C. under a nitrogen atmosphere. The mixture was stirred for 20 minutes at −78° C., allowed to warm to 0° C. for 20 minutes and then cooled back to −78° C. and tert-butyl N-[2-[methoxy(methyl)amino]-2-oxo-ethyl]carbamate (477.9 mg, 2.19 mmol) was added. After 1 hour at −78° C. the reaction was allowed to warm to room temperature and stir for 18 hours. The reaction was then poured into water (100 mL) and the resulting mixture extracted with EtOAc (2×100 mL). The combined organic layers were dried over $Na_2SO_4$, filtered and solvent removed in vacuo. The residue was purified by column chromatography using an eluent of 0-100% EtOAc in petroleum ether to give tert-butyl N-[2-(4-methoxy-2-thienyl)-2-oxo-ethyl]carbamate (93 mg, 0.34 mmol, 16% yield) and tert-butyl N-[2-(3-methoxy-2-thienyl)-2-oxo-ethyl]carbamate (170 mg, 0.63 mmol, 29% yield) as yellow oils.

N-[2-(4-methoxy-2-thienyl)-2-oxo-ethyl]carbamate: UPLCMS (ES+, short acidic): 1.62 min, m/z 294.0 [M+Na]$^+$. $^1$H NMR (400 MHz, CDCl$_3$) δ/ppm: 7.37 (1H, d, J=1.6 Hz), 6.67 (1H, d, J=1.6 Hz), 5.39 (1H, br s), 4.53-4.52 (2H, m), 3.83 (3H, s), 1.45 (9H, s).

N-[2-(3-methoxy-2-thienyl)-2-oxo-ethyl]carbamate: UPLCMS (ES+, short acidic): 1.60 min, m/z 272.0 [M+H]$^+$, 294.0 [M+Na]$^+$. $^1$H NMR (400 MHz, CDCl$_3$) δ/ppm: 7.59 (1H, d, J=5.6 Hz), 6.86 (1H, d, J=5.6 Hz), 5.56 (1H, br s), 4.52-4.50 (2H, m), 4.00 (3H, s), 1.47 (9H, s).

Step 2—2-amino-1-(4-methoxy-2-thienyl)ethanone Hydrochloride

Hydrogen Chloride (0.26 mL, 1.03 mmol-4M in dioxane) was added to a stirred solution of tert-butyl N-[2-(4-methoxy-2-thienyl)-2-oxo-ethyl]carbamate (93 mg, 0.34 mmol) and DCM (5 mL) at room temperature. The reaction was allowed to stir for 18 hours after which time the solvent was removed in vacuo to give 2-amino-1-(4-methoxy-2-thienyl)ethanone hydrochloride (71 mg, 0.34 mmol, 100% yield) as a yellow solid, which was used in the next step without further purification. UPLCMS (ES+, short acidic), 0.47 min, m/z 171.9 [M+H]$^+$.

Step 3—N-[2-(4-methoxy-2-thienyl)-2-oxo-ethyl]-6-[(7-oxo-6,8-dihydro-5H-1,8-naphthyridin-4-yl)oxy]chromane-3-carboxamide Propylphosphonic anhydride (0.31 mL, 0.51 mmol) was added to a stirred solution of 6-[(7-oxo-6,8-dihydro-5H-1,8-naphthyridin-4-yl)oxy]chromane-3-carboxylic acid (116.4 mg, 0.34 mmol), 2-amino-1-(4-methoxy-2-thienyl)ethanone hydrochloride (71 mg, 0.34 mmol), triethylamine (0.1 mL, 0.68 mmol) and THF (5 mL). The reaction was heated to 65° C. and stirred for 18 hours. The reaction was then cooled to room temperature and solvent removed in vacuo. The residue was partitioned between water (50 mL) and DCM (50 mL). The organic layer was separated, dried over $Na_2SO_4$, filtered and solvent removed in vacuo. The residue was purified by column chromatography using an eluent of 0-5% MeOH in DCM to give N-[2-(4-methoxy-2-thienyl)-2-oxo-ethyl]-6-[(7-oxo-6,8-dihydro-5H-1,8-naphthyridin-4-yl)oxy]chromane-3-carboxamide (52 mg, 0.11 mmol, 31% yield) as a white solid. UPLCMS (ES+, short acidic): 1.47 min, m/z 494.1 [M+H]$^+$.

Step 4—5-[3-[5-(3-methoxy-2-thienyl)-1H-imidazol-2-yl]chroman-6-yl]oxy-3,4-dihydro-1H-1,8-naphthyridin-2-one N-[2-(4-methoxy-2-thienyl)-2-oxo-ethyl]-6-[(7-oxo-6,8-dihydro-5H-1,8-naphthyridin-4-yl)oxy]chromane-3-carboxamide (52 mg, 0.11 mmol) and ammonium acetate (243.7 mg, 3.16 mmol) were taken up in butyric acid (2 mL, 21.88 mmol) in a sealable vial, which was sealed and heated at 175° C. for 2 hours. The reaction mixture was evaporated to dryness and then treated with aq. $K_2CO_3$ solution and extracted with DCM (15 ml). The organic layer was passed through a phase separator and then evaporated to dryness. The residue was chromatographed via preparative LCMS to give 5-[3-[5-(4-methoxy-2-thienyl)-1H-imidazol-2-yl]chroman-6-yl]oxy-3,4-dihydro-1H-1,8-naphthyridin-2-one (8 mg, 0.016 mmol, 15% yield) as an off white solid product. UPLC-MS (ES+, final purity): 2.80 min, m/z 475.1 [M+H]$^+$. $^1$H NMR (400 MHz, DMSO-d$_6$) δ/ppm: 10.67 (1H, s), 8.05-7.91 (2H, m), 7.69 (1H, d, J=1.5 Hz), 7.25 (TH, d, J=1.7 Hz), 7.05 (1H, d, J=2.5 Hz), 7.02-6.88 (2H, in), 6.76 (1H, d, J=1.8 Hz), 6.32 (1H, d, J=6.0 Hz), 4.56 (1H, dd, J=10.9 Hz, 3.2 Hz), 4.35 (1H, dd, J=11.0 Hz, 8.6 Hz), 3.79 (3H, s), 3.87-3.69 (TH, in), 3.35-3.23 (2H, in), 2.95 (2H, t, J=7.7 Hz), 2.60-2.53 (2H, in).

The compounds in the table below were made in an analogous manner to Example 21, using the appropriate reagent in place of tert-butyl N-[2-(4-methoxy-2-thienyl)-2-oxo-ethyl]carbamate in step 2:

| Comp. No | Structure and Name | Data |
|---|---|---|
| 123 | 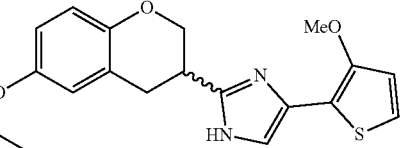<br>5-[3-[5-(3-methoxy-2-thienyl)1H-imidazol-2-yl]chroman-6-yl]oxy-3,4-dihydro-1H-1,8-naphthyridin-2-one | UPLC-MS (ES+, final purity): 2.70 min, m/z 475.1 [M + H]$^+$. $^1$H NMR (400 MHz, DMSO-$d_6$) δ/ppm: 10.59 (1H, s), 7.99 (1H, d, J = 5.9 Hz), 7.74 (1H, s), 7.68 (1H, d, J = 5.5 Hz), 7.21 (1H, d, J = 5.5 Hz), 7.04 (1H, d, J = 2.7 Hz), 7.01-6.91 (2H, m), 6.30 (1H, d, J = 5.9 Hz), 4.55 (1H, ddd, J = 10.8 Hz, 3.3 Hz, 1.3 Hz), 4.33 (1H, dd, J = 10.8 Hz, 8.9 Hz), 3.95 (3H, s), 3.80 (1H, dq, J = 8.8 Hz, 2.9 Hz), 3.38-3.19 (2H, m), 2.94 (2H, dd, J = 8.4 Hz, 7.0 Hz), 2.59-2.53 (2H, m), 2.53 (1H, d, J = 3.9 Hz). |
| 116 | 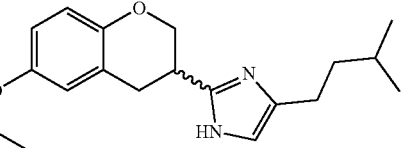<br>5-[3-(5-isopentyl-1H-imidazol-2-yl)chroman-6-yl]oxy-3,4-dihydro-1H-1,8-naphthyridin-2-one | UPLC-MS (ES+, final purity): 2.83 min, m/z 433.2 [M + H]$^+$. $^1$H NMR (400 MHz, DMSO-$d_6$ + CF$_3$CO$_2$D) δ/ppm: 14.08 (1H, m), 10.66 (1H, s), 7.99 (1H, d, J = 5.9 Hz), 7.41 (1H, s), 7.02 (1H, d, J = 2.8 Hz), 6.96 (1H, dd, J = 8.8 Hz, 2.8 Hz), 6.91 (1H, d, J = 8.8 Hz), 6.30 (1H, d, J = 6.0 Hz), 4.49 (1H, dd, J = 11.0 Hz, 3.1 Hz), 4.34 (1H, dd, J = 11.0 Hz, 8.0 Hz), 3.84-3.71 (1H, m), 3.33-3.19 (2H, m), 2.94 (2H, t, J = 7.7 Hz), 2.65-2.59 (2H, m), 2.55 (2H, dd, J = 8.4 Hz, 7.0 Hz), 1.63-1.40 (3H, m), 0.90 (6H, d, J = 6.3 Hz). |

Example 22. Synthesis of 5-[3-[4-(3,3-dimethylbutyl)-1H-imidazol-2-yl]chroman-6-yl]oxy-3,4-dihydro-1H-1,8-naphthyridin-2-one (Compound 115)

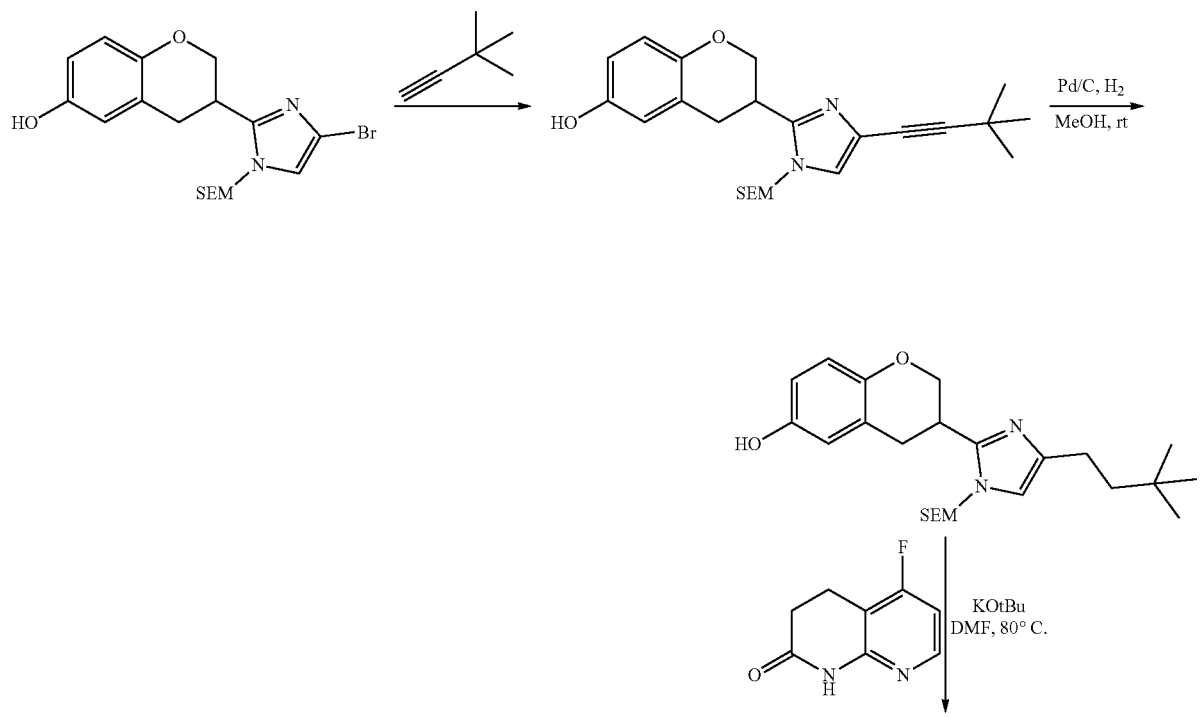

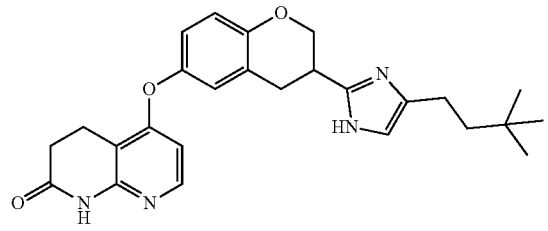 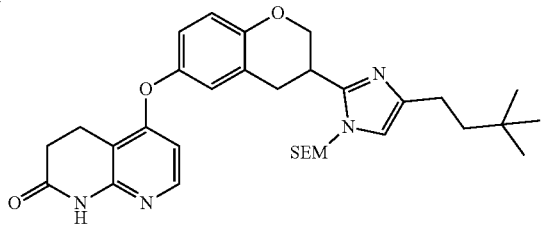

115

Step 1—3-[4-(3,3-dimethylbut-1-ynyl)-1-(2-trimethylsilylethoxymethyl)imidazol-2-yl]chroman-6-ol Tetrakis(triphenylphosphine)palladium(0) (54.3 mg, 0.05 mmol) was added to a stirred mixture of 3-[4-bromo-1-(2-trimethylsilylethoxymethyl)imidazol-2-yl]chroman-6-ol (200 mg, 0.47 mmol), 3,3-dimethyl-1-butyne (0.17 mL, 1.41 mmol), copper(I) iodide (9.0 mg, 0.05 mmol), $K_2CO_3$ (130 mg, 0.94 mmol), monoglyme (2 mL) and water (0.5 mL) in a sealable vial at room temperature under a nitrogen atmosphere. The vial was sealed and the reaction heated to 90° C. and stirred for 18 hours. After this time, the reaction mixture was cooled to room temperature and the solvent removed in vacuo. The residue was taken up in DCM, filtered through a celite plug and the filter cake washed with DCM (10 mL). The filtrate was diluted with DCM (50 mL) and the solution washed with water sat aq. $NaHCO_3$ (10 mL), brine (50 mL), dried over $Na_2SO_4$, filtered and the solvent removed in vacuo. The residue was purified by column chromatography using as eluent a gradient of 0-10% EtOAc in petroleum ether to give 3-[4-(3,3-dimethylbut-1-ynyl)-1-(2-trimethylsilylethoxymethyl)imidazol-2-yl]chroman-6-ol (156.5 mg, 0.37 mmol, 78% yield) as a yellow solid. UPLC-MS (ES+, short acidic): 2.04 min, m/z 427.6 [M+H]$^+$. $^1$H NMR (400 MHz, CDCl$_3$) δ/ppm: 7.13 (1H, s), 6.73 (1H, d, J=9.2 Hz), 6.64-6.60 (1H, m), 6.59-6.56 (1H, m), 5.37 (2H, s), 4.69 (1H, s), 4.43-4.37 (1H, m), 4.07 (1H, t, J=10.0 Hz), 3.60-3.55 (2H, m), 3.46-3.27 (2H, m), 2.95-2.88 (1H, m), 1.32 (9H, s), 0.95-0.88 (2H, m), 0.00 (9H, s).

Step 2—3-[4-(3,3-dimethylbutyl)-1-(2-trimethylsilylethoxymethyl)imidazol-2-yl]chroman-6-ol 3-[4-(3,3-dimethylbut-1-ynyl)-1-(2-trimethylsilylethoxymethyl)imidazol-2-yl]chroman-6-ol (233. mg, 0.55 mmol) was stirred in MeOH (10 mL) at room temperature under a nitrogen atmosphere followed by the addition of palladium, 10 wt. % on carbon powder, dry (30 mg). The reaction was fitted with a $H_2$ balloon and subjected to 3×vacuum/$H_2$ cycles and then left to stir under a $H_2$ atmosphere for 18 hours. The crude was filtered over celite, which was washed with MeOH (10 mL) and the filtrate concentrated in vacuo to give 3-[4-(3,3-dimethylbutyl)-1-(2-trimethylsilylethoxymethyl)imidazol-2-yl]chroman-6-ol (170 mg, 0.39 mmol, 72% yield) as a yellow solid. The compound was used in the next step without further purification. UPLC-MS (ES+, short acidic): 1.76 min, m/z 431.9 [M+H]$^+$. $^1$H NMR (400 MHz, CDCl$_3$) δ/ppm: 6.77 (1H, s), 6.67 (1H, d, J=8.8 Hz), 6.61 (1H, dd, J=8.8 Hz, 2.4 Hz), 6.56 (1H, d, J=2.4 Hz), 5.24-5.18 (2H, m), 4.33-4.27 (1H, m), 4.05 (1H, t, J=10.8 Hz), 3.57-3.52 (2H, m), 3.43-3.36 (1H, m), 3.30-3.21 (1H, m), 2.86-2.79 (1H, m), 2.57-2.51 (2H, m), 1.59-1.53 (2H, m), 0.97 (9H, s), 0.96-0.91 (2H, m), 0.00 (9H, s). Exchangeable proton not seen.

Step 3—5-[3-[4-(3,3-dimethylbutyl)-1-(2-trimethylsilylethoxymethyl)imidazol-2-yl]chroman-6-yl]oxy-3,4-dihydro-1H-1,8-naphthyridin-2-one Potassium tert-butoxide (132.9 mg, 1.18 mmol) was added to a stirred solution of 5-fluoro-3,4-dihydro-1H-1,8-naphthyridin-2-one (65.6 mg, 0.39 mmol), 3-[4-(3,3-dimethylbutyl)-1-(2-trimethylsilylethoxymethyl)imidazol-2-yl]chroman-6-ol (170 mg, 0.39 mmol) and DMF (2 mL) at room temperature under a nitrogen atmosphere in a sealable vial. The vial was sealed and the reaction was heated to 80° C. and stirred for 72 hours. The reaction was cooled to room temperature and solvent removed in vacuo. The residue was partitioned between water (20 mL) and DCM (20 mL). The organic layer was separated, passed through a phase separator and solvent removed in vacuo. The residue was purified by column chromatography using as eluent a gradient of 0-5% MeOH in DCM to give 5-[3-[4-(3,3-dimethylbutyl)-1-(2-trimethylsilylethoxymethyl)imidazol-2-yl]chroman-6-yl]oxy-3,4-dihydro-1H-1,8-naphthyridin-2-one (116 mg, 0.20 mmol, 51% yield) as a yellow solid. UPLCMS (ES+, short acidic): 1.76 min, m/z 577.5 [M+H]$^+$.

Step 4—5-[3-[4-(3,3-dimethylbutyl)-1H-imidazol-2-yl]chroman-6-yl]oxy-3,4-dihydro-1H-1,8-naphthyridin-2-one Trifluoroacetic acid (0.5 mL, 6.53 mmol) was added to a stirred solution of 5-[3-[4-(3,3-dimethylbutyl)-1-(2-trimethylsilylethoxymethyl)imidazol-2-yl]chroman-6-yl]oxy-3,4-dihydro-1H-1,8-naphthyridin-2-one (116 mg, 0.20 mmol) and DCM (2 mL) in a sealable vial at room temperature under a nitrogen atmosphere. The vial was sealed and the reaction was heated to 40° C. and stirred for 18 hours. After this time the reaction was cooled to room temperature and solvent removed in vacuo and the residue loaded on to an SCX-2 column using the minimum amount of MeOH. MeOH (10 mL) was passed through the column followed by $NH_3$ in MeOH (10 mL) to elute the product. Product containing fractions were concentrated in vacuo and the residue purified by column chromatography using an eluent of 0-5% MeOH in DCM to give 5-[3-[4-(3,3-dimethylbutyl)-1H-imidazol-2-yl]chroman-6-yl]oxy-3,4-dihydro-1H-1,8-naphthyridin-2-one (10 mg, 0.022 mmol, 11% yield) as a white solid. UPLC-MS (ES+, final purity): 2.94 min, m/z 447.2 [M+H]$^+$. $^1$H NMR (400 MHz, DMSO-d$_6$) δ/ppm: 11.67 (0.5H, s), 11.58 (0.5H, s), 10.45 (1H, s), 7.95 (1H, d, J=5.6 Hz), 6.99-6.97 (1H, m), 6.93-6.85 (2H, m), 6.76 (0.5H, s), 6.49 (0.5H, s), 6.26 (1H, d, J=5.6 Hz), 4.46-4.40 (1H, m), 4.02 (1H, t, J=10.8 Hz), 3.29-3.23 (1H, m), 3.18-3.10 (1H, m), 3.06-2.99 (1H, m), 2.93 (2H, t, J=7.2 Hz), 2.55-2.50 (2H, m, (under DMSO)), 2.44-2.36 (2H, m), 1.50-1.43 (2H, m), 0.93-0.91 (9H, m).

Example 23. Synthesis of 5-[3-[3-[2-(trifluoromethyl)phenyl]-1H-pyrazol-5-yl]chroman-6-yl]oxy-3,4-dihydro-1H-1,8-naphthyridin-2-one (Compound 35)

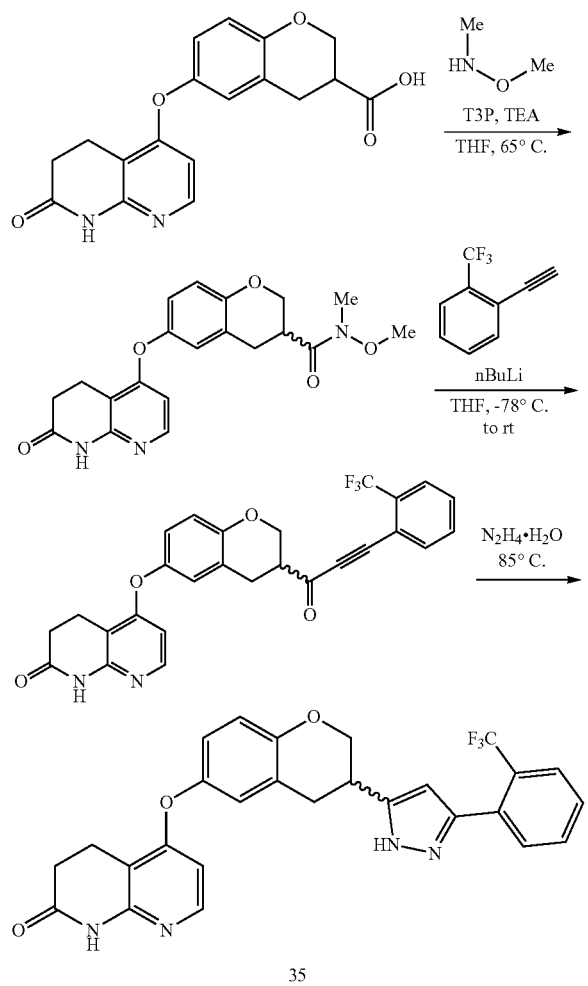

35

Step 1—N-methoxy-N-methyl-6-[(7-oxo-6,8-dihydro-5H-1,8-naphthyridin-4-yl)oxy]chromane-3-carboxamide Propylphosphonic anhydride (50% in EtOAc-1.31 mL, 2.2 mmol) was added to a stirred solution of 6-[(7-oxo-6,8-dihydro-5H-1,8-naphthyridin-4-yl)oxy]chromane-3-carboxylic acid (500 mg, 1.47 mmol), N,O-dimethylhydroxylamine hydrochloride (158 mg, 1.62 mmol), triethylamine (0.31 mL, 2.2 mmol) and THF (100 mL) at rt under a nitrogen atmosphere. The reaction was heated to 65° C. and stirred for 18 hours, then cooled to rt and solvent removed in vacuo. The residue was partitioned between water (100 mL) and DCM (100 mL). The organic layer was separated, dried over Na$_2$SO$_4$, filtered and solvent removed in vacuo. The crude was purified by column chromatography using an eluent of 0-100% EtOAc in petroleum ether to give N-methoxy-N-methyl-6-[(7-oxo-6,8-dihydro-5H-1,8-naphthyridin-4-yl)oxy]chromane-3-carboxamide (337 mg, 0.88 mmol, 60% yield) as a white solid. UPLC-MS (ES+, short acidic): 1.39 min, m/z 384.3 [M+H]$^+$. $^1$H NMR (400 MHz, CDCl$_3$) δ/ppm: 8.13 (1H, s), 7.99 (1H, d, J=6.0 Hz), 6.92-6.89 (1H, m), 6.87-6.83 (2H, m), 6.32 (1H, d, J=6.0 Hz), 4.48-4.43 (1H, m), 4.06 (1H, t, J=10.4 Hz), 3.79 (3H, s), 3.45-3.35 (1H, m), 3.26 (3H, s), 3.23-3.14 (1H, m), 3.08 (2H, t, J=7.2 Hz), 2.93-2.86 (1H, m), 2.72 (2H, t, J=7.2 Hz).

Step 2—5-[3-[3-[2-(trifluoromethyl)phenyl]prop-2-ynoyl]chroman-6-yl]oxy-3,4-dihydro-1H-1,8-naphthyridin-2-one n-Butyllithium solution (2.5M in hexane—0.35 mL, 0.88 mmol) was added dropwise to a stirred solution of 2-ethynyl-α,α,α-trifluorotoluene (0.12 mL, 0.88 mmol) in THF (20 mL) at −78° C. under a nitrogen atmosphere. After stirring for 30 minutes a solution of N-methoxy-N-methyl-6-[(7-oxo-6,8-dihydro-5H-1,8-naphthyridin-4-yl)oxy]chromane-3-carboxamide (168 mg, 0.44 mmol) in THF (10 mL) was slowly added and the resultant reaction allowed to stir at −78° C. for 1 hour, after which time it was warmed to rt and quenched with sat. aq. NH$_4$Cl (100 mL). This mixture was extracted with EtOAc (2×50 mL), the combined organic layers dried over Na$_2$SO$_4$, filtered and solvent removed in vacuo. The residue was purified by column chromatography using an eluent of 0-5% MeOH in DCM to give 5-[3-[3-[2-(trifluoromethyl)phenyl]prop-2-ynoyl]chroman-6-yl]oxy-3,4-dihydro-1H-1,8-naphthyridin-2-one (163 mg, 0.33 mmol, 76% yield) as a yellow solid. UPLC-MS (ES+, short acidic): 1.85 min, m/z 493.3 [M+H]$^+$. $^1$H NMR (400 MHz, CDCl$_3$) δ/ppm: 8.00 (1H, s), 7.97 (1H, d, J=6.0 Hz), 7.81-7.77 (2H, m), 7.65-7.62 (2H, m), 6.92-6.83 (3H, m), 6.32 (1H, d, J=5.6 Hz), 4.62-4.57 (1H, m), 4.46-4.40 (1H, m), 3.33-3.24 (2H, m), 3.16-3.11 (1H, m), 3.08 (2H, t, J=8.0 Hz), 2.72 (2H, t, J=8.0 Hz).

Step 3—5-[3-[3-[2-(trifluoromethyl)phenyl]-1H-pyrazol-5-yl]chroman-6-yl]oxy-3,4-dihydro-1H-1,8-naphthyridin-2-one Hydrazine Hydrate (0.03 mL, 0.66 mmol) was added to a stirred solution of 5-[3-[3-[2-(trifluoromethyl)phenyl]prop-2-ynoyl]chroman-6-yl]oxy-3,4-dihydro-1H-1,8-naphthyridin-2-one (163. mg, 0.3300 mmol) and t-BuOH (2 mL) at rt. The reaction was heated to 85° C. for 1 hour, after which time it was poured into sat. aq. NH$_4$Cl (100 mL) and extracted with DCM (2×50 mL). The combined organic layers were dried over Na$_2$SO$_4$, filtered and solvent removed in vacuo. The residue was purified by column chromatography using an eluent of 0-5% MeOH in DCM to give 5-[3-[3-[2-(trifluoromethyl)phenyl]-1H-pyrazol-5-yl]chroman-6-yl]oxy-3,4-dihydro-1H-1,8-naphthyridin-2-one (112 mg, 0.22 mmol, 67% yield) as a white solid. UPLC-MS (ES+, final purity): 3.94 min, m/z 507.3 [M+H]$^+$. $^1$H NMR (400 MHz, DMSO-d$_6$) δ/ppm: 13.05 (0.6H, s), 13.00 (0.4H, s), 10.46 (1H, s), 7.95 (1H, d, J=5.6 Hz), 7.90-7.54 (4H, br m), 7.01-6.98 (1H, m), 6.95-6.86 (2H, m), 6.39-6.33 (1H, m), 6.28-6.23 (1H, m), 4.50-4.41 (1H, in), 4.19-4.04 (1H, in), 3.52-3.42 (1H, in), 3.21-3.01 (2H, in), 2.93 (2H, t, J=7.6 Hz), 2.54 (2H, t, J=7.6 Hz).

The compounds in the table below were made in an analogous manner to Example 23, using the appropriate arylacetylene in place of 2-ethynyl-α,α,α-trifluorotoluene in step 2:

| Comp. No | Structure and Name | Data |
|---|---|---|
| 38 | 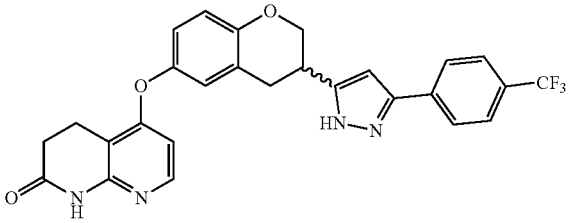<br>5-[3-[4-(p-tolyl)-1H-imidazol-2-yl]chroman-6-yl]oxy-3,4-dihydro-1H-1,8-naphthyridin-2-one | UPLC-MS (ES+, final purity): 4.13 min, m/z 507.3 [M + H]+. 1H NMR (400 MHz, DMSO-d6) δ/ppm: 13.37 (0.3H, s), 13.09 (0.7H, s), 10.47 (1H, s), 8.04-7.92 (3H, m), 7.86-7.72 (2H, m), 7.01-6.73 (4H, m), 6.27 (1H, d, J = 6.0 Hz), 4.50-4.42 (1H, m), 4.19-4.08 (1H, m), 3.50-3.39 (1H, m), 3.22-3.05 (2H, m), 2.93 (2H, t, J = 7.2 Hz), 2.54 (2H, t, J = 7.2 Hz). |
| 41 | 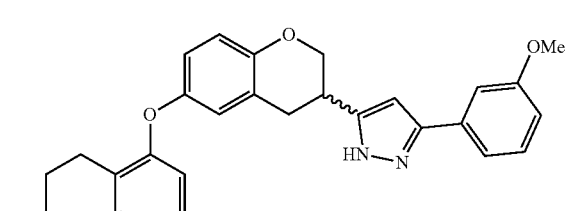<br>5-[3-[3-(3-methoxyphenyl)-1H-pyrazol-5-yl]chroman-6-yl]oxy-3,4-dihydro-1H-1,8-naphthyridin-2-one | UPLC-MS (ES+, final purity): 3.72 min, m/z 469.2 [M + H]+. 1H NMR (400 MHz, DMSO-d6) δ/ppm: 13.11-12-85 (1H, m), 10.47 (1H, s), 7.99-7.93 (1H, m), 7.39-7.26 (2.5H, m), 7.01-6.80 (4H, m), 6.71-7.61 (1H, m), 6.30-6.23 (1H, m), 5.85 (0.5H, s), 4.50-4.31 (1H, m), 4.18-4.04 (1H, m), 3.84-3.77 (3H, m), 3.48-3.38 (1H, m), 3.17-3.06 (2H, m), 2.93 (2H, t, J = 7.6 Hz), 2.59-2.53 (2H, m, (partly under DMSO peak)). |
| 40 | 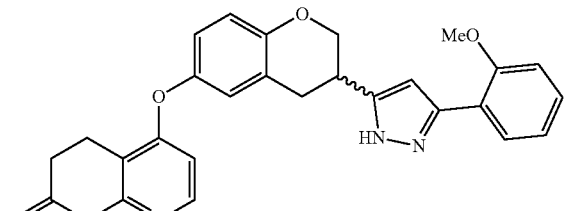<br>5-[3-[3-(2-methoxyphenyl)-1H-pyrazol-5-yl]chroman-6-yl]oxy-3,4-dihydro-1H-1,8-naphthyridin-2-one | UPLC-MS (ES+, final purity): 3.80 min, m/z 469.3 [M + H]+. 1H NMR (400 MHz, DMSO-d6) δ/ppm: 12.89-12.72 (1H, m), 10.46 (1H, s), 7.95 (1H, d, J = 5.6 Hz), 7.90-7.86 (0.2H, m), 7.70-7.62 (0.8 Hz, m), 7.38-7.25 (1H, m), 7.17-6.86 (5H, m), 6.68-6.60 (1H, m), 6.26 (1H, d, J = 5.6 Hz), 4.50 (1H, m), 4.15-4.05 (1H, m), 3.91-3.81 (3H, m), 3.45-3.36 (1H, m), 3.16-3.06 (2H, m), 2.93 (2H, t, J = 8.0 Hz), 2.93 (2H, t, J = 8.0 Hz, partly under DMSO)). |
| 43 | 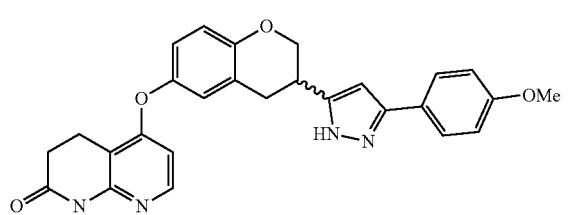<br>5-[3-[3-(4-methoxyphenyl)-1H-pyrazol-5-yl]chroman-6-yl]oxy-3,4-dihydro-1H-1,8-naphthyridin-2-one | UPLC-MS (ES+, final purity): 3.67 min, m/z 469.3 [M + H]+. 1H NMR (400 MHz, DMSO-d6) δ/ppm: 12.96 (0.5H, s), 12.72 (0.5H, s), 10.46 (1H, s), 7.96 (1H, d, J = 5.6 Hz), 7.73-7.61 (2H, m), 7.05-6.85 (5H, m), 6.57-6.50 (1H, m), 6.27 (1H, d, J = 5.6 Hz), 4.49-4.40 (1H, m), 4.16-4.04 (1H, m), 3.82-3.75 (3H, m), 3.45-3.37 (1H, m), 3.18-3.06 (2H, m), 2.93 (2H, t, J = 7.6 Hz), 2.53 (2H, t, J = 7.6 Hz, (partly under DMSO)). |
| 36 | 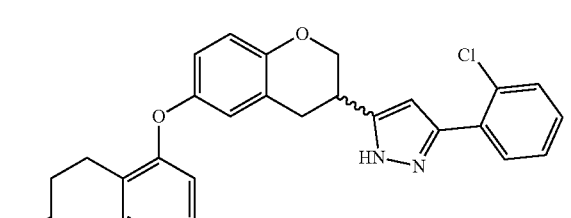<br>5-[3-[3-(2-chlorophenyl)-1H-pyrazol-5-yl]chroman-6-yl]oxy-3,4-dihydro-1H-1,8-naphthyridin-2-one | UPLC-MS (ES+, final purity): 3.88 min, m/z 473.2, 475.2 [M + H]+. 1H NMR (400 MHz, DMSO-d6) δ/ppm: 13.06 (1H, m), 10.47 (1H, m), 7.95 (1H, d, J = 6.0 Hz), 7.80-7.31 (4H, m), 7.01-6.98 (1H, m), 6.96-6.86 (2H, m), 6.64 (1H, s), 6.28-6.24 (1H, m), 4.52-4.42 (1H, m), 4.21-4.07 (1H, m), 3.53-3.35 (1H, m), 3.19-3.06 (2H, m), 2.94 (2H, t, J = 8.0 Hz), 2.57-2.53 (2H, m, (under DMSO peak)). |

| Comp. No | Structure and Name | Data |
|---|---|---|
| 37 | 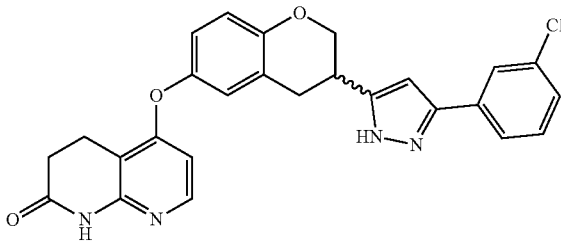<br>5-[3-[3-(3-chlorophenyl)-1H-pyrazol-5-yl]chroman-6-yl]oxy-3,4-dihydro-1H-1,8-naphthyridin-2-one | UPLC-MS (ES+, final purity): 4.00 min, m/z 473.2, 475.2 [M + H]+. 1H NMR (400 MHz, DMSO-d6) δ/ppm: 13.23 (0.4H, s), 13.00 (0.6H, s), 10.47 (1H, s), 7.96 (1H, d, J = 5.6 Hz), 7.84-7.67 (2H, m), 7.51-7.32 (2H, m), 7.00-6.97 (1H, m), 6.95-6.86 (2H, m), 6.80-6.70 (1H, m), 6.26 (1H, d, J = 5.6 Hz), 4.49-4.41 (1H, m), 4.18-4.05 (1H, m), 3.48-3.36 (1H, m), 3.17-3.05 (2H, m), 2.93 (2H, t, J = 7.6 Hz), 2.53 (2H, t, J = 7.6 Hz, (partly under DMSO)). |
| 39 | 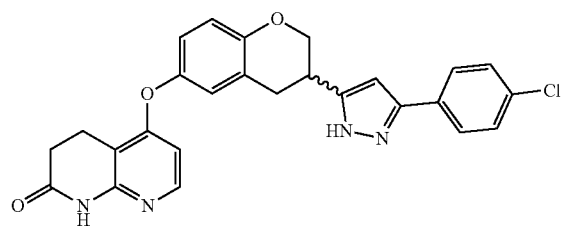<br>5-[3-[3-(4-chlorophenyl)-1H-pyrazol-5-yl]chroman-6-yl]oxy-3,4-dihydro-1H-1,8-naphthyridin-2-one | UPLC-MS (ES+, final purity): 4.01 min, m/z 473.2, 475.2 [M + H]+. 1H NMR (400 MHz, DMSO-d6) δ/ppm: 13.19 (0.4H, s), 12.94 (0.6H, s), 10.47 (1H, s), 7.96 (1H, d, J = 5.6 Hz), 7.82-7.71 (2H, m), 7.57-7.42 (2H, m), 7.00-6.97 (1H, m), 6.95-6.86 (2H, m), 6.73-6.62 (1H, m), 6.26 (1H, d, J = 5.6 Hz), 4.48-4.41 (1H, m), 4.19-4.05 (1H, m), 3.49-3.38 (1H, m), 3.19-3.05 (2H, m), 2.93 (2H, t, J = 7.6 Hz), 2.53 (2H, t, J = 7.6 Hz, (partly under DMSO)). |
| 42 | 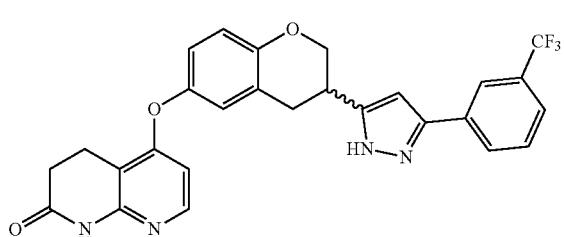<br>5-[3-[3-[3-(trifluoromethyl)phenyl]-1H-pyrazol-5-yl]chroman-6-yl]-oxy-3,4-dihydro-1H-1,8-naphthyridin-2-one | UPLC-MS (ES+, final purity): 4.11 min, m/z 507.3 [M + H]+. 1H NMR (400 MHz, DMSO-d6,) δ/ppm: 13.33 (0.3H, s), 13.05 (0.7H, s), 10.47 (1H, s), 8.13-8.00 (2H, m), 7.96 (1H, d, J = 5.6 Hz), 7.72-7.62 (2H, m), 7.01-6.98 (1H, m), 6.96-6.86 (2.3H, m), 6.81-6.78 (0.7H, m), 6.26 (1H, d, J = 5.6 Hz), 4.50-4.43 (1H, m), 4.18-4.06 (1H, m), 3.48-3.35 (1H, m), 3.18-3.06 (2H, m), 2.93 (2H, t, J = 7.6 Hz), 2.53 (2H, t, J = 7.6 Hz, (partly under DMSO peak)). |

Example 24. Synthesis of 5-[3-[6-(trifluoromethyl)-1H-benzimidazol-2-yl]chroman-6-yl]oxy-3,4-dihydro-1H-1,8-naphthyridin-2-one (Compound 22)

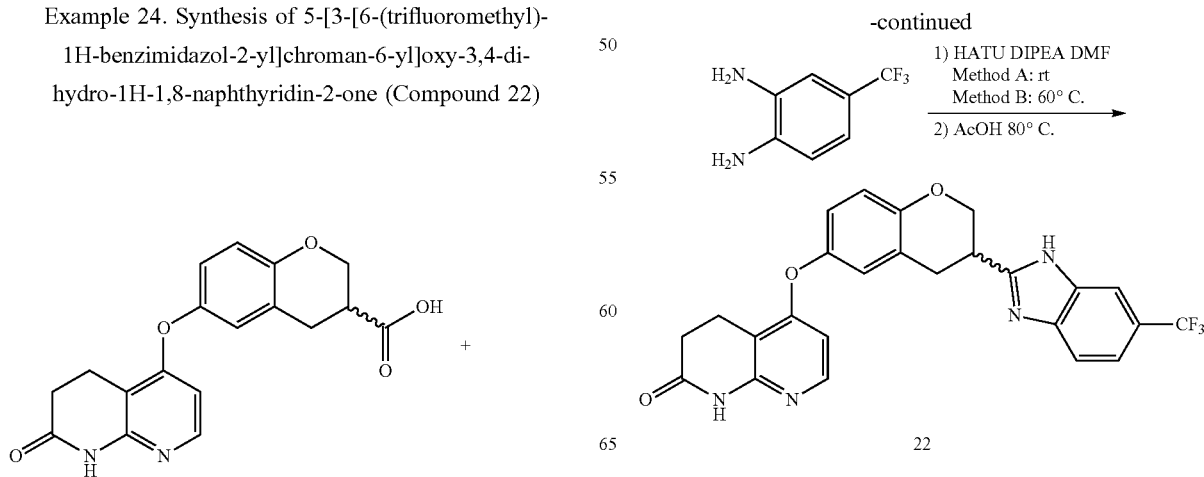

2-(7-Aza-1H-benzotriazole-1-yl)-1,1,3,3-tetramethyluronium hexafluorophosphate (HATU) (246 mg, 0.65 mmol) was added to a stirred solution of 6-[(7-oxo-6,8-dihydro-5H-1,8-naphthyridin-4-yl)oxy]chromane-3-carboxylic acid (200 mg, 0.59 mmol), 3,4-diaminobenzotrifluoride (114 mg, 0.65 mmol), DIPEA (0.31 mL, 1.76 mmol) and DMF (3 mL) at rt under a nitrogen atmosphere and stirred for 1 hour. Solvent was removed in vacuo and the residue partitioned between water (50 mL) and DCM (50 mL). The organic layer was separated, dried over Na$_2$SO$_4$, filtered and solvent removed in vacuo. The residue was then stirred at 80° C. in acetic acid (3 mL) for 18 hours, after which time the reaction was cooled to rt and solvent removed in vacuo. The residue was partitioned between sat. aq. NaHCO$_3$ (100 mL) and DCM (100 mL) and the organic layer separated, dried over Na$_2$SO$_4$, filtered and concentrated in vacuo. The residue was purified by column chromatography using an eluent of 0-5% MeOH in DCM to give 5-[3-[6-(trifluoromethyl)-1H-benzimidazol-2-yl]chroman-6-yl]oxy-3,4-dihydro-1H-1,8-naphthyridin-2-one (75 mg, 0.16 mmol, 26% yield) as a white solid. UPLC-MS (ES+, final purity): 3.41 min, m/z 481.2 [M+H]$^+$. $^1$H NMR (400 MHz, DMSO-d$_6$) δ/ppm: 12.92 (1H, br s), 10.48 (1H, s), 7.95 (1H, d, J=9.2 Hz), 7.89-7.76 (1H, m), 7.76-7.70 (1H, m), 7.50 (1H, d, J=8.8 Hz), 7.06-7.03 (1H, m), 6.93 (1H, dd, J=9.2 Hz, 2.8 Hz), 6.89 (1H, d, 8.8 Hz), 6.27 (1H, d, J=6.0 Hz), 4.65 (1H, m), 4.33 (1H, t, J=9.2 Hz), 3.71-3.62 (1H, m), 3.38-3.22 (2H, m), 2.93 (2H, t, J=8.4 Hz), 2.53 (2H, t, J=8.4 Hz, (partly under DMSO)).

The compounds in the table below were made in an analogous manner, using the appropriate diamine (either commercially available or synthesised) in place of 3,4-diaminobenzotrifluoride:

| Comp. No | Structure and Name | Data |
|---|---|---|
| 23 | 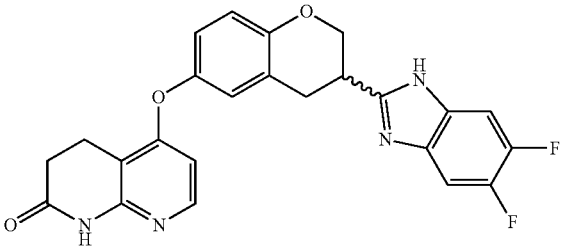  5-[3-(5,6-difluoro-1H-benzimidazol-2-yl)chroman-6-yl]oxy-3,4-dihydro-1H-1,8-naphthyridin-2-one  Method A | UPLC-MS (ES+, final purity): 3.17 min, m/z 449.2 [M + H]$^+$. $^1$H NMR (400 MHz, DMSO-d$_6$) δ/ppm: 12.68 (1H, s), 10.47 (1H, s), 7.96 (1H, d, J = 6.0 Hz), 7.68-7.53 (2H, m), 7.02 (1H, d, J = 2.8 Hz), 6.92 (1H, dd, J = 8.4 Hz, 2.4 Hz), 6.88 (1H, d, J = 8.4 Hz), 6.26 (1H, d, J = 6.0 Hz), 4.61-4.56 (1H, m), 4.27 (1H, dd, J = 11.2 Hz, 9.6 Hz), 3.63-3.55 (1H, m), 3.30-3.17 (2H, m), 2.93 (2H, t, J = 7.6 Hz), 2.53 (2H, t, J = 7.6 Hz, (partly under DMSO)). |
| 24 | 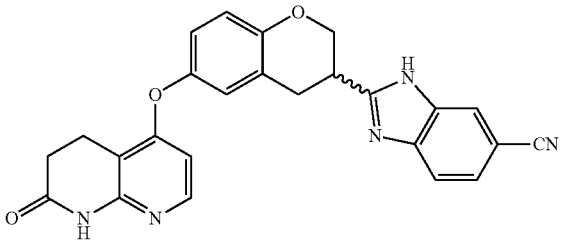  2-[6-[(7-oxo-6,8-dihydro-5H-1,8-naphthyridin-4-yl)oxy]chroman-3-yl]-3H-benzimidazole-5-carbonitrile  Method A | UPLC-MS (ES+, final purity): 3.11 min, m/z, 438.3 [M + H]$^+$. $^1$H NMR (400 MHz, DMSO-d$_6$) δ/ppm: 13.02 (1H, s), 10.47 (1H, s), 8.10 (1H, s), 7.97 (1H, d, J = 5.6 Hz), 7.70 (1H, d, J = 8.4 Hz), 7.57 (1H, dd, J = 8.4 Hz, 1.6 Hz), 7.04 (1H, d, 2.8 Hz), 6.93 (1H, dd, J = 8.4 Hz, 2.4 Hz), 6.89 (1H, d, J = 8.4 Hz), 6.27 (1H, d, 5.6 Hz), 4.64 (1H, m), 4.32 (1H, dd, J = 10.8 Hz, 8.8 Hz), 3.71-3.63 (1H, m), 3.31-3.21 (2H, m), 2.94 (2H, t, J = 8.0 Hz), 2.54 (2H, t, J = 8.0 Hz, (partly under DMSO)). |
| 25 | 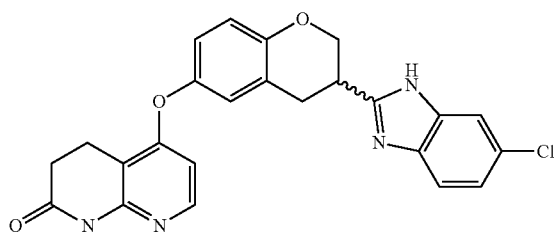  5-[3-(6-chloro-1H-benzimidazol-2-yl)chroman-6-yl]oxy-3,4-dihydro-1H-1,8-naphthyridin-2-one  Method A | UPLC-MS (ES+, final purity): 3.13 min, m/z 447.2, 449.2 [M + H]$^+$. $^1$H NMR (400 MHz, DMSO-d$_6$) δ/ppm: 12.66 (1H, br s), 10.48 (1H, s), 7.96 (1H, d, J = 5.6 Hz), 7.65-7.50 (2H, m), 7.23-7.17 (1H, m), 7.03 (1H, d, J = 2.8 Hz), 6.93 (1H, dd, J = 8.8 Hz, 2.4 Hz), 6.89 (1H, d, J = 8.8 Hz), 6.27 (1H, d, J = 5.6 Hz), 4.62-4.57 (1H, m), 4.28 (1H, dd, J = 11.2 Hz, 9.6 Hz), 3.65-3.55 (1H, m), 3.31-3.18 (2H, m), 2.94 (2H, t, J = 7.6 Hz), 2.54 (2H, t, J = 7.6 Hz, (partly under DMSO)). |

| Comp. No | Structure and Name | Data |
|---|---|---|
| 26 | 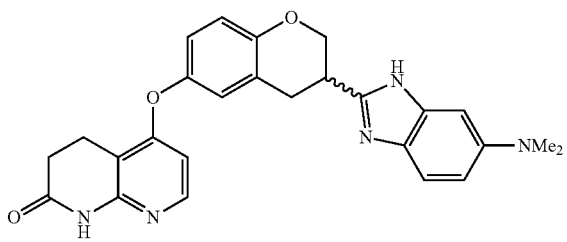<br>5-[3-[6-(dimethylamino)-1H-benzimidazol-2-yl]chroman-6-yl]oxy-3,4-dihydro-1H-1,8-naphthyridin-2-one<br>Method A | UPLC-MS (ES+, final purity): 2.52 min, m/z 456.3 [M + H]$^+$. $^1$H NMR (400 MHz, DMSO-$d_6$) δ/ppm: 12.14 (1H, br s), 10.47 (1H, s), 7.96 (1H, d, J = 5.2 Hz), 7.35 (1H, d, J = 8.8 Hz), 7.02 (1H, d, J = 2.8 Hz), 6.92 (1H, dd, J = 8.8 Hz, 2.8 Hz), 6.88 (1H, d, J = 8.8 Hz), 6.78-6.73 (2H, m), 6.27 (1H, d, J = 5.6 Hz), 4.59-4.54 (1H, m), 4.23 (1H, dd, J = 10.8 Hz, 9.6 Hz), 3.56-3.48 (1H, m), 3.30-3.15 (2H, m), 2.94 (2H, t, J = 7.2 Hz), 2.88 (6H, s), 2.54 (2H, t, J = 7.2 Hz, (partly under DMSO)). |
| 27 | 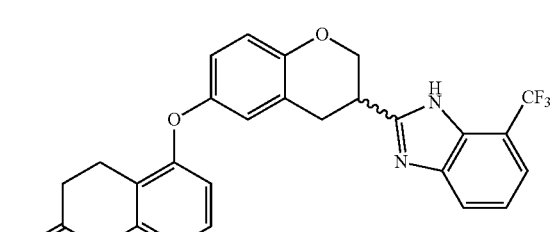<br>5-[3-[7-(trifluoromethyl)-1H-benzimidazol-2-yl]chroman-6-yl]-oxy-3,4-dihydro-1H-1,8-naphthyridin-2-one<br>Method A | UPLC-MS (ES+, final purity): 3.62 min, m/z 481.3 [M + H]$^+$. $^1$H NMR (400 MHz, DMSO-$d_6$) δ/ppm: 13.01-12.80 (1H, m), 10.48 (1H, s), 7.93-7.89 (1.4H, m), 7.82-7.78 (0.6H, m), 7.57-7.48 (1H, m), 7.38-7.32 (1H, m), 7.07-7.04 (1H, m), 6.96-6.90 (2H, m), 6.29-6.27 (1H, m), 4.66-4.59 (1H, m), 4.27 (1H, t, J = 10.4 Hz), 3.72-3.62 (1H, m), 3.40-3.35 (1H, m), 3.28-3.19 (1H, m), 2.94 (2H, t, J = 7.6 Hz), 2.56-2.53 (2H, m, (partly under DMSO)). |
| 29 | 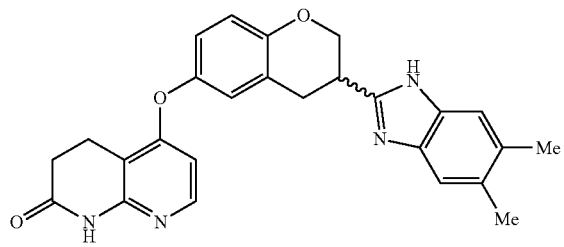<br>5-[3-(5,6-dimethyl-1H-benzimidazol-2-yl)chroman-6-yl]oxy-3,4-dihydro-1H-1,8-naphthyridin-2-one<br>Method A | UPLC-MS (ES+, final purity): 2.77 min, m/z 441.3 [M + H]$^+$. $^1$H NMR (400 MHz, DMSO-$d_6$) δ/ppm: 12.18 (1H, s), 10.47 (1H, s), 7.96 (1H, d, J = 6.0 Hz), 7.33 (1H, s), 7.24 (1H, s), 7.02 (1H, d, J = 8.0 Hz), 6.92 (1H, dd, J = 8.8 Hz, 2.8 Hz), 6.88 (1H, d, J = 8.8 Hz), 6.27 (1H, d, J = 6.4 Hz), 4.61-4.55 (1H, m), 4.24 (1H, t, J = 10.4 Hz), 3.57-3.49 (1H, m), 3.30-3.15 (2H, m), 2.94 (2H, t, J = 7.2 Hz), 2.54 (2H, t, J = 7.2 Hz, (partially under DMSO)), 2.31 (3H, s), 2.85 (3H, s). |
| 30 | 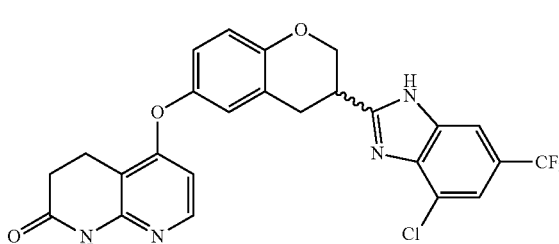<br>5-[3-[4-chloro-6-(trifluoromethyl-1H-benzimidazol-2-yl]chroman-6-yl]oxy-3,4-dihydro-1H-1,8-naphthyridin-2-one<br>Method B | UPLC-MS (ES+, final purity): 4.03 min, m/z 515.2 [M + H]$^+$. $^1$H-NMR (400 MHz, DMSO-$d_6$) δ/ppm: 13.29 (1H, br s), 10.47 (1H, s), 7.99-7.86 (2H, m), 7.66-7.58 (1H, m), 7.09-7.00 (1H, m), 6.96-6.87 (2H, m), 6.30-6.23 (1H, m), 4.66-4.58 (1H, m), 4.38-4.27 (1H, m), 3.74-3.64 (1H, m), 3.41-3.37 (1H, m (partly under water)), 3.28-3.19 (1H, m), 2.96-2.89 (2H, m), 2.56-2.53 (2H, m, (partly under DMSO)). |

| Comp. No | Structure and Name | Data |
|---|---|---|
| 31 | 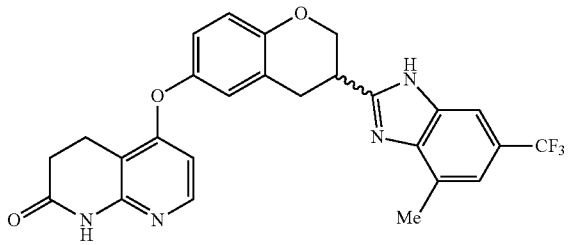<br>5-[3-[4-methyl-6-(trifluoromethyl)-1H-benzimidazol-2-yl]chroman-6-yl]oxy-3,4-dihydro-1H-1,8-naphthyridin-2-one<br>Method A | UPLC-MS (ES+, final purity): 3.69 min, m/z 495.3 [M + H]$^+$.<br>$^1$H-NMR (400 MHz, DMSO-d$_6$) δ/ppm: 12.81 (1H, br s), 10.46 (1H, s), 7.96 (1H, d, J = 5.6 Hz), 7.75 (0.6H, br s), 7.64 (0.4H, br s), 7.31 (1H, br s), 7.04 (1H, d, J = 2.4 Hz), 6.95-6.88 (2H, m), 6.27 (1H, d, J = 5.6 Hz), 4.68-4.55 (1H, m), 4.29 (1H, t, J = 10.0 Hz), 3.70-3.58 (1H, m), 3.40-3.35 (1H, m), 3.23 (1H, dd, J = 16.4 Hz, 5.6 Hz), 2.93 (2H, t, J = 7.6 Hz), 2.58 (3H, s), 2.53 (2H, t, J = 7.6 Hz, (partly under DMSO peak)). |
| 32 | 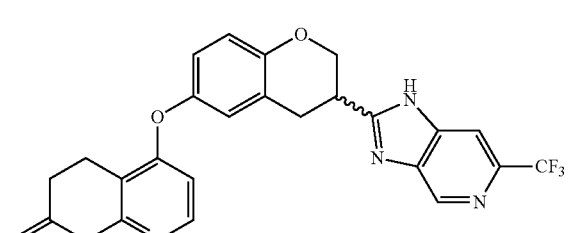<br>5-[3-[6-(trifluoromethyl)-1H-imidazo[4,5-c]pyridin-2-yl]chroman-6-yl]oxy-3,4-dihydro-1H-1,8-naphthyridin-2-one<br>Method A | UPLC-MS (ES+, final purity): 3.26 min, m/z 482.3 [M + H]$^+$.<br>$^1$H-NMR (400 MHz, DMSO-d$_6$) δ/ppm: 13.42 (1H, br s), 10.46 (1H, s), 8.98 (1H, s), 8.03 (1H, s), 7.96 (1H, d, J = 5.6 Hz), 7.04 (1H, d, J = 2.8 Hz), 6.93 (1H, dd, J = 8.8 Hz, 2.8 Hz), 6.89 (1H, d, J = 8.8 Hz), 6.27 (1H, d, J = 5.6 Hz), 4.65-4.59 (1H, m), 4.37-4.30 (1H, m), 3.75-3.66 (1H, m), 3.39-3.35 (1H, m, (partly under water)), 3.29-3.22 (1H, m), 2.93 (2H, t, J = 7.6 Hz), 2.56-2.53 (2H, m, (party under DMSO)). |
| 34 | 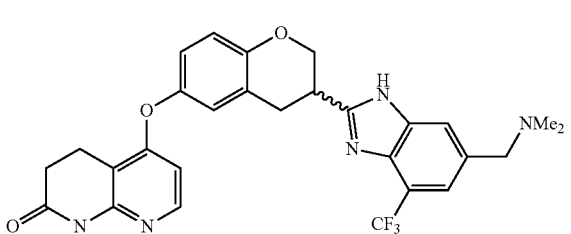<br>5-[3-[6-[(dimethylamino)methyl]-4-(trifluoromethyl)-1H-benzimidazol-2-yl]chroman-6-yl]oxy-3,4-dihydro-1H-1,8-naphthyridin-2-one<br>Method A | UPLC-MS (ES+, final purity): 2.72 min, m/z 538.2 [M + H]$^+$.<br>$^1$H-NMR (400 MHz, DMSO-d$_6$) δ/ppm: 12.93 (0.8H, s), 12.84 (0.2H, s), 10.46 (1H, s), 8.49 (0.2H, d, J = 4.4 Hz), 8.26 (0.2H, d, J = 8.0 Hz), 7.95 (0.8H, d, J = 6.0 Hz), 7.79 (0.2H, s), 7.69 (0.8H, s), 7.50 (0.2H, s), 7.45 (0.8H, s), 7.28 (0.2H, dd, J = 8.4 Hz, 4.4 Hz), 7.05 (0.8H, s), 6.96-6.86 (1.8H, m), 6.27 (0.8H, d, J = 5.6 Hz), 6.23 (0.2H, d, J = 6.0 Hz), 4.64-4.56 (1H, m), 2.46 (1H, t, J = 10.4 Hz), 3.71-3.60 (3H, m), 3.41-3.37 (1H, m (partly under water)), 3.26-3.18 (1H, m), 2.93 (2H, t, J = 7.6 Hz), 2.53 (2H, t, J = 7.6 Hz, (partly under DMSO)), 2.22 (6H, s). |
| 28 | 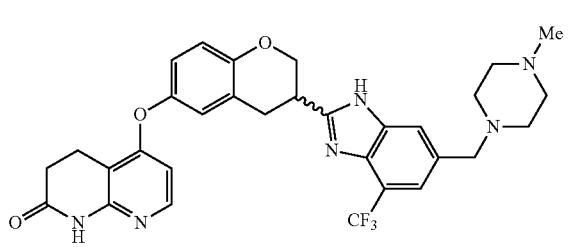<br>5-[3-[6-[(4-methylpiperazin-1-yl)methyl]-4-(trifluoromethyl)-1H-benzimidazol-2-yl]chroman-6-yl]oxy-3,4-dihydro-1H-1,8-naphthyridin-2-one<br>Method A | UPLC-MS (ES+, final purity): 2.75 min, m/z 593.4 [M + H]$^+$.<br>$^1$H-NMR (400 MHz, DMSO-d$_6$) δ/ppm: 12.89 (0.75H, br s), 12.81 (0.25H, br s), 10.46 (1H, s), 8.42 (0.25H, dd, J = 4.0 Hz, 1.2 Hz), 8.19 (0.25H, dd, J = 8.4 Hz, 1.2 Hz), 7.99-7.78 (0.75H, m), 7.81-7.58 (1H, m), 7.50-7.34 (1H, m), 7.22 (0.25H, dd, J = 8.4 Hz, 4.4 Hz), 7.04 (0.75H, s), 6.97-6.81 (1.75H, m), 6.27 (0.75H, d, J = 6.0 Hz), 6.23 (0.25H, d, J = 6.0 Hz), 4.64-4.57 (1H, m), 4.26 (1H, t, J = 10.0 Hz), 3.70-3.58 (3H, m), 3.41-3.37 (1H, m, (partly under water)), |

| Comp. No | Structure and Name | Data |
|---|---|---|
| | | 3.26-3.19 (1H, m), 2.93 (2H, t, J = 7.6 Hz), 2.55-2.53, (2H, m (partly under DMSO)), 2.46 (8H, br s), 2.19 (3H, s). |
| 33 | 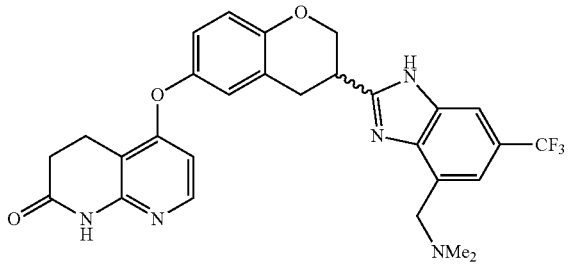<br>5-[3-[4-[(dimethylamino)methyl]-6-(trifluoromethyl)-1H-benzimidazol-2-yl]chroman-6-yl]oxy-3,4-dihydro-1H-1,8-naphthyridin-2-one<br>Method A | UPLC-MS (ES+, final purity): 2.79 min, m/z 538.4 [M + H]+. 1H-NMR (400 MHz, DMSO-d6) δ/ppm: 12.94 (0.3H, br s), 11.99 (0.7H, br s), 10.47 (1H, s), 7.96 (1H, d, J = 6.0 Hz), 7.83 (1H, br s), 7.45 (1H, br s), 7.04 (1H, d, J = 2.4 Hz), 6.95-6.88 (2H, m), 6.27 (1H, d, J = 6.0 Hz), 4.64-4.58 (1H, m), 4.28 (1H, t, J = 10.0 Hz), 3.80 (2H, br s), 3.73-3.62 (1H, m), 3.34 (1H, dd, J = 16.4 Hz, 10.0 Hz), 3.23 (1H, dd, J = 16.4 Hz, 5.6 Hz), 2.93 (2H, t, J = 7.6 Hz), 2.54 (2H, t, J = 7.6 Hz, (partly under DMSO)), 2.27 (6H, br s). |

Example 25. Synthesis of 5-[3-(3H-imidazo[4,5-c]pyridin-2-yl)chroman-6-yl]oxy-3,4-dihydro-1H-1,8-naphthyridin-2-one (Compound 134)

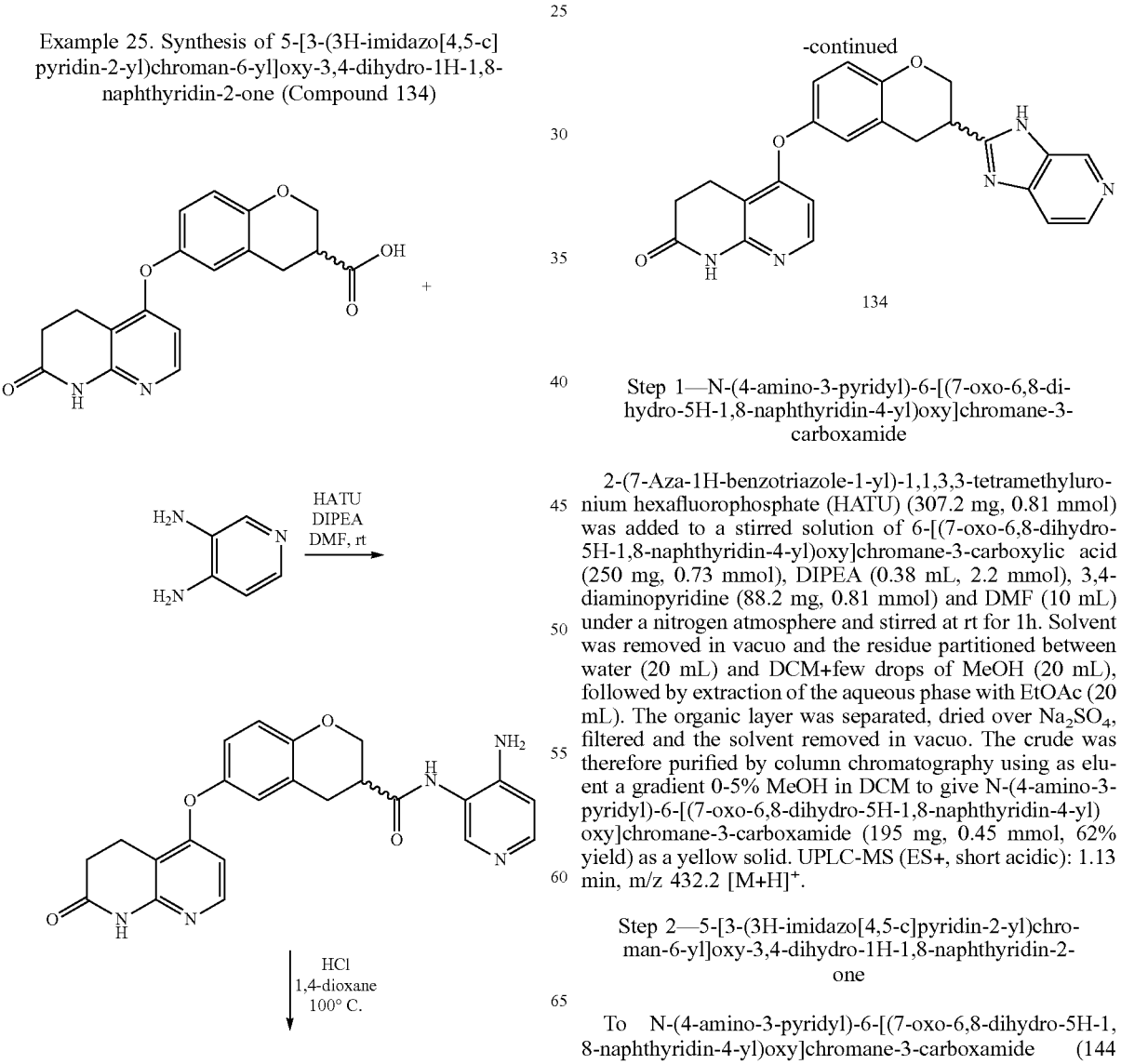

Step 1—N-(4-amino-3-pyridyl)-6-[(7-oxo-6,8-dihydro-5H-1,8-naphthyridin-4-yl)oxy]chromane-3-carboxamide 2-(7-Aza-1H-benzotriazole-1-yl)-1,1,3,3-tetramethyluronium hexafluorophosphate (HATU) (307.2 mg, 0.81 mmol) was added to a stirred solution of 6-[(7-oxo-6,8-dihydro-5H-1,8-naphthyridin-4-yl)oxy]chromane-3-carboxylic acid (250 mg, 0.73 mmol), DIPEA (0.38 mL, 2.2 mmol), 3,4-diaminopyridine (88.2 mg, 0.81 mmol) and DMF (10 mL) under a nitrogen atmosphere and stirred at rt for 1h. Solvent was removed in vacuo and the residue partitioned between water (20 mL) and DCM+few drops of MeOH (20 mL), followed by extraction of the aqueous phase with EtOAc (20 mL). The organic layer was separated, dried over Na$_2$SO$_4$, filtered and the solvent removed in vacuo. The crude was therefore purified by column chromatography using as eluent a gradient 0-5% MeOH in DCM to give N-(4-amino-3-pyridyl)-6-[(7-oxo-6,8-dihydro-5H-1,8-naphthyridin-4-yl)oxy]chromane-3-carboxamide (195 mg, 0.45 mmol, 62% yield) as a yellow solid. UPLC-MS (ES+, short acidic): 1.13 min, m/z 432.2 [M+H]+.

Step 2—5-[3-(3H-imidazo[4,5-c]pyridin-2-yl)chroman-6-yl]oxy-3,4-dihydro-1H-1,8-naphthyridin-2-one To N-(4-amino-3-pyridyl)-6-[(7-oxo-6,8-dihydro-5H-1,8-naphthyridin-4-yl)oxy]chromane-3-carboxamide (144 mg, 0.33 mmol) in 1,4-dioxane (3 mL) was added HCl (4M in dioxane—0.67 mL, 2.68 mmol) in a sealed vial. The reaction was irradiated at 100° C. for 2 hours, after which time the solvent was removed under reduce pressure. The reaction was quenched with sat. aq. NaHCO₃ and extracted with DCM+MeOH. The organic phase was dried over Na₂SO₄, filtered and the solvent removed in vacuo. The crude was purified by automated column chromatography using as eluent a gradient 0-12% MeOH in DCM to give 5-[3-(3H-imidazo[4,5-c]pyridin-2-yl)chroman-6-yl]oxy-3,4-dihydro-1H-1,8-naphthyridin-2-one (42.5 mg, 0.10 mmol, 31% yield) as a white solid. UPLC-MS (ES+, final purity): 2.30 min, m/z 414.2 [M+H]⁺. ¹H-NMR (400 MHz, DMSO-d₆) δ/ppm: 13.00-12.79 (1H, m), 10.47 (1H, s), 8.87 (1H, s), 8.28 (1H, d, J=5.2 Hz), 7.96 (1H, d, J=5.6 Hz), 7.61-7.50 (1H, m), 7.03 (1H, d, J=2.4 Hz), 6.95-6.87 (2H, m), 6.27 (1H, d, J=5.6 Hz), 4.64-4.58 (1H, m), 4.31 (1H, t, J=10.0 Hz), 3.70-3.60 (1H, m), 3.36-3.19 (2H, m, (partly under water)), 2.93 (2H, t, J=7.6 Hz), 2.53 (2H, t, 8.0 Hz, (partly under DMSO)).

Example 26. Synthesis of 5-[[2-(3-phenyl-1H-1,2,4-triazol-5-yl)-3,4-dihydro-1H-isoquinolin-7-yl]oxy]-3,4-dihydro-1H-1,8-naphthyridin-2-one hydrochloride (Compound 44)

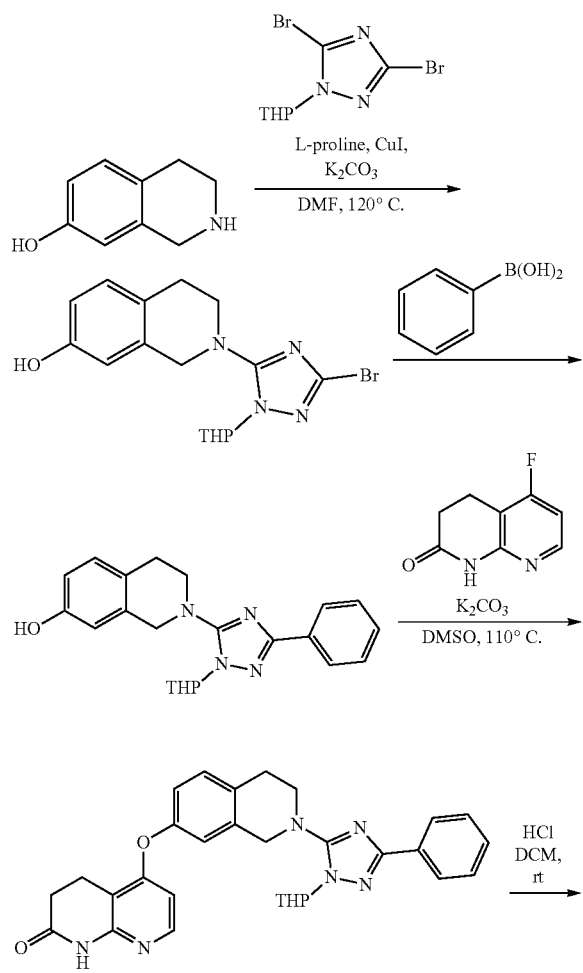

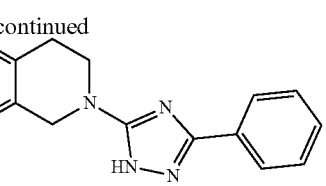

44

Step 1—2-(5-bromo-2-tetrahydropyran-2-yl-1,2,4-triazol-3-yl)-3,4-dihydro-1H-isoquinolin-7-ol 3,5-dibromo-1-tetrahydropyran-2-yl-1,2,4-triazole (1.042 g, 3.35 mmol), 1,2,3,4-tetrahydroisoquinolin-7-ol (500 mg, 3.35 mmol), L-proline (38.6 mg, 0.34 mmol), copper(I) iodide (63.8 mg, 0.34 mmol), K₂CO₃ (1.39 g, 10.05 mmol) and DMF (3 mL) were combined in a sealed and heated to 120° C. for 18 hours. The reaction was allowed to cool to rt, solvent removed in vacuo and the residue partitioned between water (100 mL) and DCM (100 mL). The organic layer was separated, dried over Na₂SO₄, filtered and solvent removed in vacuo. The residue was purified by column chromatography using an eluent of 0-100% EtOAc in petroleum ether to give 2-(5-bromo-2-tetrahydropyran-2-yl-1,2,4-triazol-3-yl)-3,4-dihydro-1H-isoquinolin-7-ol (508 mg, 1.34 mmol, 40% yield) as a brown solid. UPLC-MS (ES+, short acidic): 1.64 min, m/z 379.1, 381.1 [M+H]⁺.

Step 2—2-(5-phenyl-2-tetrahydropyran-2-yl-1,2,4-triazol-3-yl)-3,4-dihydro-1H-isoquinolin-7-ol

[1,1'-Bis(diphenylphosphino)ferrocene]Palladium(II) chloride dichloromethane complex (173.6 mg, 0.21 mmol) was added to a stirred mixture of 2-(5-bromo-2-tetrahydropyran-2-yl-1,2,4-triazol-3-yl)-3,4-dihydro-1H-isoquinolin-7-ol (806 mg, 2.13 mmol), phenylboronic acid (311 mg, 2.55 mmol), K₂CO₃ (881 mg, 6.38 mmol), 1,4-dioxane (9 mL) and water (1 mL) at rt under an inert atmosphere. The reaction was heated to 80° C. for 3 hours, after which time it was cooled to rt and solvent removed in vacuo. The residue was suspended in DCM (10 mL), filtered over celite, which was washed with DCM (10 mL). The residue was concentrated in vacuo and purified by column chromatography using an eluent of 0-100% EtOAc in petroleum ether to give 2-(5-phenyl-2-tetrahydropyran-2-yl-1,2,4-triazol-3-yl)-3,4-dihydro-1H-isoquinolin-7-ol (510 mg, 1.35 mmol, 64% yield) as a yellow solid. UPLC-MS (ES+, short acidic): 1.85 min, m/z 399.3 [M+Na]⁺, 293.2 [M-THP]⁺. ¹H NMR (400 MHz, DMSO-d₆) δ/ppm: 9.23 (1H, s), 7.98-7.93 (2H, m), 7.48-7.37 (3H, m), 6.98 (1H, d, 8.4 Hz), 6.61 (1H, dd, J=8.4 Hz, 2.8 Hz), 6.57 (1H, d, J=2.8 Hz), 5.31 (1H, dd, J=10.0 Hz, 2.0 Hz), 4.50-4.46 (1H, m), 4.35-4.31 (1H, m), 4.10-4.03 (1H, m), 3.72-3.64 (2H, m), 3.45-3.35 (1H, m), 3.10-3.01 (1H, m), 2.85-2.76 (1H, m), 2.06-1.95 (2H, m), 1.90-1.53 (4H, m).

Step 3—5-[[2-(5-phenyl-2-tetrahydropyran-2-yl-1,2,4-triazol-3-yl)-3,4-dihydro-1H-isoquinolin-7-yl]oxy]-3,4-dihydro-1H-1,8-naphthyridin-2-one 2-(5-Phenyl-2-tetrahydropyran-2-yl-1,2,4-triazol-3-yl)-3,4-dihydro-1H-isoquinolin-7-ol (510 mg, 1.35 mmol), 5-fluoro-3,4-dihydro-1H-1,8-naphthyridin-2-one (225.1 mg, 1.35 mmol), K$_2$CO$_3$ (936 mg, 6.77 mmol) and DMSO (10 mL) were combined in a sealed vial and stirred at 110° C. for 18 hours. The reaction was cooled to rt and the solvent removed in vacuo. The residue was purified by column chromatography using an eluent of 0-100% EtOAc in petroleum ether to give 5-[[2-(5-phenyl-2-tetrahydropyran-2-yl-1,2,4-triazol-3-yl)-3,4-dihydro-1H-isoquinolin-7-yl]oxy]-3,4-dihydro-1H-1,8-naphthyridin-2-one (192 mg, 0.37 mmol, 27% yield) as a yellow solid. UPLC-MS (ES+, short acidic): 1.92 min, m/z 523.3 [M+H]$^+$. $^1$H NMR (400 MHz, DMSO-d$_6$) δ/ppm: 10.56 (1H, s), 8.00-7.93 (2H, m), 7.48-7.39 (3H, m), 7.31-7.28 (1H, m), 7.03 (1H, dd, J=2.8 Hz), 6.99 (1H, dd, J=8.4 Hz, 2.8 Hz), 6.34 (1H, d, =5.6 Hz), 5.34 (1H, dd, J=10.0 Hz, 2.4 Hz), 4.56 (1H, d, J=16.0 Hz), 4.44 (1H, d, J=16.0 Hz), 4.08-4.00 (1H, m), 3.81-3.65 (2H, m), 3.50-3.42 (1H, m), 3.25-3.14 (1H, m), 3.00-2.88 (3H, m), 2.55-2.50 (3H, m), 1.90-1.54 (6H, m).

Step 4—5-[[2-(3-phenyl-1H-1,2,4-triazol-5-yl)-3,4-dihydro-1H-isoquinolin-7-yl]oxy]-3,4-dihydro-1H-1,8-naphthyridin-2-one hydrochloride HCl (4M in 1,4-dioxane—0.37 mL, 1.47 mmol) was added to 5-[[2-(5-phenyl-2-tetrahydropyran-2-yl-1,2,4-triazol-3-yl)-3,4-dihydro-1H-isoquinolin-7-yl]oxy]-3,4-dihydro-1H-1,8-naphthyridin-2-one (192. mg, 0.37 mmol) in DCM (10 mL) at rt under a nitrogen atmosphere and the reaction was stirred for 18 hours. Solvent was removed in vacuo and the residue purified by column chromatography using an eluent of 0-10% MeOH in DCM to give 5-[[2-(3-phenyl-1H-1,2,4-triazol-5-yl)-3,4-dihydro-1H-isoquinolin-7-yl]oxy]-3,4-dihydro-1H-1,8-naphthyridin-2-one hydrochloride (50 mg, 0.11 mmol, 29% yield) as a yellow solid. UPLC-MS (ES+, final purity): 3.39 min, m/z 439.2 [M+H]$^+$. $^1$H NMR (400 MHz, DMSO-d$_6$) δ/ppm: 10.63 (1H, s), 8.04-7.95 (3H, m), 7.52-7.44 (3H, m), 7.30 (1H, d, J=7.6 Hz), 7.05-6.99 (2H, m), 6.39 (1H, d, J=6.0 Hz), 4.72-4.67 (2H, m), 3.83-3.77 (2H, m), 2.99-2.91 (3H, m), 2.59-2.54 (3H, m). Broad peak at 5.4 ppm will include 1 exchangeable and HCl salt.

Example 27. Synthesis of 7-[(7-oxo-6,8-dihydro-5H-1,8-naphthyridin-4-yl)oxy]-N-phenyl-3,4-dihydro-1H-isoquinoline-2-carboxamide (Compound 46)

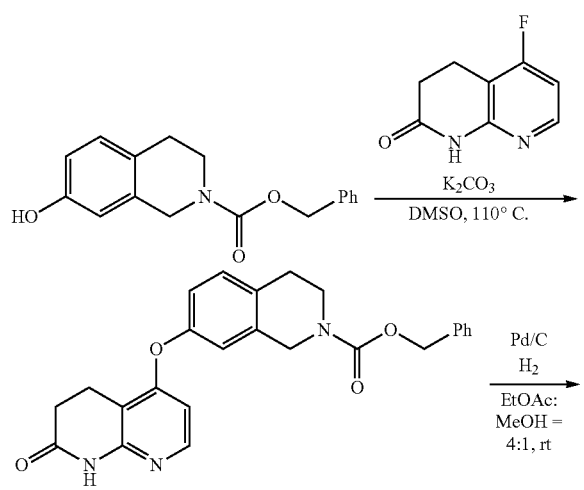

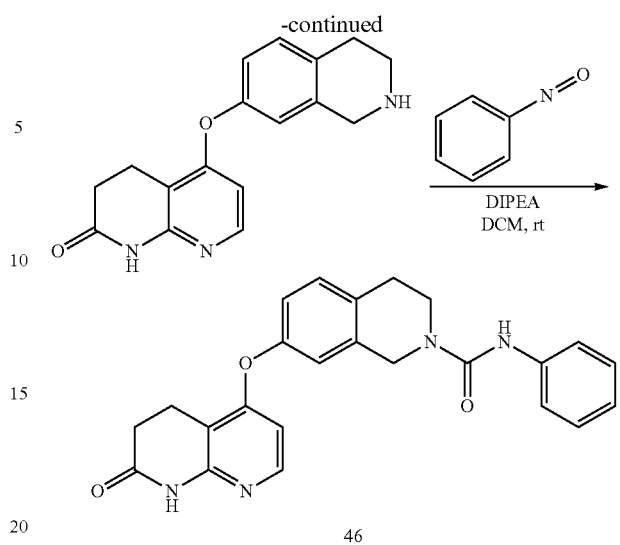

Step 1—benzyl 7-[(7-oxo-6,8-dihydro-5H-1,8-naphthyridin-4-yl)oxy]-3,4-dihydro-1H-isoquinoline-2-carboxylate Benzyl 7-hydroxy-3,4-dihydro-1H-isoquinoline-2-carboxylate (500 mg, 1.76 mmol), 5-fluoro-3,4-dihydro-1H-1,8-naphthyridin-2-one (0.29 g, 1.76 mmol) and K$_2$CO$_3$ (0.91 g, 6.55 mmol) were suspended in DMSO (50 mL) and heated to 110° C. 18 hours. The reaction was cooled to rt, carefully poured an aq. solution of citric acid (1.36 g, 7.06 mmol in 50 mL of H$_2$O), which caused fizzing, and left stirring for 1 hour. Water (200 mL) was added and the resulting mixture extracted with DCM (2×100 mL). The combined organic layers were dried over Na$_2$SO$_4$, filtered and solvent removed in vacuo. The residue was purified by column chromatography using an eluent of 0-75% EtOAc in petroleum ether to give benzyl 7-[(7-oxo-6,8-dihydro-5H-1,8-naphthyridin-4-yl)oxy]-3,4-dihydro-1H-isoquinoline-2-carboxylate (510 mg, 1.19 mmol, 67% yield) as a white solid. UPLC-MS (ES+, short acidic): 1.69 min, m/z 430.3 [M+H]$^+$. $^1$H NMR (400 MHz, DMSO-d$_6$) δ/ppm: 10.50 (1H, s), 7.97 (1H, d, J=5.6 Hz), 7.41-7.35 (5H, m), 7.25 (1H, d, J=8.4 Hz), 7.03 (1H, d, J=6.8 Hz), 6.96 (1H, dd, J=8.0 Hz, 2.4 Hz), 6.31 (1H, d, J=5.5 Hz), 5.13 (2H, s), 4.66-4.55 (2H, m), 3.70-3.62 (2H, m), 2.90 (2H, t, J=7.2 Hz), 2.82 (2H, J=5.6 Hz), 2.55-2.53 (2H, m (partly under DMSO)).

Step 2—5-(1,2,3,4-tetrahydroisoquinolin-7-yloxy)-3,4-dihydro-1H-1,8-naphthyridin-2-one Palladium, 10 wt. % on carbon powder, dry (50 mg) was added to a stirred solution of benzyl 7-[(7-oxo-6,8-dihydro-5H-1,8-naphthyridin-4-yl)oxy]-3,4-dihydro-1H-isoquinoline-2-carboxylate (510. mg, 1.19 mmol) in EtOAc (20 mL) and MeOH (5 mL) at rt under a nitrogen atmosphere. The reaction was fitted with a H$_2$ balloon and subjected to 3×vacuum/H$_2$ cycles and then left to stir under a H$_2$ atmosphere for 24 hours. The crude was filtered over celite, which was washed with MeOH (10 mL) and the filtrate concentrated in vacuo to give 5-(1,2,3,4-tetrahydroisoquinolin-7-yloxy)-3,4-dihydro-1H-1,8-naphthyridin-2-one (222 mg, 0.75 mmol, 63% yield) as a yellow solid. The product was used in the next step without further purification. UPLC-MS (ES+, short acidic): 0.91 min, m/z 296.2

[M+H]⁺. ¹H NMR (400 MHz, CDCl₃) a/ppm: 8.17 (1H, s), 7.99 (1H, d, J=6.0 Hz), 7.15 (1H, d, J=8.4 Hz), 6.86 (1H, dd, J=8.4 Hz, 2.8 Hz), 6.76 (1H, d, J=2.8 Hz), 6.34 (1H, d, J=6.0 Hz), 4.03 (2H, s), 3.18 (2H, t, J=6.0 Hz), 3.08 (2H, t, J=8.0 Hz), 2.83 (2H, t, J=6.0 Hz), 2.72 (2H, t, J=8.0 Hz). Exchangeable proton not seen.

Step 3—7-[(7-oxo-6,8-dihydro-5H-1,8-naphthyridin-4-yl)oxy]-N-phenyl-3,4-dihydro-1H-isoquinoline-2-carboxamide Phenyl isocyanate (0.02 mL, 0.19 mmol) was added to a stirred solution of 5-(1,2,3,4-tetrahydroisoquinolin-7-yloxy)-3,4-dihydro-1H-1,8-naphthyridin-2-one (50 mg, 0.17 mmol) and DIPEA (0.06 mL, 0.34 mmol) in DCM (5 mL) at rt under a nitrogen atmosphere. The reaction stirred for 1 hour, after which time it was diluted with water (20 mL) and DCM (15 mL). The organic layer was separated, passed through a phase separator and solvent removed in vacuo. The residue was purified by column chromatography using an eluent of 0-100% EtOAc in petroleum ether to give 7-[(7-oxo-6,8-dihydro-5H-1,8-naphthyridin-4-yl)oxy]-N-phenyl-3,4-dihydro-1H-isoquinoline-2-carboxamide (29 mg, 0.07 mmol, 41% yield) as a white solid. UPLC-MS (ES+, final purity): 3.35 min, m/z 415.3 [M+H]⁺. ¹H NMR (400 MHz, DMSO-d₆) δ/ppm: 10.51 (1H, s), 8.58 (1H, s), 7.98 (1H, d, J=5.6 Hz), 7.50-7.46 (2H, m), 7.30-7.22 (3H, m), 7.00-6.92 (3H, m), 6.34 (1H, d, J=5.6 Hz), 4.64 (2H, s), 3.73 (2H, t, J=6.0 Hz), 2.94-2.85 (4H, m), 2.55-2.53 (2H, m, (partly under DMSO peak)).

The compounds in the table below were made in an analogous manner, using the appropriate aryl isocyanate in place of phenyl isocyanate in step 3:

| Comp. No | Structure and Name | Data |
|---|---|---|
| 49 | 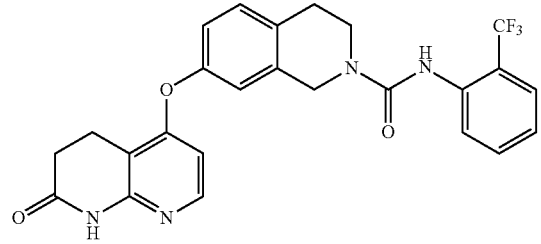<br>7-[(7-oxo-6,8-dihydro-5H-1,8-naphthyridin-4-yl)oxy]-N-[2-(trifluoromethyl)phenyl]-3,4-dihydro-1H-isoquinoline-2-carboxamide | UPLC-MS (ES+, final purity): 3.63 min, m/z 483.4 [M + H]⁺. ¹H NMR (400 MHz, DMSO-d₆) δ/ppm: 10.51 (1H, s), 8.30 (1H, s), 7.98 (1H, d, J = 6.0 Hz), 7.71-7.62 (2H, m), 7.48-7.39 (2H, m), 7.31-7.27 (1H, m), 7.00-6.96 (2H, m), 6.33 (1H, d, J = 6.0 Hz), 4.63 (2H, s), 3.72 (2H, t, J = 6.4 Hz), 2.94-2.85 (4H, m), 2.57-2.53 (2H, m, (under DMSO peak)). |
| 47 | 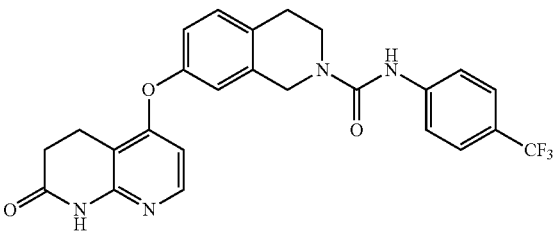<br>7-[(7-oxo-6,8-dihydro-5H-1,8-naphthyridin-4-yl)oxy]-N-[4-(trifluoromethyl)phenyl]-3,4-dihydro-1H-isoquinoline-2-carboxamide | UPLC-MS (ES+, final purity): 3.91 min, m/z 483.3 [M + H]⁺. ¹H NMR (400 MHz, DMSO-d₆) δ/ppm: 10.51 (1H, s), 8.99 (1H, s), 7.98 (1H, d, J = 6.0 Hz), 7.71 (2H, d, J = 8.8 Hz), 7.60 (2H, d, J = 8.8 Hz), 7.28 (1H, d, J = 8.4 Hz), 7.00-6.96 (2H, m), 6.33 (1H, d, J = 6.0 Hz), 4.67 (2H, s), 3.75 (2H, t, J = 5.6 Hz), 2.94-2.86 (4H, m), 2.54-2.52 (2H, m, (under DMSO peak)). |
| 50 | 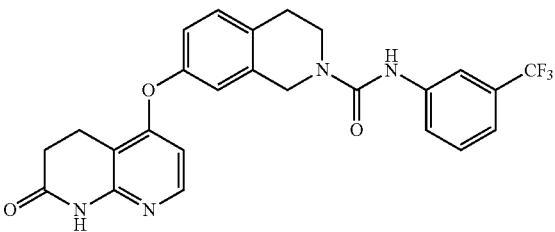<br>7-[(7-oxo-6,8-dihydro-5H-1,8-naphthyridin-4-yl)oxy]-N-[3-(trifluoromethyl)phenyl]-3,4-dihydro-1H-isoquinoline-2-carboxamide | UPLC-MS (ES+, final purity): 3.90 min, m/z 483.3 [M + H]⁺. ¹H NMR (400 MHz, DMSO-d₆) δ/ppm: 10.51 (1H, s), 8.93 (1H, s), 7.98 (1H, d, J = 6.0 Hz), 7.94 (1H, d, J = 7.6 Hz), 7.78 (1H, d, J = 8.0 Hz), 7.48 (1H, t, J = 8.0 Hz), 7.31-7.26 (2H, m), 7.02-6.96 (2H, m), 6.34 (1H, d, J = 6.0 Hz), 4.66 (2H, s), 3.74 (2H, t, J = 6.0 Hz), 2.95-2.86 (4H, m), 2.56-2.52 (2H, m, (under DMSO peak)). |

| Comp. No | Structure and Name | Data |
|---|---|---|
| 48 | 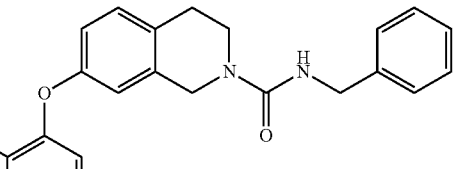

N-benzyl-7-[(7-oxo-6,8-dihydro-5H-1,8-naphthyridin-4-yl)oxy]-3,4-dihydro-1H-isoquinoline-2-carboxamide | UPLC-MS (ES+, final purity): 3.34 min, m/z 429.3 [M + H]⁺.<br>¹H NMR (400 MHz, CDCl₃) δ/ppm: 10.50 (1H, s), 7.97 (1H, d, J = 6.0 Hz), 7.32-7.15 (7H, m), 6.97-6.91 (2H, m), 6.32 (1H, d, J = 6.0 Hz), 4.53 (2H, s), 4.27 (2H, d, J = 6.0 Hz), 3.62 (2H, t, J = 6.0 Hz), 2.91 (2H, t, J = 7.6 Hz), 2.80 (2H, t, J = 6.0 Hz), 2.55 (2H, m, (under DMSO peak)).<br>Exchangeable proton not seen. |

Example 28. Synthesis of 5-[[2-(1H-benzimidazol-2-yl)-3,4-dihydro-1H-isoquinolin-7-yl]oxy]-3,4-dihydro-1H-1,8-naphthyridin-2-one (Compound 159)

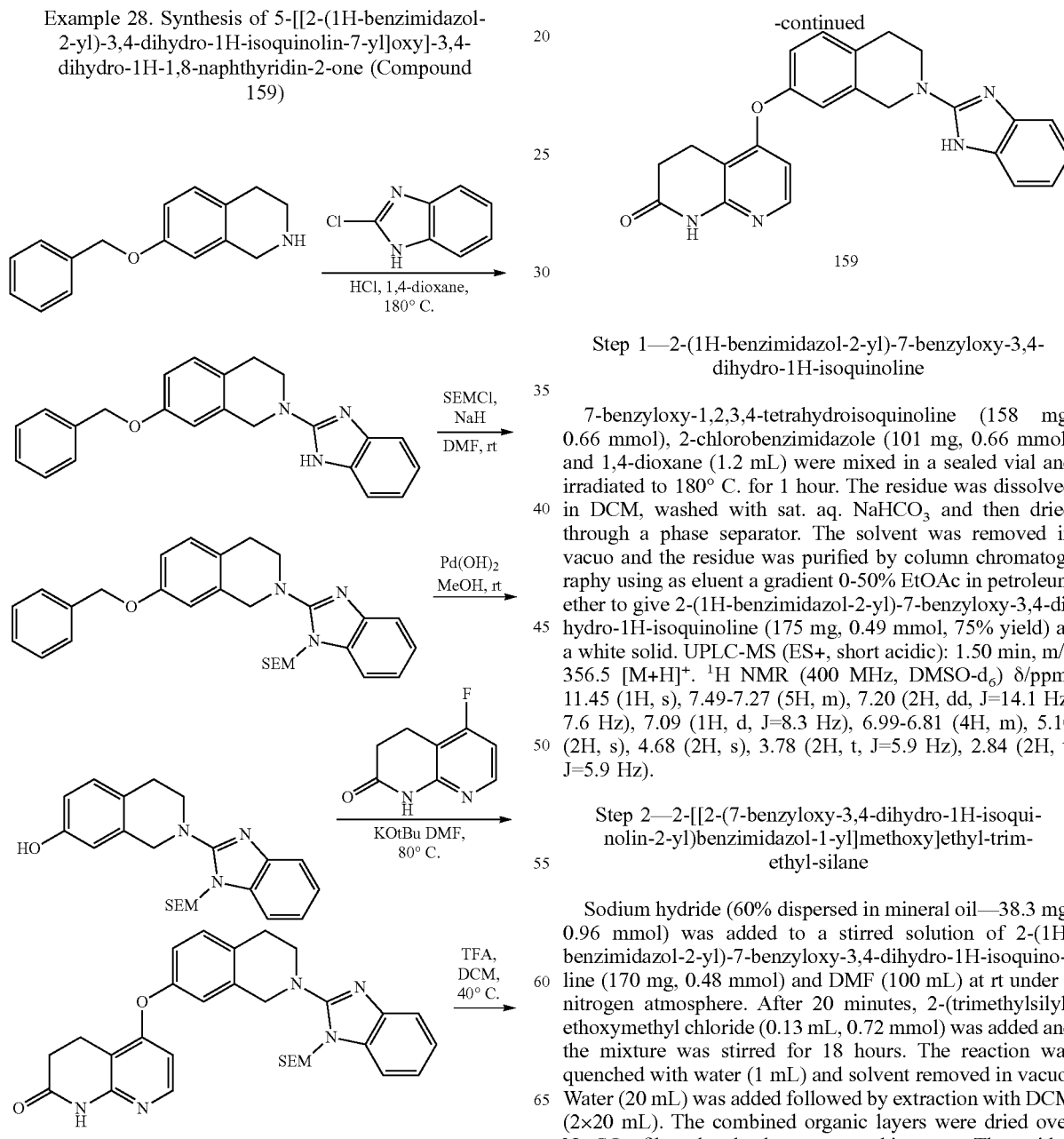

Step 1—2-(1H-benzimidazol-2-yl)-7-benzyloxy-3,4-dihydro-1H-isoquinoline 7-benzyloxy-1,2,3,4-tetrahydroisoquinoline (158 mg, 0.66 mmol), 2-chlorobenzimidazole (101 mg, 0.66 mmol) and 1,4-dioxane (1.2 mL) were mixed in a sealed vial and irradiated to 180° C. for 1 hour. The residue was dissolved in DCM, washed with sat. aq. NaHCO₃ and then dried through a phase separator. The solvent was removed in vacuo and the residue was purified by column chromatography using as eluent a gradient 0-50% EtOAc in petroleum ether to give 2-(1H-benzimidazol-2-yl)-7-benzyloxy-3,4-dihydro-1H-isoquinoline (175 mg, 0.49 mmol, 75% yield) as a white solid. UPLC-MS (ES+, short acidic): 1.50 min, m/z 356.5 [M+H]⁺. ¹H NMR (400 MHz, DMSO-d₆) δ/ppm: 11.45 (1H, s), 7.49-7.27 (5H, m), 7.20 (2H, dd, J=14.1 Hz, 7.6 Hz), 7.09 (1H, d, J=8.3 Hz), 6.99-6.81 (4H, m), 5.10 (2H, s), 4.68 (2H, s), 3.78 (2H, t, J=5.9 Hz), 2.84 (2H, t, J=5.9 Hz).

Step 2—2-[[2-(7-benzyloxy-3,4-dihydro-1H-isoquinolin-2-yl)benzimidazol-1-yl]methoxy]ethyl-trimethyl-silane Sodium hydride (60% dispersed in mineral oil—38.3 mg, 0.96 mmol) was added to a stirred solution of 2-(1H-benzimidazol-2-yl)-7-benzyloxy-3,4-dihydro-1H-isoquinoline (170 mg, 0.48 mmol) and DMF (100 mL) at rt under a nitrogen atmosphere. After 20 minutes, 2-(trimethylsilyl)ethoxymethyl chloride (0.13 mL, 0.72 mmol) was added and the mixture was stirred for 18 hours. The reaction was quenched with water (1 mL) and solvent removed in vacuo. Water (20 mL) was added followed by extraction with DCM (2×20 mL). The combined organic layers were dried over Na₂SO₄, filtered and solvent removed in vacuo. The residue was purified by column chromatography using as eluent a gradient 0-40% EtOAc in petroleum ether to give 2-[[2-(7-benzyloxy-3,4-dihydro-1H-isoquinolin-2-yl)benzimidazol-1-yl]methoxy]ethyl-trimethyl-silane (200 mg, 0.41 mmol, 86% yield) as a colourless gum. UPLC-MS (ES+, Short acidic): 1.93 min, m/z 486.9 [M+H]+. 1H NMR (400 MHz, CDCl3) δ/ppm: 7.64-7.55 (1H, m), 7.45-7.28 (6H, m), 7.24-7.15 (2H, m), 7.10 (1H, d, J=8.4 Hz), 6.85 (1H, dd, J=8.4 Hz, 2.7 Hz), 6.76 (1H, d, J=2.6 Hz), 5.34 (2H, s), 5.05 (2H, s), 4.60 (2H, s), 3.78-3.66 (4H, m), 3.02 (2H, t, J=5.9 Hz), 1.01-0.96 (2H, m), 0.00 (9H, s).

Step 3—2-[1-(2-trimethylsilylethoxymethyl)benzimidazol-2-yl]-3,4-dihydro-1H-isoquinolin-7-ol 2-[[2-(7-benzyloxy-3,4-dihydro-1H-isoquinolin-2-yl)benzimidazol-1-yl]methoxy]ethyl-trimethyl-silane (195 mg, 0.40 mmol) was dissolved in MeOH (4 mL) and Pd(OH)2 (56 mg, 0.40 mmol) added under inert atmosphere. The reaction was fitted with a H2 balloon and subjected to 3×vacuum/H2 cycles and then left to stir under a H2 atmosphere overnight. The crude was filtered over celite, flushed with MeOH and the filtrate concentrated in vacuo. The residue was purified by column chromatography using as eluent a gradient 0-50% EtOAc in petroleum ether to give 2-[1-(2-trimethylsilylethoxymethyl)benzimidazol-2-yl]-3,4-dihydro-1H-isoquinolin-7-ol (120 mg, 0.30 mmol, 76% yield) as a colourless gum which crystallised on standing. UPLC-MS (ES+, short acidic): 1.58 min, m/z 396.6 [M+H]+. 1H NMR (400 MHz, CDCl3) δ/ppm: 8.45 (1H, s), 7.61-7.55 (1H, m), 7.33-7.28 (1H, m), 7.21-7.14 (2H, m), 6.93 (1H, d, J=8.3 Hz), 6.68 (1H, dd, J=8.3 Hz, 2.6 Hz), 6.63 (1H, d, J=2.5 Hz), 5.35 (2H, s), 4.57 (2H, s), 3.81-3.69 (4H, m), 2.92 (2H, t, J=5.8 Hz), 1.03-0.96 (2H, m), 0.00 (9H, s).

Step 4—5-[[2-[1-(2-trimethylsilylethoxymethyl)benzimidazol-2-yl]-3,4-dihydro-1H-isoquinolin-7-yl]oxy]-3,4-dihydro-1H-1,8-naphthyridin-2-one Potassium tert-butoxide (37.4 mg, 0.33 mmol) was added to a stirred solution of 5-fluoro-3,4-dihydro-1H-1,8-naphthyridin-2-one (50.4 mg, 0.30 mmol) and 2-[1-(2-trimethylsilylethoxymethyl)benzimidazol-2-yl]-3,4-dihydro-1H-isoquinolin-7-ol (120 mg, 0.30 mmol) in DMF (2 mL) and the reaction was heated at 80° C. for 18 hours. The reaction was cooled to rt and the solvent removed in vacuo. The residue was partitioned between EtOAc and water; the organics were washed with saturated brine, dried over a phase separator and the solvent removed in vacuo. The residue was purified by column chromatography eluting with 25-100% EtOAc in petroleum ether to give 5-[[2-[1-(2-trimethylsilylethoxymethyl)benzimidazol-2-yl]-3,4-dihydro-1H-isoquinolin-7-yl]oxy]-3,4-dihydro-1H-1,8-naphthyridin-2-one (94 mg, 0.17 mmol, 57% yield) as a colourless gum. UPLC-MS (ES+, Short acidic): 1.65 min, m/z 542.5 [M+H]+. 1H NMR (400 MHz, CDCl3) δ/ppm: 8.69 (1H, s), 8.01 (1H, d, J=5.9 Hz), 7.63-7.58 (1H, m), 7.34-7.30 (1H, m), 7.25-7.16 (3H, m), 6.93-6.85 (2H, m), 6.35 (1H, d, J=5.9 Hz), 5.36 (2H, s), 4.65 (2H, s), 3.82-3.72 (4H, m), 3.13-3.02 (4H, m), 2.70 (2H, dd, J=8.4 Hz, 7.0 Hz), 1.03-0.96 (2H, m), 0.00 (9H, s).

Step 5—5-[[2-(1H-benzimidazol-2-yl)-3,4-dihydro-1H-isoquinolin-7-yl]oxy]-3,4-dihydro-1H-1,8-naphthyridin-2-one Trifluoroacetic acid (0.64 mL, 8.31 mmol) was added to a stirred solution of 5-[[2-[1-(2-trimethylsilylethoxymethyl)benzimidazol-2-yl]-3,4-dihydro-1H-isoquinolin-7-yl]oxy]-3,4-dihydro-1H-1,8-naphthyridin-2-one (90 mg, 0.17 mmol) in DCM (2 mL) in a sealed vial and heated to 40° C. for 18 hours, after which time the solvent was removed in vacuo. The residue was loaded into an SCX-2 column and flushed at first with MeOH (2×10 mL) and then NH3 in MeOH (10 mL) to elute the product. The reside was then purified by column chromatography using as eluent a gradient 1-8% MeOH in DCM to give a colourless gum, which was triturated in MeCN/Et2O to give a white solid. The solid was filtered, washed with Et2O and dried to give 5-[[2-(1H-benzimidazol-2-yl)-3,4-dihydro-1H-isoquinolin-7-yl]oxy]-3,4-dihydro-1H-1,8-naphthyridin-2-one (29 mg, 0.070 mmol, 42% yield) as a white solid. UPLC-MS (ES+, final purity): 2.52 min, m/z 412.4 [M+H]+. 1H NMR (400 MHz, DMSO-d6) δ/ppm: 12.21 (1H, s), 10.52 (1H, s), 7.99 (1H, d, J=5.8 Hz), 7.33-7.25 3H, m), 7.07-6.97 (4H, m), 6.35 (1H, d, J=5.8 Hz), 4.76 (2H, s), 3.85 (2H, t, J=5.9 Hz), 2.98 (2H, t, J=5.9 Hz), 2.92 (2H, t, J=7.9 Hz), 2.57-2.52 (2H, t, J=7.9 Hz, (partly under DMSO)).

The compounds in the table below were made in an analogous manner, using the appropriate heteroaryl chloride in place of 2-chlorobenzimidazole in step 1:

| Comp. No | Structure and Name | Data |
|---|---|---|
| 160 | 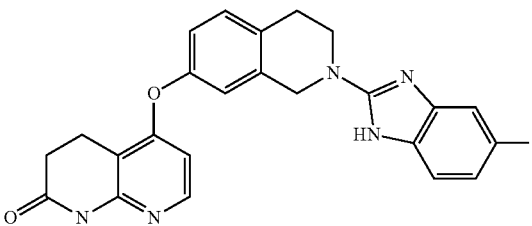<br>5-[[2-[5-(trifluoromethyl)-1H-benzimidazol-2-yl]-3,4-dihydro-1H-isoquinolin-7-yl]oxy]-3,4-dihydro-1H-1,8-naphthyridin-2-one | UPLC-MS (ES+, final purity): 2.88 min, m/z 480.3 [M + H]+. 1H NMR (400 MHz, DMSO-d6) δ/ppm: 11.89 (1H, s), 10.51 (1H, s), 7.99 (1H, dd, J = 5.7 Hz, 0.7 Hz), 7.48 (1H, s), 7.35 (1H, d, J = 8.1 Hz), 7.31-7.27 (2H, m), 7.05 (1H, d, J = 2.5 Hz), 6.99 (1H, dd, J = 8.3 Hz, 2.6 Hz), 6.35 (1H, d, J = 5.7 Hz), 4.78 (2H, s), 3.86 (2H, t, J = 5.9 Hz), 3.00-2.88 (4H, m), 2.59-2.50 (2H, m). |

Example 29. Synthesis of 5-[[2-(5-phenyl-1H-benzimidazol-2-yl)-3,4-dihydro-1H-isoquinolin-7-yl]oxy]-3,4-dihydro-1H-1,8-naphthyridin-2-one (Compound 162)

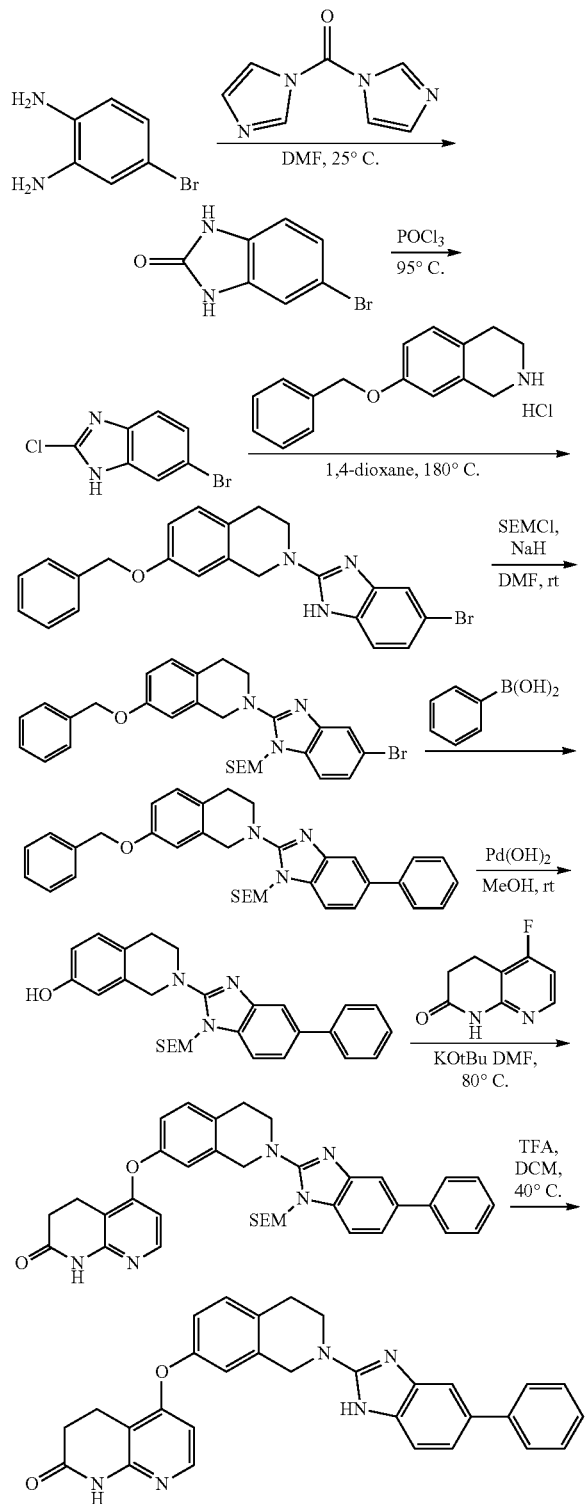

162

Step 1—5-bromo-1,3-dihydrobenzimidazol-2-one 1,1'-Carbonyldiimidazole (1.73 g, 10.69 mmol) was added to a stirred solution of 4-bromo-1,2-diaminobenzene (1 g, 5.35 mmol) in DMF (10 mL) at 25° C. under a nitrogen atmosphere and the reaction was stirred for 18 hours. The solvent was reduced in vacuo and the residue was diluted with water and EtOAc, causing a solid to crash out. The solid was filtered, slurried in water, sonicated, filtered, washed with further water and dried to give 5-bromo-1,3-dihydrobenzimidazol-2-one (912 mg, 4.28 mmol, 80% yield) as a brown solid. UPLC-MS (ES+, Short acidic): 1.28 min, m/z 212.9, 214.9 [M+H]$^+$. $^1$H NMR (400 MHz, DMSO-d$_6$) δ/ppm: 10.79-10.73 (2H, m), 7.08 (1H, dd, J=8.2 Hz, 2.0 Hz), 7.05 (1H, d, J=1.9 Hz), 6.87 (1H, d, J=8.2 Hz).

Step 2—6-bromo-2-chloro-1H-benzimidazole 5-bromo-1,3-dihydrobenzimidazol-2-one (912 mg, 4.28 mmol) was dissolved in POCl3 (7.98 mL, 85.62 mmol) and the reaction was heated to 95° C. for 4 hours, after which time the reaction was reduced in vacuo and the residue was azeotroped with toluene. The residue was quenched with saturated NaHCO$_3$ solution causing a solid to crash out, which was sonicated, filtered, washed with water and dried to give 6-bromo-2-chloro-1H-benzimidazole (855 mg, 3.69 mmol, 86% yield) as a pale brown solid. The compound was used without further purification in the following step. UPLC-MS (ES+, Short acidic): 1.44 min, m/z 230.8, 232.8, 234.8 [M+H]$^+$. $^1$H NMR (400 MHz, DMSO-d$_6$) δ/ppm: 7.74 (1H, d, J=1.9 Hz), 7.49 (1H, d, J=8.6 Hz), 7.38 (1H, dd, J=8.6 Hz, 2.0 Hz). Exchangeable proton missing.

Step 3—7-benzyloxy-2-(5-bromo-1H-benzimidazol-2-yl)-3,4-dihydro-1H-isoquinoline

Eight separate microwave vials each with 7-benzyloxy-1,2,3,4-tetrahydroisoquinoline hydrochloride (50 mg, 0.18 mmol) and 6-bromo-2-chloro-1H-benzimidazole (46 mg, 0.2 mmol), and 1,4-Dioxane (2.5 mL) were sealed and heated to 180° C. in the microwave for 60 min. Each vial precipitated a solid, all the reaction mixtures were filtered and the combined solid washed with further dioxane and dried to give 7-benzyloxy-2-(5-bromo-1H-benzimidazol-2-yl)-3,4-dihydro-1H-isoquinoline (626 mg, 1.4 mmol, 99% yield) as a green/brown solid. UPLC-MS (ES+, Short acidic): 1.59 min, m/z 434.1; 436.0 [M+H]+ (67%)

Step 4—2-[[2-(7-benzyloxy-3,4-dihydro-1H-isoquinolin-2-yl)-5-bromo-benzimidazol-1-yl]methoxy]ethyl-trimethyl-silane Sodium hydride (60% dispersed in mineral oil—168.9 mg, 4.22 mmol) was added to a stirred solution of 7-benzyloxy-2-(5-bromo-1H-benzimidazol-2-yl)-3,4-dihydro-1H-isoquinoline (692 mg, 1.12 mmol) and DMF (10 mL) at room temperature under a nitrogen atmosphere. After 20 minutes 2-(trimethylsilyl)ethoxymethyl chloride (0.3 mL, 1.67 mmol) was added and the reaction was allowed to stir for 2 hours. The reaction was quenched with water (1 mL) and solvent removed in vacuo. The residue was then partitioned between water (20 mL) and EtOAc (20 mL). The organic layer was separated and the aqueous extracted with DCM (20 mL). The combined organic layers were dried over Na$_2$SO$_4$, filtered and the solvent removed in vacuo. The residue was purified by column chromatography using an eluent of 0-40% EtOAc in petroleum ether to give 2-[[2-(7- benzyloxy-3,4-dihydro-1H-isoquinolin-2-yl)-5-bromo-benzimidazol-1-yl]methoxy]ethyl-trimethyl-silane (442 mg, 0.78 mmol, 70% yield) as a pale yellow gum. UPLC-MS (ES+, Short acidic): 2.27 and 2.29 min, m/z 564.3, 566.2 [M+H]+. Presence of two SEM isomers.

Step 5 (Method A)—2-[[2-(7-benzyloxy-3,4-dihydro-1H-isoquinolin-2-yl)-5-phenyl-benzimidazol-1-yl]methoxy]ethyl-trimethyl-silane Potassium carbonate (151.3 mg, 1.09 mmol), 2-[[2-(7-benzyloxy-3,4-dihydro-1H-isoquinolin-2-yl)-5-bromo-benzimidazol-1-yl]methoxy]ethyl-trimethyl-silane (206 mg, 0.36 mmol), phenylboronic acid (48.9 mg, 0.40 mmol), 1,4-dioxane (4 mL) and water (1 mL) were combined and stirred at room temperature under a nitrogen atmosphere, followed by addition of [1,1'-bis(diphenylphosphino)ferrocene]palladium(II) chloride dichloromethane complex (29.8 mg, 0.04 mmol). The reaction was heated to 90° C. for 18 hours, after which time the reaction was cooled to room temperature and the solvent removed under reduce pressure. The residue was purified by column chromatography using an eluent of 0-35% EtOAc in petroleum ether to give 2-[[2-(7-benzyloxy-3,4-dihydro-1H-isoquinolin-2-yl)-5-phenyl-benzimidazol-1-yl]methoxy]ethyl-trimethyl-silane (150 mg, 0.27 mmol, 73% yield) as a pale yellow oil. UPLC-MS (ES+, short acidic): 2.11 min, m/z 562.8 [M+H]+.

Step 6—2-[5-phenyl-1-(2-trimethylsilylethoxymethyl)benzimidazol-2-yl]-3,4-dihydro-1H-isoquinolin-7-ol 2-[[2-(7-benzyloxy-3,4-dihydro-1H-isoquinolin-2-yl)-5-phenyl-benzimidazol-1-yl]methoxy]ethyl-trimethyl-silane (150 mg, 0.27 mmol) was dissolved in MeOH (4 mL) and palladium hydroxide (3.04 mg, 0.02 mmol) was added under an atmosphere of nitrogen. The reaction was fitted with a H$_2$ balloon, subjected to 3×vacuum/H$_2$ cycles and then left to stir under a H$_2$ atmosphere overnight. The crude was filtered over celite, washed with MeOH and the solvent removed in vacuo to give 2-[5-phenyl-1-(2-trimethylsilylethoxymethyl)benzimidazol-2-yl]-3,4-dihydro-1H-isoquinolin-7-ol (117 mg, 0.25 mmol, 93% yield) as a colourless gum. UPLC-MS (ES+, short acidic):1.81 min, m/z 472.6 [M+H]+.

Step 7—5-[[2-[5-phenyl-1-(2-trimethylsilylethoxymethyl)benzimidazol-2-yl]-3,4-dihydro-1H-isoquinolin-7-yl]oxy]-3,4-dihydro-1H-1,8-naphthyridin-2-one ol Potassium tert-butoxide (83.5 mg, 0.74 mmol) was added to a stirred solution of 5-fluoro-3,4-dihydro-1H-1,8-naphthyridin-2-one (41.2 mg, 0.25 mmol) in DMF (2 mL) in a sealable vial. The vial was sealed and and heated at 80° C. for 18 hours. The reaction was cooled to room temperature and the solvent reduced in vacuo. The crude was partitioned between EtOAc and water. The organic phase was separated, washed with saturated brine, dried over a phase separator and the solvent removed under reduce pressure. The residue was purified by column chromatography using as eluent a gradient 25-100% EtOAc in petroleum ether to give 5-[[2-[5-phenyl-1-(2-trimethylsilylethoxymethyl)benzimidazol-2-yl]-3,4-dihydro-1H-isoquinolin-7-yl]oxy]-3,4-dihydro-1H-1,8-naphthyridin-2-one (90 mg, 0.15 mmol, 59% yield) as a colourless gum. UPLC-MS (ES+, Short acidic): 1.87 min, m/z 618.5 [M+H]+.

Step 8—5-[[2-(5-phenyl-1H-benzimidazol-2-yl)-3,4-dihydro-1H-isoquinolin-7-yl]oxy]-3,4-dihydro-1H-1,8-naphthyridin-2-one Trifluoroacetic acid (0.56 mL, 7.29 mmol) was added to a stirred solution of 5-[[2-[5-phenyl-1-(2-trimethylsilylethoxymethyl)benzimidazol-2-yl]-3,4-dihydro-1H-isoquinolin-7-yl]oxy]-3,4-dihydro-1H-1,8-naphthyridin-2-one (90 mg, 0.15 mmol) in DCM (2 mL) in a sealable vial. The vial was sealed and and heated to 40° C. for 18 hours. The reaction was reduced in vacuo and loaded onto an SCX-2 column, which was flushed at first with methanol (2×), then NH$_3$ in MeOH followed by 20% DCM in MeOH/NH$_3$ to elute the product. The crude was purified by column chromatography using as eluent a gradient 1-8% MeOH in DCM to give a colourless gum, which was triturated in MeCN/Et20 to give a white solid. The solid was filtered, washed with Et20, followed by sonication in MeOH to precipitate a white solid. The whole suspension was evaporated and dried to give 5-[[2-(5-phenyl-1H-benzimidazol-2-yl)-3,4-dihydro-1H-isoquinolin-7-yl]oxy]-3,4-dihydro-1H-1,8-naphthyridin-2-one (27 mg, 0.053 mmol, 36% yield) as an off white solid. UPLC-MS (ES+, final purity): 3.04 min, m/z 488.4 [M+H]+. $^1$H NMR (400 MHz, DMSO-d$_6$) δ/ppm: 11.57 (1H, s), 10.51 (1H, s), 7.99 (1H, dd, J=5.7 Hz, 0.7 Hz), 7.66-7.59 (2H, m), 7.52-7.38 (3H, m), 7.33-7.18 (3H, m), 7.05 (1H, d, J=2.5 Hz), 6.98 (1H, dd, J=8.3 Hz, 2.6 Hz), 6.35 (1H, d, J=5.8 Hz), 4.76 (2H, s), 3.85 (2H, t, J=5.9 Hz), 3.00-2.89 (4H, m), 2.58-2.52 (3H, m, (partly under DMSO)).

As alternative, Step 5 could have been performed using Method B:

2-[[2-(7-benzyloxy-3,4-dihydro-1H-isoquinolin-2-yl)-5-bromo-benzimidazol-1-yl]methoxy]ethyl-trimethyl-silane (255 mg, 0.45 mmol), potassium phosphate tribasic (0.29 g, 1.35 mmol) and 1,3-dimethyl-5-(4,4,5,5-tetramethyl-1,3,2-dioxaborolan-2-yl)-1H-pyrazole (150.5 mg, 0.68 mmol) were suspended in toluene (2 mL) and water (1 mL) and degassed under a nitrogen atmosphere in a sealable vial. Tricyclohexylphosphine (0.03 g, 0.09 mmol) and palladium (II) acetate (0.01 g, 0.03 mmol) were then added followed by further degassing, the vial was sealed and heated at 90° C. for 18 hours. The reaction was cooled and the water removed. The organics were reduced in vacuo onto silica and the product was purified by silica column chromatography using as eluent a gradient 0-80% EtOAc in petroleum ether to give 2-[[2-(7-benzyloxy-3,4-dihydro-1H-isoquinolin-2-yl)-5-(2,5-dimethylpyrazol-3-yl)benzimidazol-1-yl]methoxy]ethyl-trimethyl-silane (110 mg, 0.19 mmol, 42% yield) as a colourless gum. UPLC-MS (ES+, Short acidic): 2.02 and 2.05 min, m/z 580.5 [M+H]+ (2 SEM-protected isomers).

The compounds in the table below were made in an analogous manner using the appropriate boronic acid/ester and applying the appropriate method:

| Comp. No | Structure and Name | Data |
|---|---|---|
| 163 | 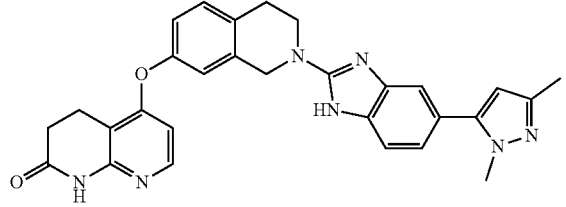<br>5-[[2-[5-(2,5-dimethylpyrazol-3-yl)-1H-benzimidazol-2-yl]-3,4-dihydro-1H-isoquinolin-7-yl]oxy]-3,4-dihydro-1H-1,8-naphthyridin-2-one | UPLC-MS (ES+, final purity): 2.69 min, m/z 506.3 [M + H]+. $^1$H NMR (400 MHz, DMSO-$d_6$) δ/ppm: 11.64 (1H, m), 10.50 (1H, s), 8.01-7.88 (1H, d, J = 5.8 Hz), 7.31-7.20 (3H, m), 7.10-6.89 (3H, m), 6.34 (1H, d, J = 5.8 Hz), 6.07 (1H, d, J = 5.7 Hz), 4.75 (2H, s), 3.84 (2H, t, J = 5.9 Hz), 3.75-3.70 (3H, br s), 2.93 (4H, m), 2.56-2.52 (2H, m), 2.15 (3H, s). |
Example 30. Synthesis of 5-[[2-(5-propyl-1H-benzimidazol-2-yl)-3,4-dihydro-1H-isoquinolin-7-yl]oxy]-3,4-dihydro-1H-1,8-nahphthyridin-2-one (Compound 161)
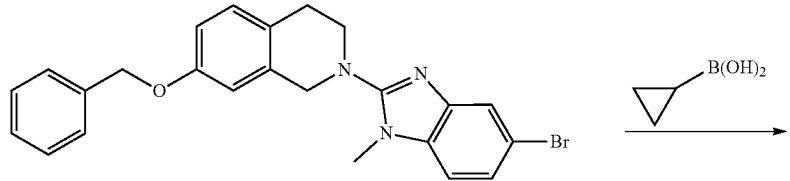
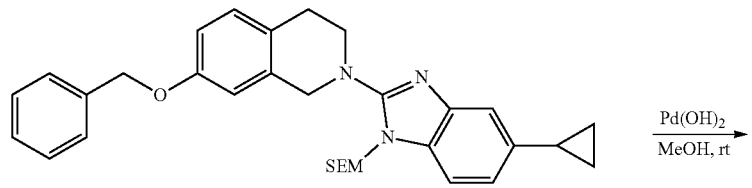
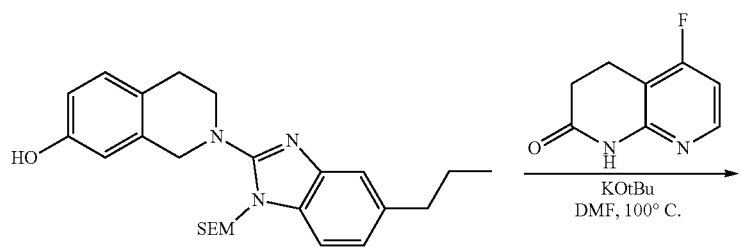
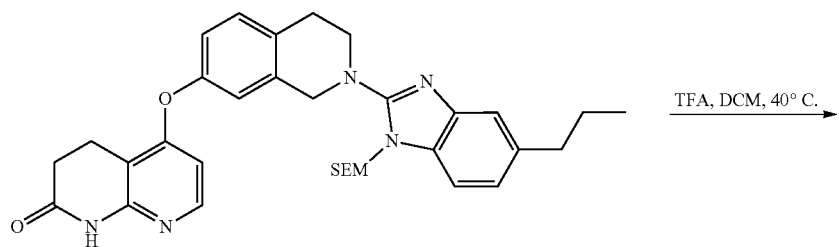

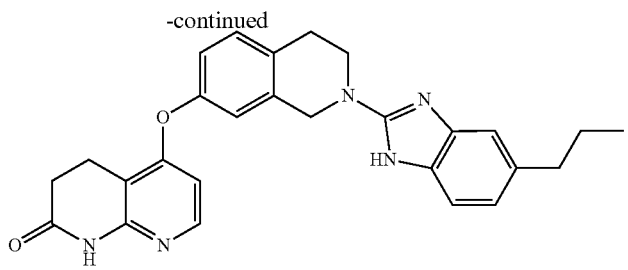

161

Step 1—2-[[2-(7-benzyloxy-3,4-dihydro-1H-isoquinolin-2-yl)-5-cyclopropyl-benzimidazol-1-yl]methoxy]ethyl-trimethyl-silane 2-[[2-(7-benzyloxy-3,4-dihydro-1H-isoquinolin-2-yl)-5-bromo-benzimidazol-1-yl]methoxy]ethyl-trimethyl-silane (205 mg, 0.36 mmol), cyclopropylboronic acid (0.08 g, 0.91 mmol) and potassium phosphate tribasic (0.23 g, 1.09 mmol) were suspended in toluene (2 mL) and water (1 mL) at room temperature and degassed under nitrogen atmosphere in a sealable vial. Tricyclohexylphosphine (0.02 g, 0.07 mmol) and palladium (II) acetate (0.01 g, 0.03 mmol) were then added, the vial sealed and heated 100° C. for 2 hours. The reaction was cooled and the water removed. The organics were reduced in vacuo onto silica and the product was purified by column chromatography using as eluent a gradient 0-35% EtOAc in petroleum ether to give 2-[[2-(7-benzyloxy-3,4-dihydro-1H-isoquinolin-2-yl)-5-cyclopropyl-benzimidazol-1-yl]methoxy]ethyl-trimethyl-silane (155 mg, 0.29 mmol, 81% yield) as a colourless gum. UPLC-MS (ES+, Short acidic): 1.98 min, m/z 526.9 [M+H]$^+$.

Step 2—2-[5-propyl-1-(2-trimethylsilylethoxymethyl)benzimidazol-2-yl]-3,4-dihydro-1H-isoquinolin-7-ol 2-[[2-(7-benzyloxy-3,4-dihydro-1H-isoquinolin-2-yl)-5-cyclopropyl-benzimidazol-1-yl]methoxy]ethyl-trimethyl-silane (155 mg, 0.29 mmol) was dissolved in methanol (4 mL) and palladium hydroxide (3.36 mg, 0.02 mmol) was added under an atmosphere of nitrogen. The reaction was fitted with a H$_2$ balloon, subjected to 3×vacuum/H$_2$ cycles and then left to stir under a H$_2$ atmosphere overnight. The crude was filtered over celite, washed with MeOH and the solvent removed in vacuo to give 2-[5-propyl-1-(2-trimethylsilylethoxymethyl)benzimidazol-2-yl]-3,4-dihydro-1H-isoquinolin-7-ol (107 mg, 0.24 mmol, 83% yield) as a colourless gum. UPLC-MS (ES+, short acidic): 1.78 min, m/z 438.6 [M+H]$^+$.

Step 3—5-[[2-[5-propyl-1-(2-trimethylsilylethoxymethyl)benzimidazol-2-yl]-3,4-dihydro-1H-isoquinolin-7-yl]oxy]-3,4-dihydro-1H-1,8-naphthyridin-2-one Potassium tert-butoxide (83.5 mg, 0.74 mmol) was added to a stirred solution of 5-fluoro-3,4-dihydro-1H-1,8-naphthyridin-2-one (40.6 mg, 0.24 mmol) and 2-[5-propyl-1-(2-trimethylsilylethoxymethyl)benzimidazol-2-yl]-3,4-dihydro-1H-isoquinolin-7-ol (107 mg, 0.24 mmol) in DMF (2 mL) in a sealable vial, which was sealed and heated at 100° C. for 72 hours. Reaction was cooled to room temperature and the solvent reduced in vacuo. The crude was partitioned between EtOAc and water. The organic layer was separated, washed with saturated brine, dried over a phase separator and the solvent removed under reduce pressure. The residue was purified by column chromatography using as eluent a gradient 25-100% EtOAc in petroleum ether to give 5-[[2-[5-propyl-1-(2-trimethylsilylethoxymethyl)benzimidazol-2-yl]-3,4-dihydro-1H-isoquinolin-7-yl]oxy]-3,4-dihydro-1H-1,8-naphthyridin-2-one (41 mg, 0.07 mmol, 29% yield) as a colourless gum. UPLC-MS (ES+, Short acidic): 1.81 min, m/z 584.5 [M+H]$^+$.

Step 3—5-[[2-(5-propyl-1H-benzimidazol-2-yl)-3,4-dihydro-1H-isoquinolin-7-yl]oxy]-3,4-dihydro-1H-1,8-naphthyridin-2-one Trifluoroacetic acid (0.27 mL, 3.51 mmol) was added to a stirred solution of 5-[[2-[5-propyl-1-(2-trimethylsilylethoxymethyl)benzimidazol-2-yl]-3,4-dihydro-1H-isoquinolin-7-yl]oxy]-3,4-dihydro-1H-1,8-naphthyridin-2-one (41. mg, 0.07 mmol) in DCM (2 mL) in a sealable vial. The reaction was sealed and heated to 40° C. for 18 hours. The reaction was reduced in vacuo and loaded onto an SCX cartridge, which was flushed at first with MeOH and then MeOH/NH$_3$ followed by 20% DCM:MeOH/NH$_3$ to elute the product. The product was then purified by silica column chromatography using as eluent a gradient 1-8% MeOH/DCM to give a colourless gum. The compound was re-purified using reverse column chromatography using as eluent a gradient 0-30% (acetonitrile+0.1% formic acid) in (water+0.1% formic acid). Fractions containing the product were re-purified using preparative LCMS (early method). Fractions containing compound were loaded onto an SCX column which was flushed at first with MeOH and then MeOH/NH$_3$ to elute the product giving 5-[[2-(5-propyl-1H-benzimidazol-2-yl)-3,4-dihydro-1H-isoquinolin-7-yl]oxy]-3,4-dihydro-1H-1,8-naphthyridin-2-one (8 mg, 0.018 mmol, 25% yield) as an off white solid. UPLC-MS (ES+, final purity): 3.03 min, m/z 454.3 [M+H]. $^1$H NMR (400 MHz, DMSO-d$_6$) δ/ppm: 11.80 (1H, s), 10.50 (1H, s), 7.98 (1H, d, J=5.8 Hz), 7.27 (1H, d, J=8.3 Hz), 7.13 (1H, d, J=8.0 Hz), 7.07-6.94 (3H, m), 6.81 (1H, dd, J=8.0 Hz, 1.6 Hz), 6.34 (1H, d, J=5.8 Hz), 4.72 (2H, s), 3.81 (2H, t, J=5.9 Hz), 2.98-2.87 (4H, m), 2.62-2.51 (4H, m), 1.65-1.51 (2H, m), 0.88 (3H, t, J=7.3 Hz).

Example 31. Synthesis of N-[4-[3-[4-(4-fluorophenyl)-1H-imidazol-2-yl]chroman-6-yl]oxy-2-pyridyl]cyclopropanecarboxamide (Compound 155)

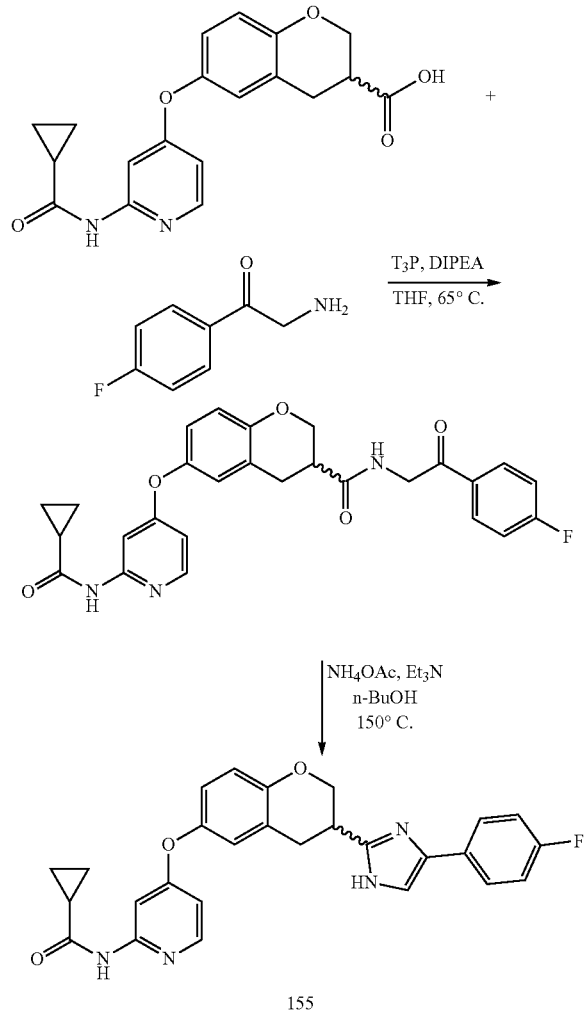

Step 1—6-[[2-(cyclopropanecarbonylamino)-4-pyridyl]oxy]-N-[2-(4-fluorophenyl)-2-oxo-ethyl]chromane-3-carboxamide To a solution of 6-[[2-(cyclopropanecarbonylamino)-4-pyridyl]oxy]chromane-3-carboxylic acid (65 mg, 0.18 mmol) and 2-amino-1-(4-fluorophenyl)ethanone hydrochloride (54.7 mg, 0.20 mmol) in THF (1.8 mL) were added T3P (164 µL, 0.28 mmol) and DIPEA (99 µL, 0.57 mmol) and the mixture was heated at 65° C. for 1 hour. After cooling to rt, the solvent was removed under reduce pressure and the residue dissolved in EtOAc (25 mL). The organic layer was washed with water (2×10 mL) and brine (10 mL), dried over $Na_2SO_4$, filtered and the solvent removed in vacuo to afford 6-[[2-(cyclopropanecarbonylamino)-4-pyridyl]oxy]-N-[2-(4-fluorophenyl)-2-oxo-ethyl]chromane-3-carboxamide (86 mg, 0.17 mmol, 95% yield) as a yellow solid. The compound was used in the next step without further purification. UPLC-MS (ES+, short acidic): 1.46 min, m/z 490.6 [M+H]$^+$.

Step 2—N-[4-[3-[4-(4-fluorophenyl)-1H-imidazol-2-yl]chroman-6-yl]oxy-2-pyridyl]cyclopropanecarboxamide To a suspension of 6-[[2-(cyclopropanecarbonylamino)-4-pyridyl]oxy]-N-[2-(4-fluorophenyl)-2-oxo-ethyl]chromane-3-carboxamide (85.5 mg, 0.17 mmol) in n-BuOH (1 mL) were added $NH_4OAc$ (134.6 mg, 1.75 mmol) and Et3N (26 µL, 0.18 mmol) and the mixture was irradiated at 150° C. for 1 hour. After cooling to rt, the solvent was removed under reduce pressure and the residue dissolved in EtOAc (25 mL). The organic layer was washed with sat. aq. $NaHCO_3$ (10 mL), water (2×10 mL) and brine (10 mL), dried over $Na_2SO_4$, filtered and the solvent removed in vacuo. The residue was purified by flash chromatography using as eluent a gradient 0-10% MeOH in DCM, followed by purification by preparative LC-MS. Fractions containing the product were dried and loaded into an SCX-2 column, which was flushed at first with MeOH (10 mL) and then $NH_3$ in MeOH (10 mL) to elute the product. The filtrate was concentrated to give N-[4-[3-[4-(4-fluorophenyl)-1H-imidazol-2-yl]chroman-6-yl]oxy-2-pyridyl]cyclopropanecarboxamide (10 mg, 0.022 mmol, 13% yield) as a white solid. UPLC-MS (ES+, final purity): 2.73 min, m/z 471.3 [M+H]$^+$. $^1$H NMR (400 MHz, DMSO-$d_6$) δ/ppm: 12.33 & 12.10 (0.2 & 0.8H, 2 s, mixture of tautomers), 10.80 (1H, s), 8.16 (1H, d, J=5.7 Hz), 7.80-7.42 (2H, m), 7.65 (1H, d, J=2.5 Hz), 7.57 (1H, br s), 7.25-7.10 (2H, m), 7.02 (1H, d, J=2.5 Hz), 6.94-6.86 (2H, m*), 6.62 (1H, dd, J=5.7 Hz, 2.4 Hz), 4.54-4.48 (1H, m), 4.16-4.08 (1H, m), 3.44-3.34 (1H, m), 3.28-3.18 (1H, m), 3.15-3.07 (1H, m), 1.97 (1H, quint, J=6.2 Hz), 0.77 (4H, d, J=6.2 Hz).

Example 32. Synthesis of 4-[3-(4-phenyl-1H-imidazol-2-yl)chroman-6-yl]oxy-N-(2-pyridyl)pyridin-2-amine (Compound 140)

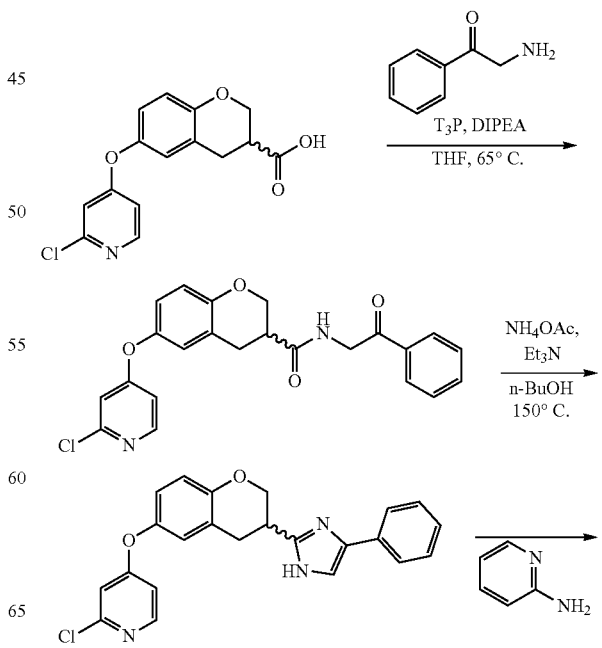

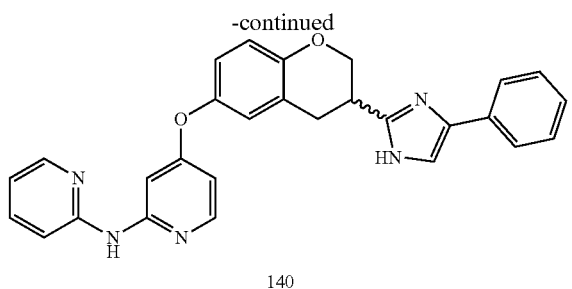

140

Step 1—6-[(2-chloro-4-pyridyl)oxy]-N-phenacyl-chromane-3-carboxamide

To a solution of 6-[(2-chloro-4-pyridyl)oxy]chromane-3-carboxylic acid (437 mg, 1.43 mmol) and 2-aminoacetophenone hydrochloride (270 mg, 1.57 mmol) in THF (14 mL) were added T3P (1.28 mL, 2.14 mmol) and DIPEA (0.8 mL, 4.58 mmol) and the mixture was heated at 65° C. for 1.5 hours. After cooling to rt, the solvent was removed under reduce pressure and the residue dissolved in EtOAc (60 mL). The organic layer was washed with water (2×20 mL) and brine (20 mL), dried over $Na_2SO_4$, filtered and the solvent removed in vacuo to give 6-[(2-chloro-4-pyridyl)oxy]-N-phenacyl-chromane-3-carboxamide (604.5 mg, 1.43 mmol, 100% yield) as a light beige solid. The compound was used in the next step without further purification. UPLC-MS (ES+, short acidic): 1.72 min, m/z 423.3 [M+H]$^+$.

Step 2—2-chloro-4-[3-(4-phenyl-1H-imidazol-2-yl)chroman-6-yl]oxy-pyridine

To a suspension of 6-[(2-chloro-4-pyridyl)oxy]-N-phenacyl-chromane-3-carboxamide (513 mg, 1.21 mmol) in n-BuOH (10 mL) were added $NH_4OAc$ (935.2 mg, 12.13 mmol) and Et3N (169 μL, 1.21 mmol). The vial was sealed and the mixture irradiated at 150° C. for 1 hr. After cooling to rt, the solvent was removed under reduce pressure and the residue dissolved in EtOAc (60 mL). The organic layer was washed with sat. aq. $NaHCO_3$ (20 mL), water (2×20 mL) and brine (20 mL), dried over $Na_2SO_4$, filtered and the solvent removed in vacuo. The residue was purified by column chromatography using as eluent a gradient 0-100% EtOAc in petroleum ether to give 2-chloro-4-[3-(4-phenyl-1H-imidazol-2-yl)chroman-6-yl]oxy-pyridine (314.9 mg, 0.78 mmol, 64% yield) as a beige solid. UPLC-MS (ES+, short acidic): 1.43 min, m/z 404.3 [M+H]$^+$. $^1$H NMR (400 MHz, DMSO-d$_6$) δ/ppm: 8.27 (1H, dd, J=5.6, 0.3 Hz), 7.77-7.73 (2H, m), 7.69 (1H, br s), 7.43-7.36 (2H, m), 7.28-7.22 (1H, m), 7.10 (1H, d, J=2.8 Hz), 7.00 (1H, dd, J=8.8, 2.8 Hz), 6.96-6.92 (3H, m), 4.57-4.51 (1H, m), 4.25-4.18 (1H, m), 3.53 (1H, br s), 3.32-3.25 (2H, m), 3.18 (1H, dd, J=16.6, 5.3 Hz), 0.89-0.79 (1H, m).

Step 3—4-[3-(4-phenyl-1H-imidazol-2-yl)chroman-6-yl]oxy-N-(2-pyridyl)pyridin-2-amine A solution of 2-chloro-4-[3-(4-phenyl-1H-imidazol-2-yl)chroman-6-yl]oxy-pyridine (50 mg, 0.12 mmol), 2-aminopyridine (17.5 mg, 0.19 mmol), XPhos Pd G2 (9.8 mg, 0.01 mmol), XPhos (5.9 mg, 0.01 mmol) and $K_2CO_3$ (51.3 mg, 0.3700 mmol) in tert-butanol under a nitrogen atmosphere (0.6 mL) was irradiated at 130° C. for 1 hour. After this time, additional 2-aminopyridine (17.5 mg, 0.1900 mmol), $K_2CO_3$ (51.3 mg, 0.37 mmol), XPhos Pd G2 (9.8 mg, 0.01 mmol) and XPhos (5.9 mg, 0.01 mmol) were added and the mixture was irradiated at 160° C. for 1 hour, after which time it was through a plug of celite and the filter cake washed with EtOAc. The filtrate was concentrated and the residue purified by column chromatography using as eluent a gradient 0-10% MeOH in DCM, followed by purification by preparative LC-MS. Fractions containing the product were dried and loaded into an SCX-2 column, which was flushed at first with MeOH (10 mL) and then $NH_3$ in MeOH (10 mL) to elute the product. The filtrate was concentrated to give 4-[3-(4-phenyl-1H-imidazol-2-yl)chroman-6-yl]oxy-N-(2-pyridyl)pyridin-2-amine (11.5 mg, 0.025 mmol, 20% yield) as a white solid. UPLC-MS (ES+, final purity): 2.47 min, m/z 462.3 [M+H]$^+$. $^1$H NMR (400 MHz, DMSO-d$_6$) δ/ppm: 12.37 (1H, br s), 9.66 (1H, br s), 8.17-8.14 (1H, m), 8.08 (1H, d, J=5.8 Hz), 7.76-7.70 (2H, m), 7.69-7.60 (2H, m), 7.55 (1H, br s), 7.40-7.31 (3H, m), 7.21-7.15 (1H, m), 7.04 (1H, d, J=2.7 Hz), 6.94 (1H, dd, J=8.8 Hz, 2.7 Hz), 6.90 (1H, d, J=8.8 Hz), 6.87-6.82 (1H, m), 6.41 (1H, dd, J=5.8 Hz, 2.1 Hz), 4.56-4.49 (1H, m), 4.17-4.10 (1H, m), 3.45-3.36 (1H, m), 3.26 (1H, dd, J=16.7 Hz, 10.6 Hz), 3.18-3.09 (1H, m).

The compound in the table below was made in an analogous manner, using the appropriate amine in step 3:

| Comp. No | Structure and Name | Data |
|---|---|---|
| 141 | N-[4-[3-(4-phenyl-1H-imidazol-2-yl)chroman-6-yl]oxy-2-pyridyl]-thiazol-2-amine | UPLC-MS (ES+, final purity): 2.81 min, m/z 468.2 [M + H]$^+$. $^1$H NMR (400 MHz, DMSO-d$_6$) δ/ppm: 12.15 (1H, br s), 11.02 (1H, s), 8.16 (1H, d, J = 5.7 Hz), 7.73 (2H, d, J = 7.5 Hz), 7.57 (1H, br s), 7.39-7.31 (3H, s), 7.22-7.15 (1H, m), 7.06 (1H, d, J = 2.6 Hz), 6.99-6.94 (2H, m), 6.92 (1H, d, J = 8.8 Hz), 6.53 (1H, d, J = 2.2 Hz), 6.52 (1H, dd, J = 5.7 Hz, 2.2 Hz), 4.56-4.50 (1H, m), 4.17-4.10 (1H, m), 3.46-3.36 (1H, m), 3.31-3.21 (1H, m), 3.19-3.10 (1H, m). |

Example 33. Synthesis of 2,2-difluoro-N-[4-[3-(4-phenyl-1H-imidazol-2-yl)chroman-6-yl]oxy-2-pyridyl]cyclopropanecarboxamide (Compound 137)

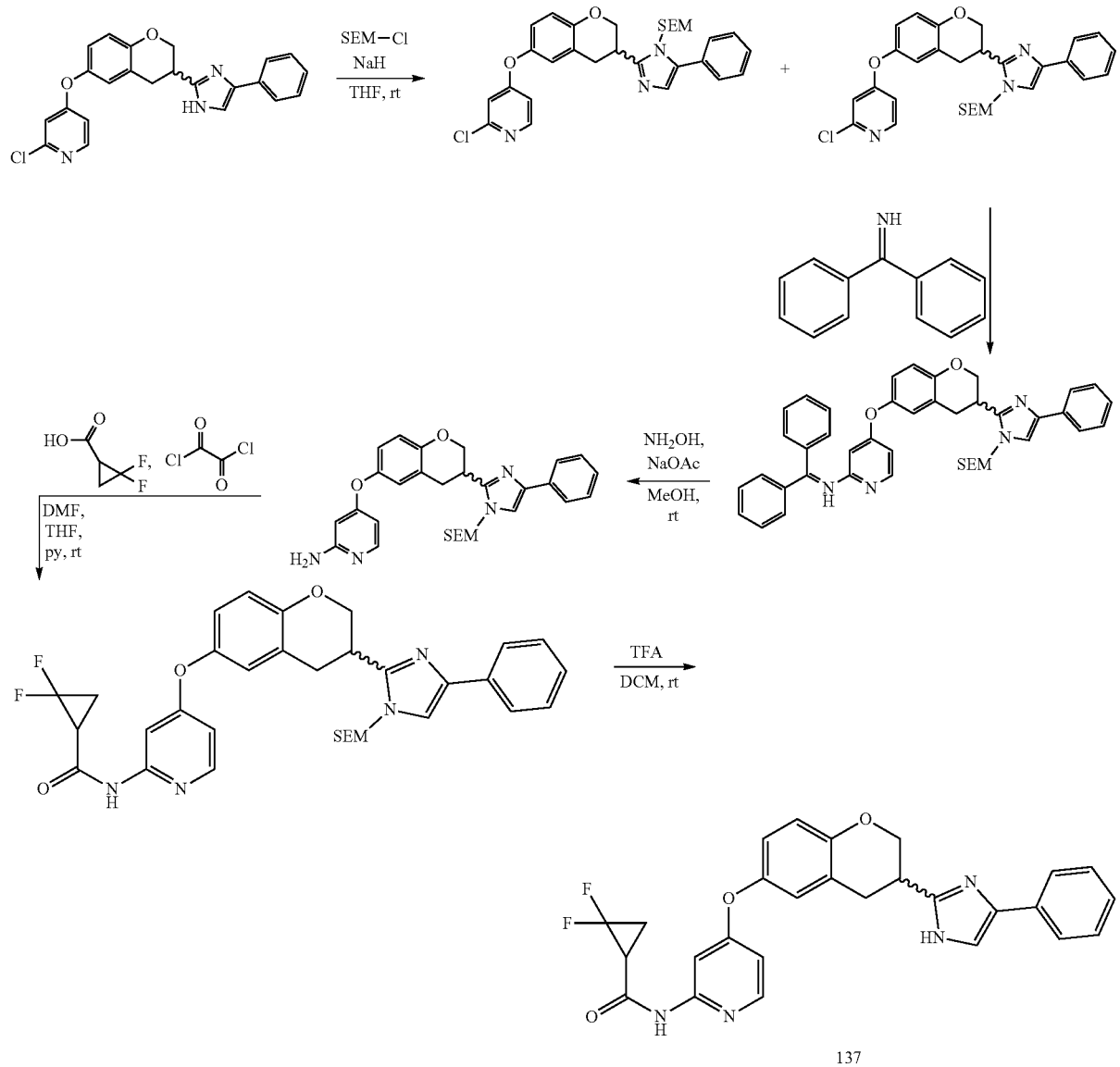

Step 1—2-[[2-[6-[(2-chloro-4-pyridyl)oxy]chroman-3-yl]-4-phenyl-imidazol-1-yl]methoxy]ethyl-trimethyl-silane and ~2-[[2-[6-[(2-chloro-4-pyridyl)oxy]chroman-3-yl]-5-phenyl-imidazol-1-yl]methoxy]ethyl-trimethyl-silane To a solution of 2-chloro-4-[3-(4-phenyl-1H-imidazol-2-yl)chroman-6-yl]oxy-pyridine (553 mg, 1.37 mmol) in anhydrous THF (13.7 mL) at 0° C. under a nitrogen atmosphere was added NaH (60% in mineral oil—82.1 mg, 2.05 mmol) and the mixture was stirred at 0° C. for 45 minutes. 2-(trimethylsilyl)ethoxymethyl chloride (300 µL, 1.7 mmol) was added dropwise and the mixture was stirred for 2 hours at 0° C. The reaction mixture was quenched with water (15 mL) and extracted with EtOAc (3×10 mL). The combined organic layers were dried over $Na_2SO_4$, filtered and the solvent removed in vacuo. The residue was purified by column chromatography using as eluent a gradient 0-50% EtOAc in petroleum ether to give 2-[[2-[6-[(2-chloro-4-pyridyl)oxy]chroman-3-yl]-4-phenyl-imidazol-1-yl]methoxy]ethyl-trimethyl-silane (444 mg, 0.83 mmol, 61% yield) and 2-[[2-[6-[(2-chloro-4-pyridyl)oxy]chroman-3-yl]-5-phenyl-imidazol-1-yl]methoxy]ethyl-trimethyl-silane (120.4 mg, 0.23 mmol, 16% yield), both as yellow gums.

2-[[2-[6-[(2-chloro-4-pyridyl)oxy]chroman-3-yl]-4-phenyl-imidazol-1-yl]methoxy]ethyl-trimethyl-silane: UPLC-MS (ES+, short acidic): 2.23 min, m/z 535.3 [M+H]⁺. ¹H NMR (400 MHz, DMSO-d₆) δ/ppm: 8.29-8.26 (1H, m), 7.77 (1H, s), 7.76-7.72 (2H, m), 7.37-7.32 (2H, m), 7.22-7.16 (1H, m), 7.08 (1H, d, J=2.8 Hz), 7.00 (1H, dd, J=8.8 Hz, 2.8 Hz), 6.97-6.92 (3H, m), 5.48 (1H, d, J=11.1 Hz), 5.42 (1H, d, J=11.1 Hz), 4.50-4.44 (1H, m), 4.11-4.04 (1H, m), 3.61-3.52 (3H, m), 3.32-3.25 (1H, m), 3.08-2.99 (1H, m), 0.93-0.86 (2H, m), −0.02 (9H, s).

2-[[2-[6-[(2-chloro-4-pyridyl)oxy]chroman-3-yl]-5-phenyl-imidazol-1-yl]methoxy]ethyl-trimethyl-silane: UPLC- MS (ES+, short acidic): 2.00 min, m/z 535.5 [M+H]⁺. ¹H NMR (400 MHz, DMSO-d₆) δ/ppm: 8.29-8.26 (1H, m), 7.51-7.38 (5H, m), 7.07 (1H, d, J=2.8 Hz), 7.02 (1H, s), 7.00 (1H, dd, J=8.8 Hz, 2.8 Hz), 6.97-6.92 (3H, m), 5.39 (1H, d, J=11.1 Hz), 5.33 (1H, d, J=11.1 Hz), 4.51-4.45 (1H, m), 4.12-4.05 (1H, m), 3.65-3.55 (1H, m), 3.44-3.38 (2H, m), 3.30-3.20 (1H, m), 3.09-3.01 (1H, m), 0.88-0.77 (2H, m), −0.08 (9H, s).

Step 2—1,1-diphenyl-N-[4-[3-[4-phenyl-1-(2-trimethylsilylethoxymethyl)imidazol-2-yl]chroman-6-yl]oxy-2-pyridyl]methanimine To a solution of 2-[[2-[6-[(2-chloro-4-pyridyl)oxy]chroman-3-yl]-4-phenyl-imidazol-1-yl]methoxy]ethyl-trimethyl-silane (444 mg, 0.83 mmol), benzophenone imine (210 µL, 1.25 mmol) and Cs₂CO₃ (677.1 mg, 2.08 mmol) in dry 1,4-dioxane (4 mL) under a nitrogen atmosphere were added (+/−)-BINAP (103.5 mg, 0.17 mmol) and tris(dibenzylideneacetone)dipalladium (0) (76.1 mg, 0.08 mmol) and the mixture was heated at 110° C. for 18 hours. After cooling to rt, the mixture was filtered through celite and the filter cake washed with EtOAc. The solvent was removed in vacuo and the residue purified by column chromatography using as eluent a gradient 0-100% EtOAc in petroleum ether to give 1,1-diphenyl-N-[4-[3-[4-phenyl-1-(2-trimethylsilylethoxymethyl)imidazol-2-yl]chroman-6-yl]oxy-2-pyridyl]methanimine (564.3 mg, 0.83 mmol, 100% yield) as an orange solid. The compound was used in the next step without further purification. UPLC-MS (ES+, short acidic): 2.12 min, m/z 679.5 [M+H]⁺.

Step 3—acetic acid; 4-[3-[4-phenyl-1-(2-trimethylsilylethoxymethyl)imidazol-2-yl]chroman-6-yl]oxypyridin-2-amine To a solution of 1,1-diphenyl-N-[4-[3-[4-phenyl-1-(2-trimethylsilylethoxymethyl)imidazol-2-yl]chroman-6-yl]oxy-2-pyridyl]methanimine (564.3 mg, 0.83 mmol) in MeOH (8.3 mL) were added NaOH (204.6 mg, 2.49 mmol) and hydroxylamine hydrochloride (127.1 mg, 1.83 mmol) and the mixture was stirred at rt for 1 hour. The solvent was removed in vacuo and the residue purified by column chromatography using as eluent a gradient 0-10% MeOH in DCM to give acetic acid; 4-[3-[4-phenyl-1-(2-trimethylsilylethoxymethyl)imidazol-2-yl]chroman-6-yl]oxypyridin-2-amine (366.4 mg, 0.64 mmol, 77% yield) as an orange solid. UPLC-MS (ES+, short acidic): 1.70 min, m/z 515.4 [M+H]⁺. ¹H NMR (400 MHz, DMSO-d₆) δ/ppm: 7.79-7.72 (4H, m), 7.38-7.32 (2H, m), 7.22-7.17 (1H, m), 7.00-6.97 (1H, m), 6.92-6.89 (2H, m), 6.13 (1H, dd, J=5.9 Hz, 2.3 Hz), 5.96 (2H, br s), 5.82 (1H, d, J=2.3 Hz), 5.48 (1H, d, J=11.1 Hz), 5.42 (1H, d, J=11.1 Hz), 4.49-4.43 (1H, m), 4.07-4.00 (1H, m), 3.60-3.48 (3H, m), 3.35-3.28 (1H, m, (partly under water peak)), 3.07-2.99 (1H, m), 1.91 (3H, s, AcOH), 0.94-0.83 (2H, m), −0.02 (9H, s).

Step 4—2,2-difluoro-N-[4-[3-[4-phenyl-1-(2-trimethylsilylethoxymethyl)imidazol-2-yl]chroman-6-yl]oxy-2-pyridyl]cyclopropanecarboxamide To a solution of 2,2-difluorocyclopropanecarboxylic acid (63.7 mg, 0.52 mmol) in anhydrous THF (0.7 mL) at 0° C. under a nitrogen atmosphere were added DMF (2 µL, 0.0300 mmol) and oxalyl chloride (44.6 µL, 0.53 mmol) and the reaction was stirred at 0° C. for 30 minutes. The mixture was then added to a solution of acetic acid; 4-[3-[4-phenyl-1-(2-trimethylsilylethoxymethyl)imidazol-2-yl]chroman-6-yl]oxypyridin-2-amine (60 mg, 0.10 mmol) in anhydrous Pyridine (0.70 mL) and stirred at rt for 1 hr. The mixture was diluted with EtOAc (30 mL) and washed with sat. aq. NaHCO₃ (10 mL), water (10 mL) and brine (10 mL). The organic layer was dried over Na₂SO₄, filtered and the solvent removed in vacuo. The residue was purified by column chromatography using as eluent a gradient 0-100% EtOAc in petroleum ether to give 2,2-difluoro-N-[4-[3-[4-phenyl-1-(2-trimethylsilylethoxymethyl)imidazol-2-yl]chroman-6-yl]oxy-2-pyridyl]cyclopropanecarboxamide (47.3 mg, 0.076 mmol, 73% yield) as a glassy solid. UPLC-MS (ES+, short acidic): 2.06 min, m/z 619.5 [M+H]⁺. ¹H NMR (400 MHz, DMSO-d₆) δ/ppm: 11.03 (1H, s), 8.20 (1H, d, J=5.7 Hz), 7.77 (1H, s), 7.76-7.72 (2H, m), 7.62 (1H, br s), 7.37-7.32 (2H, m), 7.22-7.16 (1H, m), 7.05 (1H, d, J=2.6 Hz), 6.96 (1H, dd, J=8.8 Hz, 2.6 Hz), 6.92 (1H, d, J=8.8 Hz), 6.67 (1H, ddd, J=5.7 Hz, 4.1 Hz, 2.3 Hz), 5.48 (1H, d, J=11.1 Hz), 5.42 (1H, d, J=11.1 Hz), 5.50-5.44 (1H, m), 4.05 (1H, td, J=10.7 Hz, 1.7 Hz), 3.60-3.54 (3H, m), 3.32-3.25 (1H, m), 3.07-2.90 (2H, m), 2.04-1.93 (2H, m), 0.93-0.85 (2H, m), −0.03 (9H, s).

Step 5—2,2-difluoro-N-[4-[3-(4-phenyl-1H-imidazol-2-yl)chroman-6-yl]oxy-2-pyridyl]cyclopropanecarboxamide To a solution of 2,2-difluoro-N-[4-[3-[4-phenyl-1-(2-trimethylsilylethoxymethyl)imidazol-2-yl]chroman-6-yl]oxy-2-pyridyl]cyclopropanecarboxamide (47.3 mg, 0.08 mmol) in DCM (1 mL) was added trifluoroacetic acid (0.5 mL, 6.53 mmol) and the mixture was stirred at rt for 72h. The solvent was removed in vacuo and the residue loaded into loaded into an SCX-2 column, which was flushed at first with MeOH (10 mL) and then NH₃ in MeOH (10 mL) to elute the product. The residue was purified by column chromatography using as eluent a gradient 0-6% MeOH in DCM to give 2,2-difluoro-N-[4-[3-(4-phenyl-1H-imidazol-2-yl)chroman-6-yl]oxy-2-pyridyl]cyclopropanecarboxamide (28.8 mg, 0.059 mmol, 77% yield) as a white solid. UPLC-MS (ES+, final purity): 2.94 min m/z 489.3 [M+H]⁺. ¹H NMR (400 MHz, DMSO-d₆) δ/ppm: 12.32 (0.2H, br s), 12.10 (0.8H, br s), 11.03 (1H, s), 8.19 (1H, d, J=5.7 Hz), 7.79-7.56 (3.78H, m), 7.44-7.12 (3.22, N), 7.06-7.03 (1H, m), 6.94 (1H, dd, J=8.8 Hz, 2.8 Hz), 6.90 (1H, d, J=8.8 Hz), 6.67 (1H, ddd, J=5.7 Hz, 2.3 Hz, 0 Hz), 4.55-4.49 (1H, m), 4.17-4.09 (1H, d), 3.45-3.36 (1H, m), 3.29-3.19 (1H, m), 3.18-3.07 (1H, m), 3.01-2.90 (1H, m), 2.05-1.91 (2H, m).

The compounds in the table below were made in an analogous manner, using the appropriate acid in step 4:

| Comp. No | Structure and Name | Data |
|---|---|---|
| 138 | 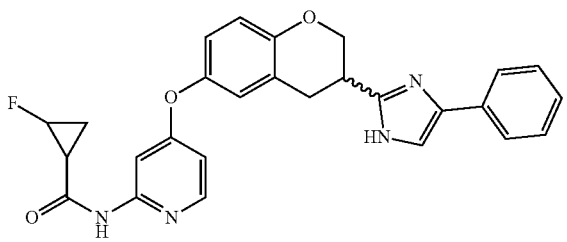<br>1-fluoro-N-[4-[3-(4-phenyl)-1H-imidazol-2-yl)chroman-6-yl]oxy-2-pyridyl]cyclopropanecarboxamide | UPLC-MS (ES+, final purity): 3.00 min, m/z 471.2 [M + H]$^+$. $^1$H NMR (400 MHz, DMSO-d$_6$) δ/ppm: 12.32 (0.2H, br s), 12.06 (0.8H, br s), 10.21 (1H, d, J = 1.3 Hz), 8.23 (1H, d, J = 5.7 Hz), 7.77-7.73 (1.6H, m), 7.65-7.61 (0.4H, m), 7.60-7.56, (1.8H, m), 7.43-7.37 (0.4H, m), 7.36-7.29 (1.6H, m), 7.29-7.20 (0.4H, m), 7.19-7.13 (0.8H, m), 7.07-7.04 (1H, m), 6.95 (1H, dd, J = 8.8, 2.8 Hz), 6.90 (1H, d, J = 8.8 Hz), 6.73 (1H, dd, J = 8.8, 2.4 Hz), 4.55-4.49 (1H, m), 4.16-4.08 (1H, m), 3.45-3.35 (1H, m), 3.29-3.19 (1H, m), 3.16-3.07 (1H, m), 1.46-1.27 (4H, m). |
| 139 | 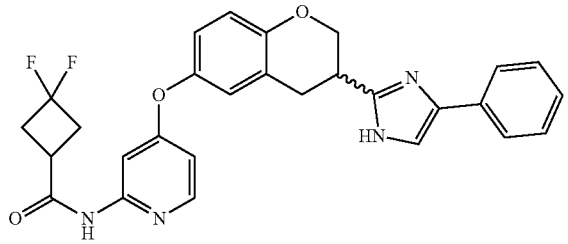<br>3,3-difluoro-N-[4-[3-(4-phenyl-1H-imidazol-2-yl)chroman-6-yl]oxy-2-pyridyl]cyclobutanecarboxamide | UPLC-MS (ES+, final purity): 2.99 min, m/z 503.3 [M + H]$^+$. $^1$H NMR (400 MHz, DMSO-d$_6$) δ/ppm: 12.32 (0.2H, br s), 12.10 (0.8H, br s), 10.70 (1H, s), 8.17 (1H, d, J = 5.7 Hz), 7.78-7.72 (1.6H, m), 7.72-7.57 (2.2H, m), 7.43-7.37 (0.4H, m), 7.36-7.29 (1.6H, m), 7.29-7.20 (0.4H, m), 7.19-7.13 (0.8H, m), 7.06-7.02 (1H, m), 6.94 (1H, dd, J = 8.8, 2.6 Hz), 6.90 (1H, d, J = 8.8 Hz), 6.65 (1H, dd, J = 5.7, 2.4 Hz), 4.56-4.50 (1H, m), 4.17-4.10 (1H, m), 3.46-3.36 (1H, m), 3.27-3.07 (3H, m), 2.82-2.69 (4H, m). |
| 157 | 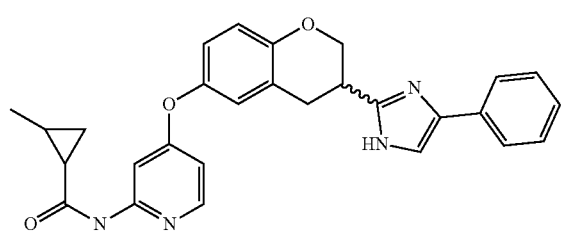<br>2-methyl-N-[4-[3-(4-phenyl-1H-imidazol-2-yl)chroman-6-yl]oxy-2-pyridyl]cyclopropanecarboxamide | UPLC-MS (ES+, final purity): 2.79 & 2.81 min, m/z 467.3 [M + H]$^+$ (0.14/1 mixture of diastereoisomers). 1H NMR (400 MHz, DMSO-d$_6$) δ/ppm: 12.31 (0.2H, br s), 12.09 (0.8H, br s), 10.71 (1H, s), 8.15 (1H, d, J = 5.7 Hz), 7.77-7.73 (1.6H, m), 7.71-7.57 (2.2H, m), 7.43-7.37 (0.4H, m), 7.36-7.29, (1.6H, m), 7.29-7.20 (0.4H, m), 7.19-7.13 (0.8H, m), 7.05-7.00 (1H, m), 6.96-6.86 (2H, m), 6.61 & 6.57 (1H, dd, J = 5.7, 2.3 Hz), 4.55-4.49 (1H, m), 4.16-4.08 (1H, m), 3.45-3.35 (1H, m), 3.28-3.18 (1H, m), 3.16-3.06 (1H, m), 1-76-1.70 (1H, m), 2.03-1.95 & 1.27-1.14 (2H, m), 1.09-1.04 (3H, m), 0.66-0.59 (1H, m). |

Example 34. Synthesis of N-[4-[3-(4-phenyl-1H-imidazol-2-yl)chroman-6-yl]oxy-2-pyridyl]acetamide (Compound 156)

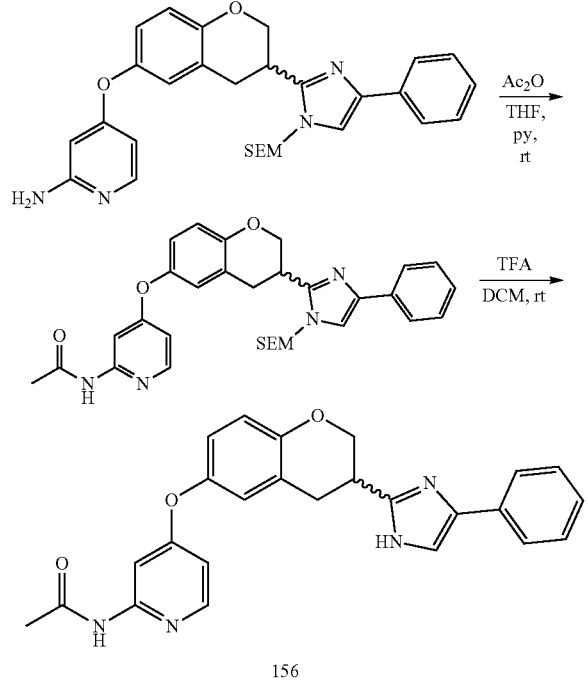

Step 1—N-[4-[3-[4-phenyl-1-(2-trimethylsilylethoxymethyl)imidazol-2-yl]chroman-6-yl]oxy-2-pyridyl]acetamide To a solution of acetic acid; 4-[3-[4-phenyl-1-(2-trimethylsilylethoxymethyl)imidazol-2-yl]chroman-6-yl]oxypyridin-2-amine (69.5 mg, 0.12 mmol) in pyridine (0.6 mL) was slowly added a solution of acetic anhydride (23 μL, 0.24 mmol) in THF (0.6 mL) and the mixture was stirred at rt for 72 hrs. The mixture was diluted with EtOAc (30 mL) and washed with sat. aq. NaHCO₃ (10 mL), water (10 mL) and brine (10 mL). The organic layer was dried over Na$_2$SO$_4$, filtered and the solvent removed in vacuo. The residue was purified by column chromatography using as eluent a gradient 0-100% EtOAc in petroleum ether to give N-[4-[3-[4-phenyl-1-(2-trimethylsilylethoxymethyl)imidazol-2-yl] chroman-6-yl]oxy-2-pyridyl]acetamide (47.5 mg, 0.085 mmol, 71% yield) as a white solid. UPLC-MS (ES+, short acidic): 1.90 min, m/z 557.5 [M+H]$^+$. $^1$H NMR (400 MHz, DMSO-d$_6$) δ/ppm: 10.50 (1H, s), 8.15 (1H, d, J=5.7 Hz), 7.77 (1H, s), 7.76-7.72 (2H, m), 7.66 (1H, d, J=2.1 Hz), 7.38-7.32 (2H, m), 7.22-7.17 (1H, m), 7.02 (1H, d, J=2.4 Hz), 6.97-6.90 (2H, m), 6.60 (1H, dd, J=5.7 Hz, 2.4 Hz), 5.49 (1H, d, J=11.1 Hz), 5.42 (1H, d, J=11.1 Hz), 4.50-4.43 (1H, m), 4.09-4.01 (1H, m), 3.61-3.50 (3H, m), 3.31-3.25 (1H, m), 3.07-2.98 (1H, m), 2.05 (3H, s), 0.93-0.86 (2H, m), −0.02 (9H, s).

Step 2—N-[4-[3-(4-phenyl-1H-imidazol-2-yl)chroman-6-yl]oxy-2-pyridyl]acetamide To a solution of N-[4-[3-[4-phenyl-1-(2-trimethylsilylethoxymethyl)imidazol-2-yl]chroman-6-yl]oxy-2-pyridyl] acetamide (39.4 mg, 0.07 mmol) in DCM (1 mL) was added TFA (0.5 mL, 6.53 mmol) and the mixture was stirred at rt for 22 hrs. The solvent was removed under reduce pressure and the residue was loaded into an SCX-2 column and flushed at first with MeOH (10 mL) and then NH$_3$ in MeOH (10 mL) to elute the product. The solvent was removed in vacuo and the residue was purified by column chromatography using as eluent a gradient 0-8% MeOH in DCM to give N-[4-[3-(4-phenyl-1H-imidazol-2-yl)chroman-6-yl] oxy-2-pyridyl]acetamide (20.2 mg, 0.047 mmol, 70% yield) as a white solid. UPLC-MS (ES+, final purity): 2.45 min, m/z 427.2 [M+H]$^+$. $^1$H NMR (400 MHz, DMSO-d$_6$) δ/ppm: 12.32 (0.2, br s), 12.10 (0.8H, br s), 10.50 (1H, s), 8.15 (1H, d, J=5.7 Hz), 7.78-7.73 (1.6H, m), 7.68-7.57 (2.2H, m), 7.43-7.37 (0.4H, m), 7.36-7.29 (1.6H, m), 7.29-7.20 (0.4H, m), 7.18-7.13 (0.8H, m), 7.05-7.01 (1H, m), 6.93 (1H, dd, J=8.8 Hz, 2.7 Hz), 6.89 (1H, d, J=8.8 Hz), 6.60 (1H, dd, J=5.7 Hz, 2.4 Hz), 4.55-4.49 (1H, m), 4.16-4.08 (1H, m), 3.45-3.35 (1H, m), 3.29-3.19 (1H, m), 3.16-3.07 (1H, m), 2.05 (3H, s).

Example 35. Synthesis of N-cyclopropyl-4-[3-(4-phenyl-1H-imidazol-2-yl)chroman-6-yl]oxy-pyridine-2-carboxamide (Compound 158)

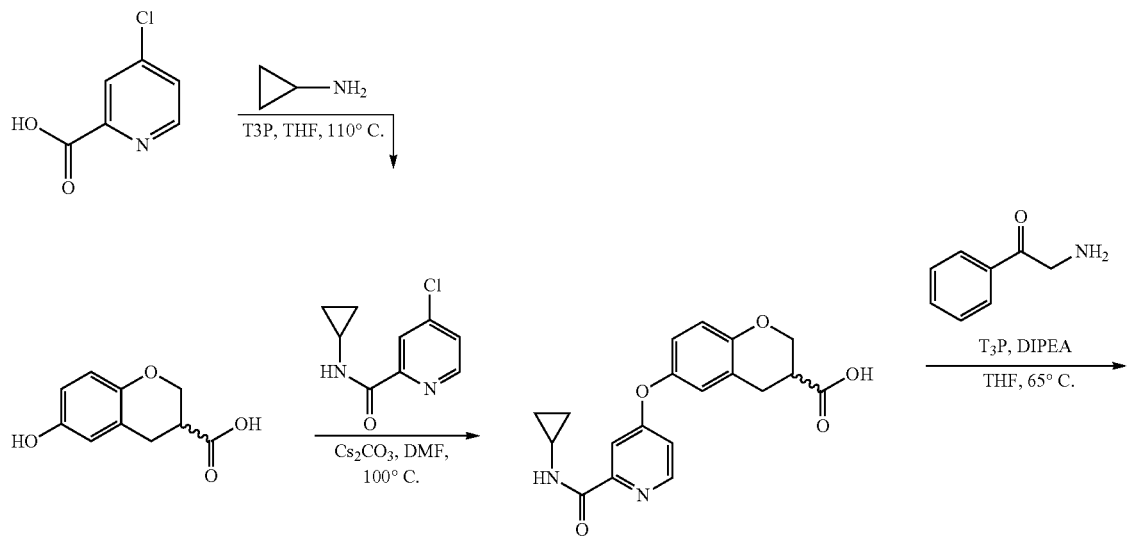

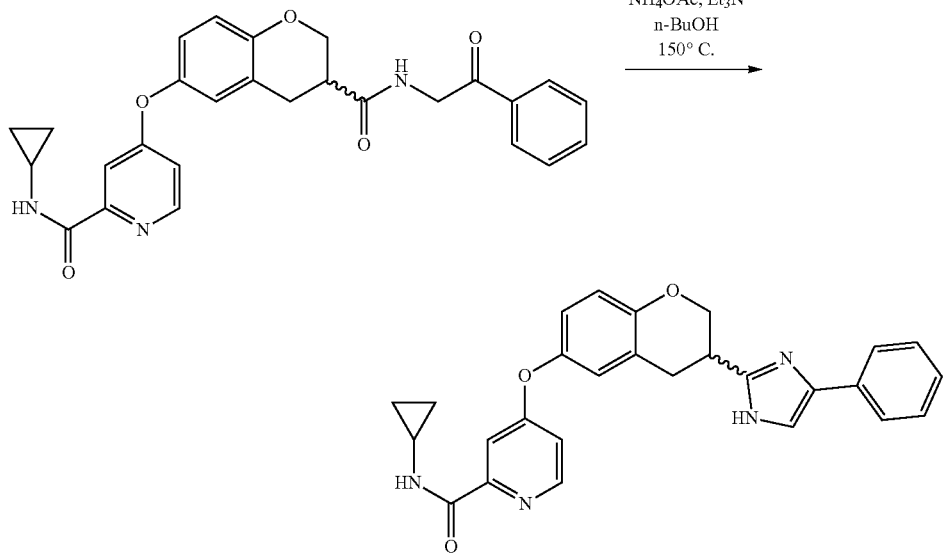

Step 1—4-chloro-N-cyclopropyl-pyridine-2-carboxamide

To a suspension of 4-chloro-2-pyridinecarboxylic acid (500 mg, 3.17 mmol) and cyclopropylamine (242 µL, 3.49 mmol) in THF (32 mL) were added T3P (2.8 mL, 4.7 mmol) and DIPEA (1.1 mL, 6.32 mmol) and the mixture was heated at 65° C. for 2.5 hours. The solvent was removed under reduce pressure and the residue dissolved in EtOAc (100 mL). The organic layer was washed with sat. aq. NaHCO$_3$ (25 mL), water (2×25 mL) and brine (25 mL), dried over Na$_2$SO$_4$, filtered and the solvent removed in vacuo to give 4-chloro-N-cyclopropyl-pyridine-2-carboxamide (499.8 mg, 2.54 mmol, 80% yield) as an off-white solid. The compound used in the next step without further purification. UPLC-MS (ES+, short acidic): 1.35 min, m/z 197.0 [M+H]. $^1$H NMR (400 MHz, DMSO-d$_6$) δ/ppm: 8.82 (1H, d, J=4.4 Hz), 8.59 (1H, dd, J=5.3, 0.6 Hz), 8.01 (1H, dd, J=2.2 Hz, 0.6 Hz), 7.75 (1H, dd, J=5.3 Hz, 2.2 Hz), 2.95-2.87 (1H, m), 0.72-0.65 (4H, m).

Step 2—6-[[2-(cyclopropylcarbamoyl)-4-pyridyl]oxy]chromane-3-carboxylic Acid To a solution of 4-chloro-N-cyclopropyl-pyridine-2-carboxamide (200 mg, 1.02 mmol) in DMF (10 mL) under a nitrogen atmosphere were added Cs$_2$CO$_3$ (994.3 mg, 3.05 mmol) and 6-hydroxychromane-3-carboxylic acid (197.8 mg, 1.02 mmol) and the mixture was heated at 100° C. overnight. Additional 6-hydroxychromane-3-carboxylic acid (49.4 mg, 0.25 mmol) and Cs$_2$CO$_3$ (165.7 mg, 0.51 mmol) were added and the mixture was heated at 100° C. for 72 hours. After cooling to rt, the mixture was poured into cold water and the aqueous was acidified to pH 2 with 1N aq. HCl followed by with EtOAc (4×50 mL). The combined organic layers were dried over Na$_2$SO$_4$, filtered and the solvent removed in vacuo. The residue was purified by column chromatography using as eluent a gradient 0-10% MeOH in DCM to give 6-[[2-(cyclopropylcarbamoyl)-4-pyridyl]oxy]chromane-3-carboxylic acid (192.9 mg, 0.54 mmol, 54% yield) as a beige solid. UPLC-MS (ES+, short acidic): 1.47 min, m/z 355.4 [M+H]$^+$. $^1$H NMR (400 MHz, DMSO-d$_6$) δ/ppm: 12.69 (1H, s), 8.71 (1H, d, J=5.0 Hz), 8.47 (1H, dd, J=5.6 Hz, 0.4 Hz), 7.34 (1H, dd, J=2.7 Hz, 0.4 Hz), 7.12 (1H, dd, J=5.6 Hz, 2.7 Hz), 7.04 (1H, d, J=2.8 Hz), 6.94 (1H, dd, J=8.8 Hz, 2.8 Hz), 6.88 (1H, d, J=8.8 Hz), 4.36 (1H, dd, J=10.8 Hz, 3.1 Hz), 4.17 (1H, dd, J 10.8 Hz, 7.7 Hz), 3.06-2.95 (3H, m), 2.89-2.82 (1H, m), 0.69-0.63 (4H, m).

Step 3—N-cyclopropyl-4-[3-(phenacylcarbamoyl)chroman-6-yl]oxy-pyridine-2-carboxamide To a solution of 6-[[2-(cyclopropylcarbamoyl)-4-pyridyl]oxy]chromane-3-carboxylic acid (190.6 mg, 0.54 mmol) and 2-aminoacetophenone hydrochloride (101.6 mg, 0.59 mmol) in THF (5.3 mL) were added T3P (480 µL, 0.81 mmol) and DIPEA (290 µL, 1.66 mmol) and the mixture was heated at 65° C. for 2 hours. After cooling to rt, the solvent was removed in vacuo and the residue dissolved in EtOAc (50 mL). The organic layer was washed with water (2×15 mL) and brine (15 mL), dried over Na$_2$SO$_4$, filtered and the solvent removed under reduce pressure. The residue was suspended in petroleum ether, filtered and dried to give N-cyclopropyl-4-[3-(phenacylcarbamoyl)chroman-6-yl]oxy-pyridine-2-carboxamide (228 mg, 0.48 mmol, 90% yield) as a cream solid. UPLC-MS (ES+, short acidic): 1.64 min, m/z 472.5 [M+H]$^+$. $^1$H NMR (400 MHz, DMSO-d$_6$) δ/ppm: 8.72 (1H, d, J=5.0 Hz), 8.58-8.53 (1H, m), 8.47 (1H, dd, J=5.6 Hz, 0.3 Hz), 8.02-7.97 (2H, m), 7.70-7.65 (1H, m), 7.58-7.52 (2H, m), 7.35 (1H, dd, J=2.6 Hz, 0.3 Hz), 7.13 (1H, dd, J=5.6 Hz, 2.6 Hz), 7.06 (1H, d, J=2.8 Hz), 6.96 (1H, dd, J=8.8 Hz, 2.8 Hz), 6.90 (1H, d, J=8.8 Hz), 4.67 (2H, d, J=5.6 Hz), 4.43-4.37 (1H, m), 4.03-3.95 (1H, m), 3.07-2.82 (4H, m), 0.69-0.62 (4H, m).

Step 4—N-cyclopropyl-4-[3-(4-phenyl-1H-imidazol-2-yl)chroman-6-yl]oxy-pyridine-2-carboxamide To a suspension of N-cyclopropyl-4-[3-(phenacylcarbamoyl)chroman-6-yl]oxy-pyridine-2-carboxamide (227.6 mg, 0.48 mmol) in 1-butanol (4.8 mL) were added ammonium acetate (372.1 mg, 4.82 mmol) and triethylamine (67 μL, 0.48 mmol) and the mixture was irradiated at 150° C. for 45 minutes. The solvent was removed under reduce pressure and the residue purified by column chromatography using as eluent a gradient 0-4% MeOH in DCM, followed by purification by reverse column chromatography using as eluent a gradient 0-50% (MeCN+0.1% formic acid) in (water+0.1% formic acid). Fractions containing product were combined, the solvent removed in vacuo and the residue loaded into a SCX-2 which was flushed at first with MeOH and then MeOH+NH$_3$ to elute the product. The solvent was removed in vacuo to give N-cyclopropyl-4-[3-(4-phenyl-1H-imidazol-2-yl)chroman-6-yl]oxy-pyridine-2-carboxamide (75.7 mg, 0.17 mmol, 67% yield) as a white solid. UPLC-MS (ES+, final purity): 3.12 min, m/z 453.4 [M+H]$^+$. $^1$H NMR (400 MHz, DMSO-d$_6$) δ/ppm: 12.24 (1H, br s), 8.72 (1H, d, J=5.0 Hz), 8.47 (1H, dd, J=5.6 Hz, 0.3 Hz), 7.76-7.70 (2H, m), 7.55 (1H, br s), 7.39-7.32 (3H, m), 7.22-7.16 (1H, m), 7.15 (1H, dd, J=5.6 Hz, 2.6 Hz), 7.09 (1H, d, J=2.8 Hz), 6.99 (1H, dd, J=8.8 Hz, 2.8 Hz), 6.94 (1H, d, J=8.8 Hz), 4.57-4.51 (1H, m), 4.20-4.13 (1H, m), 3.49-3.39 (1H, m), 3.30-3.22 (1H, m), 3.19-3.10 (1H, m), 2.91-2.82 (1H, m), 0.71-0.62 (4H, m).

Example 36. Synthesis of N-cyclobutyl-4-[3-(4-phenyl-1H-imidazol-2-yl)chroman-6-yl]oxy-pyridin-2-amine (Compound 142)

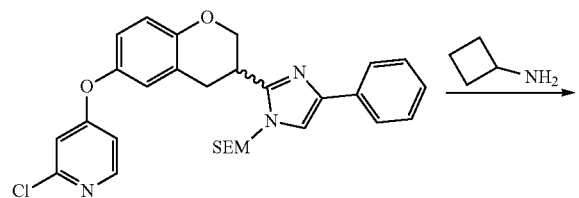

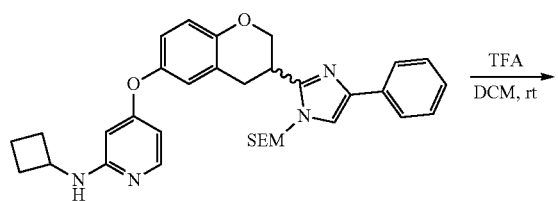

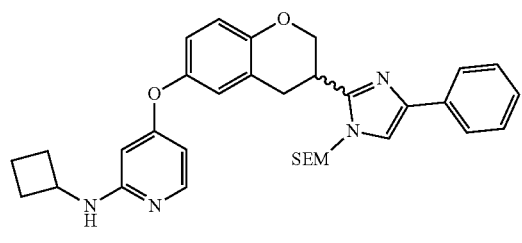

142

Step 1—N-cyclobutyl-4-[3-[5-phenyl-1-(2-trimethylsilylethoxymethyl)imidazol-2-yl]chroman-6-yl]oxy-pyridin-2-amine A solution of 2-[[2-[6-[(2-chloro-4-pyridyl)oxy]chroman-3-yl]-5-phenyl-imidazol-1-yl]methoxy]ethyl-trimethyl-silane (125 mg, 0.23 mmol; Example 33, Step 1), tris(dibenzylideneacetone)dipalladium (0) (21.5 mg, 0.02 mmol), (+/−)-BINAP (29.2 mg, 0.05 mmol) and Cs$_2$CO$_3$ (152.5 mg, 0.47 mmol) in 1,4-Dioxane (2.2 mL) was degassed under a nitrogen atmosphere for 10 minutes then cyclobutanamine (40 μL, 0.47 mmol) was added. The vial was sealed and the mixture heated at 100° C. for 20 hours. After cooling to rt, the mixture was filtered through diatomaceous earth and the filter cake was washed with EtOAc. The filtrate was concentrated and the residue purified by column chromatography using as eluent a gradient 0-10% MeOH in DCM to give N-cyclobutyl-4-[3-[5-phenyl-1-(2-trimethylsilylethoxymethyl)imidazol-2-yl]chroman-6-yl]oxy-pyridin-2-amine (133.1 mg, 0.23 mmol, 100% yield) as an orange foam. The compound was used in the next step without further purification. UPLC-MS (ES+, short acidic): 1.83 min, m/z 569.3 [M+H]$^+$.

Step 2—N-cyclobutyl-4-[3-(4-phenyl-1H-imidazol-2-yl)chroman-6-yl]oxy-pyridin-2-amine To a solution of N-cyclobutyl-4-[3-[4-phenyl-1-(2-trimethylsilylethoxymethyl)imidazol-2-yl]chroman-6-yl]oxy-pyridin-2-amine (133.1 mg, 0.23 mmol) in DCM (3.6 mL) was added TFA (1.8 mL, 23.51 mmol) and the mixture was stirred at 25° C. for 18 hours. The solvent was removed under reduce pressure, the residue loaded into an SCX-2 column and flushed at first with MeOH (10 mL) and then NH$_3$ in MeOH (10 mL) to elute the product. The residue was purified by column chromatography using as eluent a gradient 0-6% MeOH in DCM, followed by reverse column chromatography using as eluent a gradient 0-50% (MeCN+0.1% formic acid) in (water+0.1% formic acid). Fractions containing the product were loaded onto a SCX-2 column and flushed at first with MeOH (10 mL) and then NH$_3$ in MeOH (10 mL) to give N-cyclobutyl-4-[3-(4-phenyl-1H-imidazol-2-yl)chroman-6-yl]oxy-pyridin-2-amine (30 mg, 0.068 mmol, 29% yield) as a white solid. UPLC-MS (ES+, final purity): 2.45 min, m/z 439.2 [M+H]$^+$. $^1$H NMR (400 MHz, DMSO-d$_6$) δ/ppm: 12.12 (1H, br s), 7.82 (1H, d, J=5.8 Hz), 7.73 (2H, m), 7.55 (1H, br s), 7.38-7.30 (2H, m), 7.21-7.14 (1H, m), 6.99-6.96 (1H, m), 6.91-6.85 (2H, m), 6.77 (1H, d, J=6.6 Hz, broad), 6.10 (1H, dd, J=5.8, 2.2 Hz), 5.76 (1H, d, J=2.2 Hz), 4.54-4.48 (1H, m), 4.27-4.15 (1H, m), 4.15-4.06 (1H, m), 3.43-3.34 (1H, m), 3.28-3.19 (1H, m), 3.15-3.07 (1H, m), 2.25-2.16 (2H, m), 1.85-1.73 (2H, m), 1.69-1.53 (2H, m).

Example 37. Synthesis of 1-methyl-N-[4-[3-(4-phenyl-1H-imidazol-2-yl)chroman-6-yl]oxy-2-pyridyl]piperidine-4-carboxamide (Compound 147)

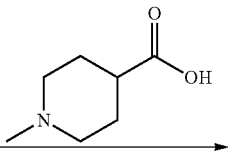

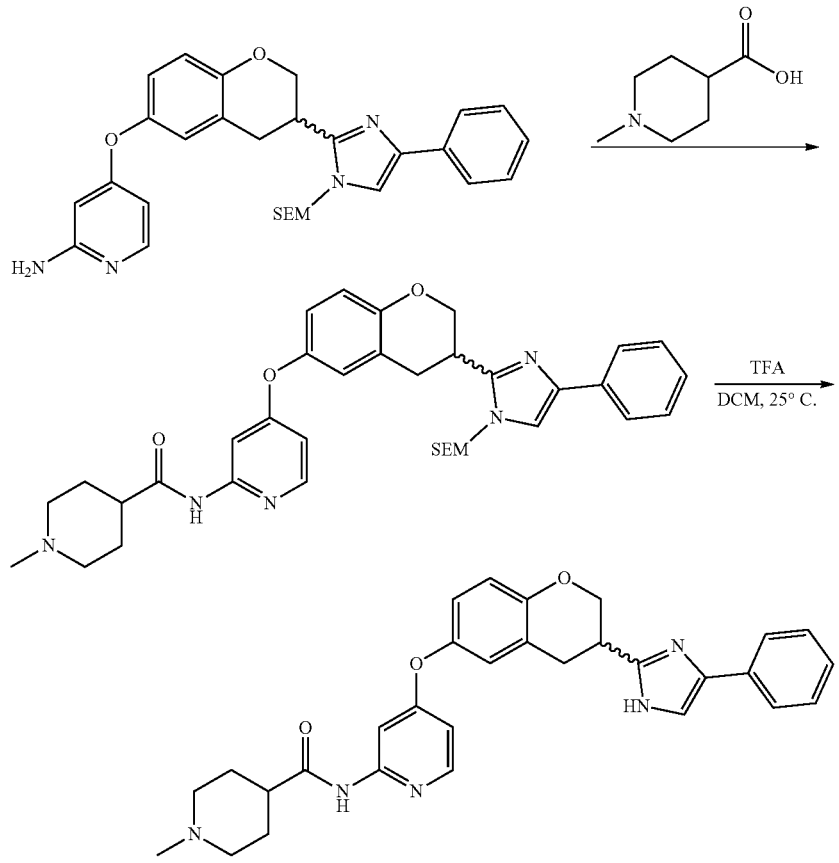

Step 1—1-methyl-N-[4-[3-[4-phenyl-1-(2-trimethylsilylethoxymethyl)imidazol-2-yl]chroman-6-yl]oxy-2-pyridyl]piperidine-4-carboxamide A solution of 4-[3-[4-phenyl-1-(2-trimethylsilylethoxymethyl)imidazol-2-yl]chroman-6-yl]oxypyridin-2-amine (60 mg, 0.12 mmol), 1-methylpiperidine-4-carboxylic acid (18.4 mg, 0.13 mmol), propylphosphonic anhydride (104 µL, 0.17 mmol) and N,N-diisopropylethylamine (41 µL, 0.23 mmol) in THF (1.2 mL) was heated at 65° C., in a sealed tube, overnight. Additional 1-methylpiperidine-4-carboxylic acid (18.4 mg, 0.13 mmol), propylphosphonic anhydride (104 µL, 0.17 mmol) and N,N-diisopropylethylamine (41 µL, 0.23 mmol) were added in a sealable vial. The vial was sealed and the mixture heated at 65° C. for 2 hours. After cooling to room temperature, the mixture was concentrated and the residue purified by column chromatography using as eluent a gradient 0-20% MeOH in DCM, followed by 20% NH₃ 2N in MeOH in DCM to give 1-methyl-N-[4-[3-[4-phenyl-1-(2-trimethylsilylethoxymethyl)imidazol-2-yl]chroman-6-yl]oxy-2-pyridyl]piperidine-4-carboxamide (38.4 mg, 0.060 mmol, 51% yield) as an off-white solid. UPLC-MS (ES+, Short acidic): 1.71 min, m/z 640.3 [M+H]⁺.

Step 2—1-methyl-N-[4-[3-(4-phenyl-1H-imidazol-2-yl)chroman-6-yl]oxy-2-pyridyl]piperidine-4-carboxamide To a solution of 1-methyl-N-[4-[3-[4-phenyl-1-(2-trimethylsilylethoxymethyl)imidazol-2-yl]chroman-6-yl]oxy-2-pyridyl]piperidine-4-carboxamide (38.4 mg, 0.060 mmol) in DCM (1 mL) was added trifluoroacetic acid (0.5 mL, 6.53 mmol) in a sealable vial. The vial was sealed and the mixture stirred at 25° C. for 18 hours. The mixture was concentrated and the residue purified by reverse column chromatography using as eluent a gradient 0-50% of acetonitrile+0.1% formic acid in water+0.1% formic acid. Fraction containing the product were combined, the solvent removed in vacuo and loaded into an SCX-2 column. The column was washed at first with MeOH and then MeOH+NH₃ to give 1-methyl-N-[4-[3-(4-phenyl-1H-imidazol-2-yl)chroman-6-yl]oxy-2-pyridyl]piperidine-4-carboxamide (16 mg, 0.031 mmol, 52% yield) as a white solid. UPLC-MS (ES+, final purity): 2.26 min, m/z 510.3 [M+H]⁺. ¹H NMR (400 MHz, DMSO-d₆) δ/ppm: 12.31 (0.2H, br s), 12.09 (0.8H, br s), 10.45 (1H, s), 8.15 (1H, d, J=5.7 Hz), 7.77-7.73 (1.6H, m), 7.67 (1H, d, J=2.4 Hz), 7.66-7.61 (0.4H, m), 7.61-7.57 (0.8H, m), 7.43-7.37 (0.4H, m), 7.36-7.29 (1.6H, m), 7.29-7.20 (0.4H, m), 7.19-7.13 (0.8H, m), 7.04-7.01 (1H, m), 6.93 (1H, dd, J=8.8, 2.6 Hz), 6.90 (1H, d, J=8.8 Hz), 6.62 (1H, dd, J=5.7, 2.4 Hz), 4.56-4.49 (1H, m), 4.17-4.09 (1H, m), 3.46-3.36 (1H, m), 3.29-3.20 (1H, m), 3.17-3.07 (1H, m), 2.85-2.75 (2H, m), 2.43-2.36 (1H, m), 2.16 (3H, s), 1.92-1.69 (2H, m), 1.74-1.65 (2H, m), 1.64-1.51 (2H, m).

The compounds in the table below were made in an analogous manner, using the appropriate acid in step 1:

| Comp. No | Structure and Name | Data |
|---|---|---|
| 144 | 2-imidazol-1-yl-N-[4-[3-(4-phenyl-1H-imidazol-2-yl)chroman-6-yl]oxy-2-pyridyl]acetamide | UPLC-MS (ES+, final purity): 2.30 min, m/z 493.2 [M + H]⁺. ¹H NMR (400 MHz, DMSO-d₆) δ/ppm: 12.31 (1H, br s), 10.89 (1H, s), 8.20 (1H, d, J = 5.8 Hz), 7.76-7.69 (3H, m), 7.56 (1H, br s), 7.51 (1H, s), 7.37-7.31 (2H, m), 7.21-7.14 (2H, m), 7.02 (1H, d, J = 2.5 Hz), 6.95 (1H, br s), 6.91 (1H, dd, J = 8.8 Hz, 2.5 Hz), 6.88 (1H, d, J = 8.8 Hz), 6.69 (1H, dd, J = 5.8 Hz, 2.3 Hz), 4.96 (2H, s), 4.54-4.47 (1H, m), 4.16-4.08 (1H, m), 3.44-3.36 (1H, m, (partly under water peak)), 3.28-3.16 (1H, m, (partly under water peak)), 3.14-3.06 (1H, m). |
| 152 | N-[4-[3-(4-phenyl-1H-imidazol-2-yl)chroman-6-yl]oxy-2-pyridyl]-2-pyrrolidin-1-yl-acetamide | UPLC-MS (ES+, final purity): 2.34 min, m/z 496.2 [M + H]⁺. ¹H NMR (400 MHz, DMSO-d₆) δ/ppm: 12.33 & 12.10 (0.2 & 0.8H, 2 × br s, mixture of tautomers), 10.02 (1H, br s), 8.16 (1H, d, J = 5.7 Hz), 7.79-7.71 (1.6H, m), 7.69-7.56 (2H, m), 7.43-7.25 (2.4H, m), 7.24-7.12 (1H, m), 7.05 (1H, d, J = 2.6 Hz), 6.94 (1H, dd, J = 8.8 Hz, 2.6 Hz), 6.90 (1H, d, J = 8.8 Hz), 6.64 (1H, dd, J = 5.7 Hz, 2.4 Hz), 4.56-4.49 (1H, m), 4.17-4.09 (1H, m), 3.45-3.35 (2H, m), 3.29-3.20 (1H, m), 3.16-3.08 (1H, m), 2.73-2.62 (4H, m), 1.80-1.72 (4H, m). (1H missing (underneath water and/or DMSO peak)). |
| 154 | N-[4-[3-(4-phenyl-1H-imidazol-2-yl)chroman-6-yl]oxy-2-pyridyl]-2-(1,2,4-triazol-1-yl)acetamide | UPLC-MS (ES+, final purity): 2.64 min, m/z 494.2 [M + H]⁺. ¹H NMR (400 MHz, DMSO-d₆) δ/ppm: 12.14 (1H, br s), 10.98 (1H, s), 8.50 (1H, s), 8.21 (1H, d, J = 5.7 Hz), 7.97 (1H, s), 7.76-7.69 (2H, m), 7.60-7.47 (2H, m), 7.38-7.30 (2H, m), 7.21-7.14 (1H, m), 7.02 (1H, d, J = 2.7 Hz), 6.92 (1H, dd, J = 8.8 Hz, 2.7 Hz), 6.88 (1H, d, J = 8.8 Hz), 6.70 (1H, dd, J = 5.7 Hz, 2.4 Hz), 5.18 (2H, s), 4.54-4.47 (1H, m), 4.16-4.08 (1H, m), 3.44-3.35 (1H, m), 3.27-3.18 (1H, m), 3.15-3.06 (1H, m). |

Example 38. Synthesis of 2-(4-methylpiperazin-1-yl)-N-[4-[3-(4-phenyl-1H-imidazol-2-yl)chroman-6-yl]oxy-2-pyridyl]acetamide (Compound 146)

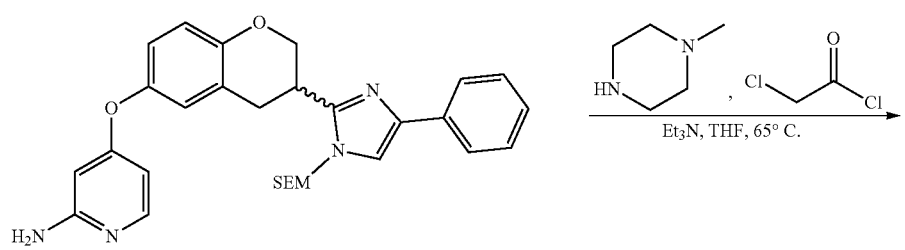

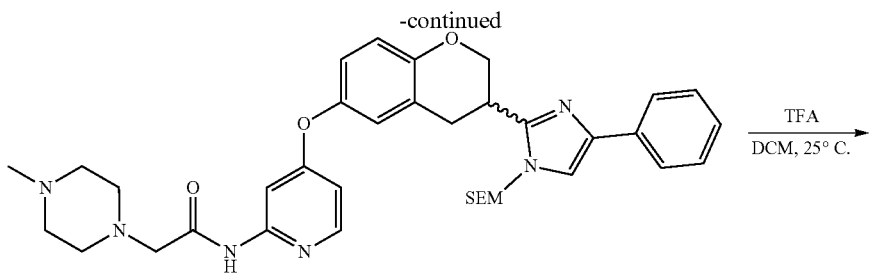

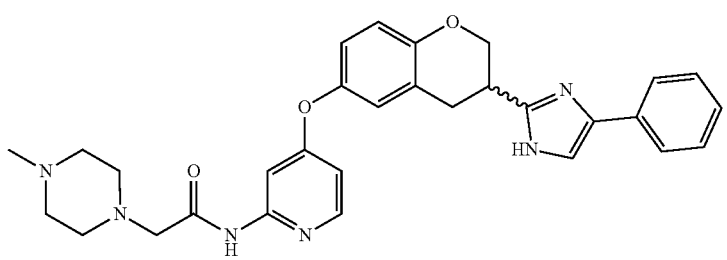

146

Step 1—2-(4-methylpiperazin-1-yl)-N-[4-[3-[4-phenyl-1-(2-trimethylsilylethoxymethyl)imidazol-2-yl]chroman-6-yl]oxy-2-pyridyl]acetamide To a solution of 4-[3-[4-phenyl-1-(2-trimethylsilylethoxymethyl)imidazol-2-yl]chroman-6-yl]oxypyridin-2-amine (100 mg, 0.19 mmol) and Et3N (68 μL, 0.49 mmol) in anhydrous THF (2 mL) at 0° C. under a nitrogen atmosphere was slowly added a solution of chloroacetyl chloride (16 μL, 0.20 mmol) in THF (0.5 mL) and the mixture was stirred at 25° C. for 1 hour. A solution of 1-methylpiperazine (26 μL, 0.23 mmol) in anhydrous THF (0.5 mL) was then added dropwise and the mixture was stirred at 25° C. for 18 hrs. Additional 1-methylpiperazine (26 μL, 0.23 mmol) was added and the mixture heated at 65° C. for 4 hours. After cooling to room temperature, the solvent was removed under reduce pressure and the residue purified by column chromatography using as eluent a gradient 0-20% MeOH in DCM to give 2-(4-methylpiperazin-1-yl)-N-[4-[3-[4-phenyl-1-(2-trimethylsilylethoxymethyl)imidazol-2-yl]chroman-6-yl]oxy-2-pyridyl]acetamide (50.5 mg, 0.077 mmol, 40% yield) as a yellow solid. UPLC-MS (ES+, Short acidic): 1.68 min, m/z 655.4 [M+H]+.

Step 2—2-(4-methylpiperazin-1-yl)-N-[4-[3-(4-phenyl-1H-imidazol-2-yl)chroman-6-yl]oxy-2-pyridyl]acetamide To a solution of 2-(4-methylpiperazin-1-yl)-N-[4-[3-[4-phenyl-1-(2-trimethylsilylethoxymethyl)imidazol-2-yl]chroman-6-yl]oxy-2-pyridyl]acetamide (49.3 mg, 0.0800 mmol) in DCM (1.2 mL) was added trifluoroacetic acid (0.6 mL, 7.84 mmol) and the mixture was stirred at 25° C., in a sealed tube, for 22 hrs. The mixture was concentrated and the residue purified by flash chromatography (C18, 12 g column, gradient 0-50% MeCN in H2O+0.1% HCO2H). Pure fractions were loaded onto a SCX-2 column pre-equilibrated with methanol. The column was washed with methanol and the filtrate was discarded. The product was then eluted with NH3 2N in methanol and the filtrate was concentrated to afford 2-(4-methylpiperazin-1-yl)-N-[4-[3-(4-phenyl-1H-imidazol-2-yl)chroman-6-yl]oxy-2-pyridyl]acetamide (26 mg, 0.050 mmol, 66% yield) as a white solid. UPLC-MS (ES+, final purity): 2.29 min, m/z 525.3 [M+H]+. 1H NMR (400 MHz, DMSO-d6) δ/ppm: 12.31 (0.2H, br s), 12.09 (0.8H, br s), 9.89 (1H, s), 8.17 (1H, d, J=5.8 Hz), 7.77-7.73 (1.6H, m), 7.66 (1H, d, J=2.4 Hz), 7.65-7.61 (0.4H, m), 7.61-7.57 (0.8H, m), 7.43-7.37 (0.4H, m), 7.36-7.29 (1.6H, m), 7.29-7.20 (0.4H, m), 7.19-7.13 (0.8H, m), 7.06-7.02 (1H, m), 6.94 (1H, dd, J=8.8, 2.7 Hz), 6.90 (1H, d, J=8.8 Hz), 6.66 (1H, dd, J=5.8, 2.4 Hz), 4.55-4.49 (1H, m), 4.17-4.09 (1H, m), 3.45-3.35 (1H, m), 3.26-3.19 (1H, m), 3.16-3.07 (3H, m), 2.37 (4H, m, seen as a br s), 2.18 (3H, s). 4H missing (underneath DMSO/water peaks).

The compounds in the table below were made in an analogous manner, using the appropriate amine in step 1:

| Comp. No | Structure and Name | Data |
|---|---|---|
| 149 | 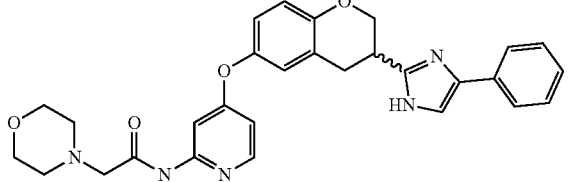<br>2-morpholino-N-[4-[3-(4-phenyl-1H-imidazol-2-yl)chroman-6-yl]oxy-2-pyridyl]acetamide<br>*first step at 60° C. | UPLC-MS (ES+, final purity): 2.39 min, m/z 512.3 [M + H]⁺. $^1$H NMR (400 MHz, DMSO-$d_6$) δ/ppm: 12.15 (1H, br s), 10.02 (1H, s), 8.17 (1H, d, J = 5.7 Hz), 7.76-7.70 (2H, m), 7.66 (1H, d, J = 2.3 Hz), 7.54 (1H, br s), 7.38-7.31 (2H, m), 7.21-7.15 (1H, m), 7.04 (1H, d, J = 2.7 Hz), 6.94 (1H, dd, J = 8.8 Hz, 2.7 Hz), 6.90 (1H, d, J = 8.8 Hz), 6.66 (1H, dd, J = 5.7 Hz, 2.3 Hz), 4.56-4.49 (1H, m), 4.17-4.10 (1H, m), 3.65-3.59 (4H, m), 3.46-3.36 (1H, m), 3.30-3.08 (4H, m), 2.59-2.51 (3H, m). (1H missing (underneath DMSO or water peak)) |
| 145 | 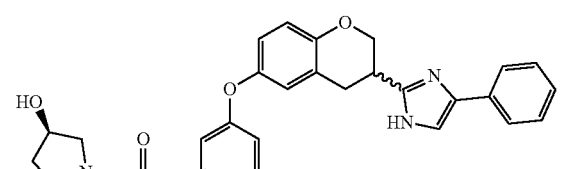<br>2-[(3R)-3-hydroxypyrrolidin-1-yl]-N-[4-[3-(4-phenyl-1H-imidazol-2-yl)chroman-6-yl]oxy-2-pyridyl]acetamide<br>*first step at 60° C. | UPLC-MS (ES+, final purity): 2.30 min, m/z 512.2 [M + H]⁺. $^1$H NMR (400 MHz, DMSO-$d_6$) δ/ppm: 12.33 & 12.10 (0.2 & 0.8H, 2 × br s, mixture of tautomers), 10.03 (1H, br s), 8.17 (1H, d, J = 5.7 Hz), 7.80-7.54 (3.8H, m), 7.42-7.28 (2.2H, m), 7.22-7.12 (1H, m), 7.04 (1H, d, J = 2.7 Hz), 6.94 (1H, dd, J = 8.8 Hz, 2.7 Hz), 6.90 (1H, d, J = 8.8 Hz), 6.66 (1H, dd, J = 5.7 Hz, 2.4 Hz), 4.88 (1H, br s), 4.56-4.49 (1H, m), 4.27-4.20 (1H, m), 4.17-4.09 (1H, m), 3.45-3.35 (2H, m), 3.29-3.19 (1H, m), 3.16-3.07 (1H, m), 2.91-2.77 (2H, m), 2.65-2.54 (1H, m), 2.09-1.97 (1H, m), 1.69-1.58 (1H, m). (2H missing (underneath water and/or DMSO peak)) |
| 153 | 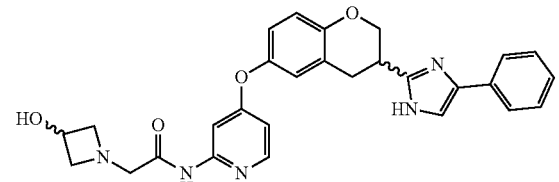<br>2-(3-hydroxyazetidin-1-yl)-N-[4-[3-(4-phenyl-1H-imidazol-2-yl)-chroman-6-yl]oxy-2-pyridyl]acetamide<br>*first step at 60° C. | UPLC-MS (ES+, final purity): 2.29 min, m/z 498.2 [M + H]⁺. $^1$H NMR (400 MHz, DMSO-$d_6$) δ/ppm: 12.32 & 12.10 (0.2 & 0.8H, 2 × br s), 9.96 (1H, s), 8.16 (1H, d, J = 5.7 Hz), 7.78-7.71 (1.6H, m), 7.66-7.56 (2H, m), 7.44-7.25 (2.4H, m), 7.21-7.12 (1H, m), 7.04 (1H, d, J = 2.7 Hz), 6.93 (1H, dd, J = 8.8 Hz, 2.7 Hz), 6.90 (1H, d, J = 8.8 Hz), 6.65 (1H, dd, J = 5.7 Hz, 2.4 Hz), 5.41 (1H, d, J = 6.5 Hz), 4.56-4.48 (1H, m), 4.30-4.21 (1H, m), 4.17-4.08 (1H, m), 3.71-3.63 (2H, m), 3.45-3.35 (1H, m), 3.29-3.19 (1H, m), 3.16-3.07 (1H, m), 3.06-2.93 (2H, m). (2H missing (underneath water and/or DMSO peak)) |

Example 39. Synthesis of 2-morpholino-N-[4-[3-(4-phenyl-1H-imidazol-2-yl)chroman-6-yl]oxy-2-pyridyl]propenamide (Compound 150)

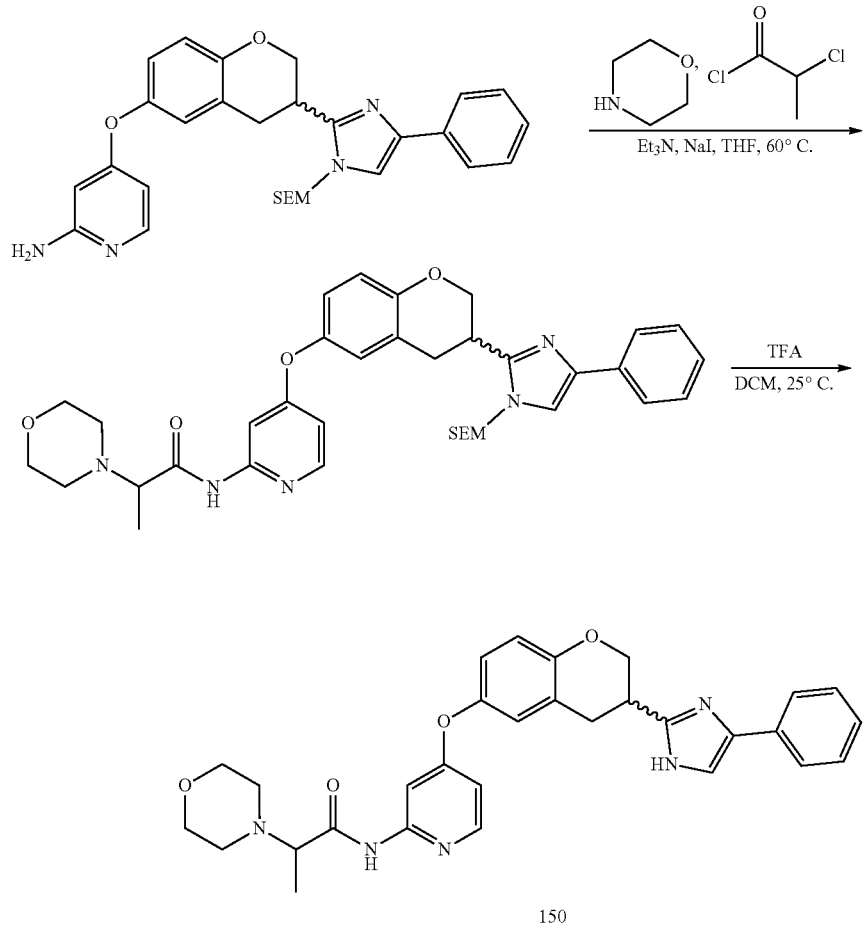

Step 1—2-morpholino-N-[4-[3-[4-phenyl-1-(2-trimethylsilylethoxymethyl)imidazol-2-yl]chroman-6-yl]oxy-2-pyridyl]propanamide To a solution of 4-[3-[4-phenyl-1-(2-trimethylsilylethoxymethyl)imidazol-2-yl]chroman-6-yl]oxypyridin-2-amine (68 mg, 0.13 mmol) and triethylamine (55 µL, 0.40 mmol) in anhydrous THF (1.3 mL) at 0° C. under a nitrogen atmosphere slowly added solution of chloropropionyl chloride (16 µL, 0.16 mmol) in anhydrous THF (0.5 mL) and the mixture was stirred at room temperature for 2 hrs. To this mixture was added morpholine (23 µL, 0.26 mmol) and sodium iodide (40 mg, 0.26 mmol) and the reaction was heated at 60° C. for 72 hours. After cooling to room temperature, the mixture was concentrated and the residue purified by column chromatography using as eluent a gradient 0-4% MeOH in DCM to give 2-morpholino-N-[4-[3-[4-phenyl-1-(2-trimethylsilylethoxymethyl)imidazol-2-yl]chroman-6-yl]oxy-2-pyridyl]propanamide (43 mg, 0.065 mmol, 49% yield) as an off-white solid. UPLC-MS (ES+, Short acidic): 1.82 min, m/z 656.5 [M+H]+.

Step 2—2-morpholino-N-[4-[3-(4-phenyl-1H-imidazol-2-yl)chroman-6-yl]oxy-2-pyridyl]propenamide To a solution of 2-morpholino-N-[4-[3-[4-phenyl-1-(2-trimethylsilylethoxymethyl)imidazol-2-yl]chroman-6-yl]oxy-2-pyridyl]propanamide (42 mg, 0.06 mmol) in DCM (1 mL) was added trifluoroacetic acid (490 µL, 6.4 mmol) and the mixture was stirred at 25° C. in a sealed tube for 22 hrs. The mixture was concentrated and the residue purified by column chromatography using as eluent a gradient 0-50% (acetonitrile+0.1% formic acid):(water+0.1% formic acid). Fractions containing the product were loaded onto a SCX-2 column, which was flushed with MeOH and then MeOH+ NH$_3$ to give 2-morpholino-N-[4-[3-(4-phenyl-1H-imidazol-2-yl)chroman-6-yl]oxy-2-pyridyl]propanamide (23 mg, 0.043 mmol, 68% yield) as a white solid. UPLC-MS (ES+, final purity): 2.46 min, m/z 526.3 [M+H]+. $^1$H NMR (400 MHz, DMSO-d$_6$) δ/ppm: 12.16 (1H, br s), 10.13 (1H, s), 8.17 (1H, d, J=5.7 Hz), 7.76-7.70 (2H, m), 7.68 (1H, d, J=2.3 Hz), 7.54 (1H, br s), 7.38-7.31 (2H, m), 7.21-7.15 (1H, m), 7.04 (1H, d, J=2.7 Hz), 6.94 (1H, dd, J=8.8 Hz, 2.7 Hz), 6.90 (1H, d, J=8.8 Hz), 6.66 (1H, dd, J=5.7 Hz, 2.3 Hz), 4.56-4.50 (1H, m), 4.18-4.10 (1H, m), 3.65-3.56 (4H, m), 3.46-3.35 (2H, m), 3.30-3.08 (2H, m), 1.15 (3H, d, J=6.7 Hz). 4H missing (underneath DMSO or water peak).

Example 40. Synthesis of N-[4-[3-(4-phenyl-1H-imidazol-2-yl)chroman-6-yl]oxypyrimidin-2-yl]cyclopropanecarboxamide (Compound 148)
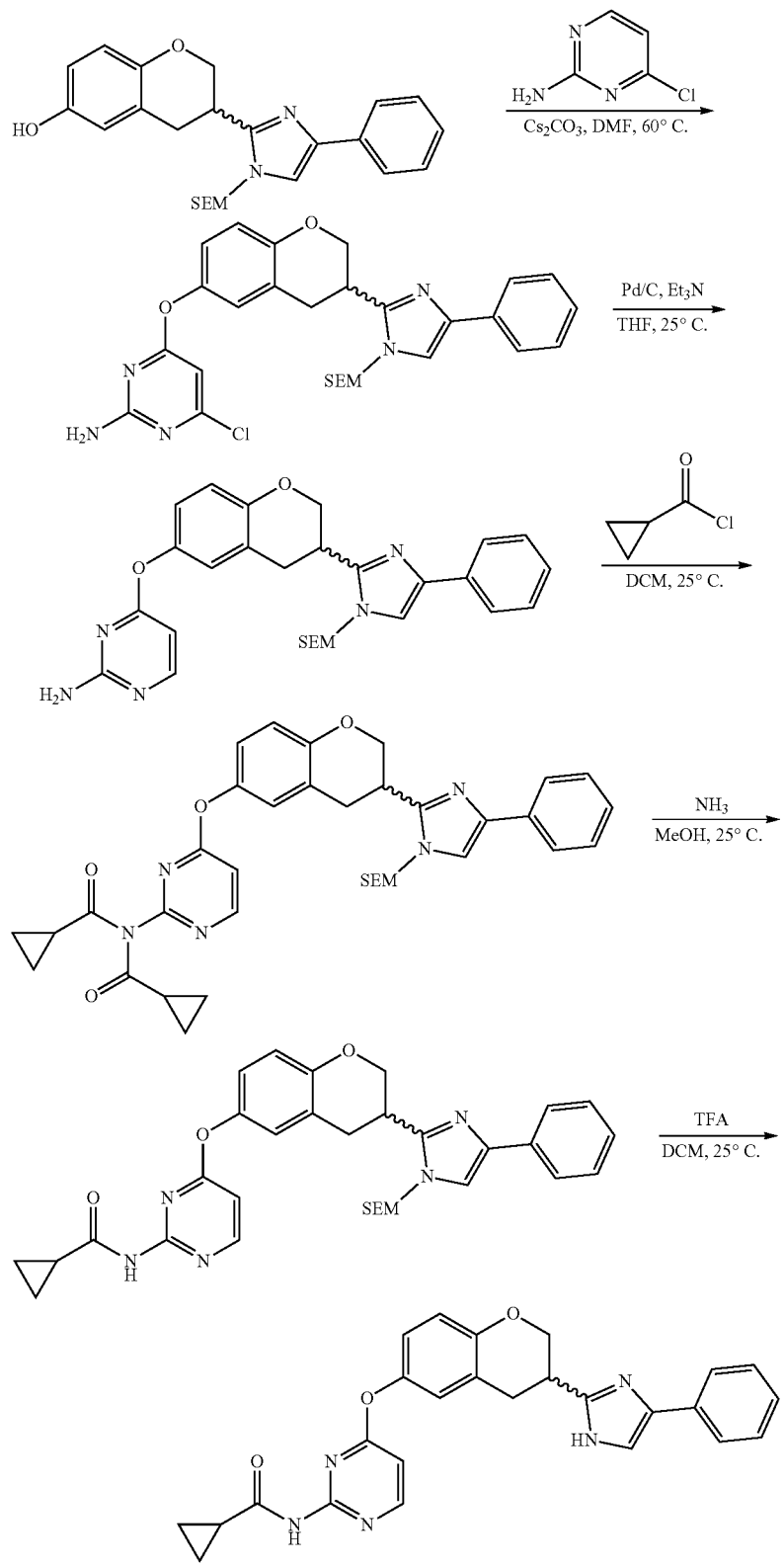

Step 1—4-chloro-6-[3-[4-phenyl-1-(2-trimethylsilylethoxymethyl)imidazol-2-yl]chroman-6-yl]oxypyrimidin-2-amine A mixture of 4,6-dichloropyrimidin-2-amine (51.2 mg, 0.31 mmol), 3-[4-phenyl-1-(2-trimethylsilylethoxymethyl)imidazol-2-yl]chroman-6-ol (132 mg, 0.31 mmol) and $Cs_2CO_3$ (152.6 mg, 0.47 mmol) in DMF (1.5 mL) was heated at 60° C. overnight. After cooling to rt, the mixture was poured into water (30 mL) and the aqueous was extracted with EtOAc (5×20 mL) then EtOAc:MeOH (10:1, 5×20 mL). The combined organic extracts were dried over $Na_2SO_4$, filtered and the solvent removed in vacuo. The residue was purified by column chromatography using as eluent a gradient 0-4% MeOH in DCM to give 4-chloro-6-[3-[4-phenyl-1-(2-trimethylsilylethoxymethyl)imidazol-2-yl]chroman-6-yl]oxy-pyrimidin-2-amine (120 mg, 0.22 mmol, 70% yield) as a white foam. UPLC-MS (ES+, short acidic): 2.10 min, m/z 550.5 [M+H]$^+$. $^1$H NMR (400 MHz, DMSO-d$_6$) δ/ppm: 7.77 (1H, s), 7.76-7.72 (2H, m), 7.38-7.32 (2H, m), 7.22-7.17 (1H, m), 7.13 (2H, br s), 7.01 (1H, d, J=2.8 Hz), 6.95 (1H, dd, J=8.8, 2.8 Hz), 6.87 (1H, d, J=8.8 Hz), 6.13 (1H, s), 5.45 (2H, m), 4.49-4.42 (1H, m), 4.08-4.00 (1H, m), 3.63-3.46 (3H, m), 3.31-3.23 (1H, m), 3.07-2.97 (1H, m), 0.94-0.85 (2H, m), −0.02 (9H, s).

Step 2—4-[3-[4-phenyl-1-(2-trimethylsilylethoxymethyl)imidazol-2-yl]chroman-6-yl]oxypyrimidin-2-amine To a mixture of 4-chloro-6-[3-[4-phenyl-1-(2-trimethylsilylethoxymethyl)imidazol-2-yl]chroman-6-yl]oxy-pyrimidin-2-amine (119 mg, 0.22 mmol) and triethylamine (33 μL, 0.24 mmol) in THF (7 mL) was added palladium, 10 wt. % on carbon powder, wet (57.5 mg, 0.05 mmol). The reaction was fitted with a $H_2$ balloon, extra $H_2$ added and subjected to 3×vacuum/$H_2$ cycles and then left to stir under a $H_2$ atmosphere for 72 hours. The mixture was filtered through a plug of diatomaceous earth and the filter cake was washed with THF and MeOH. The filtrate was concentrated and the residue partitioned between EtOAc (10 mL) and water (10 mL). The organic layer was separated and the aqueous extracted with EtOAc (3×10 mL). The combined organic extracts were washed with brine (10 mL), dried over $Na_2SO_4$, filtered and the solvent removed in vacuo to give 4-[3-[4-phenyl-1-(2-trimethylsilylethoxymethyl)imidazol-2-yl]chroman-6-yl]oxypyrimidin-2-amine (111.5 mg, 0.22 mmol, 100% yield) as a white foam. The compound was used in the next step without further purification. UPLC-MS (ES+, short acidic): 1.75 min, m/z 516.5 [M+H]$^+$.

Step 3—N-(cyclopropanecarbonyl)-N-[4-[3-[4-phenyl-1-(2-trimethylsilylethoxymethyl)imidazol-2-yl]chroman-6-yl]oxypyrimidin-2-yl]cyclopropanecarboxamide To a solution of 4-[3-[4-phenyl-1-(2-trimethylsilylethoxymethyl)imidazol-2-yl]chroman-6-yl]oxypyrimidin-2-amine (111.5 mg, 0.22 mmol) in pyridine (1.6 mL) and DCM (1.1 mL) was added cyclopropanecarbonyl chloride (25 μL, 0.27 mmol) in DCM (0.1 mL) dropwise and the mixture was stirred at 25° C. under a nitrogen atmosphere for 18 hours. A solution of cyclopropanecarbonyl chloride (98 μL, 1.08 mmol) in DCM (0.1 mL) was slowly added and the mixture was stirred at 25° C. for 5 hours. The crude was diluted with DCM (30 mL), washed with water (15 mL) and brine (15 mL), dried over $Na_2SO_4$, filtered and the solvent removed in vacuo. The residue was purified by column chromatography using as eluent a gradient 0-40% EtOAc in petroleum ether to give N-(cyclopropanecarbonyl)-N-[4-[3-[4-phenyl-1-(2-trimethylsilylethoxymethyl)imidazol-2-yl]chroman-6-yl]oxypyrimidin-2-yl]cyclopropanecarboxamide (101 mg, 0.16 mmol, 72% yield) as colourless oil, which solidified upon standing. UPLC-MS (ES+, short acidic): 2.14 min, m/z 652.9 [M+H]$^+$. $^1$H NMR (400 MHz, DMSO-d$_6$) δ/ppm: 8.76 (1H, d, J=5.8 Hz), 7.77 (1H, s), 7.77-7.72 (2H, m), 7.38-7.32 (2H, m), 7.23-7.16 (1H, m), 7.13 (1H, d, J=5.8 Hz), 7.07 (1H, d, J=2.8 Hz), 7.00 (1H, dd, J=8.8, 2.8 Hz), 6.91 (1H, d, J=8.8 Hz), 5.47 (1H, d, J=11.1 Hz), 5.43 (1H, d, J=11.1 Hz), 4.50-4.44 (1H, m), 4.09-4.02 (1H, m), 3.61-3.51 (3H, m), 3.31-3.25 (1H, m), 3.06-2.97 (1H, m), 1.95-1.87 (2H, m), 0.97-0.88 (10H, m), −0.02 (9H, s).

Step 4—N-[4-[3-[4-phenyl-1-(2-trimethylsilylethoxymethyl)imidazol-2-yl]chroman-6-yl]oxypyrimidin-2-yl]cyclopropanecarboxamide N-(cyclopropanecarbonyl)-N-[4-[3-[4-phenyl-1-(2-trimethylsilylethoxymethyl)imidazol-2-yl]chroman-6-yl]oxypyrimidin-2-yl]cyclopropanecarboxamide (96 mg, 0.15 mmol) was dissolved in $NH_3$ (7M in MeOH—3 mL, 21 mmol) and the mixture was stirred at 25° C. for 1 hour. The solvent was removed under reduce pressure and the residue was purified by column chromatography using as eluent a gradient 0-80% EtOAc in petroleum ether to give N-[4-[3-[4-phenyl-1-(2-trimethylsilylethoxymethyl)imidazol-2-yl]chroman-6-yl]oxypyrimidin-2-yl]cyclopropanecarboxamide (70 mg, 0.12 mmol, 82% yield) as a white solid. UPLC-MS (ES+, short acidic): 1.97 min, m/z 584.4 [M+H]$^+$. $^1$H NMR (400 MHz, DMSO-d$_6$) δ/ppm: 10.62 (1H, s), 8.47 (1H, d, J=5.7 Hz), 7.77 (1H, s), 7.77-7.72 (2H, m), 7.38-7.32 (2H, m), 7.22-7.17 (1H, m), 7.10 (1H, d, J=2.8 Hz), 7.02 (1H, dd, J=8.8, 2.8 Hz), 6.89 (1H, d, J=8.8 Hz), 6.63 (1H, d, J=5.7 Hz), 5.47 (1H, d, J=11.1 Hz), 5.42 (1H, d, J=11.1 Hz), 4.50-4.43 (1H, m), 4.09-4.02 (1H, m), 3.61-3.54 (2H, m), 3.54-3.47 (1H, m), 3.31-3.24 (1H, m), 3.07-2.98 (1H, m), 2.24-2.16 (1H, m), 0.93-0.86 (2H, m), 0.80-0.68 (4H, m), −0.02 (9H, s).

Step 5—N-[4-[3-(4-phenyl-1H-imidazol-2-yl)chroman-6-yl]oxypyrimidin-2-yl]cyclopropanecarboxamide To a solution of N-[4-[3-[4-phenyl-1-(2-trimethylsilylethoxymethyl)imidazol-2-yl]chroman-6-yl]oxypyrimidin-2-yl]cyclopropanecarboxamide (69 mg, 0.12 mmol) in DCM (1.8 mL) was added trifluoroacetic acid (0.9 mL, 11.75 mmol) and the mixture was stirred at 25° C. for 18 hours. The mixture was concentrated and the residue loaded onto a SCX-2 column, which was washed at first with MeOH and then $NH_3$ in MeOH to elute the product. The residue was purified by column chromatography using as eluent a gradient 0-8% MeOH in DCM. Like fractions were pooled and concentrated to afford N-[4-[3-(4-phenyl-1H-imidazol-2-yl)chroman-6-yl]oxypyrimidin-2-yl]cyclopropanecarboxamide (44 mg, 0.096 mmol, 82% yield) as a white solid. UPLC-MS (ES+, final purity): 2.65 min, m/z 454.2 [M+H]$^+$. $^1$H NMR (400 MHz, DMSO-d$_6$) δ/ppm: 12.32 (0.2H, br s), 12.10 (0.8H, br s), 10.62 (1H, s), 8.46 (1H, d, J=5.7 Hz), 7.79-7.72 (1.6H, m), 7.67-7.56 (1.2H, m), 7.45-7.36 (0.4H, m), 7.36-7.29 (1.6H, m), 7.29-7.20 (0.4H, m), 7.20-7.12 (0.8H, m), 7.10 (1H, d, J=2.8 Hz), 7.00 (1H, dd, J=8.8, 2.8 Hz), 6.86 (1H, d, J=8.8 Hz), 6.63 (1H, d, J=5.7 Hz), 4.54-4.48 (1H, m), 4.15-4.06 (1H, m), 3.43-3.33 (1H, m), 3.29-3.18 (1H, m), 3.16-3.06 (1H, m), 2.23-2.15 (1H, m), 0.80-0.66 (4H, m).

Example 41. Synthesis of 2-(4-methyl-1H-imidazol-2-yl)-4-[3-(4-phenyl-1H-imidazol-2-yl)chroman-6-yl]oxy-pyridine (Compound 143)

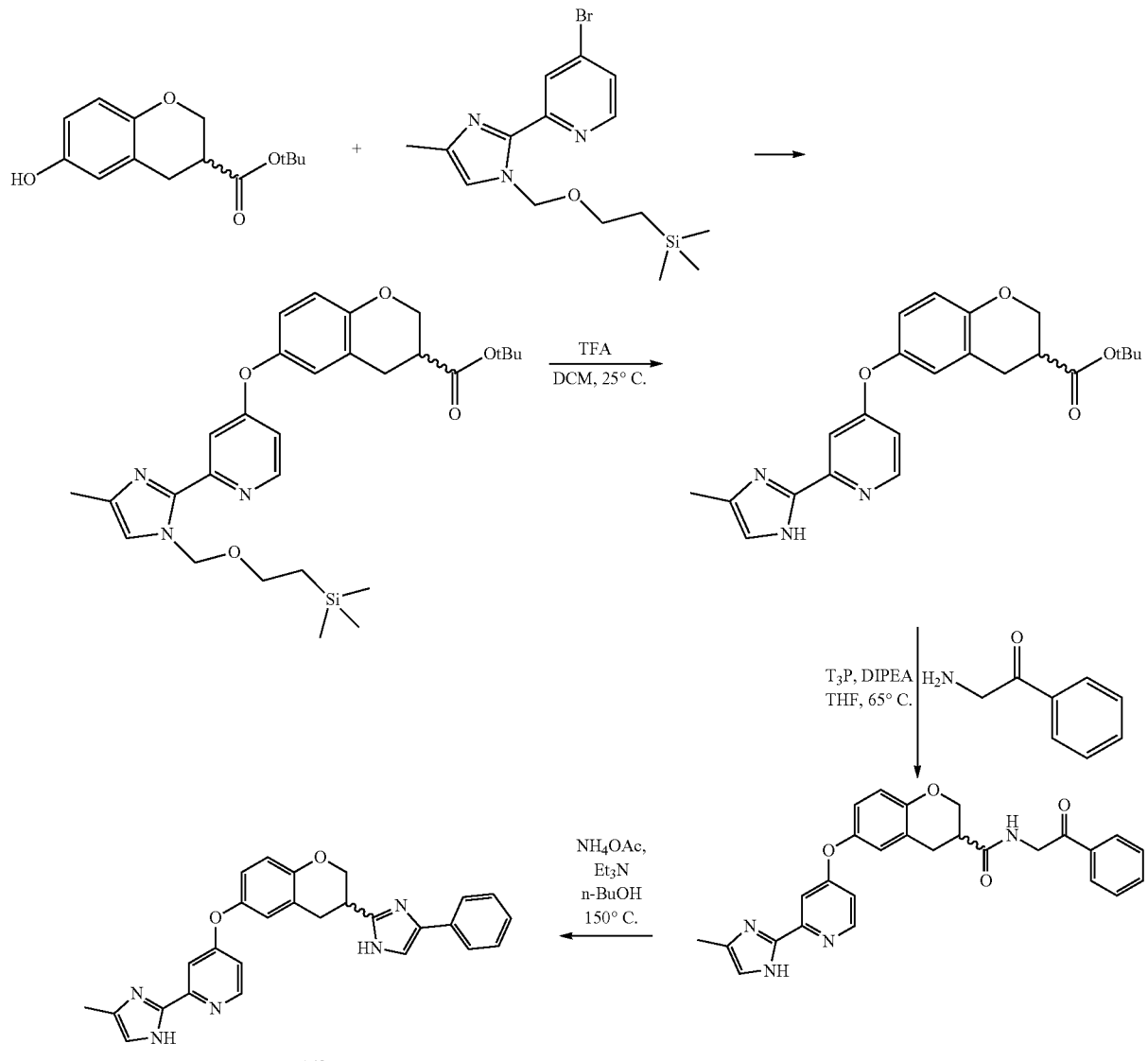

Step 1—tert-butyl 6-[[2-[4-methyl-1-(2-trimethylsilylethoxymethyl)imidazol-2-yl]-4-pyridyl]oxy]chromane-3-carboxylate A mixture of 2-[[2-(4-bromo-2-pyridyl)-4-methyl-imidazol-1-yl]methoxy]ethyl-trimethyl-silane (285 mg, 0.77 mmol), tert-butyl 6-hydroxychromane-3-carboxylate (213 mg, 0.85 mmol) and potassium phosphate tribasic (328.5 mg, 1.55 mmol) in anhydrous toluene (3.8 mL) was degassed under a nitrogen atmosphere for 10 minutes; then palladium (II) acetate (10.4 mg, 0.05 mmol) and 2-(di-tert-butylphosphino)biphenyl (27.7 mg, 0.09 mmol) were added. The vial was sealed and the mixture heated at 100° C. for 4 hours. After cooling to room temperature, the mixture was filtered through a plug of diatomaceous earth and the filter cake washed with DCM. The filtrate was concentrated and the residue purified by column chromatography using as eluent a gradient 0-100% EtOAc in petroleum ether to give tert-butyl 6-[[2-[4-methyl-1-(2-trimethylsilylethoxymethyl)imidazol-2-yl]-4-pyridyl]oxy]chromane-3-carboxylate (330 mg, 0.61 mmol, 79% yield) as a dark orange oil. UPLC-MS (ES+, Short acidic): 1.92 & 1.98 min, m/z 538.8 [M+H]$^+$. $^1$H NMR (400 MHz, DMSO-d$_6$) consistent with a ~ 2.5/1 ratio of regioisomers.

Step 2—formic acid; 6-[[2-(4-methyl-1H-imidazol-2-yl)-4-pyridyl]oxy]chromane-3-carboxylic Acid (0.4; 1)

To a solution of tert-butyl 6-[[2-[4-methyl-1-(2-trimethylsilylethoxymethyl)imidazol-2-yl]-4-pyridyl]oxy]chromane-3-carboxylate (328 mg, 0.61 mmol) in DCM (4.6 mL) was added trifluoroacetic acid (2.3 mL, 30.04 mmol) and the mixture was stirred at room temperature, in a sealed vial, overnight. The mixture was concentrated and the residue azeotroped with toluene. The residue was purified by reverse column chromatography using as eluent a gradient 0-50% acetonitrile+0.1% formic acid in water+0.1% formic acid to give formic acid; 6-[[2-(4-methyl-1H-imidazol-2-yl)-4-pyridyl]oxy]chromane-3-carboxylic acid (0.4; 1) (148 mg, 0.40 mmol, 66% yield) as a white solid. UPLC-MS (ES+, Short acidic): 1.14 min, m/z 352.4 [M+H]$^+$. $^1$H NMR (400 MHz, DMSO-d$_6$) δ/ppm: 13.26 (1H, br s), 12.72 (1H, br s), 8.47 (1H, d, J=5.7 Hz), 8.13 (0.4H, s, formate), 7.37 (1H, d, J=2.3 Hz), 7.05 (1H, d, J=2.8 Hz), 6.98-6.93 (3H, m), 6.88 (1H, d, J=8.8 Hz), 4.36 (1H, dd, J=10.8 Hz, 3.1 Hz), 4.17 (1H, dd, J=10.8 Hz, 7.7 Hz), 3.07-2.95 (3H, m), 2.19 (3H, s).

Step 3—6-[[2-(4-methyl-1H-imidazol-2-yl)-4-pyridyl]oxy]-N-phenacyl-chromane-3-carboxamide A mixture of formic acid; 6-[[2-(4-methyl-1H-imidazol-2-yl)-4-pyridyl]oxy]chromane-3-carboxylic acid (0.4; 1) (148 mg, 0.40 mmol), 2-aminoacetophenone hydrochloride (75.7 mg, 0.44 mmol), propylphosphonic anhydride (358 μL, 0.60 mmol) and N,N-diisopropylethylamine (245 μL, 1.41 mmol) in THF (4 mL) was heated at 65° C. for 2 hours. After cooling to room temperature, the mixture was concentrated and the residue taken up in EtOAc (30 mL). The organic layer was washed with water (2×10 mL) and brine (10 mL), dried over Na$_2$SO$_4$, filtered and the solvent removed in vacuo to give 6-[[2-(4-methyl-1H-imidazol-2-yl)-4-pyridyl]oxy]-N-phenacyl-chromane-3-carboxamide (188 mg, 0.40 mmol, 100% yield) as an orange solid. The compound was used in the next step without further purification. UPLC-MS (ES+, Short acidic): 1.33 min, m/z 469.5 [M+H]$^+$.

Step 4—2-(4-methyl-1H-imidazol-2-yl)-4-[3-(4-phenyl-1H-imidazol-2-yl)chroman-6-yl]oxy-pyridine To a suspension of 6-[[2-(4-methyl-1H-imidazol-2-yl)-4-pyridyl]oxy]-N-phenacyl-chromane-3-carboxamide (188 mg, 0.40 mmol) in 1-butanol (4 mL) were added ammonium acetate (309 mg, 4.01 mmol) and Et3N (56 μL, 0.40 mmol). The vial was sealed and the mixture irradiated at 150° C. for 45 minutes. After cooling to room temperature, the mixture was concentrated and the residue was purified by column chromatography using as eluent a gradient 0-20% MeOH. Fractions containing the product were combined and re-purified by reverse column chromatography using as eluent a gradient acetonitrile+0.1% formic acid. Fractions containing the product were loaded onto an SCX-2 column, which was flushed with MeOH followed by MeOH+NH$_3$ to give 2-(4-methyl-1H-imidazol-2-yl)-4-[3-(4-phenyl-1H-imidazol-2-yl)chroman-6-yl]oxy-pyridine (42 mg, 0.093 mmol, 23% yield) as a white solid. UPLC-MS (ES+, final purity): 2.35 min, m/z 450.2 [M+H]$^+$. $^1$H NMR (400 MHz, DMSO-d$_6$+few μL of CF$_3$CO$_2$D) δ/ppm: 8.65 (1H, d, J=5.7 Hz), 8.14 (1H, s), 7.84-7.80 (2H, m), 7.78 (1H, d, J=2.3 Hz), 7.58-7.51 (3H, m), 7.49-7.43 (1H, m), 7.15-7.10 (2H, m), 7.07 (1H, dd, J=8.8 Hz, 2.8 Hz), 7.01 (1H, d, J=8.8 Hz), 4.65-4.58 (1H, m), 4.40 (1H, dd, J=10.7 Hz, 9.0 Hz), 3.91-3.82 (1H, m), 3.44-3.27 (2H, m), 2.33 (3H, d, J=0.9 Hz).

Example 42. Synthesis of 6-[6-(cyclopropanecarbonylamino)pyrimidin-4-yl]oxy-N-phenacyl-chromane-3-carboxamide (Compound 151)

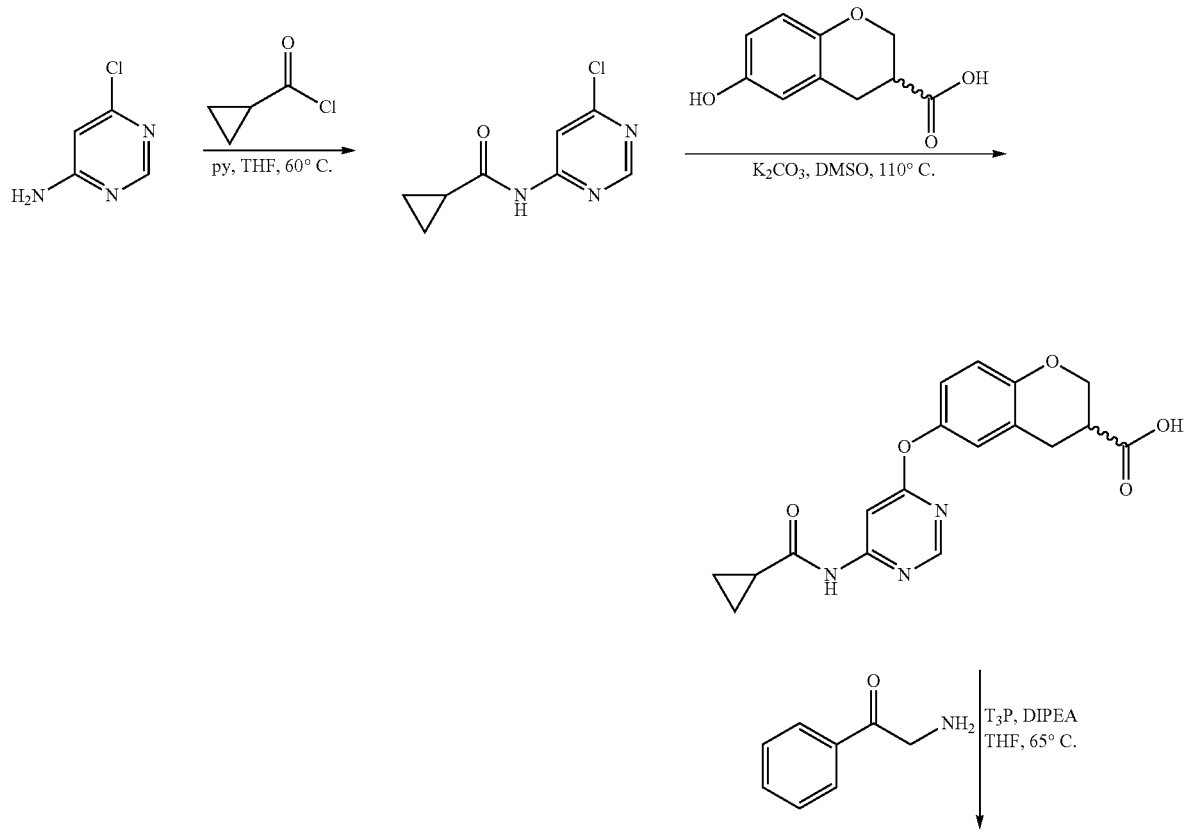

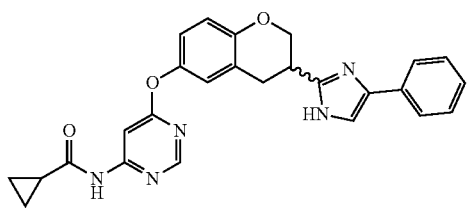

151

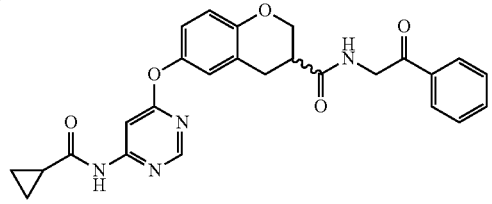

Step 1—N-(6-chloropyrimidin-4-yl)cyclopropanecarboxamide

To a solution of 6-chloropyrimidin-4-ylamine (800 mg, 6.18 mmol) and pyridine (1.25 mL, 15.46 mmol) in THF (25 mL) at 0° C., under a nitrogen atmosphere, was slowly added cyclopropanecarbonyl chloride (0.7 mL, 7.71 mmol) and the mixture was heated at 60° C. for 17 hours. After cooling to room temperature, the mixture was partitioned between water (50 mL) and EtOAc (50 mL). The two layers were separated and the aqueous extracted with EtOAc (2×50 mL). The combined organic layers were washed with brine (50 mL), dried over $Na_2SO_4$, filtered and concentrated. The residue was purified by column chromatography using as eluent a gradient 0-4% MeOH in DCM to give N-(6-chloropyrimidin-4-yl)cyclopropanecarboxamide (917 mg, 4.64 mmol, 75% yield) as a white solid. UPLC-MS (ES+, Short acidic): 1.35 min, m/z 197.9 $[M+H]^+$. $^1$H NMR (400 MHz, DMSO-$d_6$) δ/ppm: 11.54 (1H, s), 8.75 (1H, d, J=1.0 Hz), 8.10 (1H, d, J=1.0 Hz), 2.08-2.00 (1H, m), 0.93-0.86 (4H, m).

Step 2—6-[6-(cyclopropanecarbonylamino)pyrimidin-4-yl]oxychromane-3-carboxylic Acid A solution of 6-hydroxychromane-3-carboxylic acid (198 mg, 1.02 mmol), N-(6-chloropyrimidin-4-yl)cyclopropanecarboxamide (200 mg, 1.01 mmol) and potassium carbonate (560 mg, 4.05 mmol) in DMSO (1.25 mL) was heated 110° C. overnight. The reaction mixture was cooled to room temperature and poured into a solution of citric acid (777.8 mg, 4.05 mmol) in water (15 mL). The resulting precipitate was filtered, washed with water and dried to afford 6-[6-(cyclopropanecarbonylamino)pyrimidin-4-yl]oxychromane-3-carboxylic acid (316 mg, 0.89 mmol, 88% yield) as a beige solid. Compound used directly in the next step without further purification. UPLC-MS (ES+, Short acidic): 1.44 min, m/z 356.2 $[M+H]^+$ (94%). $^1$H NMR (400 MHz, DMSO-$d_6$) δ/ppm: 12.67 (1H, br s), 11.22 (1H, s), 8.48 (1H, d, J=0.9 Hz), 7.50 (1H, d, J=0.9 Hz), 6.98 (1H, d, J=2.8 Hz), 6.89 (1H, dd, J=8.8, 2.8 Hz), 6.80 (1H, d, J=8.8 Hz), 4.32 (1H, dd, J=10.8, 3.1 Hz), 4.15 (1H, dd, J=10.8, 7.5 Hz), 3.04-2.92 (3H, m), 2.06-1.98 (1H, m), 0.89-0.80 (4H, m).

Step 3—6-[6-(cyclopropanecarbonylamino)pyrimidin-4-yl]oxy-N-phenacyl-chromane-3-carboxamide A mixture of 6-[6-(cyclopropanecarbonylamino)pyrimidin-4-yl]oxychromane-3-carboxylic acid (100 mg, 0.28 mmol), 2-aminoacetophenone hydrochloride (53 mg, 0.31 mmol), propylphosphonic anhydride (250 μL, 0.42 mmol) and N,N-diisopropylethylamine (152 μL, 0.87 mmol) in THF (2.8 mL) was heated at 65° C. for 1 hour. After cooling to room temperature, the mixture was concentrated and the residue dissolved in EtOAc (30 mL). The organic layer was washed with water (2×10 mL) and brine (10 mL), dried over $Na_2SO_4$, filtered and concentrated to afford 6-[6-(cyclopropanecarbonylamino)pyrimidin-4-yl]oxy-N-phenacyl-chromane-3-carboxamide (131 mg, 0.28 mmol, 98% yield) as a beige solid. The compound used in the next step without further purification. UPLC-MS (ES+, Short acidic): 1.61 min, m/z 473.2 $[M+H]^+$.

Step 4—6-[6-(cyclopropanecarbonylamino)pyrimidin-4-yl]oxy-N-phenacyl-chromane-3-carboxamide To a suspension of 6-[6-(cyclopropanecarbonylamino)pyrimidin-4-yl]oxy-N-phenacyl-chromane-3-carboxamide (131 mg, 0.28 mmol) in 1-butanol (2.7 mL) were added ammonium acetate (213 mg, 2.77 mmol) and triethylamine (39 μL, 0.28 mmol). The vial was sealed and the mixture irradiated at 150° C. for 45 min. The mixture was concentrated and the residue purified by column chromatography using as eluent a gradient 0-20% MeOH in DCM. Fractions containing the product was re-purified by reverse column chromatography using as eluent gradient 0-40% acetonitrile+0.10% formic acid in water+0.1% formic acid. Fractions containing the product were loaded onto a SCX-2 column, which was flushed at first with MeOH and the MeOH/$NH_3$ to give N-[6-[3-(4-phenyl-1H-imidazol-2-yl)chroman-6-yl]oxypyrimidin-4-yl]cyclopropanecarboxamide (28 mg, 0.062 mmol, 22% yield) as a white solid. UPLC-MS (ES+, final purity): 2.94 min, m/z 454.3 $[M+H]^+$. $^1$H NMR (400 MHz, DMSO-$d_6$) δ/ppm: 12.30 (1H, br s), 11.23 (1H, s), 8.50 (1H, d, J=1.0 Hz), 7.76-7.70 (2H, m), 7.56 (1H, br s), 7.52 (1H, d, J=1.0 Hz), 7.38-7.32 (2H, m), 7.22-7.16 (1H, m), 7.03 (1H, d, J=2.8 Hz), 6.94 (1H, dd, J=8.8 Hz, 2.8 Hz), 6.86 (1H, d, J=8.8 Hz), 4.55-4.49 (1H, m), 4.18-4.10 (1H, m), 3.47-3.38 (1H, m), 3.29-3.19 (1H, m), 3.16-3.08 (1H, m), 2.07-1.99 (1H, m), 0.89-0.82 (4H, m).

Example 43. Synthesis of 5-[3-(5-isopropyl-3,4,6,7-tetrahydroimidazo[4,5-c]pyridin-2-yl)chroman-6-yl]oxy-3,4-dihydro-1H-1,8-naphthyridin-2-one (Compound 133)
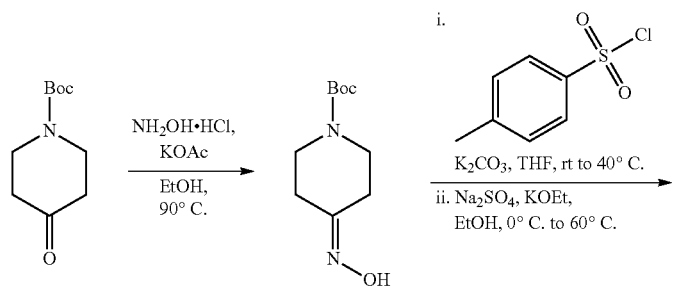
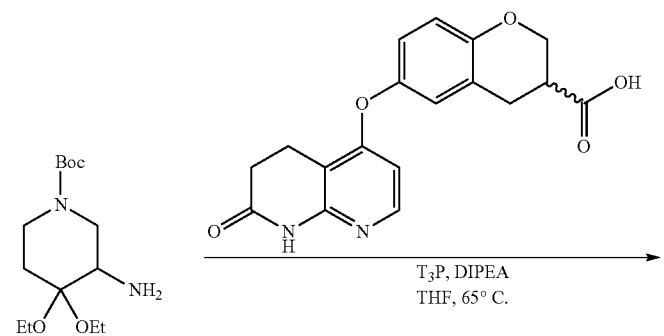
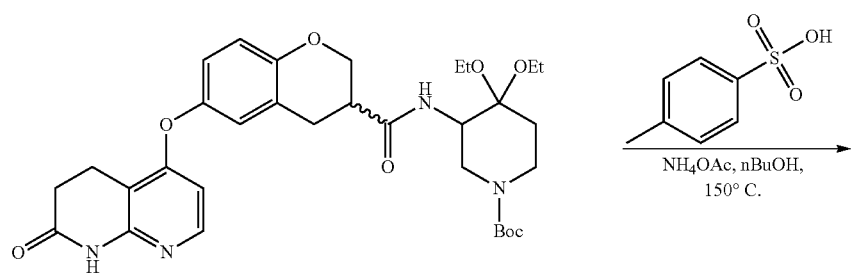
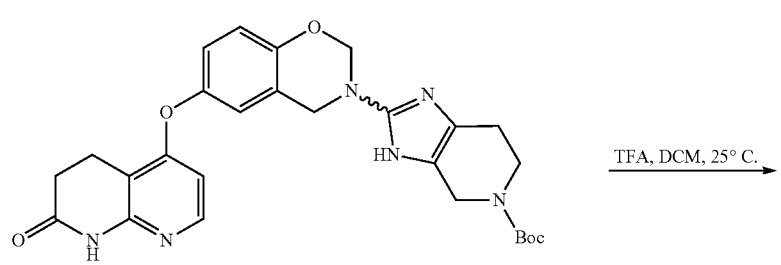

-continued

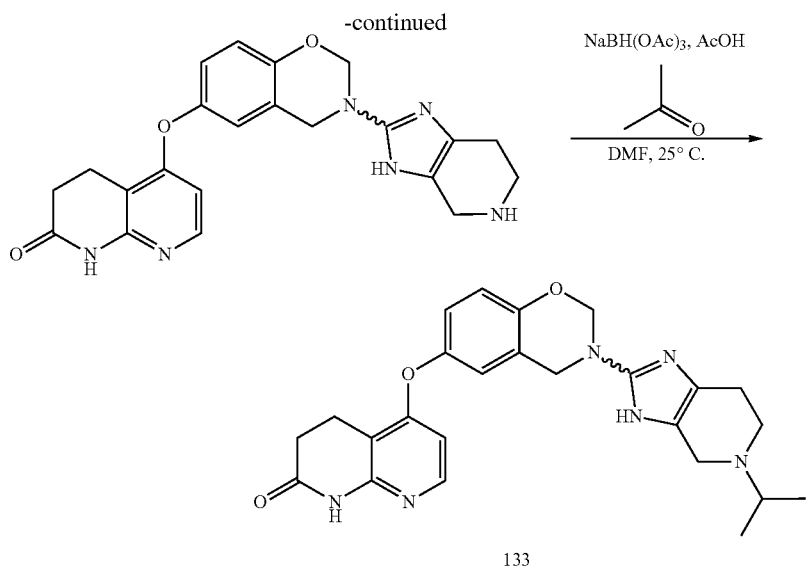

133

Step 1—tert-butyl 4-hydroxyiminopiperidine-1-carboxylate

A mixture of 1-Boc-4-piperidone (2 g, 10.04 mmol), hydroxylamine hydrochloride (1.4 g, 20.08 mmol) and potassium acetate (1.97 g, 20.07 mmol) in EtOH (20 mL) was heated at 90° C. overnight. After cooling to room temperature, the mixture was concentrated and the residue taken up in water (20 mL). The aqueous layer was extracted with EtOAc (3×20 mL). The combined organic layers were washed with sat aq. NaHCO$_3$ (25 mL) and brine (25 mL), separated, dried over Na$_2$SO$_4$, filtered and concentrated to give tert-butyl 4-hydroxyiminopiperidine-1-carboxylate (2.067 g, 9.64 mmol, 96% yield) as a white solid. UPLC-MS (ES+, Short acidic): 1.36 min, m/z 215.0 [M+H]$^+$. $^1$H NMR (400 MHz, DMSO-d$_6$) δ/ppm: 10.44 (1H, s), 3.44-3.35 (4H, m), 2.46-2.41 (2H, m), 2.24-2.19 (2H, m), 1.40 (9H, s).

Step 2—tert-butyl 3-amino-4,4-diethoxy-piperidine-1-carboxylate

A mixture of tert-butyl 4-hydroxyiminopiperidine-1-carboxylate (2.06 g, 9.63 mmol), potassium carbonate (2.66 g, 19.28 mmol) and p-toluenesulfonyl chloride (1.84 g, 9.64 mmol) in THF (50 mL) was stirred at room temperature for 24 hours then heated at 40° C. for 20 hours. After cooling to room temperature, the mixture was filtered, and the solvent removed under reduce pressure. The residue was dissolved in EtOH (20 mL) and added dropwise to a mixture of potassium ethoxide (1.62 g, 19.27 mmol) and Na$_2$SO$_4$ anhydrous (5.47 g, 38.54 mmol) in EtOH (20 mL) at 0° C. under a nitrogen atmosphere. The mixture was stirred at room temperature for 1.5 hours then heated at 60° C. for 1 hour. After cooling to room temperature, the mixture was filtered and the filter cake was washed with EtOH. The filtrate was concentrated and the residue purified by column chromatography using as eluent a gradient 0-8% MeOH in DCM to give tert-butyl 3-amino-4,4-diethoxy-piperidine-1-carboxylate (1.181 g, 4.10 mmol, 43% yield) as a thick yellow oil. UPLC-MS (ES+, Short acidic): 1.25 min, m/z 289.1 [M+H]$^+$.

Step 3—tert-butyl 4,4-diethoxy-3-[[6-[(7-oxo-6,8-dihydro-5H-1,8-naphthyridin-4-yl)oxy]chromane-3-carbonyl]amino]piperidine-1-carboxylate A mixture of 6-[(7-oxo-6,8-dihydro-5H-1,8-naphthyridin-4-yl)oxy]chromane-3-carboxylic acid (585 mg, 1.72 mmol), tert-butyl 3-amino-4,4-diethoxy-piperidine-1-carboxylate (741 mg, 2.57 mmol), propylphosphonic anhydride (2.05 mL, 3.44 mmol) and N,N-diisopropylethylamine (0.9 mL, 5.17 mmol) in THF (17.2 mL) was heated at 65° C. for 2 hours. The mixture was concentrated and the residue dissolved in EtOAc (100 mL). The organic layer was washed with water (2×30 mL) and brine (30 mL), dried over Na$_2$SO$_4$, filtered and concentrated to afford tert-butyl 4,4-diethoxy-3-[[6-[(7-oxo-6,8-dihydro-5H-1,8-naphthyridin-4-yl)oxy]chromane-3-carbonyl]amino]piperidine-1-carboxylate (1049.7 mg, 1.72 mmol, 100% yield) as a light orange foam. The compound was used directly in the next step without further purification. UPLC-MS (ES+, Short acidic): 1.79 min, m/z 611.7 [M+H]$^+$.

Step 4—tert-butyl 2-[6-[(7-oxo-6,8-dihydro-5H-1,8-naphthyridin-4-yl)oxy]chroman-3-yl]-3,4,6,7-tetrahydroimidazo[4,5-c]pyridine-5-carboxylate A mixture of tert-butyl 4,4-diethoxy-3-[[6-[(7-oxo-6,8-dihydro-5H-1,8-naphthyridin-4-yl)oxy]chromane-3-carbonyl]amino]piperidine-1-carboxylate (1.05 g, 1.72 mmol), ammonium acetate (2.65 g, 34.38 mmol) and p-toluenesulfonic acid monohydrate (65.4 mg, 0.34 mmol) in 1-butanol (11.5 mL) was irradiated at 150° C. for 1.5 hours. Additional ammonium acetate (2.65 g, 34.38 mmol) and p-toluenesulfonic acid monohydrate (65.4 mg, 0.34 mmol) were added and the mixture was further irradiated at 150° C. for 2 hours. The mixture was concentrated and the residue dissolved in EtOAc (100 mL). The organic layer was washed with sat. aq. NaHCO$_3$ (30 mL), water (30 mL) and brine (30 mL), dried over Na$_2$SO$_4$, filtered and the solvent removed in vacuo. The residue was purified by column chromatography using as eluent a gradient 0-10% MeOH in DCM to give tert-butyl 2-[6-[(7-oxo-6,8-dihydro-5H-1,8-naphthyridin-4-yl)oxy]chroman-3-yl]-3,4,6,7-tetrahydroimidazo[4,5-c]

pyridine-5-carboxylate (214 mg, 0.41 mmol, 24% yield) as an off-white solid. UPLC-MS (ES+, Short acidic): 1.27 min, m/z 518.4 [M+H]+.

Step 5—5-[3-(4,5,6,7-tetrahydro-3H-imidazo[4,5-c]pyridin-2-yl)chroman-6-yl]oxy-3,4-dihydro-1H-1,8-naphthyridin-2-one To a mixture of tert-butyl 2-[6-[(7-oxo-6,8-dihydro-5H-1,8-naphthyridin-4-yl)oxy]chroman-3-yl]-3,4,6,7-tetrahydroimidazo[4,5-c]pyridine-5-carboxylate (214 mg, 0.41 mmol) in DCM (2.5 mL) was added TFA (0.5 mL, 6.53 mmol) and stirred at 25° C. in a sealed vial for 1.5 hours. The mixture was concentrated and the residue azeotroped with toluene. The residue was dissolved in water and loaded onto an SCX-2 column. The column was washed with MeOH and then 2N NH$_3$ in methanol to elute the product. The filtrate was concentrated and dried to afford 5-[3-(4,5,6,7-tetrahydro-3H-imidazo[4,5-c]pyridin-2-yl)chroman-6-yl]oxy-3,4-dihydro-1H-1,8-naphthyridin-2-one (84 mg, 0.20 mmol, 49% yield) as a yellow solid. The compound was used in the next step without further purification. UPLC-MS (ES+, Short acidic): 0.97 min, m/z 418.1 [M+H]+.

Step 6—5-[3-(5-isopropyl-3,4,6,7-tetrahydroimidazo[4,5-c]pyridin-2-yl)chroman-6-yl]oxy-3,4-dihydro-1H-1,8-naphthyridin-2-one A mixture of 5-[3-(4,5,6,7-tetrahydro-3H-imidazo[4,5-c]pyridin-2-yl)chroman-6-yl]oxy-3,4-dihydro-1H-1,8-naphthyridin-2-one (65 mg, 0.16 mmol), acetone (22.9 μL, 0.31 mmol), sodium triacetoxyborohydride (66.1 mg, 0.31 mmol) and acetic acid (17.9 μL, 0.31 mmol) in DMF (1.5 mL) was stirred at 25° C. Additional acetone (22.9 μL, 0.31 mmol) and sodium triacetoxyborohydride (66.1 mg, 0.31 mmol) were added after 23 hours and 30 hours and the mixture was further stirred at 25° C. for 48 hours. The mixture was concentrated and the residue purified by reverse column chromatography using as eluent a gradient 0-40% (MeCN+0.1% formic acid) in (H$_2$O+0.1% formic acid). Fractions containing the product were dried and loaded onto a SCX-2 column, which was flushed at first with MeOH and then 2N NH$_3$ in MeOH to elute 5-[3-(5-isopropyl-3,4,6,7-tetrahydroimidazo[4,5-c]pyridin-2-yl)chroman-6-yl]oxy-3,4-dihydro-1H-1,8-naphthyridin-2-one (20.9 mg, 0.046 mmol, 29% yield) as a white solid. UPLC-MS (ES+, final purity): 2.05 min, m/z 460.2 [M+H]+. $^1$H NMR (400 MHz, DMSO-d$_{6+3}$ drops of CF$_3$CO$_2$D) δ/ppm: 8.03 (1H, d, J=6.1 Hz), 7.04 (1H, d, J=2.7 Hz), 6.97 (1H, dd, J=8.8 Hz, 2.7 Hz), 6.91 (1H, d, J=8.8 Hz), 6.36 (1H, d, J=6.1 Hz), 4.50-4.44 (2H, m), 4.44-4.37 (2H, m), 3.92-3.84 (1H, m), 3.83-3.68 (2H, m), 3.45-3.20 (3H, m), 3.07-2.91 (4H, m), 2.61-2.55 (2H, m), 1.33 (6H, d, J=6.6 Hz). Exchangeable protons not seen.

Example 44. Synthesis of 5-[3-(5-acetyl-3,4,6,7-tetrahydroimidazo[4,5-c]pyridin-2-yl)chroman-6-yl]oxy-3,4-dihydro-1H-1,8-naphthyridin-2-one (Compound 135)

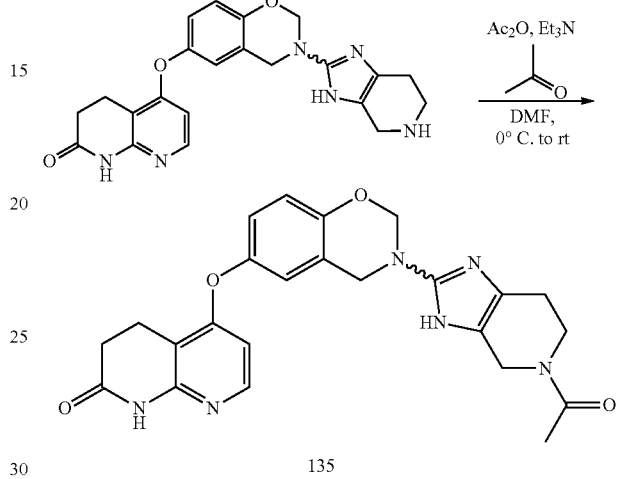

135

Compound 135 was synthesised in analogy with Example 43 with the exception of Step 6 as follows: To a solution of 5-[3-(4,5,6,7-tetrahydro-3H-imidazo[4,5-c]pyridin-2-yl)chroman-6-yl]oxy-3,4-dihydro-TH-1,8-naphthyridin-2-one (36 mg, 0.09 mmol) and triethylamine (12 μL, 0.09 mmol) in DMF (0.8 mL) was added acetic anhydride (8.2 μL, 0.09 mmol) at 0° C. and the mixture was stirred at this temperature for 2 hours. The mixture was concentrated and the residue purified by column chromatography using as eluent a gradient 0-40% (MeCN+0.1% formic acid) in (H2O+0.1% formic acid). Fractions containing the product were concentrated and loaded onto a SCX-2 column, which was flushed at first with MeOH and then NH$_3$ 2N in MeOH to give 5-[3-(5-acetyl-3,4,6,7-tetrahydroimidazo[4,5-c]pyridin-2-yl)chroman-6-yl]oxy-3,4-dihydro-TH-1,8-naphthyridin-2-one (15.5 mg, 0.034 mmol, 39% yield) as a white solid. UPLC-MS (ES+, final purity): 2.22 and 2.25 min, m/z 460.2 [M+H]+. $^1$H NMR (400 MHz, DMSO-d$_6$) δ/ppm: 12.08 (1H, br s), 10.45 (1H, s), 7.95 (1H, d, J=5.8 Hz), 6.97 (1H, d, J=2.6 Hz), 6.90 (1H, dd, J=8.8 Hz, 2.6 Hz), 6.86 (1H, d, J=8.8 Hz), 6.25 (1H, d, J=5.8 Hz), 4.46-4.31 (3H, m), 4.11-4.01 (1H, m), 3.75-3.63 (2H, m), 3.18-3.09 (1H, m), 3.09-3.00 (1H, m), 2.95-2.89 (2H, m), 2.66-2.61 (1H, m), 2.56-2.51 (3H, m), 2.08 & 2.05 (3H, 2s, acetamide rotamers). 1H missing (underneath water/DMSO peak).

Example 45. Chiral Separation of Selected Compounds

Conditions disclosed in table below can be used to separate stereoisomers of the racemic compound as shown:

| Comp. No | Structure and Name | Separation conditions |
|---|---|---|
| 32 | 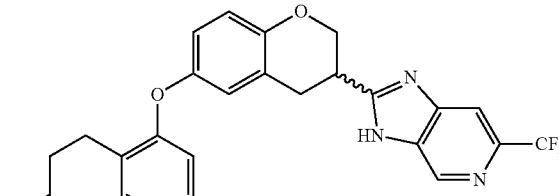<br>5-[3-[6-(trifluoromethyl)-3H-imidazo[4,5-c]pyridin-2-yl]chroman-6-yl]oxy-3,4-dihydro-1H-1,8-naphthyridin-2-one | Instrument: MG II preparative SFC(SFC-14)<br>Column: ChiralPak AD, 250 × 30 mm I.D., 10 μm<br>Mobile phase: A for CO2 and B for Ethanol(0.1% NH3H2O)<br>Gradient: B 40%<br>Flow rate: 80 mL/min<br>Back pressure: 100 bar<br>Column temperature: 38° C.<br>Wavelength: 220 nm<br>Cycle time: ~6.8 min |
| 136 | 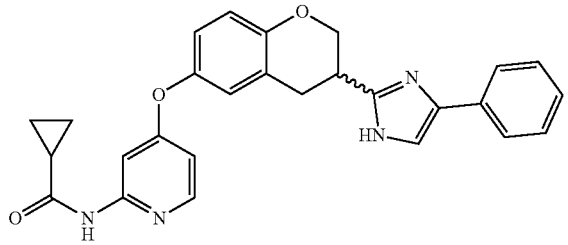<br>N-[4-[3-(4-phenyl-1H-imidazol-2-yl)chroman-6-yl]oxy-2-pyridyl]-cyclopropanecarboxamide | Instrument: MG II preparative SFC(SFC-14)<br>Column: ChiralPak AD, 250 × 30 mm I.D., 10 μm<br>Mobile phase: A for CO2 and B for Ethanol<br>Gradient: B 50%<br>Flow rate: 80 mL/min<br>Back pressure: 100 bar<br>Column temperature: 38° C.<br>Wavelength: 220 nm<br>Cycle time: ~11 min |

Example 46. Biological Assay PGP-3 0R

HCT-116 AlphaLISA SureFire pERK1/2 Cellular Assay

The human HCT-116 colorectal carcinoma cell line (ATCC CCL-247) endogenously expresses the $KRAS^{G13D}$ mutation, which leads to constitutive activation of the MAP kinase pathway and phosphorylation of ERK. To determine whether compounds inhibit constitutive ERK phosphorylation in HCT-116 cells, they were tested using AlphaLISA® SureFire® technology (Perkin Elmer p-ERK1/2 p-T202/Y204 assay kit ALSU-PERK-A10K). Assay read outs took place 2 or 24 hours after dosing with compounds. On the first day, HCT-116 cells were harvested, resuspended in growth medium (McCoys5A with Glutamax (Life Technologies 36600021) and 10% heat-inactivated fetal bovine serum (Sigma F9665)), and counted. Cells were plated in 100 μl per well in each well of a 96-well culture dish (Sigma CLS3598) to a final density of 30,000 (2 hr read) or 15,000 (24 hr read) cells per well and incubated over night at 37° C. and 5% $CO_2$. On day 2, the growth medium was exchanged for dosing medium (McCoys5A with Glutamax (Life Technologies 36600021) and 1% heat-inactivated fetal bovine serum (Sigma F9665)) and the cells were dosed with compounds to produce a 10-point dose response, where the top concentration was 1 μM and subsequent concentrations were at ⅓ log dilution intervals. A matched DMSO control was included. The cells were subsequently incubated for either 2 or 24 hours at 37° C. and 5% $CO_2$. After incubation, media was removed and the cells were incubated with lysis buffer containing phosphatase inhibitors for 15 minutes at room temperature. Cell lysates were transferred to a ½ area 96 well white Optiplate™ (Perkin Elmer 6005569) and incubated with anti-mouse IgG acceptor beads, a biotinylated anti-ERK1/2 rabbit antibody recognizing both phosphorylated and non-phosphorylated ERK1/2, a mouse antibody targeted to the Thr202/Tyr204 epitope and recognizing phosphorylated ERK proteins only, and streptavidin-coated donor beads. The biotinylated antibody binds to the streptavidin-coated donor beads and the phopsho-ERK1/2 antibody binds to the acceptor beads. Plates were read on an EnVision reader (Perkin Elmer) and excitation of the beads at 680 nm with a laser induced the release of singlet oxygen molecules from the donor beads that trigger energy transfer to the acceptor beads in close proximity, producing a signal that can be measured at 570 nm. Both antibodies bound to phosphorylated ERK proteins, bringing the donor and acceptor beads into close proximity. All data were analyzed using the Dotmatics or GraphPad Prism software packages. Inhibition of ERK phosphorylation was assessed by determination of the absolute $IC_{50}$ value, which is defined as the concentration of compound required to decrease the level of phosphorylated ERK proteins by 50% when compared to DMSO control.

WiDr AlphaLISA SureFire pERK1/2 Cellular Assay

The human WiDr colorectal adenocarcinoma cell line (ATCC CCL-218) endogenously expresses the $BRAF^{V600E}$ mutation, which leads to constitutive activation of the MAP kinase pathway and phosphorylation of ERK. To determine whether compounds inhibit constitutive ERK phosphorylation in WiDr cells, they were tested using AlphaLISA® SureFire® technology (Perkin Elmer p-ERK1/2 p-T202/Y204 assay kit ALSU-PERK-A10K). The main procedure is essentially the same as for HCT-116 cells (above), with the following adjustments to the growth medium (Eagle's Minimum Essential Medium (Sigma M2279) with 1× Glutamax (Life Technologies 35050038), 1× Sodium-Pyruvate (Sigma S8636), and 10% heat-inactivated fetal bovine serum (Sigma F9665)), the dosing medium (Eagle's Minimum Essential Medium (Sigma M2279) with 1× Glutamax (Life Technologies 35050038), 1× Sodium-Pyruvate (Sigma S8636), and 1% heat-inactivated fetal bovine serum (Sigma F9665)), and the seeding densities (2 hr: 50,000 cells per well; 24 hr: 35,000 cells per well). Moreover, the compounds were dosed in ½ log dilution intervals with the top concentration of 10 µM.

HCT-116 AlphaLISA SureFire pERK1/2 Cellular Assay (Dimer)

The human HCT-116 colorectal carcinoma cell line (ATCC CCL-247) endogenously expresses the KRAS$^{G13D}$ mutation, which leads to constitutive activation of the MAP kinase pathway and phosphorylation of ERK. First generation RAF inhibitors can promote RAF dimer formation in KRAS mutant tumours leading to a paradoxical activation of the pathway. To determine whether compounds can circumvent this problem and inhibit RAF dimers in HCT-116 cells, they were tested using AlphaLISA® SureFire® technology (Perkin Elmer p-ERK1/2 p-T202/Y204 assay kit ALSU-PERK-A10K). The main procedure is essentially the same as described above, with the following adjustments: Cells were seeded with the seeding density of 30,000 cells per well. On the second day (the day of dosing) no medium change was performed and the cells were dosed with 1 µM of Encorafenib for 1 hour (at 37° C. and 5% $CO_2$) to induce RAF dimers and promote paradoxical dimer-dependent pERK signalling. After incubation, the cells were washed, 100 µl fresh growth medium was added, and cells were dosed with compounds of interest to produce a 10-point dose response, where the top concentration was 10 µM and subsequent concentrations are at ½ log dilution intervals. Cells were incubated for another hour at 37° C. and 5% $CO_2$ before lysis and processing with the pERK AlphaLISA® SureFire® kit as described above.

A375 AlphaLISA SureFire pERK1/2 Cellular Assay (Monomer)

The human A375 melanoma cell line (ATCC CRL-1619) endogenously expresses the BRAF$^{V600E}$ mutation, which leads to constitutive activation of the MAP kinase pathway and phosphorylation of ERK. In BRAF$^{V600E}$ mutant tumours, BRAF signals as a monomer to activate ERK. To determine whether compounds can inhibit BRAF monomers in A375 cells, they were tested using AlphaLISA® SureFire® technology (Perkin Elmer p-ERK1/2 p-T202/Y204 assay kit ALSU-PERK-A10K). The main procedure is essentially the same as described above for HCT-116 cells, with the following adjustments: The A375 cells were cultivated and dosed in Dulbecco's modified Eagle's medium containing 4.5 g/L D-glucose (Sigma D6546), 10% heat-inactivated fetal bovine serum (Sigma F9665), and 1% Sodium-Pyruvate (Sigma S8636), and seeded with a seeding density of 30,000 cells per well. No media exchange was performed before dosing with compounds to produce a 10-point dose response, where the top concentration was 10 µM and subsequent concentrations were at ½ log dilution intervals. Subsequently, the cells were incubated for 1 hour at 37° C. and 5% $CO_2$ before lysis.

HCT-116 CellTiter-Glo 3D Cell Proliferation Assay

The human HCT-116 colorectal carcinoma cell line (ATCC CCL-247) endogenously expresses the KRAS$^G$13D mutation, which leads to enhanced survival and proliferative signaling. To determine whether compounds inhibit the proliferation of HCT-116 cells, they are tested using the CellTiter-Glo® 3D Cell Viability Assay Kit (Promega G9683). On the first day, HCT-116 cells were harvested, resuspended in growth medium (McCoys5A with Glutamax (Life Technologies 36600021) with 10% heat-inactivated fetal bovine serum (Sigma F9665)), and counted. Cells were plated in 100 µl per well in each well of a Corning 7007 96-well clear round bottom Ultra-Low Attachment plate (VWR 444-1020) to a final density of 1000 cells per well. Cells were seeded for pre- and post-treatment readouts. The cells were then incubated at 37° C. and 5% $CO_2$ for 3 days (72 hours) to allow spheroid formation. After 72 hours, the plate seeded for a pre-treatment read was removed from the incubator to allow equilibration to room temperature for 30 minutes, before CellTitre-Glo® reagent was added to each well. The plates were incubated at room temperature for 5 minutes shaking at 300 rpm, followed by an incubation of 25 minutes on the benchtop before being read on the Envision reader (Perkin Elmer) as described below. On the same day, the cells plated for the post-treatment readout were dosed with compounds to produce a 9-point dose response, where the top concentration was 15 µM and following concentrations were at ½ log dilution intervals. These cells were subsequently incubated at 37° C. and 5% $CO_2$ for another 4 days (96 hours). After 4 days, the plate was removed from the incubator to allow equilibration to room temperature for 30 minutes and treated with CellTitre Glo® reagent as stated above. The method allows the quantification of ATP present in the wells, which is directly proportional to the amount of viable—hence metabolically active—cells in 3D cells cultures. The CellTitre Glo® reagent lyses the cells and contains luciferin and a luciferase (Ultra-Glo™ Recombinant Luciferase), which in the presence of ATP and oxygen can produce bioluminescence from luciferin. Therefore, plates were read on an EnVision reader (Perkin Elmer) and luminescence signals were recorded. Cell proliferation was determined on 4 days after dosing relative to the pre-treatment read. All data were analyzed using the Dotmatics or GraphPad Prism software packages. Inhibition of proliferation was assessed by determination of the $GI_{50}$ value, which was defined as the concentration of compound required to decrease the level of cell proliferation by 50% when compared to DMSO control.

WiDr CellTiter-Glo 3D Cell Proliferation Assay

The human WiDr colorectal adenocarcinoma cell line (ATCC CCL-218) endogenously expresses the BRAF$^{V600E}$ mutation, which leads to enhanced survival and proliferative signaling. To determine whether compounds inhibit the proliferation of WiDr cells, they were tested using the CellTiter-Glo® 3D Cell Viability Assay Kit (Promega G9683) as stated for HCT-116 cells, with the following adjustments to the growth medium: Eagle's Minimum Essential Medium (Sigma M2279) with 1× Glutamax (Life Technologies 35050038), 1× Sodium-Pyruvate (Sigma S8636) and 10% heat-inactivated fetal bovine serum (Sigma F9665).

Microsomal Stability Assay

The stability studies were performed manually using the substrate depletion approach. Test compounds were incubated at 37° C. with cryo-preserved mouse or human liver microsomes (Corning) at a protein concentration of 0.5 mg·mL$^{-1}$ and a final substrate concentration of 1 µM. Aliquots were removed from the incubation at defined timepoints and the reaction was terminated by adding to ice-cold organic solvent. Compound concentrations were determined by LC-MS/MS analysis. The natural log of the percentage of compound remaining was plotted against each time point and the slope determined. The half-life ($t_{1/2}$) and CLint were calculated using Equations 1 and 2, respectively. Data analysis was performed using Excel (Microsoft, USA).

$$t_{1/2} \text{ (min)} = 0.693/-\text{slope} \tag{1}$$

$$CL_{int}(\mu L/min/mg) = (LN(2)/t_{1/2} \text{ (min)}) * 1000/\text{microsomal protein (mg/mL)} \tag{2}$$

HLM (human liver microsomes) and MLM (mouse liver microsomes) stability assay results are described in Tables 1-2.

Plasma Protein Binding Assay

The plasma protein binding was determined by the equilibrium dialysis method. A known concentration of compound (5 μM) in previously frozen human or mouse plasma (Sera Labs) was dialysed against phosphate buffer using a RED device (Life Technologies) for 4 hours at 37° C. The concentration of compound in the protein containing (PC) and protein free (PF) sides of the dialysis membrane were determined by LC-MS/MS and the % free compound was determined by equation 4. Data analysis was performed using Excel (Microsoft, USA).

$$\% \text{ free} = (1 - ((PC - PF)/PC)) \times 100 \tag{4}$$

hPPB (human plasma protein binding) and mPPB (mouse plasma protein binding) results are described in Tables 1-2.

FeSSIF Solubility Assay 1 mL of fed state simulated intestinal fluid (FeSSIF), prepared using FaSSIF/FeSSIF/FaSSGF powder (Biorelevant.com) and pH 5 acetate buffer, was added to 1.0 mg of compound and then incubated for 24 h (Bioshake iQ, 650 rpm, 37° C.). Following filtration under positive pressure, the concentration of compound in solution was assessed by LC-UV in comparison to the response for a calibration standard of known concentration (250 μM). FeSSIF solubility results are described in Tables 1-2.

TABLE 1

| Comp. No | pERK A375 (1 hr) pIC50 | pERK HCT116 dimer (1 hr) pIC50 | pERK HCT116 (2 hr) Abs pIC50 | pERK WiDr (2 hr) Abs pIC50 | HLM (CLint) μL/min/mg | MLM (CLint) μL/min/mg | hPPB (% free) | mPPB (% free) | Sol mg/L |
|---|---|---|---|---|---|---|---|---|---|
| 1 | 7.55 | 7.17 | nd | nd | 123.1 | 108.8 | 0.2 | 0.5 | <1.2 |
| 2 | 7.90 | 7.23 | nd | nd | 147.3 | 85.8 | 0.3 | 1 | <1.1 |
| 3 | 7.36 | 6.95 | nd | nd | 30.3 | 34.4 | 0.2 | 0.5 | nd |
| 4 | 7.01 | 6.57 | nd | nd | 261.4 | 121.2 | <0.1 | 0.5 | <1.3 |
| 5 | 6.73 | 6.72 | nd | nd | 33.9 | 28.5 | 0.3 | 0.4 | <1.2 |
| 6 | 6.01 | 6.35 | nd | nd | 33.4 | 18.1 | 2.4 | 1.3 | <1.4 |
| 7 | 6.16 | 6.72 | nd | nd | 67.9 | 39.2 | 1.9 | 0.9 | <1.4 |
| 8 | 6.50 | 6.57 | 6.76 | 6.75 | 36 | 13.9 | 1.0 | 1.1 | 18.5 (FESSIF) |
| 9 | 6.48 | 6.73 | nd | nd | 70.5 | 6.1 | 0.6 | 0.4 | <1.1 |
| 10 | 6.08 | 6.55 | nd | nd | 89.1 | 45.9 | 0.6 | 0.7 | <1.2 |
| 11 | 6.59 | 6.67 | nd | nd | 10.3 | 29.1 | 0.5 | 0.1 | <1.2 |
| 12 | 7.37 | 6.64 | 6.59 | 6.91 | 88.6 | 15.7 | <0.1 | <0.1 | <1.3 |
| 13 | 7.45 | 6.91 | nd | nd | 77.1 | 114.1 | 0.7 | 1.2 | <1.2 |
| 14 | 7.74 | 7.12 | nd | nd | 60.7 | 51.3 | 0.1 | 0.5 | <1.1 |
| 15 | 7.62 | 7.17 | nd | nd | 39.9 | 33.9 | 0.2 | 1.3 | <1.1 |
| 16 | 6.24 | 6.21 | nd | nd | nd | nd | nd | nd | <1.2 |
| 17 | 6.03 | 6.46 | nd | nd | 31.5 | 16.5 | 0.7 | 2.4 | <1.2 |
| 18 | 5 | 5.44 | nd | nd | 71.1 | 32.9 | 1.2 | 2.5 | nd |
| 19 | 5.79 | 6.46 | 6.50 | 5.96 | 27.8 | 23 | 1.9 | 1.5 | 19.6 (FESSIF) |
| 20 | 6.13 | 6.22 | nd | nd | 16.9 | 3 | 0.1 | 0.1 | <1.3 |
| 21 | 6.03 | 6.56 | nd | nd | 15.6 | 23.2 | 0.7 | 1.6 | <1.2 |
| 22 | 7.70 | 6.81 | 6.85 | 6.92 | 35.9 | 25.1 | <0.1 | <0.1 | <1.2 |
| 23 | 6.59 | 6.65 | 6.50 | 6.64 | 29.9 | 30.5 | 0.5 | 0.5 | <1.1 |
| 24 | 6.25 | 6.81 | 6.39 | 6.30 | 12.7 | 41.6 | 1.8 | 1.9 | <1.1 |
| 25 | 6.94 | 6.94 | 7.07 | 6.89 | 50.1 | 48.5 | 0.3 | 1.5 | 1.8 (FESSIF) |
| 26 | 7.19 | 6.56 | 6.38 | 6.52 | 77.5 | 89.3 | 0.7 | 1 | <1.1 |
| 27 | 6.41 | 6.42 | nd | nd | 101.7 | 148.1 | <0.1 | <0.1 | <1.2 |
| 28 | 5.74 | nd | nd | nd | 68.1 | 31.1 | 0.1 | 0.5 | nd |
| 29 | 7.49 | 6.66 | 6.88 | 6.97 | 118.6 | 77.6 | 0.2 | 0.6 | <1.1 |
| 30 | 6.79 | 5.88 | nd | nd | nd | nd | nd | nd | <1.3 |
| 31 | 6.90 | 6.06 | nd | nd | 34.6 | 26 | <0.1 | 0.2 | <1.2 |
| 32 | 6.60 | 6.40 | 6.64 | 6.69 | 11.3 | 8.3 | 1.3 | 3.2 | <1.2 |
| 33 | 6.42 | 6.18 | nd | nd | 77.3 | 37 | 2 | 3.1 | 7 |
| 34 | 5.35 | nd | nd | nd | 46.9 | 8.6 | 0.7 | 3.2 | 28.7 |
| 35 | 5.61 | 6.28 | nd | nd | 277 | 42.1 | <0.1 | nv | <1.3 |
| 36 | 6.28 | 6.76 | nd | nd | 23.5 | 18.4 | nv | <0.1 | <1.2 |
| 37 | 6.30 | 6.47 | nd | nd | nd | 18.4 | nv | nv | <1.2 |
| 38 | 5.07 | 5.40 | nd | nd | 3 | 4.3 | nv | nv | <1.3 |
| 39 | nd | nd | nd | nd | nd | 15.4 | nv | nd | <1.2 |
| 40 | 6.60 | 6.49 | nd | nd | nd | 27.1 | nv | nd | <1.2 |
| 41 | 6.29 | 6.52 | nd | nd | nd | 46.1 | nv | 1.2 | <1.2 |
| 42 | 6.05 | 6.13 | nd | nd | 10.6 | 22 | nv | <0.1 | <1.3 |
| 43 | nd | nd | nd | nd | nd | 23.2 | nv | nd | <1.2 |
| 44 | 5.92 | 6.54 | 6.27 | 6.45 | 14.2 | 11 | 0.3 | 0.9 | <1.2 |
| 45 | 6.79 | 7.05 | 7.56 | 7.18 | 58.1 | 277 | 0.2 | 0.2 | <1.2 |
| 46 | nd | nd | nd | nd | 18.4 | 45.5 | 1.9 | 2.3 | <1 |
| 47 | 6.64 | 7.19 | 7.16 | 6.93 | 24.5 | 32.5 | 0.7 | 0.3 | 27.5 (FESSIF) |
| 48 | 5.04 | 5.14 | nd | nd | 40.5 | 38.4 | 2 | 3 | <1.1 |
| 49 | 5.11 | 5.05 | nd | nd | 82.2 | 83.6 | 1.9 | 2.5 | <1.2 |
| 50 | 6.57 | 7.19 | 7.33 | 7.01 | 70.4 | 79 | 1.2 | 1.6 | <1.2 |
| 51 | nd | nd | nd | nd | 156.1 | 123.4 | 0.5 | 2.6 | 1.2 |

TABLE 2

| Comp. No | pERK A375 (1 hr) pIC50 | pERK HCT116 dimer (1 hr) pIC50 | pERK HCT116 (2 hr) Abs pIC50 | pERK WiDr (2 hr) Abs pIC50 | 3D HCT116 pGI50 | 3D WiDr pGI50 | HLM (CLint) μL/min/mg | MLM (CLint) μL/min/mg | hPPB (% free) | mPPB (% free) | FESSIF Sol mg/L |
|---|---|---|---|---|---|---|---|---|---|---|---|
| 8 | 6.50 | 6.57 | 6.76 | 6.75 | 6.86 | 6.72 | 36 | 13.9 | 1.0 | 1.1 | 18.5 |
| 101 | 6.69 | 7.20 | 6.88 | 6.74 | 7.07 | 6.51 | 29.6 | 15.2 | 1.6 | 1.1 | 5.7 |
| 103 | 6.41 | 6.97 | 6.62 | 6.57 | 6.54 | 6.27 | 11.6 | 4.4 | 0.6 | 0.6 | 5.2 |
| 104 | 5.79 | 6.46 | 6.50 | 5.96 | 6.35 | 5.94 | 27.8 | 23 | 1.9 | 1.5 | 19.6 |
| 105 | 6.38 | 7.19 | 6.75 | 6.57 | 6.61 | 6.22 | 24.8 | 2.1 | 1.0 | 0.86 | 8.6 |
| 106 | 6.03 | 6.91 | 6.56 | 6.23 | 6.36 | 5.81 | 10.5 | 17.1 | 2.4 | 3.0 | 28.1 |
| 107 | 6.75 | 7.24 | 6.72 | 6.68 | 6.64 | 6.11 | 30.3 | 12.5 | 0.7 | 0.3 | |
| 108 | 5.20 | 6.41 | <6 | | | | | | | | |
| 109 | | | <6 | | | | | | | | <1.1 |
| 110 | 6.97 | 7.30 | 7.05 | 7.15 | 7.15 | 6.70 | 48.3 | 55.5 | 0.2 | 0.1 | 8.5 |
| 111 | 6.27 | 6.97 | 6.66 | 6.49 | 6.50 | 5.99 | 48.1 | 26.9 | 1.91 | 1.73 | 70 |
| 112 | 5.75 | 6.59 | <6 | 6.00 | | | 81.5 | 55.5 | 1.4 | 2.0 | 51.1 |
| 113 | 5.33 | 6.29 | <6 | 5.83 | | | 82.1 | 38.2 | 0.6 | 1.6 | 139.6 |
| 114 | 5.59 | 6.44 | <6 | 5.87 | | | 38.5 | 12.6 | 1.2 | 2.0 | 496.7 |
| 115 | 7.86 | 6.98 | 7.34 | 8.09 | 7.17 | 7.42 | 277 | 277 | 0.3 | 0.3 | 129.1 |
| 116 | 7.33 | 7.06 | 7.17 | 7.40 | 7.18 | 6.90 | 277 | 277 | 0.13 | 0.23 | 311.4 |
| 117 | 6.14 | 6.96 | 6.97 | 6.23 | 6.67 | 6.15 | 43.3 | 13.4 | 2.6 | 2.3 | 1.4 |
| 118 | 6.20 | 6.83 | 6.57 | 6.40 | 6.40 | 5.93 | 81.2 | 40 | 1.3 | 1.0 | |
| 119 | | | 6.14 | | | | 74.2 | 35.8 | 0.6 | 0.9 | <1.2 |
| 120 | | | 6.02 | | | | 189.6 | 89 | 0.9 | 0.6 | 1.3 |
| 121 | | | <6 | | | | 206.8 | 137.3 | 0.4 | 0.4 | 38.2 |
| 122 | 6.54 | 6.79 | 6.88 | 6.45 | 6.74 | 6.29 | 80.3 | 70.8 | 0.23 | 0.21 | 123.6 |
| 123 | 7.55 | 7.23 | 7.20 | 7.47 | 7.39 | 7.27 | 97.5 | 125.8 | 0.23 | 0.25 | 156.5 |
| 124 | 5.97 | 6.57 | 6.46 | 6.18 | 6.14 | 5.84 | 65.8 | 28.2 | 2.7 | 3.9 | 3 |
| 125 | 5.35 | 6.86 | 6.45 | 6.01 | 5.95 | 4.82 | | | | | 22.0 |
| 126 | 6.10 | 6.61 | 6.30 | 5.99 | | 4.82 | 121.1 | 55.7 | 1.0 | 0.7 | <1.3 |
| 127 | 6.07 | 6.80 | 6.38 | | | | 38.7 | 13.4 | 0.6 | 0.2 | 6.0 |
| 128 | 6.08 | 6.58 | 6.41 | | | | | | 0.9 | 1.2 | 1.6 |
| 129 | | | <6 | | | | | | | | 16.7 |
| 130 | 6.00 | 6.78 | 6.85 | 6.22 | 6.21 | 5.78 | 23.6 | 23.5 | 0.1 | 0.2 | |
| 131 | | | <6 | | | | | | | | 12.2 |
| 132 | 6.12 | 6.37 | 6.46 | 6.08 | 6.18 | 5.94 | 20.7 | 9.3 | 2.6 | 10.1 | 41.9 |
| 133 | | | <6 | | | | | | | | 661 |
| 134 | <6 | 7.49 | <6 | 5.21 | 4.82 | 4.59 | 13.6 | 72.4 | 6.1 | 9.5 | |
| 135 | | | <6 | | | | | | | | 33.2 |
| 136 | 6.79 | 7.05 | 7.56 | 7.18 | 7.32 | 6.77 | 58.1 | 277 | 0.2 | 0.2 | 17.1 |
| 137 | 6.72 | 7.55 | 7.45 | 7.13 | 7.15 | 6.90 | 32.6 | 277 | 0.1 | <0.1 | 73.9 |
| 138 | 5.79 | 6.09 | 6.56 | | | | 134.1 | 277 | <0.1 | <0.1 | |
| 139 | 5.97 | 6.66 | 6.70 | | | | 99.8 | 277 | <0.1 | <0.1 | 106.6 |
| 140 | 5.23 | 5.69 | <6 | 5.90 | 5.88 | 5.72 | 48.7 | 81.1 | <0.1 | 0.2 | |
| 141 | | | <6 | | | | 1.0 | 21.8 | <0.1 | 0.5 | |
| 142 | | | <6 | | | | | | | | 135.4 |
| 143 | 6.10 | 6.24 | 6.51 | 6.52 | 6.13 | 5.82 | 36.1 | 86.1 | <0.1 | <0.1 | 44.7 |
| 144 | 6.69 | 7.22 | 7.34 | 7.02 | 7.00 | 6.42 | 27.1 | 29.3 | 0.7 | 0.8 | 317.5 |
| 145 | 6.27 | 6.75 | 6.78 | 6.48 | 6.32 | 5.20 | 57.2 | 147.3 | 0.4 | 0.53 | |
| 146 | 6.43 | 6.77 | 6.75 | 6.40 | 6.42 | 6.09 | 33.4 | 89.7 | 1.5 | 0.7 | 403.9 |
| 147 | 6.20 | 6.36 | 6.49 | 6.06 | 5.86 | 5.86 | 10.4 | 102 | 0.5 | 0.8 | 527.6 |
| 148 | 5.91 | 6.34 | 6.52 | 6.06 | 6.31 | 5.92 | 132.2 | 211 | 0.9 | 0.4 | 104.3 |
| 149 | 5.88 | 6.44 | 6.50 | 6.03 | 6.07 | 5.65 | 63.7 | 230.9 | 0.25 | 0.14 | 200 |
| 150 | | | <6 | | | | | | | | 235.4 |
| 151 | 6.46 | 6.69 | 6.75 | 6.65 | 6.42 | 5.94 | 18.3 | 161 | 0.21 | <0.1 | 86.6 |
| 152 | 6.22 | 6.56 | 6.68 | 6.66 | 6.08 | 5.25 | 29 | 258.7 | 0.48 | 0.47 | 997.1 |
| 153 | 6.30 | 6.90 | 6.70 | 6.54 | 6.37 | 5.25 | 19.2 | 92.9 | 0.39 | 0.6 | 336 |
| 154 | 7.01 | 7.42 | 7.55 | 7.48 | 7.21 | 6.18 | 22.8 | 95.2 | 0.75 | 0.7 | 170.9 |
| 155 | 6.93 | 7.14 | 7.22 | 6.99 | 7.00 | 6.20 | 28.9 | 277 | 0.1 | 0.1 | 123.8 |
| 156 | 6.75 | 7.28 | 7.37 | 6.88 | 7.05 | 6.57 | 30.3 | 151.5 | 0.5 | 0.4 | 296.2 |
| 157 | 6.28 | 6.76 | 6.95 | 6.56 | 6.58 | 6.18 | 35.7 | 277 | <0.1 | <0.1 | 116.3 |
| 158 | | | 6.13 | | | | 21.3 | 62.8 | 0.3 | 0.2 | |
| 159 | | | <6 | | | | 19.8 | 34.4 | 1.0 | 0.5 | <1.0 |
| 160 | 6.06 | 6.46 | 6.87 | 6.66 | 6.21 | 5.68 | 2.7 | 4.5 | 0.3 | <0.1 | 3.0 |
| 161 | | | 6.25 | | | | | | | | <1.1 |
| 162 | | | <6 | | | | | | | | 13.7 |
| 163 | | | <6 | | | | | | | | <1.3 |

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed:

1. A compound of formula (I), or a pharmaceutically acceptable salt, tautomer, or stereoisomer thereof,

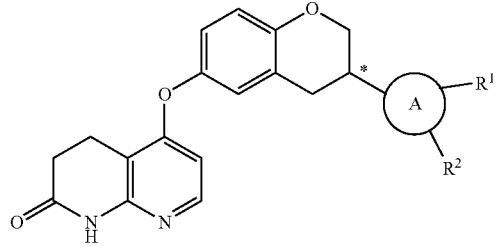

(I)

wherein:
ring A is an imidazole, a pyrazole, or a triazole;
one of $R^1$ or $R^2$ is a substituted $C_{1-8}$ alkyl, an unsubstituted $C_{5-8}$ alkyl, a substituted or unsubstituted $C_{1-8}$ haloalkyl, a substituted monocyclic aryl, substituted monocyclic heteroaryl, unsubstituted tetrahydropyran, substituted indazole, or substituted benzoimidazole, and the other $R^1$ or $R^2$ is H;
or alternatively, $R^1$ and $R^2$ together with the atoms to which they are attached forms a 5- or 6-membered saturated, partially unsaturated, or unsaturated ring containing 0, 1, or 2 heteroatoms selected from N, O, or S, wherein the ring is substituted with 1 or 2 substituents selected from methyl, ethyl, propyl, isopropyl, n-butyl, s-butyl, t-butyl, cyclopropyl, methoxy, ethoxy, isopropoxy, —$CH_2F$, —$CHF_2$, —$CF_3$, —$CH_2CH_2F$, —$CH_2CHF_2$, —$CH_2CF_3$, —$C(O)CH_3$, —CN, —OH, —$NH_2$, —$NH(C_{1-3}$ alkyl), —$N(C_{1-3}$ alkyl)$_2$, —$CH_2NH_2$, —$CH_2NH(C_{1-3}$ alkyl), or —$CH_2N(C_{1-3}$ alkyl)$_2$; and
wherein when ring A is an imidazole, then the substituted monocyclic aryl of $R^1$ or $R^2$ is not

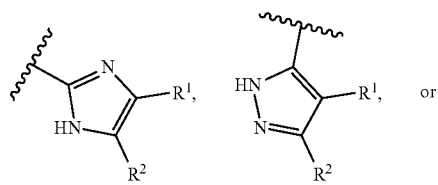

2. The compound of claim 1, wherein ring A is

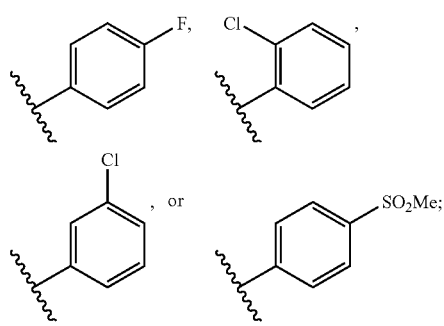

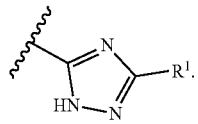

3. The compound of claim 1 having the structure of formula (I-A) or a pharmaceutically acceptable salt, tautomer, or stereoisomer thereof,

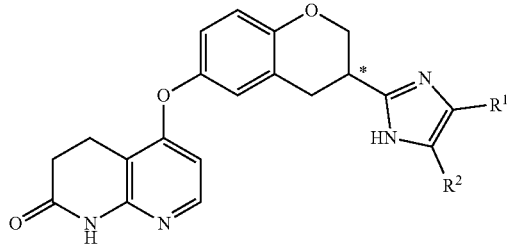

(I-A)

wherein:
one of $R^1$ or $R^2$ is a substituted or unsubstituted $C_{5-8}$ alkyl, a substituted or unsubstituted $C_{1-8}$ haloalkyl, a substituted monocyclic aryl, substituted monocyclic heteroaryl, unsubstituted tetrahydropyran, substituted indazole, or substituted benzoimidazole, and the other $R^1$ or $R^2$ is H;
or alternatively, $R^1$ and $R^2$ together with the atoms to which they are attached forms a 5- or 6-membered saturated, partially unsaturated, or unsaturated ring containing 0, 1, or 2 heteroatoms selected from N, O, or S, wherein the ring is substituted with 1 or 2 substituents selected from methyl, ethyl, propyl, isopropyl, n-butyl, s-butyl, t-butyl, cyclopropyl, methoxy, ethoxy, isopropoxy, —$CH_2F$, —$CHF_2$, —$CF_3$, —$CH_2CH_2F$, —$CH_2CHF_2$, —$CH_2CF_3$, —$C(O)CH_3$, —CN, —OH, —$NH_2$, —$NH(C_{1-3}$ alkyl), —$N(C_{1-3}$ alkyl)$_2$, —$CH_2NH_2$, —$CH_2NH(C_{1-3}$ alkyl), or —$CH_2N(C_{1-3}$ alkyl)$_2$; and
wherein the substituted monocyclic aryl of $R^1$ or $R^2$ is not

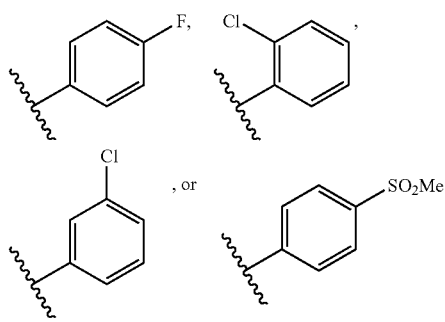

4. The compound of claim 1, wherein $R^1$ and $R^2$ together with the atoms to which they are attached forms a substituted phenyl ring, a substituted pyridyl ring, or a substituted tetrahydropyridyl ring.

5. The compound of claim 1, wherein the compound has the structure of formula (I-B), or a pharmaceutically acceptable salt, tautomer, or stereoisomer thereof, (I-B)

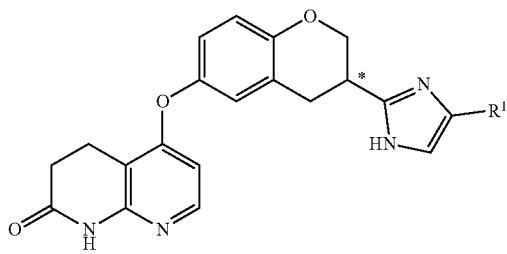

wherein R¹ is a substituted monocyclic aryl, a substituted monocyclic heteroaryl, unsubstituted tetrahydropyran, substituted indazole, or substituted benzoimidazole; and wherein the substituted monocyclic aryl is not

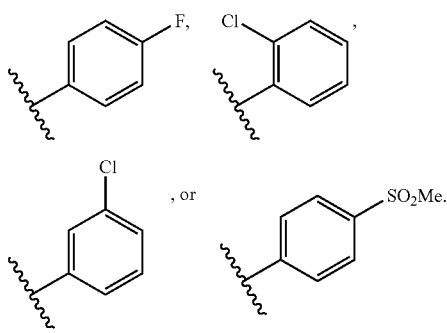

6. The compound of claim 1, wherein R¹ is a substituted monocyclic aryl, substituted monocyclic heteroaryl, substituted indazole, or substituted benzoimidazole.

7. The compound of claim 6, wherein:

a) R¹ is a substituted phenyl or a substituted 5- or 6-membered N-heteroaryl;

b) R¹ is a substituted phenyl, a substituted pyridyl, a substituted pyrazole, a substituted pyrimidinyl, or a substituted thiophenyl;

c) R¹ is a monocyclic substituted aryl or a monocyclic substituted heteroaryl;

d) R¹ is a substituted monocyclic aryl; or e) R¹ is a substituted indazole or a substituted benzoimidazole.

8. The compound of claim 5, wherein R¹ is an unsubstituted tetrahydropyran.

9. The compound of claim 1, wherein the substituent of the substituted monocyclic aryl, the substituted monocyclic heteroaryl, the substituted indazole, and the substituted benzoimidazole is selected from halogen, methyl, ethyl, propyl, isopropyl, n-butyl, s-butyl, t-butyl, cyclopropyl, methoxy, ethoxy, isopropoxy, —CH₂F, —CHF₂, —CF₃, —CH₂CH₂F, —CH₂CHF₂, —CH₂CF₃, —C(O)CH₃, —CN, —OH, —NH₂, —NH(C$_{1-3}$ alkyl), —N(C$_{1-3}$ alkyl)₂, —CH₂NH₂, —CH₂NH(C$_{1-3}$ alkyl), or —CH₂N(C$_{1-3}$ alkyl)₂.

10. The compound of claim 1, wherein the compound has (R) or (S) stereochemistry at the carbon indicated by *.

11. A compound having the structure

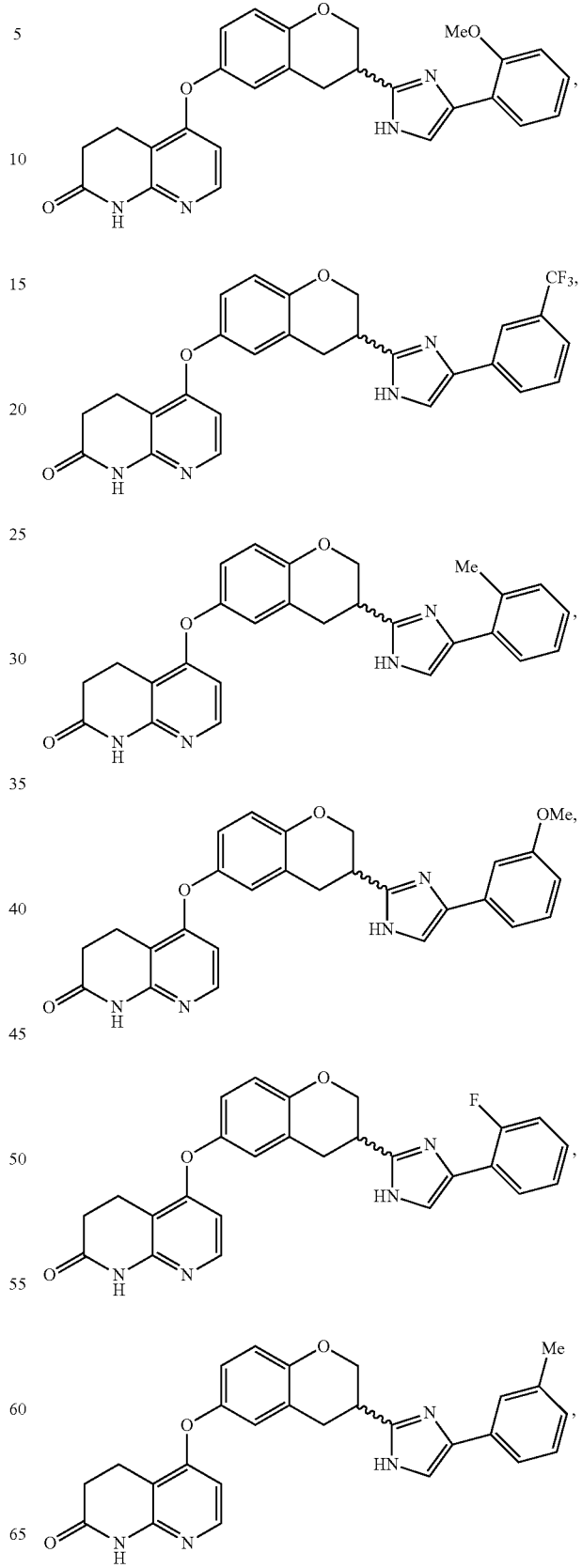

-continued

199
-continued
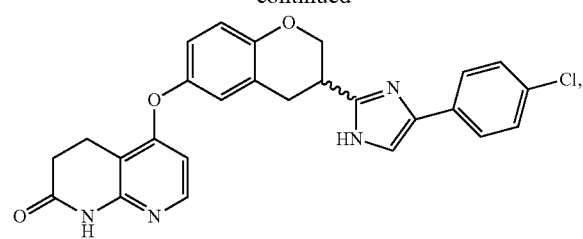
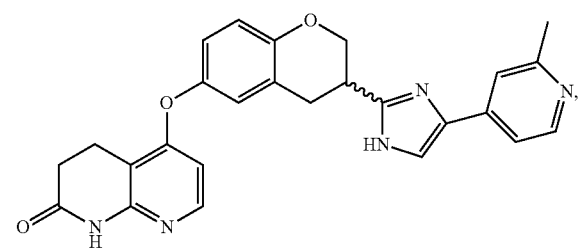
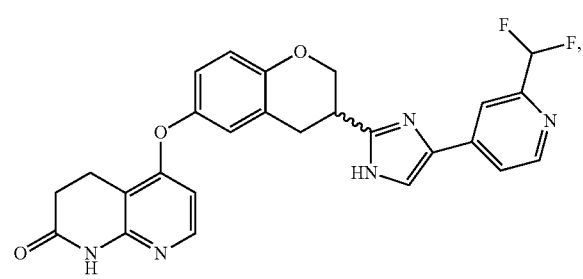
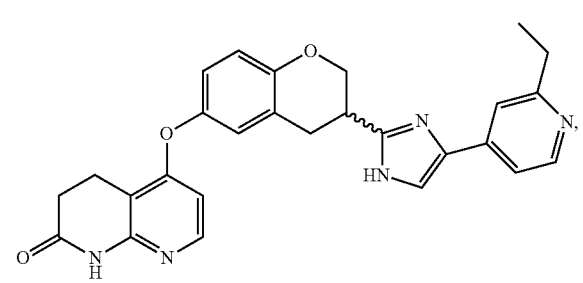
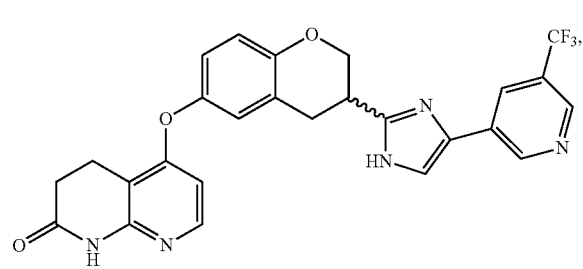
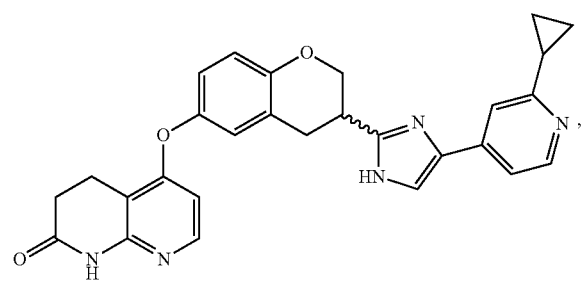
200
-continued
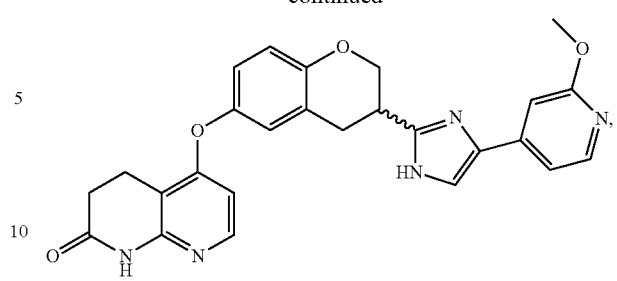
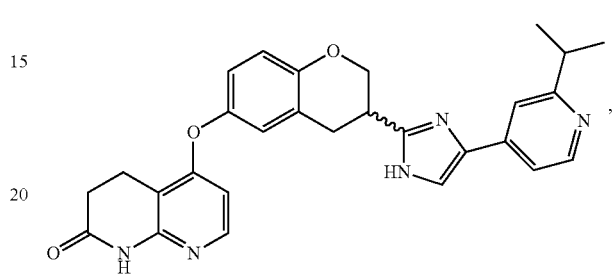
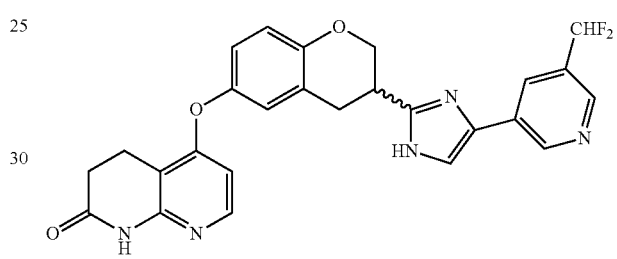
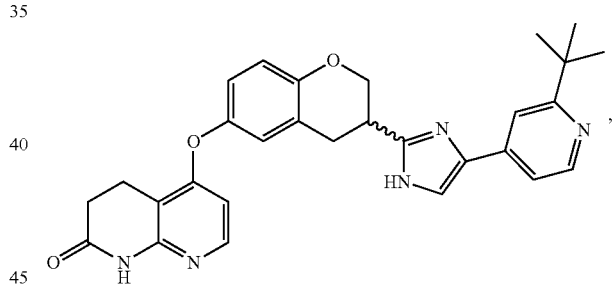
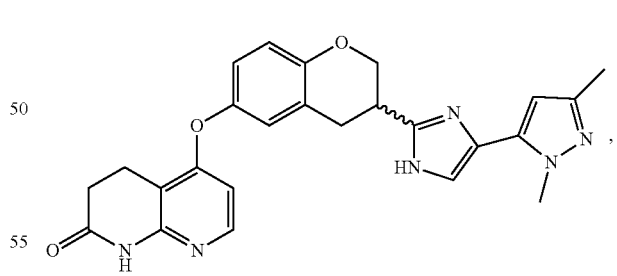
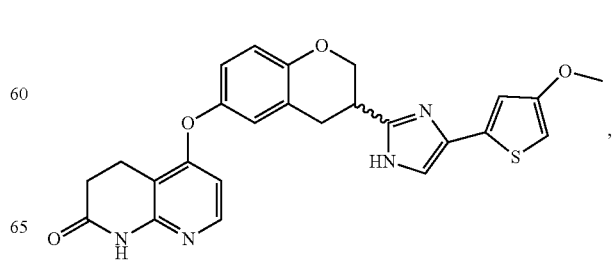

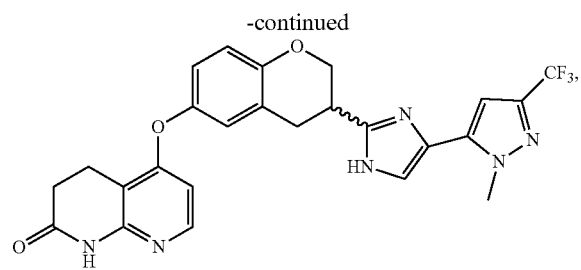
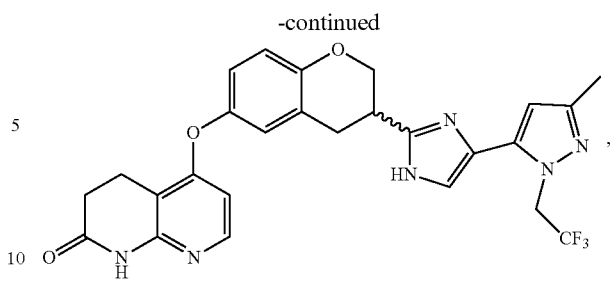
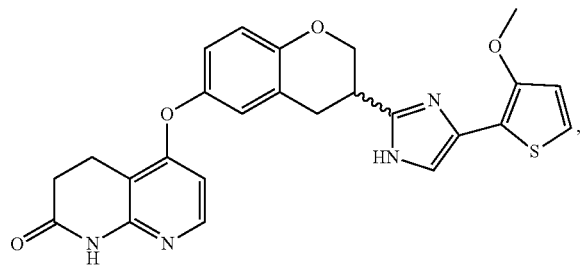
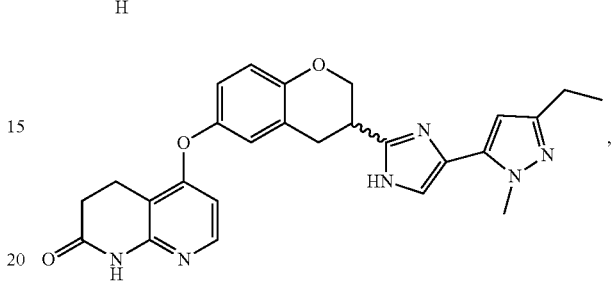
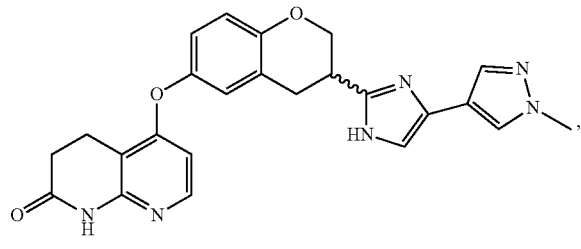
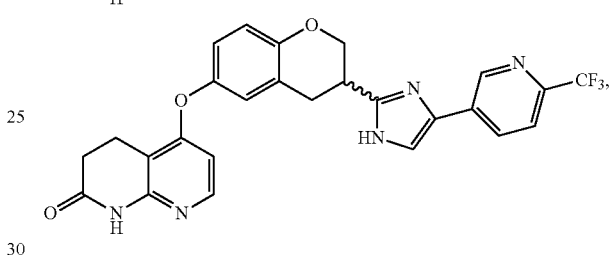
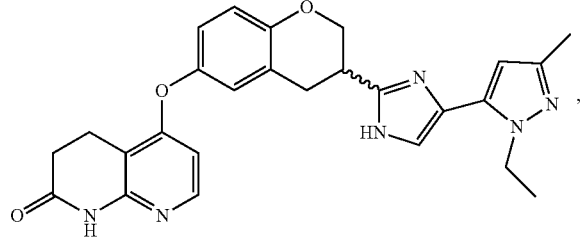
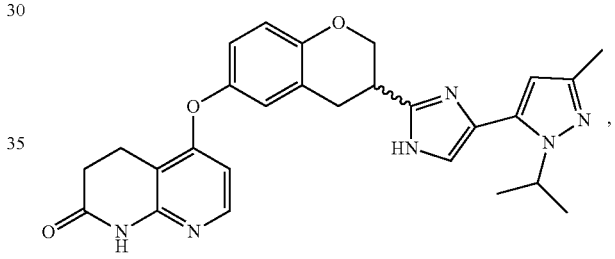
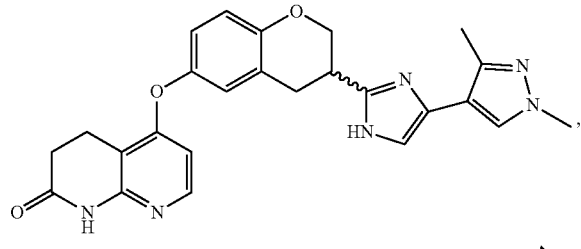
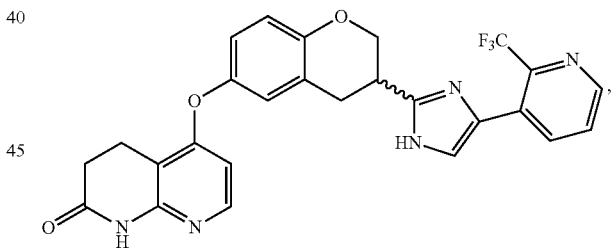
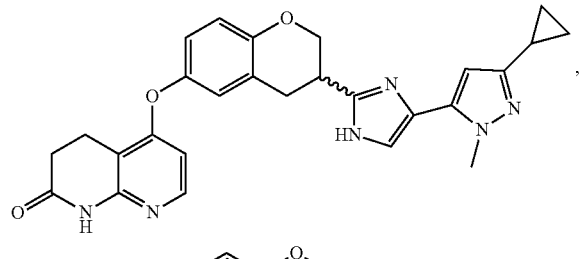
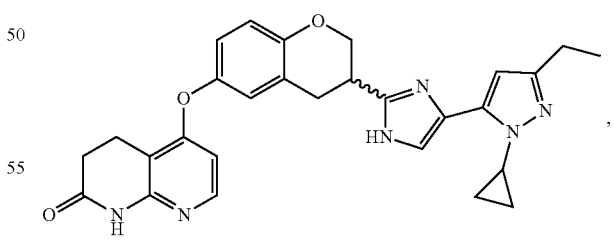
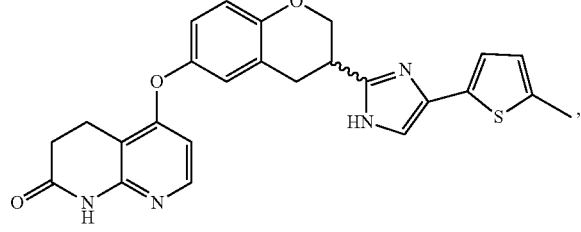
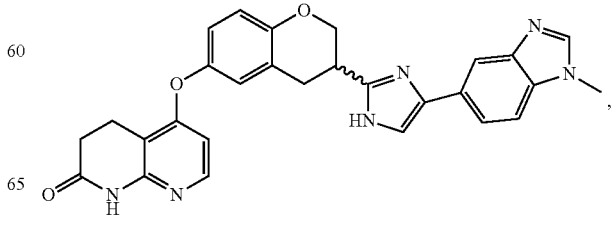

203
-continued
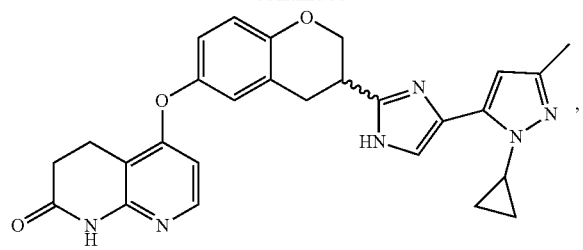
,
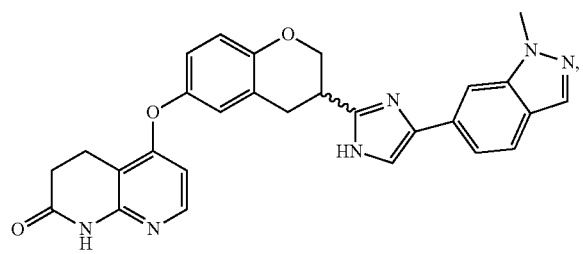
,
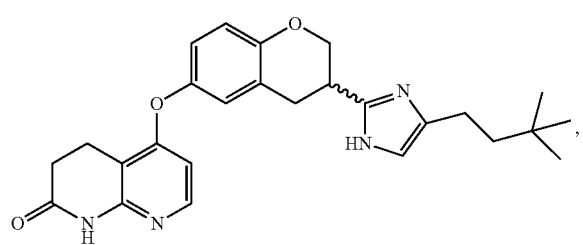
,
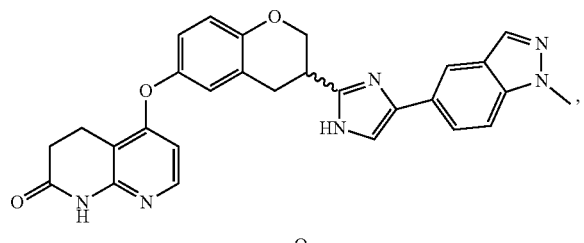
,
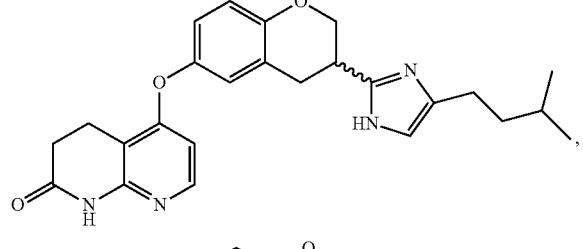
,
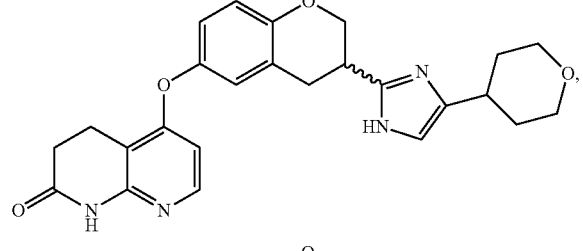
,
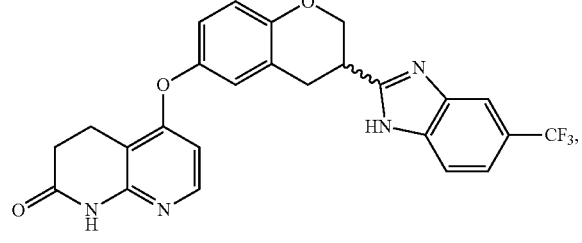
,
204
-continued
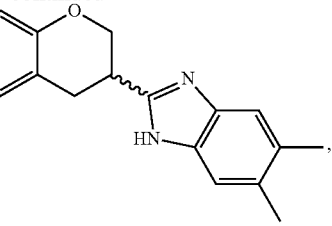
,
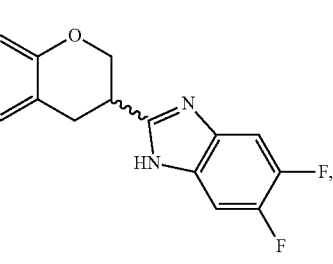
,
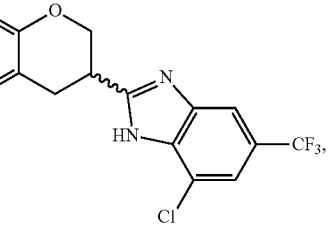
,
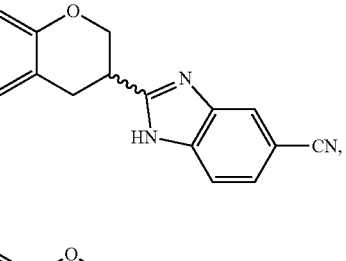
,
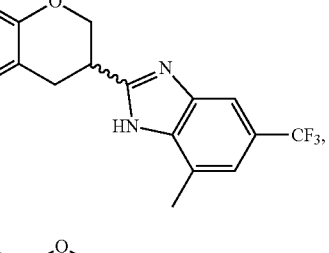
,
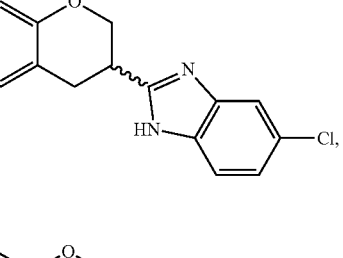
,
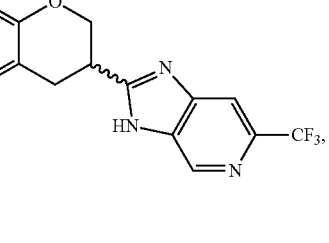
, -continued
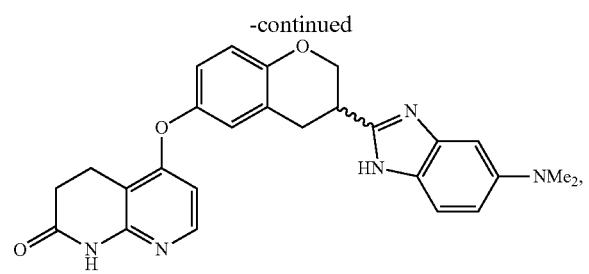
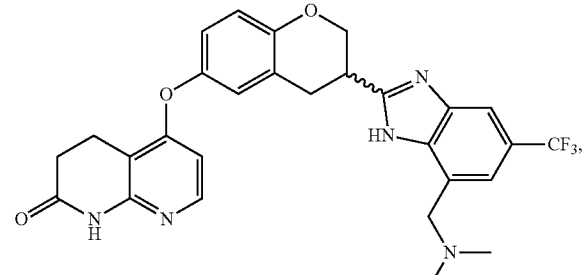
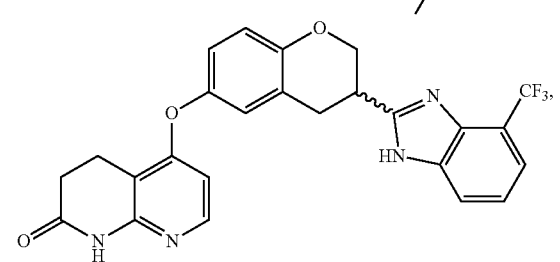
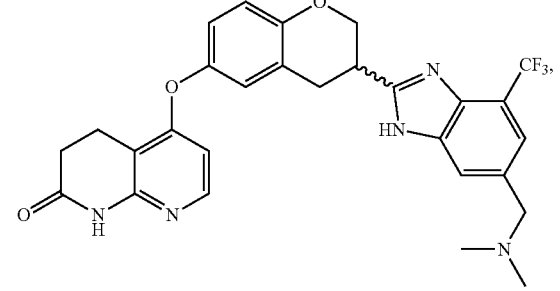
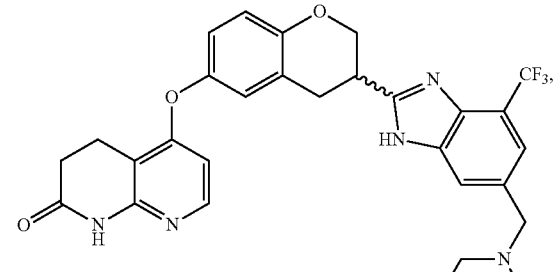
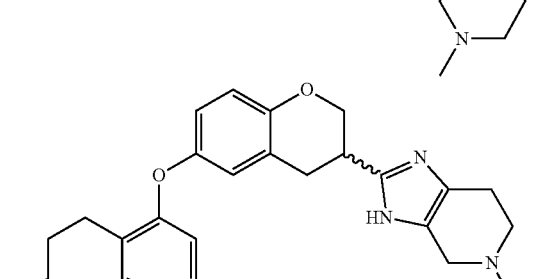
-continued
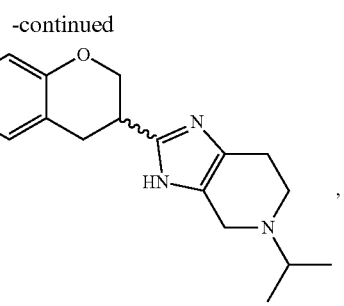
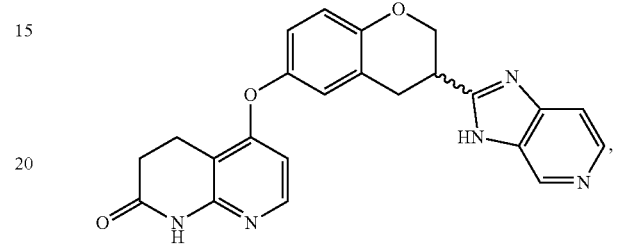
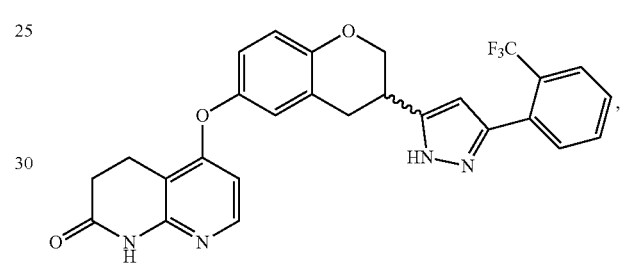
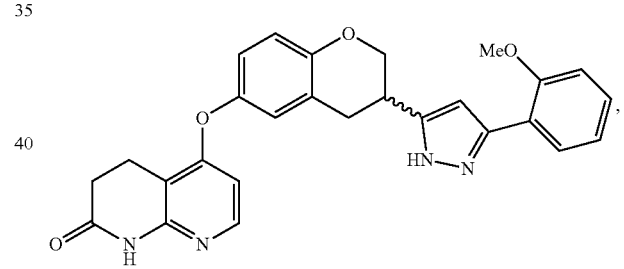
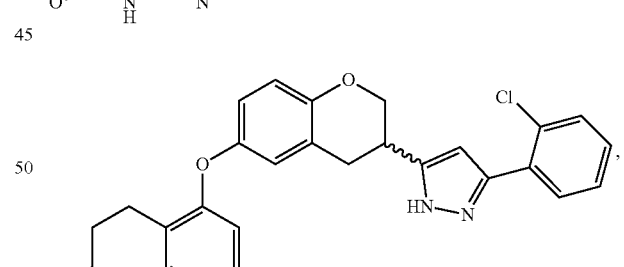
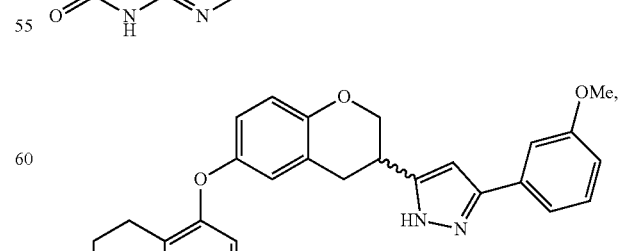

-continued

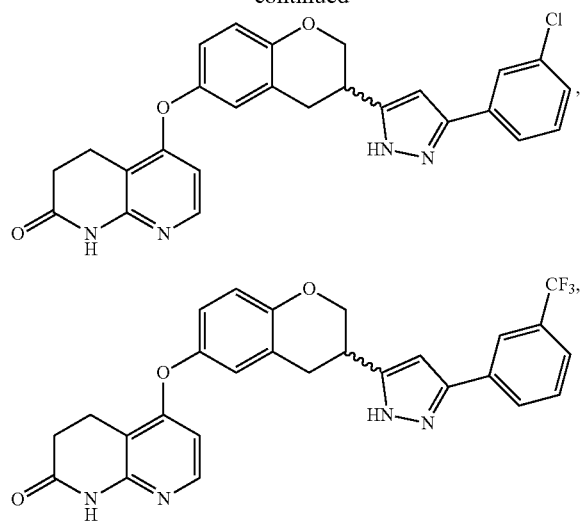

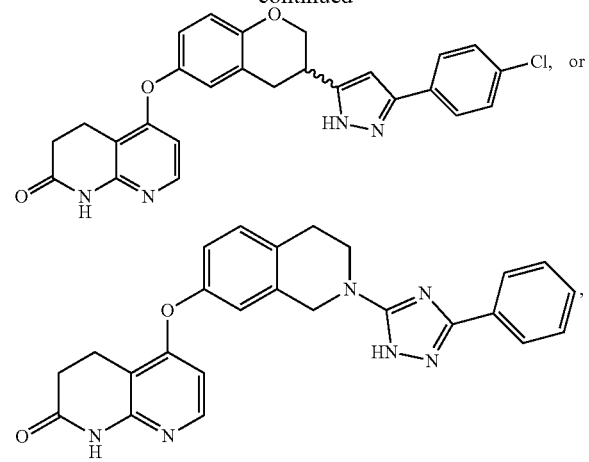

or a pharmaceutically acceptable salt, tautomer, or stereoisomer thereof.

12. A pharmaceutical composition comprising a compound of claim 1 and a pharmaceutically acceptable excipient or carrier.

13. The pharmaceutical composition of claim 12, further comprising an additional therapeutic agent.

14. The pharmaceutical composition of claim 13, wherein the additional therapeutic agent is an antiproliferative or an antineoplastic drug, a cytostatic agent, an anti-invasion agent, an inhibitor of growth factor function, an antiangiogenic agent, a steroid, a targeted therapy agent, or an immunotherapeutic agent.

15. A method of treating cancer, comprising administering an effective amount of the compound of claim 1 to a subject in need thereof, wherein the cancer is colorectal cancer or melanoma.

16. The method of claim 15, wherein the cancer comprises a $BRAF^{V600E}$ mutation.

17. The method of claim 16, wherein the cancer is $BRAF^{V600E}$ melanoma or $BRAF^{V600E}$ colorectal cancer.

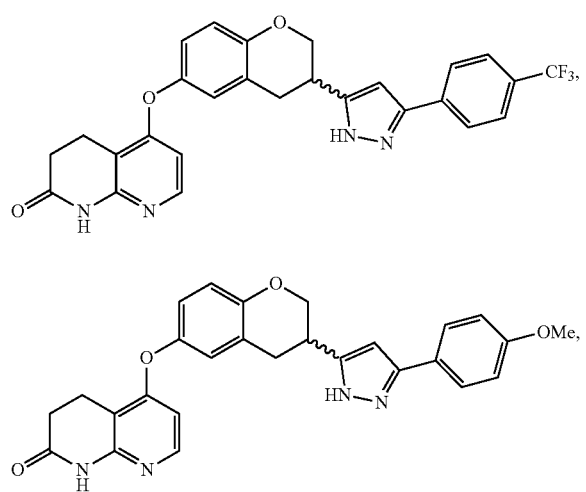

* * * * *